US011583569B2

(12) United States Patent
Gallo et al.

(10) Patent No.: US 11,583,569 B2
(45) Date of Patent: Feb. 21, 2023

(54) PSMA-TARGETING AMANITIN CONJUGATES

(71) Applicant: Heidelberg Pharma Research GmbH, Ladenburg (DE)

(72) Inventors: Francesca Gallo, Ladenburg (DE); Barbara Korsak, Ladenburg (DE); Christoph Mueller, Ladenburg (DE); Torsten Hechler, Ladenburg (DE); Andreas Pahl, Ladenburg (DE); Michael Kulke, Ladenburg (DE); Werner Simon, Ladenburg (DE); Christian Lutz, Ladenburg (DE)

(73) Assignee: Heidelberg Pharma Research GmbH, Ladenburg (DE)

( * ) Notice: Subject to any disclaimer, the term of this patent is extended or adjusted under 35 U.S.C. 154(b) by 0 days.

(21) Appl. No.: 16/649,898

(22) PCT Filed: Sep. 24, 2018

(86) PCT No.: PCT/EP2018/075789

§ 371 (c)(1),
(2) Date: Mar. 23, 2020

(87) PCT Pub. No.: WO2019/057964

PCT Pub. Date: Mar. 28, 2019

(65) Prior Publication Data

US 2020/0345807 A1 Nov. 5, 2020

(30) Foreign Application Priority Data

Sep. 22, 2017 (EP) .................................... 17192686

(51) Int. Cl.
*A61K 38/12* (2006.01)
*A61K 47/54* (2017.01)
*A61P 35/00* (2006.01)

(52) U.S. Cl.
CPC ............ *A61K 38/12* (2013.01); *A61K 47/542* (2017.08); *A61K 47/545* (2017.08); *A61P 35/00* (2018.01)

(58) Field of Classification Search
None
See application file for complete search history.

(56) References Cited

FOREIGN PATENT DOCUMENTS

| | | | | |
|---|---|---|---|---|
| WO | 2009/026177 A1 | | 2/2009 | |
| WO | 2014/078484 A1 | | 5/2014 | |
| WO | WO-2014078484 A1 | * | 5/2014 | ........... A61K 31/445 |
| WO | 2016/142049 A1 | | 9/2016 | |

OTHER PUBLICATIONS

European Patent Office, International Search Report in International Patent Application No. PCT/EP2018/075789 (dated Dec. 12, 2018).
European Patent Office, Written Opinion in International Patent Application No. PCT/EP2018/075789 (dated Mar. 28, 2019).

* cited by examiner

*Primary Examiner* — Christina Bradley

(57) ABSTRACT

The invention relates to a PSMA-targeting conjugate comprising (a) an amatoxin; (b) a small molecule PSMA-targeting moiety; and (c) optionally a linker linking said amatoxin and said small molecule PSMA-targeting moiety. The invention furthermore relates to a pharmaceutical composition comprising such conjugate.

18 Claims, 22 Drawing Sheets

Specification includes a Sequence Listing.

| | $R_1$ | $R_2$ | $R_3$ | $R_4$ |
|---|---|---|---|---|
| α-amanitin | OH | OH | $NH_2$ | OH |
| β-amanitin | OH | OH | OH | OH |
| γ-amanitin | H | OH | $NH_2$ | OH |
| ε-amanitin | H | OH | OH | OH |
| amanin | OH | OH | OH | H |
| amaninamide | OH | OH | $NH_2$ | H |
| amanullin | H | H | $NH_2$ | OH |
| amanullinic acid | H | H | OH | OH |
| γ-amanin | H | OH | OH | H |
| γ-amaninamide | H | OH | NH2 | H |

FIGURE 7:
A
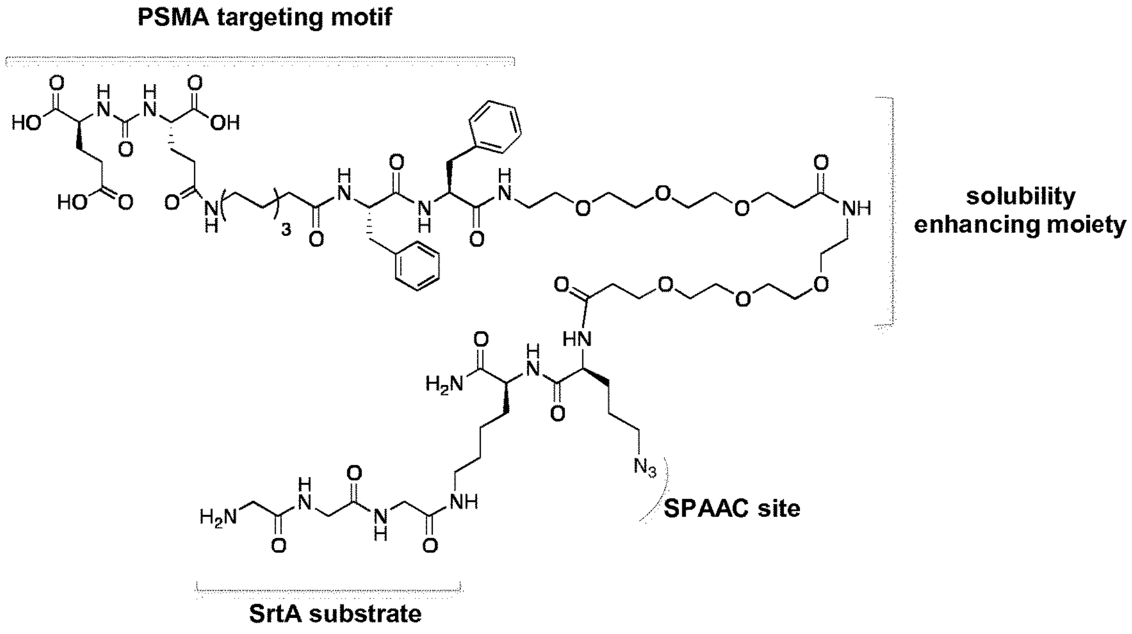
Trifunctional DUPA-containing linker.
B
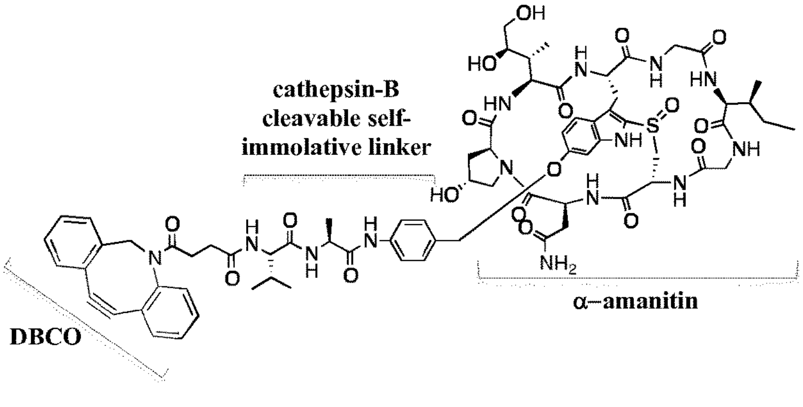
Amanitin-DBCO linker

FIGURE 8:

AENLYFQGGGGGEPKSCDKTHTCPPCPAPELLGGPSVFLFPPKPKDTLMISRTPEVTC
VVVDVSHEDPEVKFNWYVDGVEVHNAKTKPREEQYASTYRVVSVLTVLHQDWLNGKE
YKCKVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMHEALH
NHYTQKSLSLSPGGSLPETGG

Structure of the polypeptide:

A TEV cleavage site GGGG H20 region P Fc domain (CH2-CH3) SrtA tag G

A:

FIGURE 13 (contd.):
B:
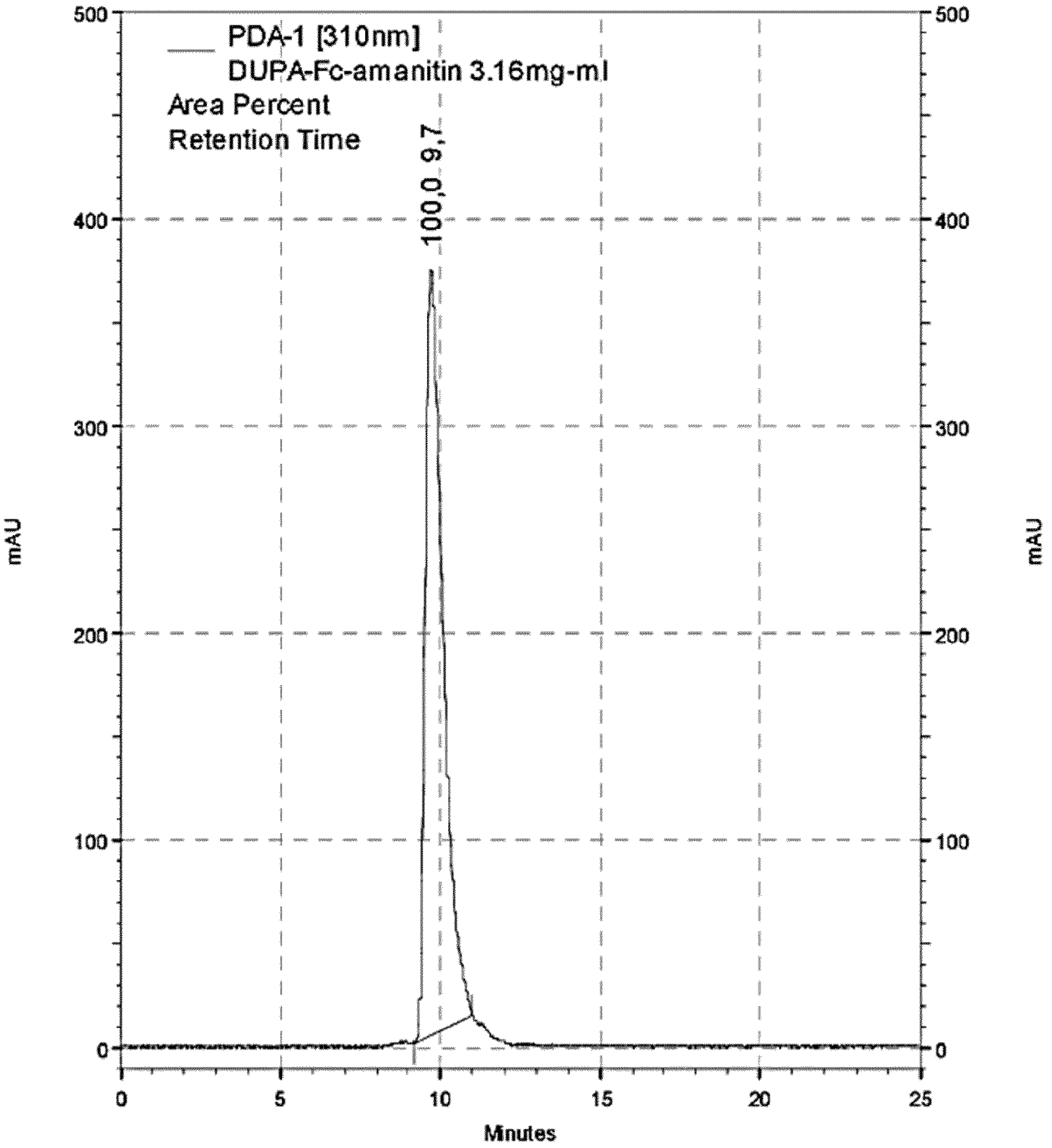

FIGURE 14A (contd.):
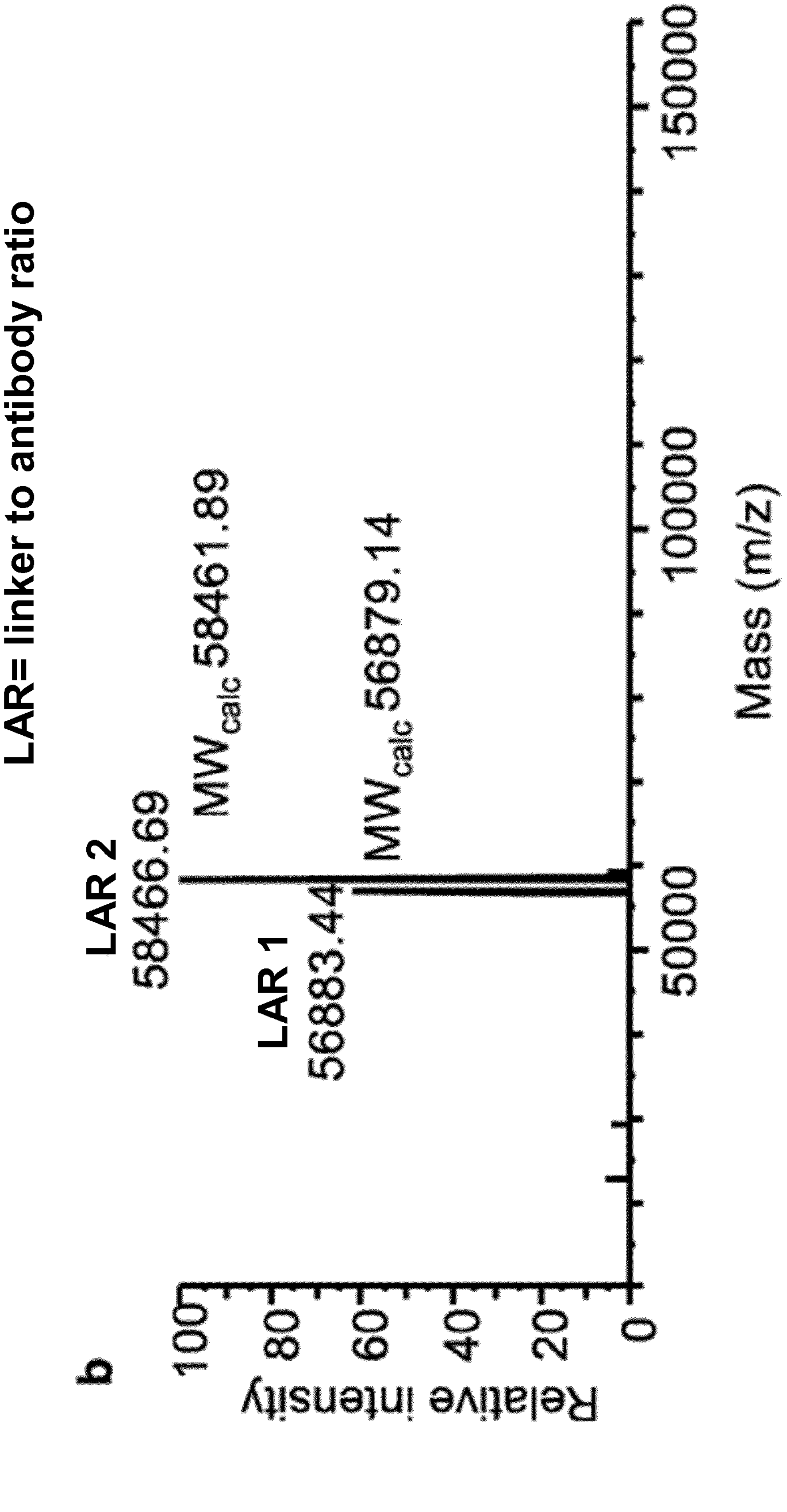

FIGURE 14A (contd.):
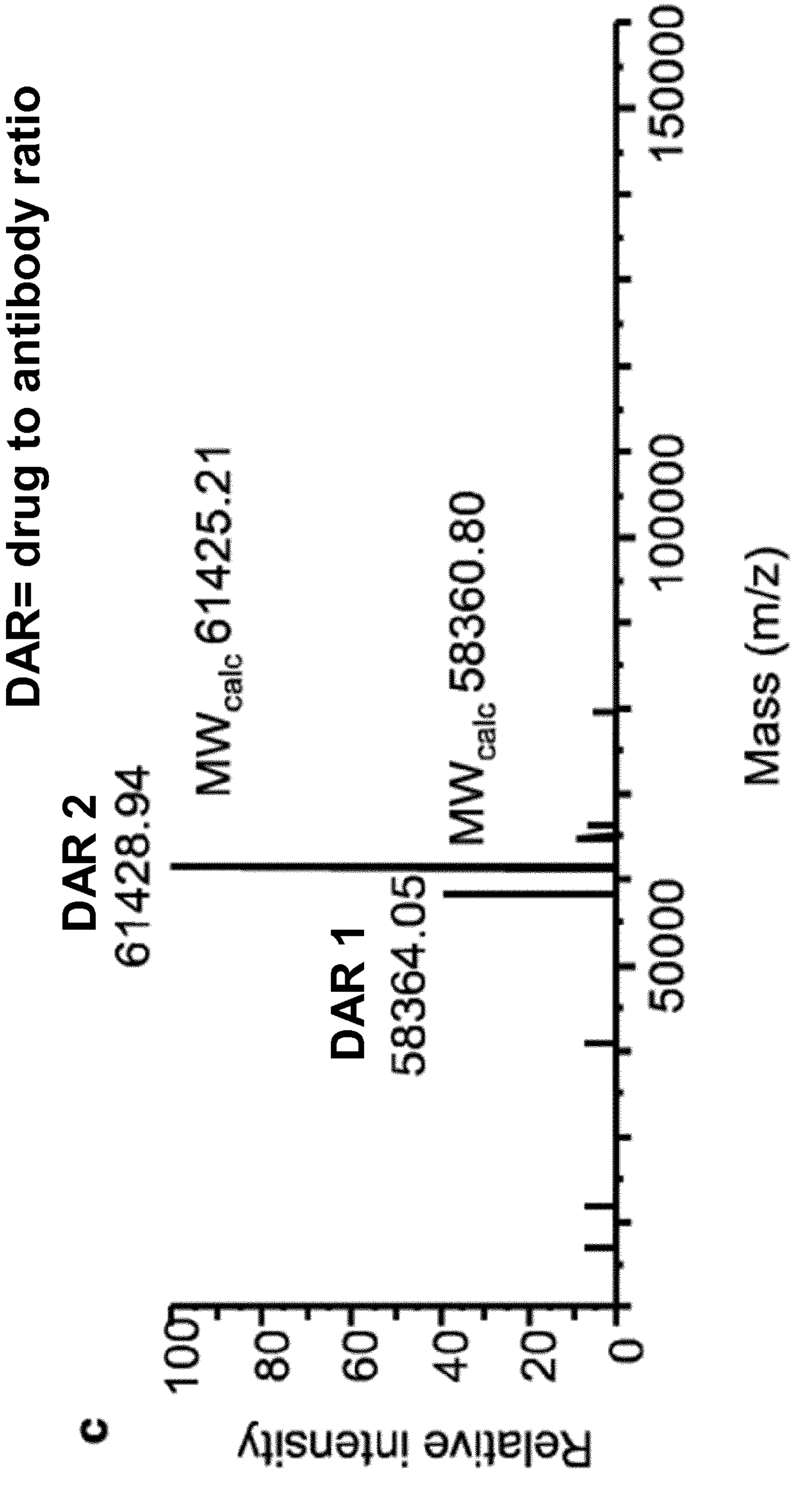

FIGURE 14 (contd.):
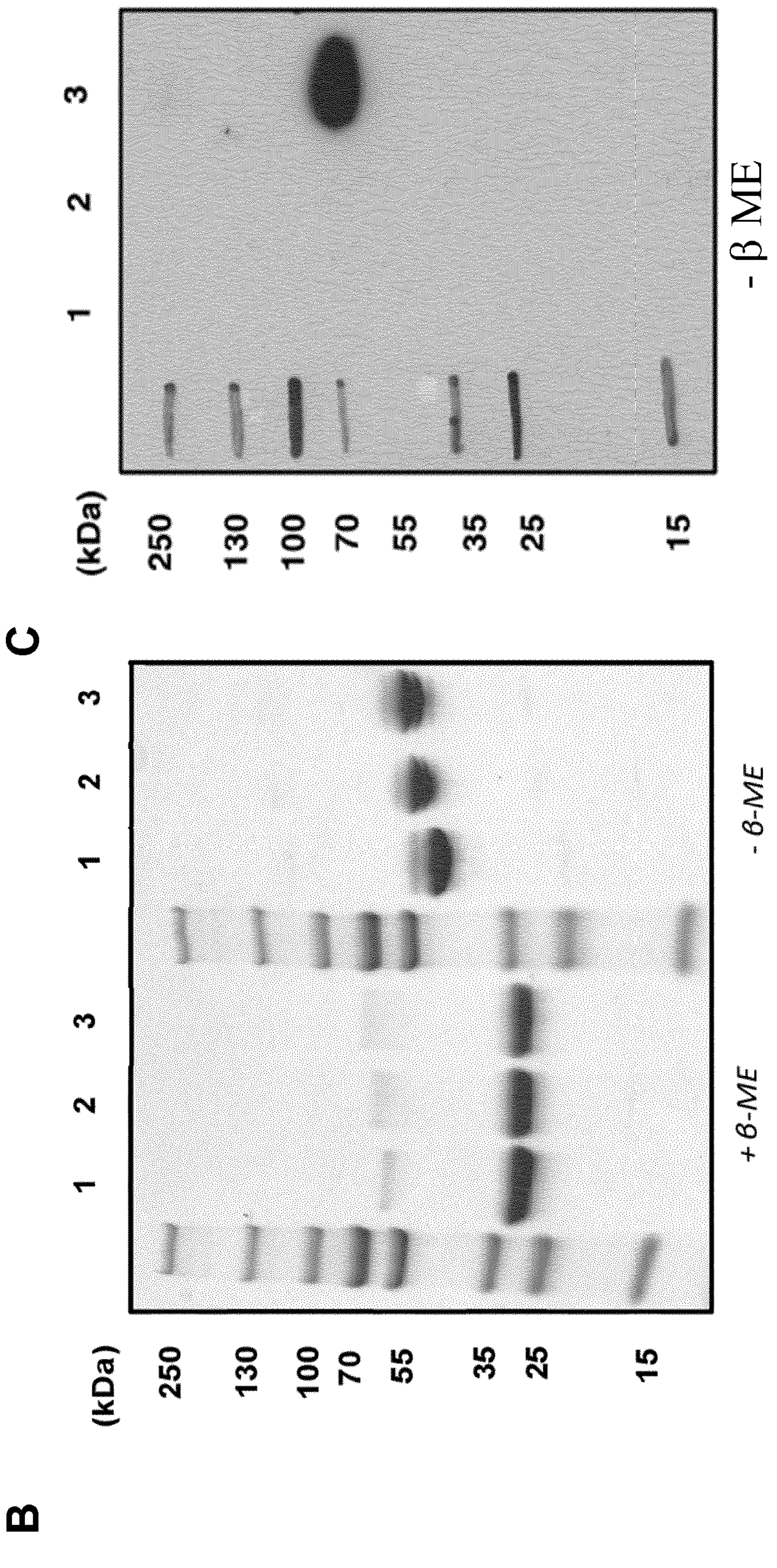

LNCaP PSMA (+++); 22RV1 PSMA) (+)

FIGURE 15 (contd.):
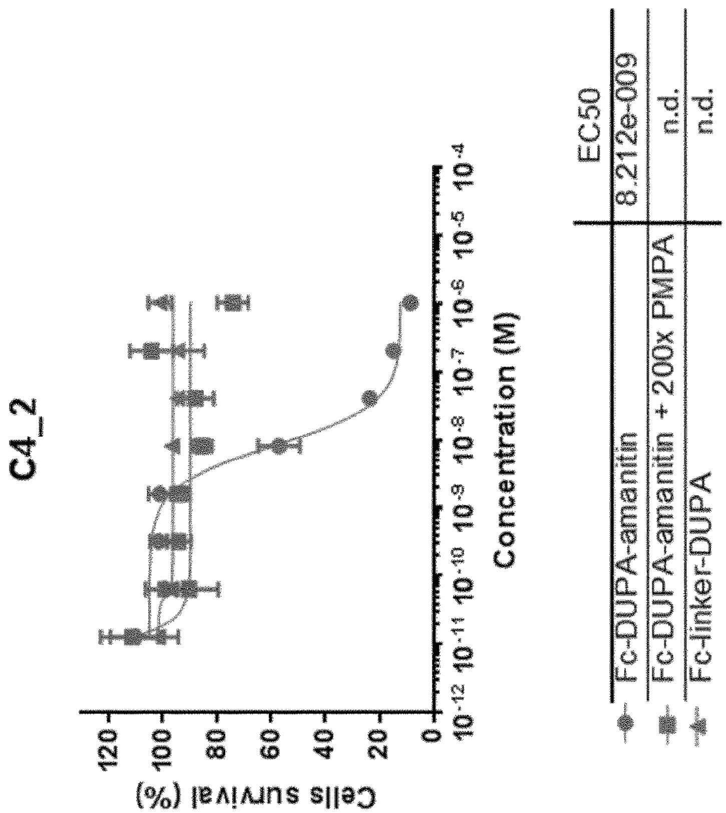
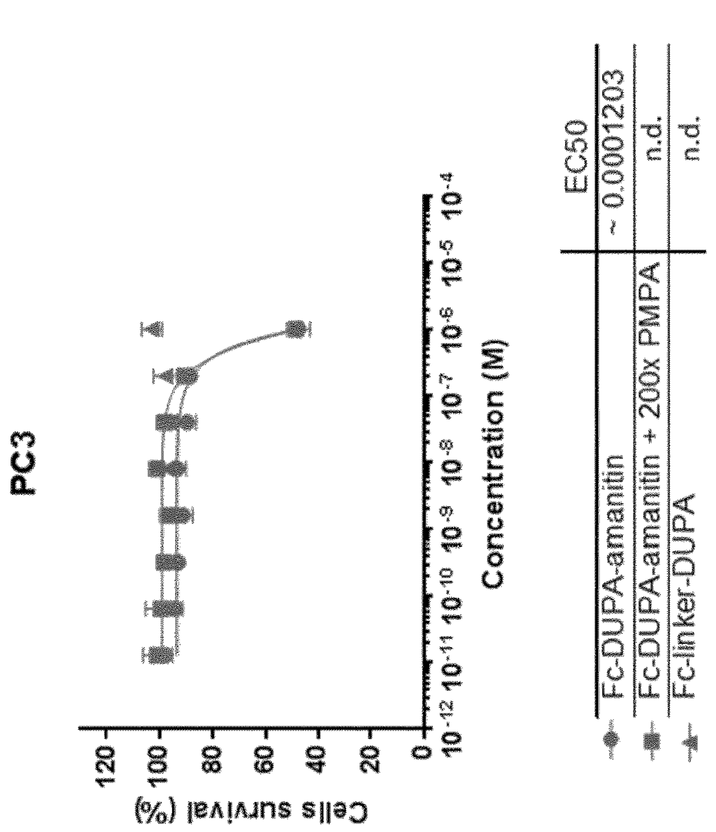
C4_2 PSMA (+++);PC 3 PSMA (-)

Blood pharmacokinetics of DUPA-Fc-α-amanitin conjugate Cb17 Scid male mice (n = 3)

| Half Life (Slow) | Half Life (Fast) |
|---|---|
| 133.4 | 1.37 |

PSMA-TARGETING AMANITIN CONJUGATES

CROSS-REFERENCE TO RELATED APPLICATIONS

This patent application is the U.S. national phase of International Patent Application No. PCT/EP2018/075789, filed on Sep. 24, 2018, which claims the benefit of European Patent Application No. 17192686.8, filed on Sep. 22, 2017, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: one 5,078 bytes ASCII (Text) file named "748984SequenceListing-Replacement.txt," created Aug. 20, 2021.

FIELD OF THE INVENTION

The invention relates to a PSMA-targeting conjugate comprising (a) an amatoxin; (b) a small molecule PSMA-targeting moiety; and (c) optionally a linker linking said amatoxin and said small molecule PSMA-targeting moiety. The invention furthermore relates to said conjugate further comprising a half-life extension moiety. The invention furthermore relates to a pharmaceutical composition comprising such conjugate.

BACKGROUND OF THE INVENTION

Amatoxins are cyclic peptides composed of 8 amino acids that are found in *Amanita phalloides* mushrooms (see FIG. 1). Amatoxins specifically inhibit the DNA-dependent RNA polymerase II of mammalian cells, and thereby also the transcription and protein biosynthesis of the affected cells. Inhibition of transcription in a cell causes stop of growth and proliferation. Though not covalently bound, the complex between amanitin and RNA-polymerase II is very tight ($K_D$=3 nM). Dissociation of amanitin from the enzyme is a very slow process, thus making recovery of an affected cell unlikely. When the inhibition of transcription lasts too long, the cell will undergo programmed cell death (apoptosis).

The use of amatoxins as cytotoxic moieties for tumour therapy had already been explored in 1981 by coupling an anti-Thy 1.2 antibody to α-amanitin using a linker attached to the indole ring of Trp (amino acid 4; see FIG. 1) via diazotation (Davis & Preston, Science 213 (1981) 1385-1388). Davis & Preston identified the site of attachment as position 7'. Morris & Venton demonstrated as well that substitution at position 7' results in a derivative, which maintains cytotoxic activity (Morris & Venton, Int. J. Peptide Protein Res. 21 (1983) 419-430).

Patent application EP 1 859 811 A1 (published Nov. 28, 2007) described conjugates, in which the γ C-atom of amatoxin amino acid 1 of β-amanitin was directly coupled, i.e. without a linker structure, to albumin or to monoclonal antibody HEA125, OKT3, or PA-1. Furthermore, the inhibitory effect of these conjugates on the proliferation of breast cancer cells (MCF-7), Burkitt's lymphoma cells (Raji) and T-lymphoma cells (Jurkat) was shown. The use of linkers was suggested, including linkers comprising elements such as amide, ester, ether, thioether, disulfide, urea, thiourea, hydrocarbon moieties and the like, but no such constructs were actually shown, and no more details, such as attachment sites on the amatoxins, were provided.

Patent applications WO 2010/115629 and WO 2010/115630 (both published Oct. 14, 2010) describe conjugates, where antibodies, such as anti-EpCAM antibodies such as humanized antibody huHEA125, are coupled to amatoxins via (i) the γ C-atom of amatoxin amino acid 1, (ii) the 6' C-atom of amatoxin amino acid 4, or (iii) via the δ C-atom of amatoxin amino acid 3, in each case either directly or via a linker between the antibody and the amatoxins. The suggested linkers comprise elements such as amide, ester, ether, thioether, disulfide, urea, thiourea, hydrocarbon moieties and the like. Furthermore, the inhibitory effects of these conjugates on the proliferation of breast cancer cells (cell line MCF-7), pancreatic carcinoma (cell line Capan-1), colon cancer (cell line Colo205), and cholangiocarcinoma (cell line OZ) were shown.

Patent application WO 2012/119787 describes that target-binding moieties can be attached to amatoxins via linkers at additional attachment sites on tryptophan amino acid 4, namely positions 1'-N, without interference with the interaction of such amatoxins with their target, the DNA-dependent RNA polymerase II of mammalian cells.

So far, amatoxins have been conjugated to large biomolecules, such as antibody molecules, as targeting moieties. Such large biomolecules, however, pose huge challenges in terms of the production processes and cost of goods. Thus, it would be highly desirable to use small molecule-based targeting moieties instead. However, there are certain serious safety concerns.

First, while it is known that amatoxins are relatively non-toxic when coupled to such large biomolecules, and that they exert their cytotoxic activity only after the biomolecule carrier is cleaved off after internalization in the target cells, it is not known so far, whether amatoxin conjugates carrying small molecule-based targeting domains would be able to maintain such toxicity profile. In light of the toxicity of amatoxins, particularly for liver cells, it is of outmost importance that amatoxin conjugates for targeted tumour therapy remain specific for their target cells. In this context, minor variations of the conjugate structure may have drastic consequences for the therapeutic window and the safety of the amatoxin conjugates for therapeutic approaches.

Second, a substantial number of Small Molecule Drug Conjugates (SMDCs) have been developed and tested so far. While many of them showed a good selectivity (selectivity (S)=$IC_{50}$ on receptor negative cells/$IC_{50}$ on receptor positive cells), the targeting index was rather poor (targeting index (TI)=$IC_{50}$ of free toxin/$IC_{50}$ of conjugate, both on receptor positive cell line). Details on known SMDCs are shown in Example A and Tables 1 to 5 below.

Thus, significant progress has already been made in the development of antibody-based amatoxin conjugates for therapeutic uses. However, there are certain problems associated with such conjugates that could not be solved satisfactorily so far.

OBJECT OF THE INVENTION

Thus, there was still a great and unmet need for the development of alternative targeting moieties that could replace antibody-based structures in amatoxin conjugates. The solution to this problem, i.e. the identification of certain derivatives of NAAG (N-acetyl aspartylglutamate) as targeting moieties was neither provided nor suggested by the prior art.

SUMMARY OF THE INVENTION

The present invention is based on the unexpected observation that amatoxins can be conjugated with a PSMA-targeting moiety based on 2-[3-(1,3-dicarboxy-propyl) ureido]pentanedioic acid (I) or 6-amino-2-[3-(1,3-dicarboxypropyl)ureido]-hexanoic acid (II), where such conjugates shows excellent selectivity and targeting index values.

I

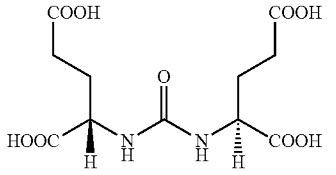

II

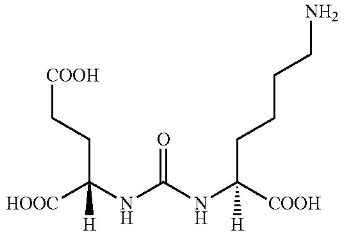

This finding was particularly surprising, since other small molecule-based amatoxin conjugates, such as conjugates with Integrin αvβ3, did not result in compounds with properties suitable for the development as pharmaceutical compounds (see Example A.2).

Thus, in one aspect the present invention relates to a conjugate comprising (a) an amatoxin; (b) a PSMA-binding moiety based on 2-[3-(1,3-dicarboxy-propyl)ureido]pentanedioic acid (I) or 6-amino-2-[3-(1,3-dicarboxypropyl) ureido]-hexanoic acid (II); and (c) a linker linking said amatoxin and said PSMA-binding moiety.

In a second aspect the present invention relates to a conjugate comprising (a) an amatoxin; (b) a PSMA-binding moiety based on 2-[3-(1,3-dicarboxy-propyl)ureido]pentanedioic acid (I) or 6-amino-2-[3-(1,3-dicarboxypropyl) ureido]-hexanoic acid (II); (c) a half-life extending moiety; and (d) at least one linker linking said amatoxin, said PSMA-binding moiety, and said half-life extending moiety.

In a third aspect, the present invention relates to a pharmaceutical composition comprising the conjugate of the present invention.

In a fourth aspect, the present invention relates to a conjugate of the present invention for use in the treatment of cancer in a patient, particularly wherein the cancer is selected from the group consisting of breast cancer, pancreatic cancer, cholangiocarcinoma, colorectal cancer, lung cancer, prostate cancer, ovarian cancer, stomach cancer, kidney cancer, malignant melanoma, leukemia, and malignant lymphoma.

BRIEF DESCRIPTION OF THE DRAWING

FIG. 7A shows the trifunctional DUPA-containing linker for programming and arming Fc. FIG. 7B shows the Amanitin-DBCO linker bearing a cathepsin B-cleavable self-immolative linker for arming the DUPA-Fc.

FIG. 8 shows the structure and amino acid sequence of the Fc-LPETG polypeptide.

FIG. 14 shows the characterization of DUPA-Fc-amanitin. FIG. 14B shows an SDS-PAGE analysis under reducing (+βME) and non-reducing (−βME) conditions. FIG. 14C shows an anti-α-amanitin Western blot under non-reducing conditions (−βME). SDS- PAGE was performed on Fc-LPETG (lane 1), DUPA-Fc (lane 2) and DUPA-Fc-amanitin (lane 3) under non-reducing conditions followed by staining with Comassie blue or Western blot analysis with immunodetection of amanitin.

DETAILED DESCRIPTION OF THE INVENTION

Figure 1:
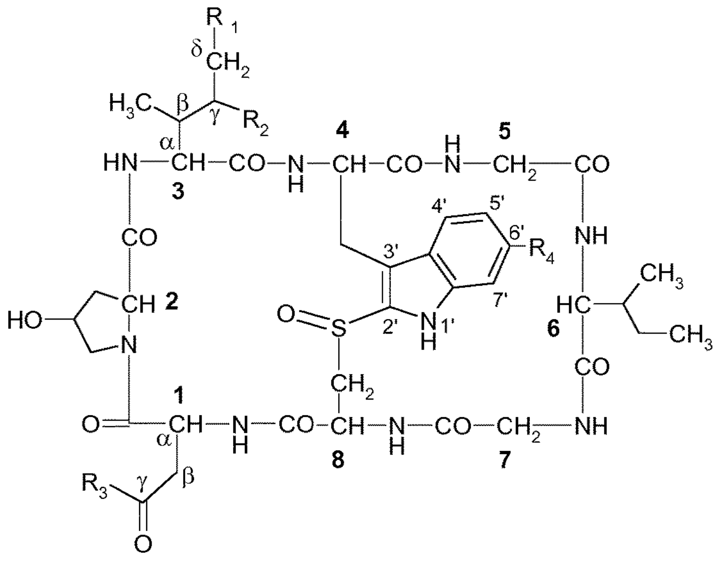
FIG. 1 shows the structural formulae of different amatoxins. The numbers in bold type (1 to 8) designate the standard numbering of the eight amino acids forming the amatoxin. The standard designations of the atoms in amino acids 1, 3 and 4 are also shown (Greek letters α to γ, Greek letters α to δ, and numbers from 1' to 7', respectively).
Figure 2:
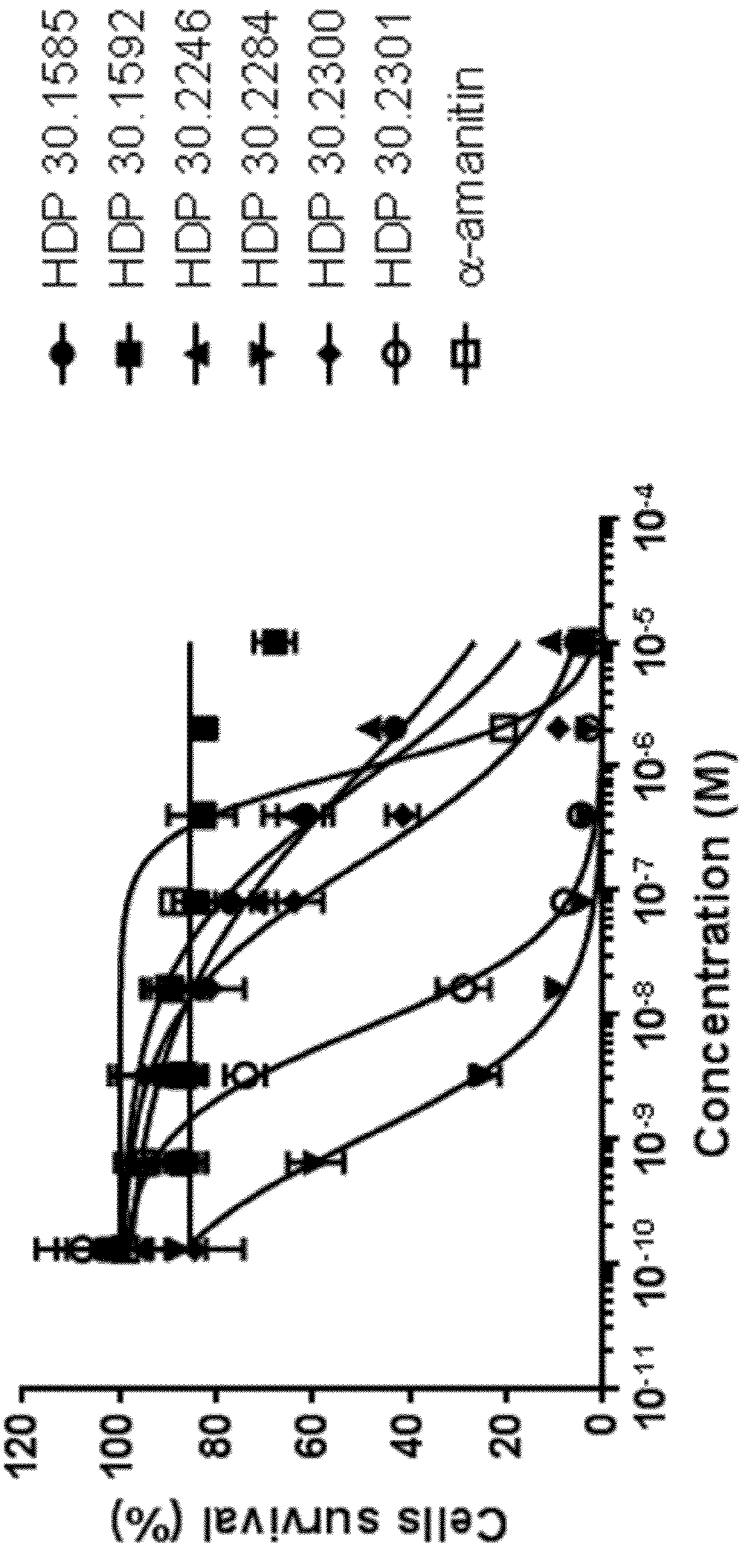
FIG. 2 shows the cytotoxicity of DUPA-α-amanitin conjugates in LNCaP (PSMA++) cell line—graphical presentation. Note: A direct comparison of all DUPA conjugates with amanitin was not performed in one experiment. The amanitin curve shown in the graph is derived from the direct comparison between HDP 30.2284 and amanitin.
Figure 3:
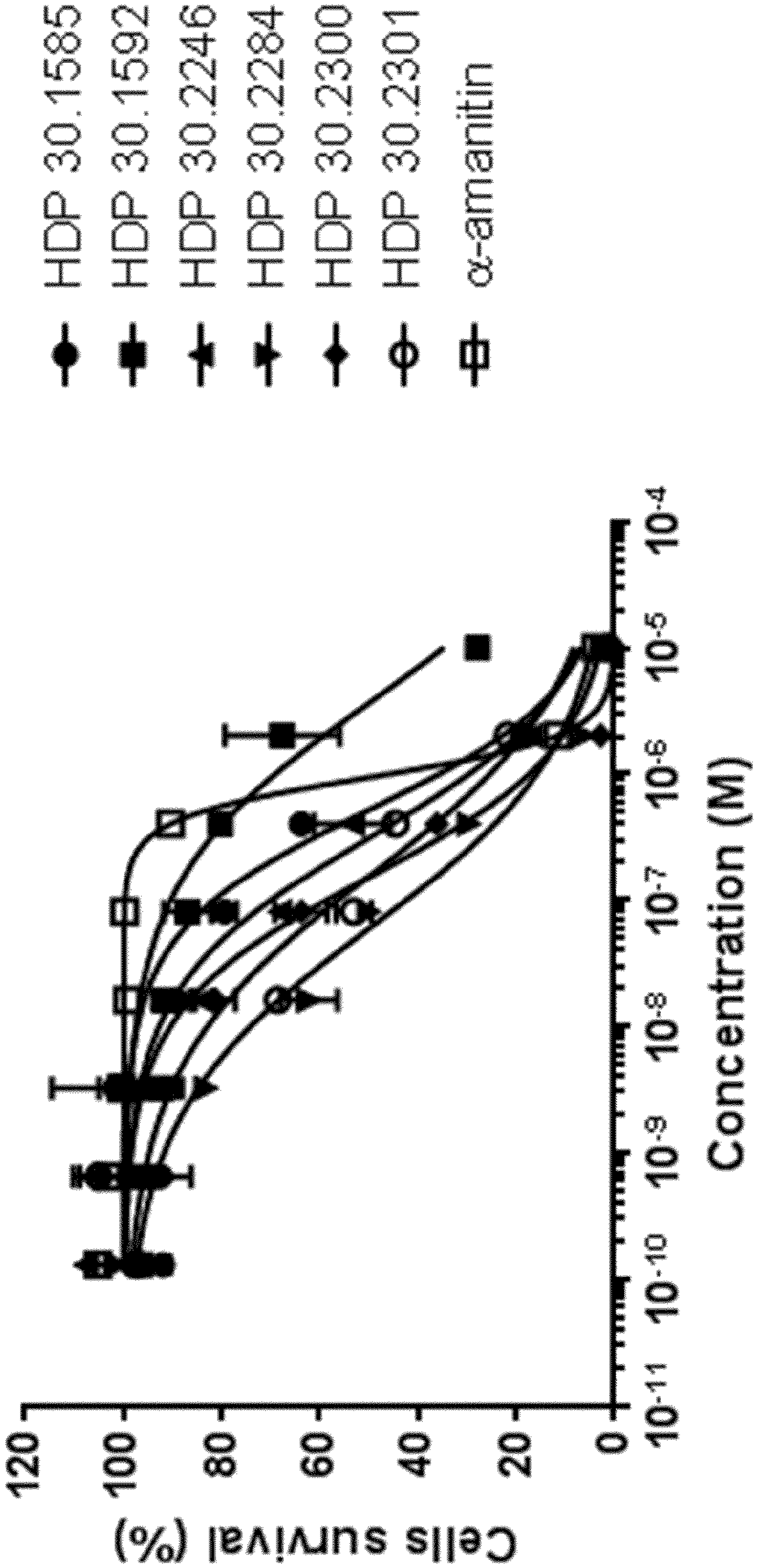
FIG. 3 shows the cytotoxicity of DUPA-α-amanitin conjugates in 22RV1 (PSMA+−) cell line—graphical presentation. Note: A direct comparison of all DUPA conjugates with amanitin was not performed in one experiment. The amanitin curve shown in the graph is derived from the direct comparison between HDP 30.2284 and amanitin
Figure 4:
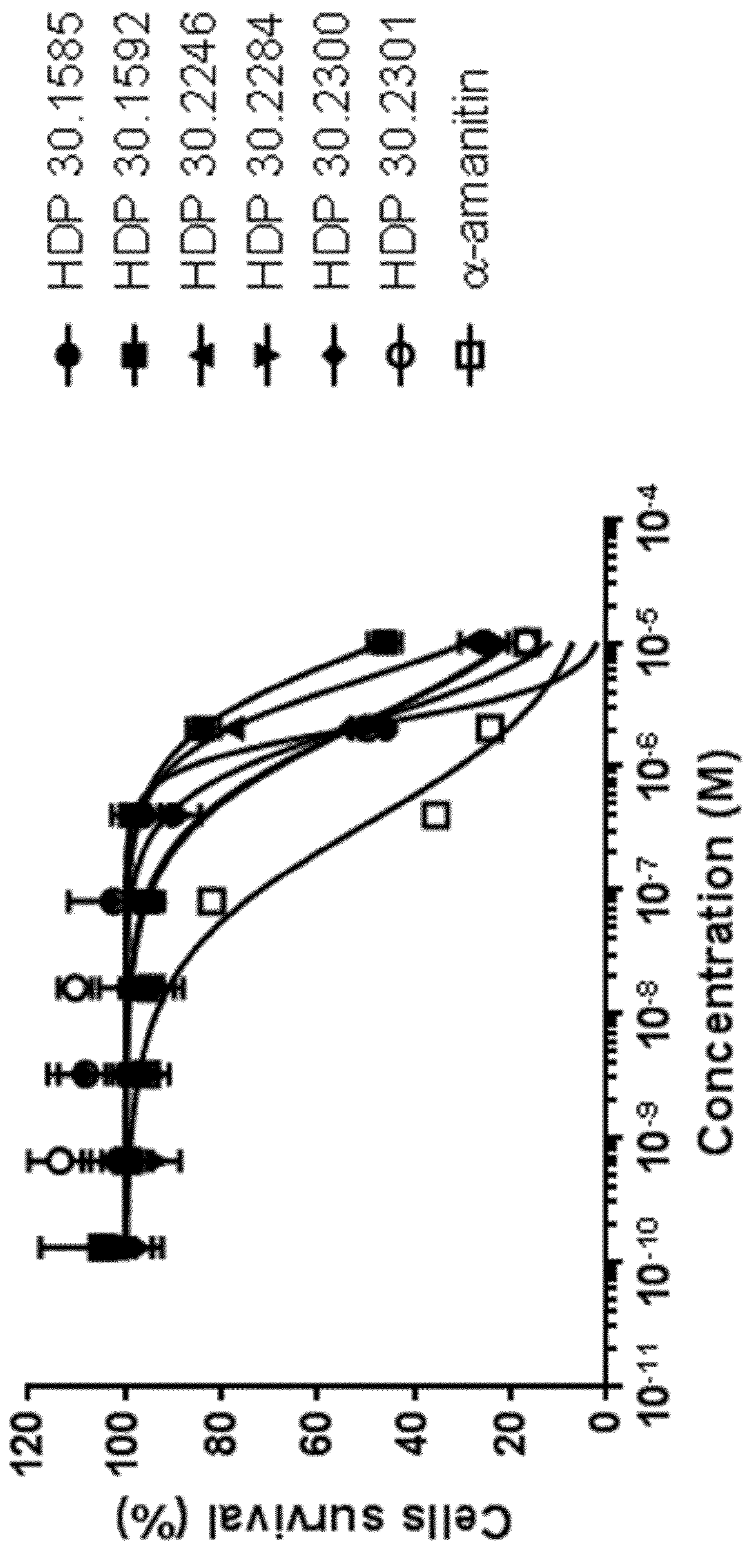
FIG. 4 shows Cytotoxicity of DUPA-α-amanitin conjugates in PC-3 (PSMA−) cell line—graphical presentation. Note: A direct comparison of all DUPA conjugates with amanitin was not performed in one experiment. The amanitin curve shown in the graph is derived from the direct comparison between HDP 30.2284 and amanitin.
Figure 5:
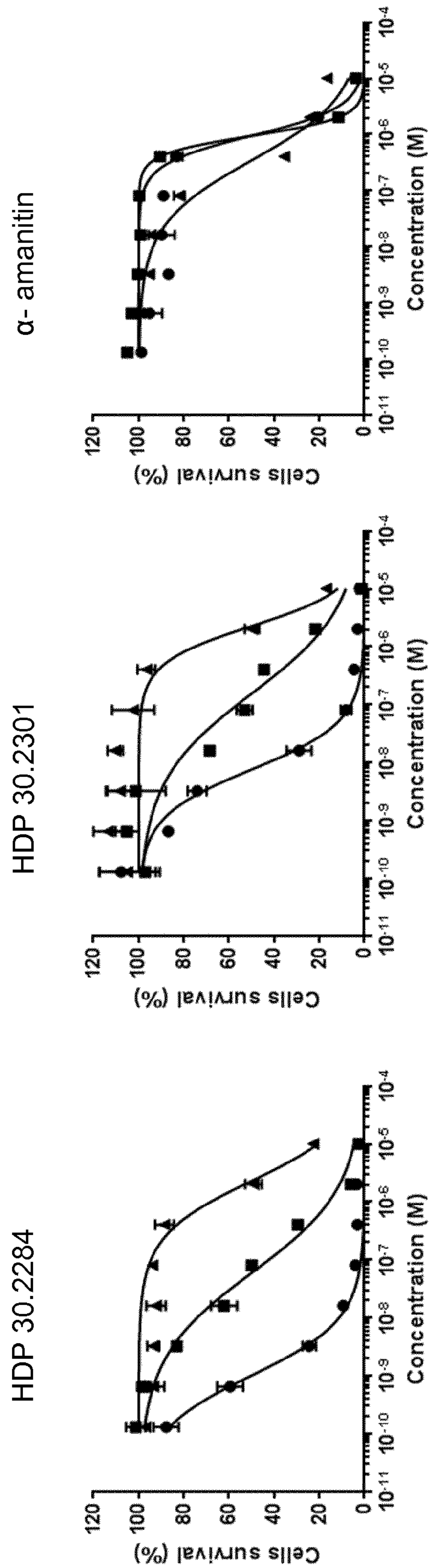
FIG. 5 shows the cytotoxicity of the two most potent DUPA α-amanitin conjugates HDP 30.2284 and HDP 30.2301 in three prostate cancer cell lines compared with unconjugated α-amanitin—graphical presentation. Note: A direct comparison of all HDP 30.2284 and HDP 30.2301 with amanitin in one experiment was not performed. The amanitin curves shown in the graph are derived from the direct comparison between HDP 30.2284 and amanitin.

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Particularly, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer, composition or step or group of integers or steps, while any additional integer, composition or step or group of integers, compositions or steps may optionally be present as well, including embodiments, where no additional integer, composition or step or group of integers, compositions or steps are present. In such latter embodiments, the term "comprising" is used coterminous with "consisting of".

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety to the extent possible under the respective patent law. Nothing herein is to be construed as an admission that the invention is not entitled to antedate such disclosure by virtue of prior invention.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The present invention is based on the unexpected observation that amatoxins can be conjugated with a PSMA-targeting moiety based on 2-[3-1,3-dicarboxy-propyl) ureido]pentanedioic acid (I) or 6-amino-2-[3-(1,3-dicarboxypropyl)ureido]-hexanoic acid (II), where such conjugates shows excellent selectivity and targeting index values.

Thus, in one aspect the present invention relates to a conjugate comprising (a) an amatoxin; (b) a PSMA-binding moiety based on 2-[3-(1,3-dicarboxy-propyl)ureido]pentanedioic acid (I) or 6-amino-2-[3-(1,3-dicarboxypropyl) ureido]-hexanoic acid (II); and (c) a linker linking said amatoxin and said PSMA-binding moiety.

In the context of the present invention, the term "amatoxin" includes all cyclic peptides composed of 8 amino acids as isolated from the genus *Amanita* and described in Wieland, T. and Faulstich H. (Wieland T, Faulstich H., CRC Crit Rev Biochem. 5 (1978) 185-260), which comprise the specific positions according to (i) (i.e. where the indole moiety of the amino acid residue tryptophan has no oxygen-containing substituent at position 6', particularly where position 6' carries a hydrogen atom) and (ii) (i.e. in which the thioether sulfoxide moiety of naturally occurring amatoxins is replaced by a sulphide or a sulfon), and furthermore includes all chemical derivatives thereof; further all semi-synthetic analogues thereof; further all synthetic or semi-synthetic analogues, in which the thioether sulfoxide moiety is replaced by a sulfide, sulfone, or by atoms different from sulfur; further all synthetic analogues thereof built from building blocks according to the master structure of the natural compounds (cyclic, 8 amino acids), further all synthetic or semisynthetic analogues containing non-hydroxylated amino acids instead of the hydroxylated amino acids, further all synthetic or semisynthetic analogues, in each case wherein any such derivative or analogue carries at least the positions (i) and (ii) mentioned above and is functionally active by inhibiting mammalian RNA polymerase II. In particular, the term "amatoxin" includes all structures shown in FIG. 1.

Functionally, amatoxins are defined as peptides or depsipeptides that inhibit mammalian RNA polymerase II. Preferred amatoxins are those with a functional group (e.g. a carboxylic group or carboxylic acid derivative such as a carboxamide or hydroxamic acid, an amino group, a hydroxy group, a thiol or a thiol-capturing group) that can be reacted with linker molecules or target-binding moieties as defined above. Amatoxins which are particularly suitable for the conjugates of the present invention are di-deoxy variants of α-amanitin, β-amanitin, γ-amanitin, ε-amanitin, amanullin, or amanullinic acid, or mono-deoxy variants of amanin, amaninamide, γ-amanin, or γ-amaninamide as shown in FIG. 1 as well as salts, chemical derivatives, semisynthetic analogues, and synthetic analogues thereof.

In a particular embodiment, the conjugate of the present invention has a purity greater than 90%, particularly greater than 95%.

In the context of the present invention, the term "purity" refers to the total amount of conjugates being present. A purity of greater than 90%, for example, means that in 1 mg of a composition comprising a conjugate of the present invention, there are more than 90%, i.e. more than 900 μg, of such conjugate. The remaining part, i.e. the impurities may include unreacted starting material and other reactants, solvents, cleavage products and/or side products.

In a particular embodiment, a composition comprising a conjugate of the present invention comprises more than 100 mg, in particular more than 500 mg, and more particularly more than 1 g of such conjugate. Thus, trace amount of a conjugate of the present invention that arguably may be present in complex preparations of conjugates of the prior art, e.g. from partial reduction of naturally occurring sulfoxides, are explicitly excluded.

In the context of the present invention the term "PSMA" is the abbreviation for prostate-specific membrane antigen, which is also known as glutamate carboxypeptidase II" (GCPII), N-acetyl-L-aspartyl-L-glutamate peptidase I (NAALADase I), or NAAG peptidase. PSMA) is an enzyme that is encoded by the FOLH1 (folate hydrolase 1) gene in humans.

In the context of the present invention the term "PSMA-binding moiety based on 2-[3-(1,3-dicarboxy-propyl)ureido] pentanedioic acid (I)" refers to a moiety consisting essentially of structure I, wherein a linker is attached to the carboxylic group in position 5 of the pentanedioic acid.

In the context of the present invention the term "PSMA-binding moiety based on . . . 6-amino-2-[3-(1,3-dicarboxy-propyl)ureido]-hexanoic acid (II)" refers to a moiety consisting essentially of structure II, wherein a linker is attached to the 6-amino group of the hexanoic acid part.

A "linker" in the context of the present invention refers to a structure that is connecting two components, each being attached to one end of the linker. In the case of the linker being a bond, a direct linkage of amatoxin to the PSMA-targeting moiety may decrease the ability of the amatoxin to interact with RNA polymerase II. In particular embodiments, the linker increases the distance between two components and alleviates steric interference between these components, such as in the present case between the PSMA-targeting moiety and the amatoxin. In particular embodiments, the linker has a continuous chain of between 1 and 70 atoms (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, and 70 atoms) in its backbone, i.e. the length of the linker is defined as the shortest connection as measured by the number of atoms or bonds between the amatoxin moiety and the PSMA-targeting moiety, wherein one side of the linker backbone has been reacted with the amatoxin and, the other side is available for reaction, or has been reacted, with the carboxylic or amino group of the PSMA-targeting moiety. In particular embodiments, the linker has a continuous chain of between 20 and 70 atoms, more particularly between 25 and 60, more particularly between 30 and 55, more particularly between 35 and 50 atoms. In the context of the present invention, a linker particularly is a $C_{1-20}$-alkylene, $C_{1-20}$-heteroalkylene, $C_{2-20}$-alkenylene, $C_{2-20}$-heteroalkenylene, $C_{2-20}$-alkynylene, $C_{2-20}$-heteroalkynylene, cycloalkylene, heterocycloalkylene, arylene, heteroarylene, aralkylene, or a heteroaralkylene group, optionally substituted. The linker may contain one or more structural elements such as carboxamide, ester, ether, thioether, disulfide, urea, thiourea, hydrocarbon moieties and the like. The linker may also contain combinations of two or more of these structural elements. Each one of these structural elements may be present in the linker more than once, e.g. twice, three times, four times, five times, or six times. In some embodiments, the linker may comprise a disulfide bond. It is understood that the linker has to be attached either in a single step or in two or more subsequent steps to the amatoxin and the PSMA-targeting moiety. To that end the linker to be will carry two groups, particularly at a proximal and distal end, which can (i) form a covalent bond to a group present in one of the components to be linked, particularly an activated group on an amatoxin or the PSMA-targeting moiety or (ii) which is or can be activated to form a covalent bond with a group on an amatoxin. Accordingly, it is preferred that chemical groups are at the distal and proximal end of the linker, which are the result of such a coupling reaction, e.g. an ester, an ether, a urethane, a peptide bond etc.

In particular embodiments, the linker L is a linear chain of between 1 and 20 atoms independently selected from C, O, N and S, particularly between 2 and 18 atoms, more particularly between 5 and 16 atoms, and even more particularly between 6 and 15 atoms. In particular embodiments, at least 60% of the atoms in the linear chain are C atoms. In particular embodiments, the atoms in the linear chain are linked by single bonds.

In particular embodiments. the linker L is an alkylene, heteroalkylene, alkenylene, heteroalkenylene, alkynylene, heteroalkynylene, cycloalkylene, heterocycloalkylene, arylene, heteroarylene, aralkylene, or a heteroaralkylene group, comprising from 1 to 4 heteroatoms selected from N, O, and S, wherein said linker is optionally substituted.

The term "alkylene" refers to a bivalent straight chain saturated hydrocarbon groups having from 1 to 20 carbon atoms, including groups having from 1 to 10 carbon atoms. In certain embodiments, alkylene groups may be lower alkylene groups. The term "lower alkylene" refers to alkylene groups having from 1 to 6 carbon atoms, and in certain embodiments from 1 to 5 or 1 to 4 carbon atoms. Examples of alkylene groups include, but are not limited to, methylene ($—CH_2—$), ethylene ($—CH_2—CH_2—$), n-propylene, n-butylene, n-pentylene, and n-hexylene.

The term "alkenylene" refers to bivalent straight chain groups having 2 to 20 carbon atoms, wherein at least one of the carbon-carbon bonds is a double bond, while other bonds may be single bonds or further double bonds. The term "alkynylene" herein refers to groups having 2 to 20 carbon atoms, wherein at least one of the carbon-carbon bonds is a triple bond, while other bonds may be single, double or further triple bonds. Examples of alkenylene groups include ethenylene ($—CH{=}CH—$), 1-propenylene, 2-propenylene, 1-butenylene, 2-butenylene, 3-butenylene, and the like. Examples of alkynylene groups include ethynylene, 1-propynylene, 2-propynylene, and so forth.

As used herein, "cycloalkylene" is intended to refer to a bivalent ring being part of any stable monocyclic or polycyclic system, where such ring has between 3 and 12 carbon atoms, but no heteroatom, and where such ring is fully saturated, and the term "cycloalkenylene" is intended to refer to a bivalent ring being part of any stable monocyclic or polycyclic system, where such ring has between 3 and 12 carbon atoms, but no heteroatom, and where such ring is at least partially unsaturated (but excluding any arylene ring). Examples of cycloalkylenes include, but are not limited to, cyclopropylene, cyclobutylene, cyclopentylene, cyclohexylene, and cycloheptylene. Examples of cycloalkenylenes include, but are not limited to, cyclopentenylene and cyclohexenylene.

As used herein, the terms "heterocycloalkylene" and "heterocycloalkenylene" are intended to refer to a bivalent ring being part of any stable monocyclic or polycyclic ring system, where such ring has between 3 and about 12 atoms, and where such ring consists of carbon atoms and at least one heteroatom, particularly at least one heteroatom independently selected from the group consisting of N, O and S, with heterocycloalkylene referring to such a ring that is fully saturated, and heterocycloalkenylene referring to a ring that is at least partially unsaturated (but excluding any arylene or heteroarylene ring).

The term "arylene" is intended to mean a bivalent ring or ring system being part of any stable monocyclic or polycyclic system, where such ring or ring system has between 3 and 20 carbon atoms, but has no heteroatom, which ring or ring system consists of an aromatic moiety as defined by the "4n+2" π electron rule, including phenylene.

As used herein, the term "heteroarylene" refers to a bivalent ring or ring system being part of any stable mono- or polycyclic system, where such ring or ring system has between 3 and 20 atoms, which ring or ring system consists of an aromatic moiety as defined by the "4n+2" π electron rule and contains carbon atoms and one or more nitrogen, sulfur, and/or oxygen heteroatoms.

In the context of the present invention, the term "substituted" is intended to indicate that one or more hydrogens present in the backbone of a linker is replaced with a selection from the indicated group(s), provided that the indicated atom's normal valency, or that of the appropriate atom of the group that is substituted, is not exceeded, and that the substitution results in a stable compound. The term "optionally substituted" is intended to mean that the linker is either unsubstituted or substituted, as defined herein, with one or more substituents, as defined herein. When a substituent is a keto (or oxo, i.e. =O) group, a thio or imino group or the like, then two hydrogens on the linker backbone atom are replaced. Exemplary substituents include, for example, alkyl, alkenyl, alkynyl, cycloalkyl, heterocycloalkyl, aryl, heteroaryl, aralkyl, heteroaralkyl, acyl, aroyl, heteroaroyl, carboxyl, alkoxy, aryloxy, acyloxy, aroyloxy, heteroaroyloxy, alkoxycarbonyl, halogen, (thio)ester, cyano, phosphoryl, amino, imino, (thio)amido, sulfhydryl, alkylthio, acylthio, sulfonyl, a sulfate, a sulfonate, a sulfamoyl, a sulfonamido, nitro, azido, haloalkyl, including perfluoroalkyl (such as trifluoromethyl), haloalkoxy, alkylsulfanyl, alkylsulfinyl, alkylsulfonyl, alkylsulfonylamino, arylsulfonoamino, phosphoryl, phosphate, phosphonate, phosphinate, alkylcarboxy, alkylcarboxyamide, oxo, hydroxy, mercapto, amino (optionally mono- or di-substituted, e.g. by alkyl, aryl, or heteroaryl), imino, carboxamide, carbamoyl (optionally mono- or di-substituted, e.g. by alkyl, aryl, or heteroaryl), amidino, aminosulfonyl, acylamino, aroylamino, (thio)ureido, (arylthio)ureido, alkyl(thio) ureido, cycloalkyl(thio)ureido, aryloxy, aralkoxy, or $—O(CH_2)_n—OH$, $—O(CH_2)_n—NH_2$, $—O(CH_2)_nCOOH$, $—(CH_2)_nCOOH$, $—C(O)O(CH_2)_nR$, $—(CH_2)_nN(H)C(O)OR$, or $—N(R)S(O)_2R$ wherein n is 1-4 and R is independently selected from hydrogen, -alkyl, -alkenyl, -alkynyl, -cycloalkyl, -cycloalkenyl, —(C-linked-heterocycloalkyl), —(C-linked-heterocycloalkenyl), -aryl, and -heteroaryl, with multiple degrees of substitution being allowed. It will be understood by those skilled in the art that substituents, such as heterocycloalkyl, aryl, heteroaryl, alkyl, etc., or functional groups such as —OH, —NHR etc., can themselves be substituted, if appropriate. It will also be understood by those skilled in the art that the substituted moieties themselves can be substituted as well when appropriate.

In particular embodiments, the linker L comprises a moiety selected from one of the following moieties: a disulfide (—S—S—), an ether (—O—), a thioether (—S—), an amine (—NH—), an ester (—O—C(=O)— or —C(=O)—O—), a carboxamide (—NH—C(=O)— or —C(=O)—NH—), a urethane (—NH—C(=O)—O— or —O—C(=O)—NH—), and a urea moiety (—NH—C(=O)—NH—).

In particular embodiments of the present invention, the linker L comprises a number of m groups selected from the list of: alkylene, alkenylene, alkynylene, cycloalkylene, heteroalkylene, heteroalkenylene, heteroalkynylene, heterocycloalkylene, arylene, heteroarylene, aralkylene, and a heteroaralkylene group, wherein each group may optionally be independently substituted, the linker further comprises a number of n moieties independently selected from one of the following moieties: a disulfide (—S—S—), an ether (—O—), a thioether (—S—), an amine (—NH—), an ester (—O—C(=O)— or —C(=O)—O—), a carboxamide (—NH—C(=O)— or —C(=O)—NH—), a urethane (—NH—C(=O)—O— or —O—C(=O)—NH—), and a urea moiety (—NH—C(=O)—NH—), wherein m=n+1. In particular embodiments, m is 2 and n is 1, or m is 3 and n is 2. In particular embodiments, the linker comprises 2 or 3 unsubstituted alkylene groups, and 1 or 2, respectively, disulfide, ether, thioether, amine, ester, carboxamide, urethane or urea moieties linking the unsubstituted alkylene groups.

In particular embodiments, the C atoms in the linear chain are independently part of optionally substituted methylene groups ($—CH_2—$). In particular such embodiments, the optional substituents are independently selected from halogen and $C_{1-6}$-alkyl, particularly methyl.

In particular embodiments, the linker L is a stable linker.

In the context of the present invention, the term "stable linker" refers to a linker that is stable (i) in the presence of enzymes, and (ii) in an intracellular reducing environment.

In particular embodiments, the stable linker does not contain (i) an enzyme-cleavable substructure, and/or (ii) a disulfide group. In particular such embodiments, the linker has a length of up to 12 atoms, particularly from 2 to 10, more particularly from 4 to 9, and most particularly from 6 to 8 atoms.

In particular other embodiments, the linker is a cleavable linker.

In the context of the present invention, the term "cleavable linker" refers to a linker that is (i) cleavable by chemical cleavage, or (ii) a reducible linker.

In certain such embodiments, the linker is cleavable by reduction. In the context of the present invention, the term "cleavable by reduction" refers to a linker that can be cleaved in the intracellular reducing environment, particularly a linker that contains a disulfide groups, resulting in the intracellular release of the toxin cargo conjugated to the target-binding moiety after internalization by the intracellular reducing environment (see Shen et al., (1985) J. Biol. Chem. 260:10905-10908).

In certain such embodiments, the linker comprises a disulfide bond, particularly a moiety

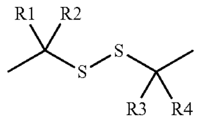

wherein R1 to R4 are independently selected from H and methyl.

In certain other such embodiments, the linker is cleavable by chemical cleavage, particularly by hydrolysis or proteolysis, particularly wherein such chemical cleavage is catalyzed by an enzyme.

In the context of the present invention, the term "chemical cleavage is catalyzed by an enzyme" refers to a linker that can be cleaved by an enzyme, particularly by a lysosomal peptidase, such as Cathepsin B, resulting in the intracellular release of the toxin cargo conjugated to the targeting antibody after internalization (see Dubowchik et al., (2002) Bioconjug Chem. 13:855-69). In particular embodiments, the cleavable linker comprises a dipeptide selected from: Phe-Lys, Val-Lys, Phe-Ala, Val-Ala, Phe-Cit and Val-Cit, particularly wherein the cleavable linker further comprises a p-aminobenzyl (PAB) spacer between the dipeptides and the toxic payload.

In certain such embodiments, the linker comprises a hydrazone group. In particular such embodiments, cleavage occurs by hydrolysis in the lysosome.

In certain embodiments, the linker is a self-immolative linker.

In the context of the present invention, the term "self-immolative linker" refers to a linker that comprises a cleavable bond, wherein after cleavage a fragmentation takes place that removes that part of the linker that is still attached to the toxin after said cleavage.

In particular such embodiments, the cleavable bond is the amide bond between the C-terminus of a polypeptide, particularly a dipeptide, and the amino group of an optionally N-substituted p-aminobenzyl (PAB) spacer.

In particular such embodiments, the cleavable linker comprises a structure $L^1$-L*-$L^2$ $L^1$-L*-$L^2$

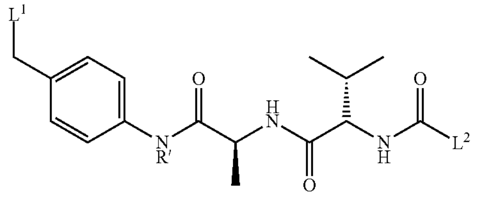

wherein R' is selected from H and methyl, $L^1$ is a part of the linker that connects L* to the amatoxin, in particular wherein $L^1$ is connected to L* via a —NH— or a —O— group, particularly a —C(=O)—NH—, a —C(=O)—NH—O— or a —C(=O)—O— group, and wherein $L^2$ is a part of the linker that connects L* to the PSMA-targeting moiety, particularly wherein $L^1$ is connected to L* via a $-(CH_2)_m-$ moiety, with m being an integer selected from 1 to 8, in particular from 1 to 5, or via a $-(CH_2CH_2O)_n-$ moiety, with n being an integer selected from 1 to 3, in particular from 1 to 2.

In particular other such embodiments, L* has the following structure

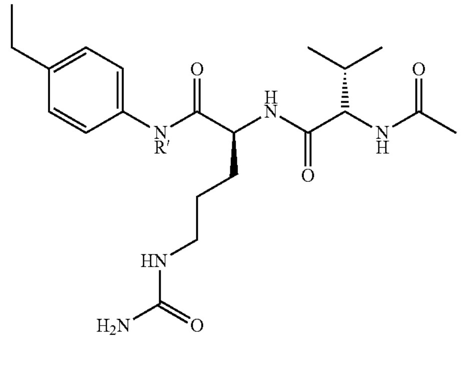

In certain embodiments, the linker part $L^1$-L*- comprises a group -(cleavable bond)—NR'-phenyl-$CH_2$—O—C(=O)—, wherein R' is selected from H and methyl, and wherein the carbonyl group is part of terminal carboxylic acid moiety of the aspartic acid residue's side chain at position 1 of the amatoxin.

In particular other embodiments, the linker part $L^1$-L*- comprises a group -(cleavable bond)-NR'-phenyl-$CH_2$—O—, wherein the oxygen atom forms an ether linkage to position 6' of the indole ring of the tryptophan residue at position 4 of the amatoxin.

In particular embodiments, the linker $L^1$ is a linear chain of between 1 and 4 atoms independently selected from C, O, N and S, particularly between 1 and 3 atoms, more particularly between 1 and 2 atoms, and even more just 1 atom. In particular embodiments, at least 50% of the atoms in the linear chain are C atoms. In particular embodiments, the atoms in the linear chain are linked by single bonds.

In particular such embodiments, the structure $L^1$-L*-$L^2$ comprised in such cleavable linker has a length of up to 20 atoms, particularly from 6 to 18, more particularly from 8 to 16, and most particularly from 10 to 15 atoms. In particular such embodiments, the part of the linker linking the amatoxin according to the present invention and the cleavable disulfide group is a linear chain of 3 or 4 C atoms, particularly 3 C atoms. In particular embodiments, the 3 or 4 C atoms in the linear chain are linked by single bonds. In particular embodiments, the linker is an n-propylene group.

Coupling of the linker to the target-binding moiety can be achieved by a variety of methods well known to one of ordinary skill in the art, particularly in the art of antibody-drug conjugates (ADCs).

In particular embodiments, the present invention relates to a conjugate having the structure III, IV, V or VI

III

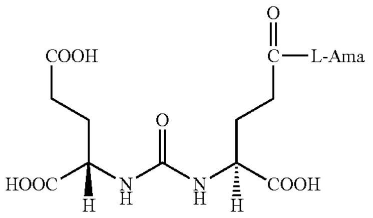

IV

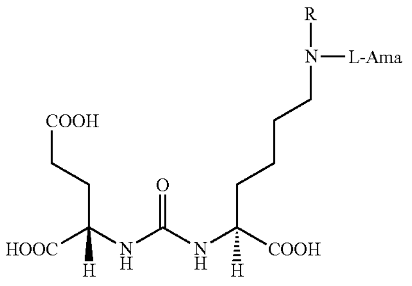

V

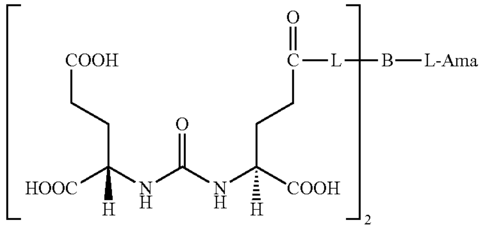

-continued

VI

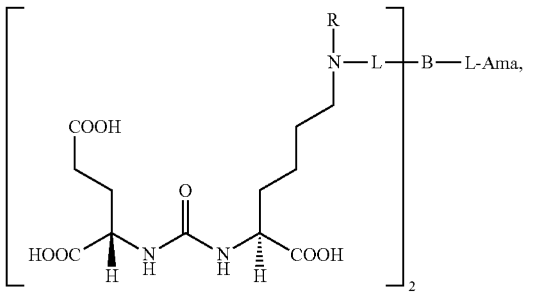

wherein each L is a linker, Ama is an amatoxin, B is a bifurcation linker element, and R is selected from H, $C_{1-6}$-alkyl and p-bromobenzyl.

In the context of the present invention, the term "bifurcation linker element" relates to an element comprising at least three attachment sites so that the incorporation of such element results in a branched construct comprising two PSMA-binding moieties being conjugated to an amatoxin.

In particular embodiments, each L independently comprises n linker elements independently selected from the list of: $—CH_2—$, $—CHR^1—$, $—C(R^2)_2—$, —O—, —S—, —NH—, $—NR^3—$, —C(═O)—, -phenylene-, 2,5-dioxo-1,3-pyrrolidinylene, wherein $R^1$ is selected from the list of: $C_{1-6}$-alkyl, —COOH, a side chain of an amino acid; $R^2$ is selected from the list of: $C_{1-6}$-alkyl; $R^3$ is selected from the list of $C_{1-6}$-alkyl, B is selected from 1,3,4-trisubstitued maleimide and 1,3,4-trisubstitued succinimide, and n is an integer independently selected from the range of 5 to 60.

In particular embodiments, a linker L is a linear chain of at least 5, particularly at least 10, more particularly between 10 and 20 atoms independently selected from C, O, N and S, particularly between 10 and 18 atoms, more particularly between 10 and 16 atoms, and even more particularly between 10 and 15 atoms. In particular embodiments, at least 60% of the atoms in the linear chain are C atoms. In particular embodiments, the atoms in the linear chain are linked by single bonds.

In particular embodiments, each L independently comprises one or more of the linker elements independently selected from: $—(CH_2)_x—$, —S—S—, —C(═O)—NH—, —NH—C(═O)—NH—, —NH—C(═O)—, a dipeptide, a tripeptide, a tetrapeptide, a pentaptpeptide, a hexapeptide, a heptapeptide, an octapeptide, $—(O—CH_2—CH_2-)_y$, $—(CH_2—CH_2—O—)_y$, N,O-disubstituted p-aminobenzyloxy, and 2,5-dioxo-1,3-pyrrolidinylene, wherein x and y are integers independently selected from the range of 2 to 14.

In particular embodiments, a linker L comprises an 8-amino octanoic acid-based element $—NH—(CH_2)_7—C(═O)—$ (Aoc element). In particular such embodiments, the amino terminus of the $—NH—(CH_2)_7—C(═O)—$ element is forming an amide bond with the terminal carboxylic acid of the PSMA-binding moiety according to structure III or V, or is part of a urea linkage to the terminal amino group of the PSMA-binding moiety according to structure IV or VI.

In particular embodiments, a linker L comprises a polypeptide selected from Phe-Phe-, -Phe-Phe-Cys-, and -Phe-Phe-His-Glu-His-Glu-Cys- (N- to C-terminus). In particular such embodiment, the N-terminus of said polypeptide forms a peptide bond with an 8-amino octanoic acid-based element $—NH—(CH_2)_7—C(═O)—$.

In particular embodiments, said linker comprises a thioether moiety.

In particular such embodiments, such conjugate results from coupling of a thiol-containing linker moiety . . . L-SH with a second linker moiety . . . L-X comprising a thiol-reactive group —X. In particular such embodiments, the thiol-containing linker moiety is the free —SH group of a cysteine residue of a polypeptide being part of the linker.

Thus, in such embodiments, the present invention relates to a conjugate of generic formula PSMA-binding moiety-L-X*—S-L-Ama or PSMA-binding moiety-L-S—X*-L-Ama, wherein —X*— is a moiety resulting from coupling of a thiol group to a thiol-reactive group.

In the context of the present invention, the term "thiol-reactive group X" refers to a group that selectively reacts with a thiol group, particularly in a pH value in the range between 6.0 and 8.0, more particularly in a pH value in the range between 6.5 and 7.5. In particular, the term "selectively" means that less than 10% of the coupling reactions of a molecule comprising a thiol-reactive group with a second moiety comprising at least one free cysteine residue are coupling reactions with non-cysteine residues of the second moiety, such as lysine residues, particularly less than 5%, more particularly less than 2%. In particular embodiments, the thiol-reactive group is selected from bromoacetamide, iodoacetamide, maleimide, a maleimide having a leaving group in position 3, in particular a leaving group selected from —Br, and substituted thiol (see, for example, U.S. Pat. No. 9,295,729), a 1,2-dihydropyridazine-3,6-dione having a leaving group in position 4, in particular a leaving group selected from —Br, and substituted thiol (see, for example, U.S. Pat. No. 9,295,729), methylsulfonyl benzothiazole, methylsulfonyl phenyltetrazole, methylsulfonyl phenyloxadiazole (see Toda et al., Angew. Chem. Int. Ed. Engl., 52 (2013) 12592-6), a 3-arylpropionitrile (see Kolodych et al, Bioconjugate Chem. 2015, 26, 197-200), and 5-nitro-pyridin-2-yl-disulfide ( . . . -L-S—S-(5-nitro-pyridine-2-yl).

In particular embodiments, a bifurcation reagent, which comprises two functional groups that each can react with a thiol group present in a PSMA-binding moiety-linker construct, is used in the coupling. As a result, two PSMA-binding moietyl-containing chains are linked to a bifurcation linker element B. In particular embodiments, the bifurcation reagent is a maleimide having two leaving groups in positions 3 and 4, in particular selected from 3,4-dibromomaleimide, 3,4-bis(arylthio)-maleimide, in particular 3,4-diphenylthio-maleimide, and 3,4-bis(heteroarylthio)-maleimide, in particular 3,4-bis(2-pyridinyl-sulfanyl)-maleimide, and. In particular other embodiments, the bifurcation reagent is a 1,2-dihydropyridazine-3,6-dione having two leaving groups in positions 4 and 5, in particular selected from 4,5-bromo-1,2-dihydropyridazine-3,6-dione, 4,5-bis(arylthio)-1,2-dihydropyridazine-3,6-dione, in particular 4,5-diphenylthio-1,2-dihydropyridazine-3,6-dione, and 4,5-bis(heteroarylthio)-1,2-dihydropyridazine-3,6-dione, in particular 4,5-bis(2-pyridinyl-sulfanyl)-1,2-dihydropyridazine-3,6-dione.

In particular embodiments, where a bifurcation linker element B is present in the conjugates according to the present invention, the linkers between the PSMA-binding moieties and said bifurcation linker element B each comprise at least a $—(O—CH_2—CH_2-)_y$- or $—(CH_2—CH_2—O—)_y$- moiety, wherein y is an integer independently selected from the range of 6 to 14, particularly from 8 to 12.

In particular embodiments, the moiety resulting from coupling of a thiol group to a thiol-reactive group is selected from: thiol-substituted acetamide; thiol-substituted succinimide; thiol-substituted succinamic acid; thiol-substituded heteroaryl, particularly thiol-substituted benzothiazole, thiol-substituted phenyltetrazole and thiol-substituted phenyloxadiazole; and a disulphide. In particular embodiments, the moiety resulting from coupling of a thiol group to a thiol-reactive group is a thiol-substituted succinimide.

In particular embodiments, the linker L in the moiety L-X*—S present in the generic formula of section [0069], is selected from the following group of moieties:

(Amatoxin side) —$(CH_2)_2$—S—S—$(CH_2)_2$—X—S—(PSMA-binding side);

(Amatoxin side) —$(CH_2)_3$—S—S—$(CH_2)_2$—X—S—(PSMA-binding side);

(Amatoxin side) —$(CH_2)_2$—S—S—$(CH_2)_3$—X—S—(PSMA-binding side);

(Amatoxin side) —$(CH_2)_3$—S—S—$(CH_2)_3$—X—S—(PSMA-binding side);

(Amatoxin side) —$(CH_2)_4$—S—S—$(CH_2)_4$—X—S—(PSMA-binding side);

(Amatoxin side) —$(CH_2)_2$—$CMe_2$-S—S—$(CH_2)_2$—X—S— (PSMA-binding side);

(Amatoxin side) —$(CH_2)_2$—S—S—$CMe_2$-$(CH_2)_2$—X—S— (PSMA-binding side);

(Amatoxin side) —$(CH_2)_3$—S—S—$CMe_2$-$(CH_2)_2$—X—S— (PSMA-binding side);

(Amatoxin side) —$(CH_2)_3$—S—S—CHMe-$(CH_2)_2$—X—S— (PSMA-binding side);

(Amatoxin side) —$(CH_2)_2$CHMe-S—S—CHMe-$(CH_2)_2$—X—S— (PSMA-binding side);

(Amatoxin side) —$(CH_2)_2$CHMe-S—S— (PSMA-binding side);

(Amatoxin side) —$(CH_2)_3$—S—S— (PSMA-binding side);

(Amatoxin side) —$CH_2$—$C_6H_4$—NH-Cit-Val-CO$(CH_2)_5$—X—S— (PSMA-binding side);

(Amatoxin side) —$CH_2$—$C_6H_4$—NH-Ala-Val-CO$(CH_2)_5$—X—S— (PSMA-binding side);

(Amatoxin side) —$CH_2$—$C_6H_4$—NH-Ala-Val-CO$(CH_2)_2$—X—S— (PSMA-binding side);

(Amatoxin side) —$CH_2$—$C_6H_4$—NH-Ala-Phe-CO$(CH_2)_2$—X—S— (PSMA-binding side);

(Amatoxin side) —$CH_2$—$C_6H_4$—NH-Lys-Phe-CO$(CH_2)_2$—X—S— (PSMA-binding side);

(Amatoxin side) —$CH_2$—$C_6H_4$—NH-Cit-Phe-CO$(CH_2)_2$—X—S— (PSMA-binding side);

(Amatoxin side) —$CH_2$—$C_6H_4$—NH-Val-Val-CO$(CH_2)_2$—X—S— (PSMA-binding side);

(Amatoxin side) —$CH_2$—$C_6H_4$—NH-Ile-Val-CO$(CH_2)_2$—X—S— (PSMA-binding side);

(Amatoxin side) —$CH_2$—$C_6H_4$—NH-His-Val-CO$(CH_2)_2$—X—S— (PSMA-binding side);

(Amatoxin side) —$CH_2$—$C_6H_4$—NH-Met-Val-CO$(CH_2)_2$—X—S— (PSMA-binding side);

(Amatoxin side) —$CH_2$—$C_6H_4$—NH-Asn-Lys-CO$(CH_2)_2$—X—S— (PSMA-binding side); and wherein —NH— and —CO— flanking the dipeptide sequences represent amino and carbonyl moieties of the linker forming amide bonds to the carboxy- and the amino-terminus of the dipeptide, respectively.

In the context of the present invention, the term "a moiety resulting from coupling of a thiol group to a thiol-reactive group" refers to a structure that results from (i) the nucleophilic substitution of a leaving group Y present in a thiol-reactive group by the sulphur atom of a cysteine residue, for example a bromo acetamide group, a iodo acetamide, a 4,6-dichloro-1,3,5-triazin-2-ylamino group, an alkylsulfone or a heteroarylsulfone; (ii) the addition of the HS-group of a cysteine residue to an activated double bond of a thiol-reactive group, for example maleimide, or (iii) an disulfide exchange of an activated disulfide or methanethiosulfonate with the sulphur atom of a cysteine residue, for example with pyridine-2-thiol, 5-nitropyridine-2-thiol or methanesulfinate as leaving group; or (iv) any other chemical reaction that results in a stable bond between the sulphur atom of a cysteine residue and a reactive moiety being part of the thiol-reactive group.

The primary moiety resulting from coupling of thiol group may be optionally further derivatized, e.g. the succinimidyl thioether resulting from a maleimide can be hydrolysed to succinamic acid thioethers.

In alternative embodiments, the linker comprises at least one five-membered ring that results from the reaction of a 1,3 dipole with a double or triple bond in a 1,3-dipolar cycloaddition (click chemistry).

In particular embodiments, said PSMA-binding moiety is conjugated to the linker L, in the case of structure III or V, via a carboxamide group —C(═O)—NH—, or, in the case of structure IV or VI, via a carboxamide group —NR—C(═O)— or urea group —NR—C(═O)—NH—.

In particular embodiments, wherein said linker is connected to the PSMA-targeting moiety moiety via a urea moiety, the urea moiety results from a reaction of the primary amino group originally present in the PSMA-targeting moiety according to structure II with a carbamic acid derivative . . . -linker-NH—C(═O)—Z, wherein Z is a leaving group that can be replaced by a primary amine.

In particular embodiments of conjugates of the present invention having the structure III or V, the linker L has the generic structure (Aoc element)$_a$-(polypeptide)$_b$-(alkylene)$_c$-(PEG)$_d$-(thiol element)$_e$-(alkylene)$_f$-(self-immolative element)$_g$ wherein each of the factors a to g is independently selected from 0 and 1, provided that that at least one of said factors is 1.

In such embodiments, the term "Aoc element" refers to a group as defined above, the term "polypeptide" refers to a dipeptide, a tripeptide, a tetrapeptide, a pentapteptide, a hexapeptide, a heptapeptide, an octapeptide, particularly to a polypeptide as defined above. The term "alkylene" independently refers to a group $(CH_2)_n$, optionally substituted with up to n $C_{1-6}$-alkyl groups, with n being an integer selected from the range of 2 to 8. The term "PEG" refers to a group —(O—$CH_2$—$CH_2$-$)_y$ or —($CH_2$—$CH_2$—O—$)_y$, with y being an integer selected from the range of 6 to 14. The term "thiol element" refers to a thioether, a disulfide or an element —S—X—, wherein X refers to a group as defined above, and the term "self-immolative element" refers to an enzyme-cleavable structure as defined above. As will be immediately apparent to one of ordinary skill in the art, the generic concept described in this Section implicitly includes certain linkage elements that are required to form an appropriate linkage between the individual components of said generic concept in accordance with the present invention. For example, in the case of a urea linkage between the PSMA-binding moiety according to structure II and an Aoc element, an additional carbonyl moiety will be present, and in the case of a polypeptide-alkylene linkage, said linkage includes an amino group forming an amide bond between the alkylene group and the C-terminal end of the polypeptide.

In particular embodiments of conjugates of the present invention having the structure IV or VI, the linker (L-$)_2$-B-L has the structure

[(Aoc element)$_a$-(polypeptide)$_b$-(PEG)]2-B-alkylene)$_c$-(self-immolative element)$_d$ wherein each of the factors a to d is independently selected from 0 and 1, provided that at least one of said factors is 1.

In such embodiments, the terms are used as defined above.

In particular embodiments, said amatoxin is conjugated to the linker L via the side chain of the aspartic acid residue at position 1.

In particular such embodiments, said amatoxin is conjugated via an ester linkage Ama-C(═O)—O-L- . . . or via a hydroxamic acid linkage Ama-C(═O)—NH—O-L- . . . .

In particular other embodiments, said amatoxin is conjugated via a carboxamide linkage.

In particular such embodiments, said conjugate is compound HDP 30.2597.

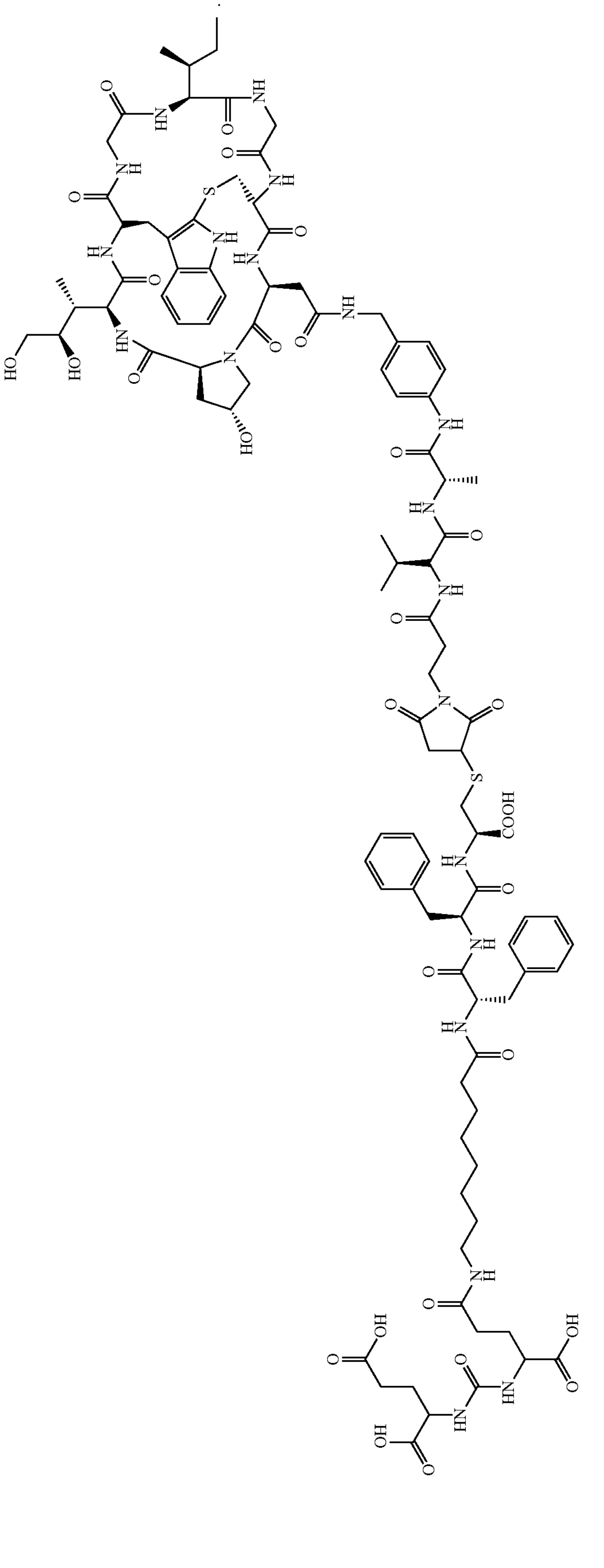

In particular embodiments, said amatoxin is conjugated to the linker L via the side chain of the dihydroxyisoleucine residue at position 3.

In particular embodiments, said amatoxin is conjugated to the linker L the indole nitrogen atom of the tryptophan residue at position 4.

In particular embodiments, said amatoxin is conjugated to the linker L via the phenylene part of the indole ring of the tryptophan residue at position 4.

In particular such embodiments, said amatoxin is conjugated to position 6' of said indole ring via an ether linkage.

In particular such embodiments, said conjugate is a compound selected from the list of:

HDP 30.1585

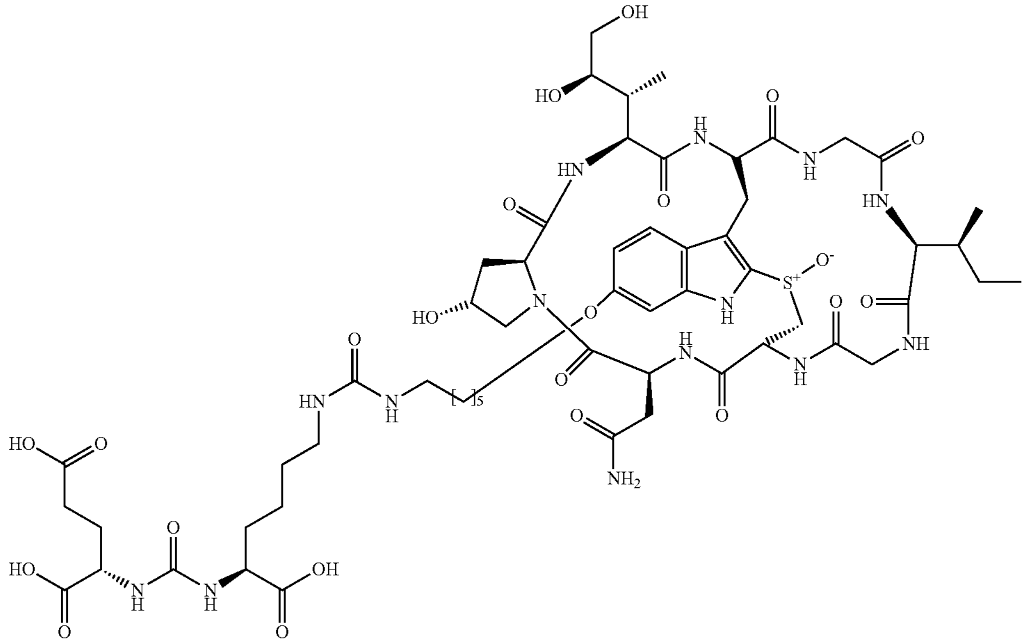

HDP 30.1592

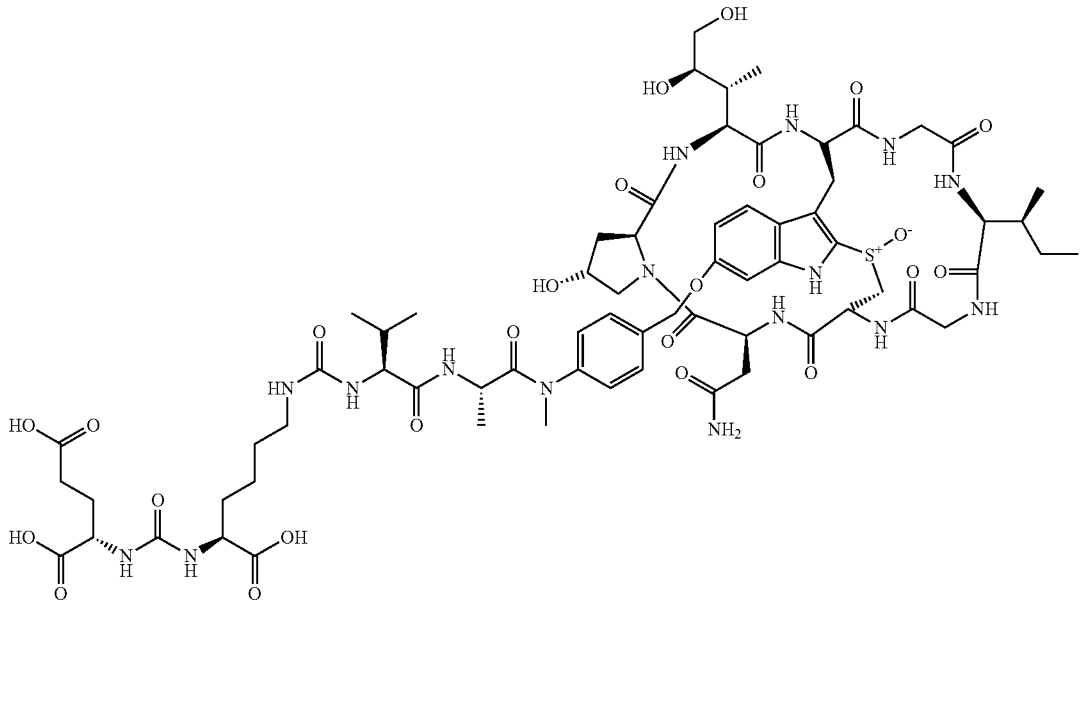

-continued
HDP 30.2246
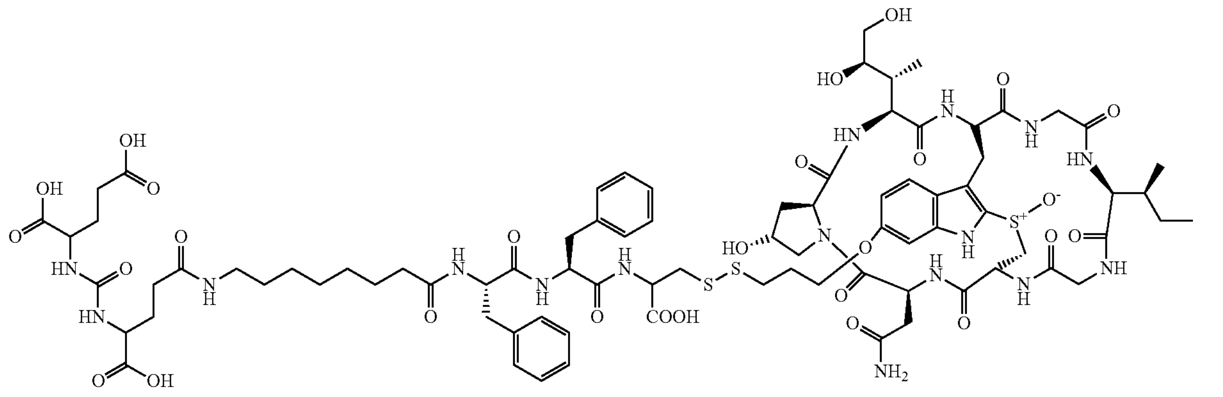
HDP 30.2589
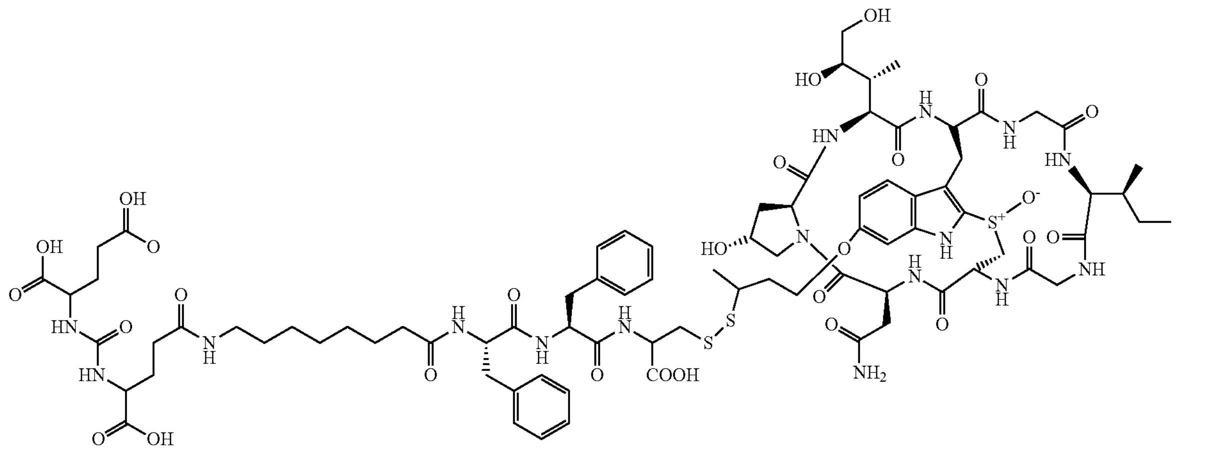
HDP 30.2609
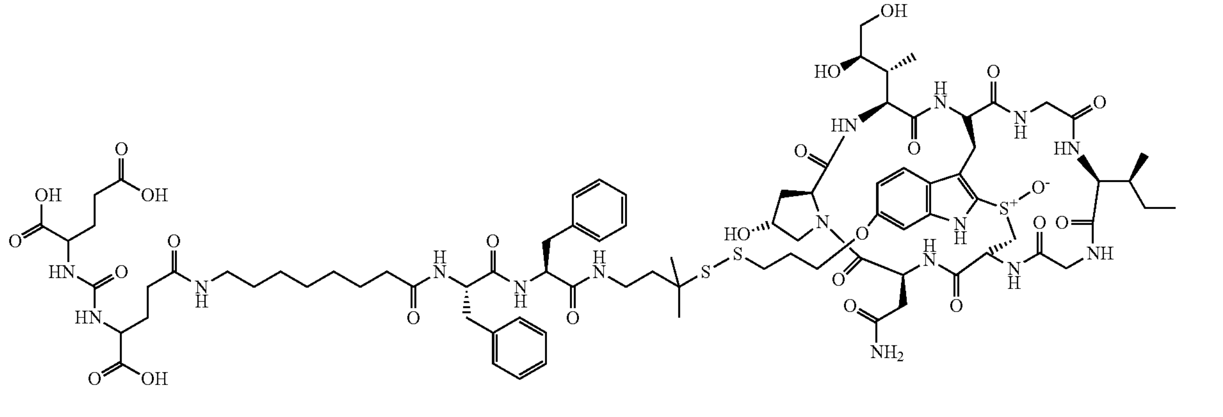

-continued
HDP 30.2618
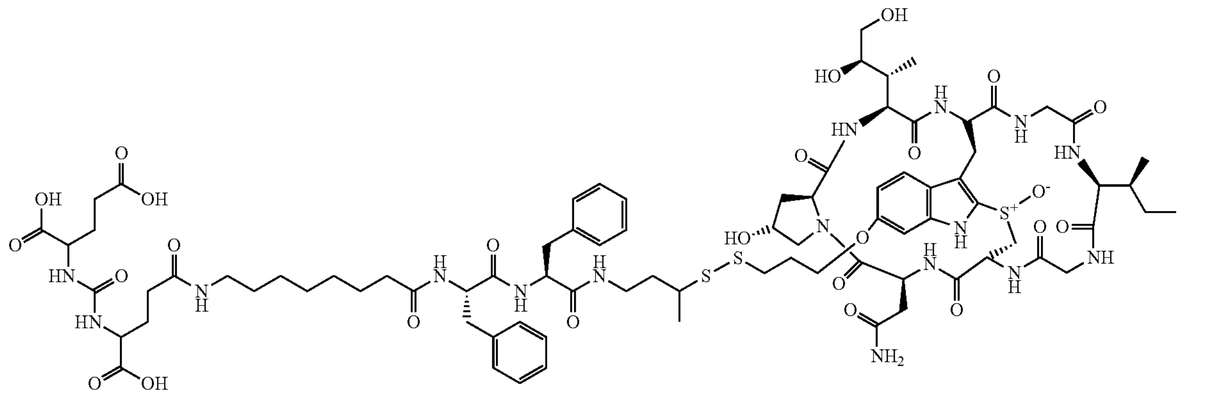
HDP 30.2619
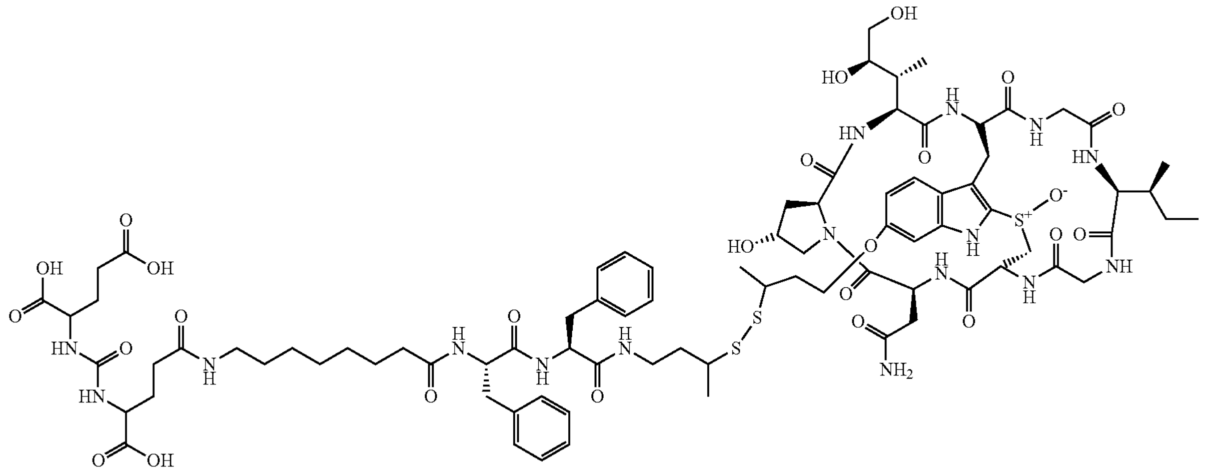
HDP 30.2284
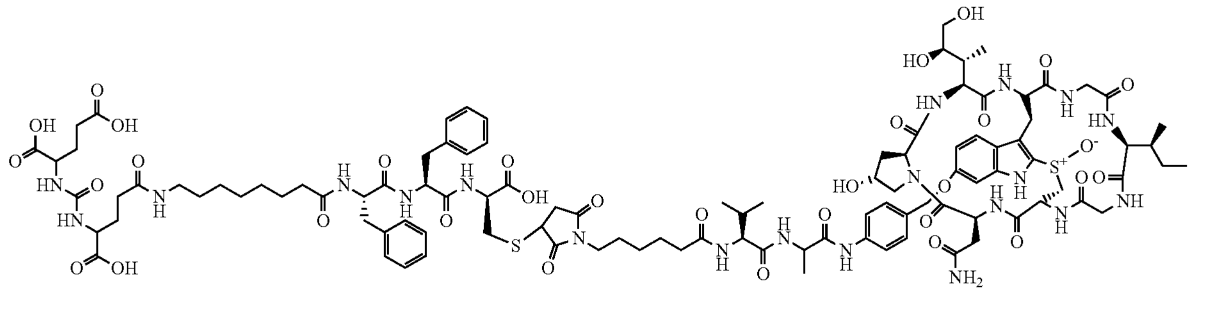

-continued
HDP 30.2535
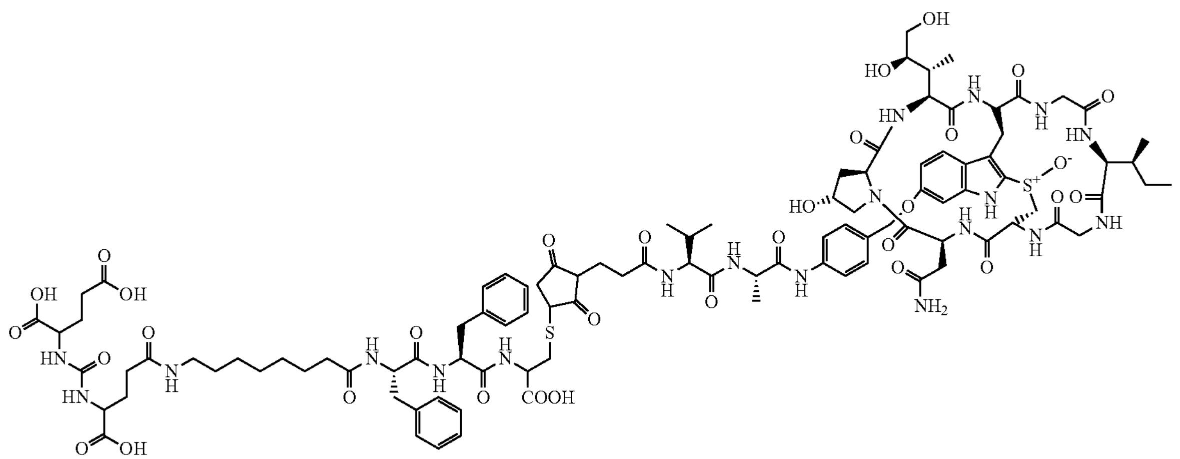
HDP 30.2537
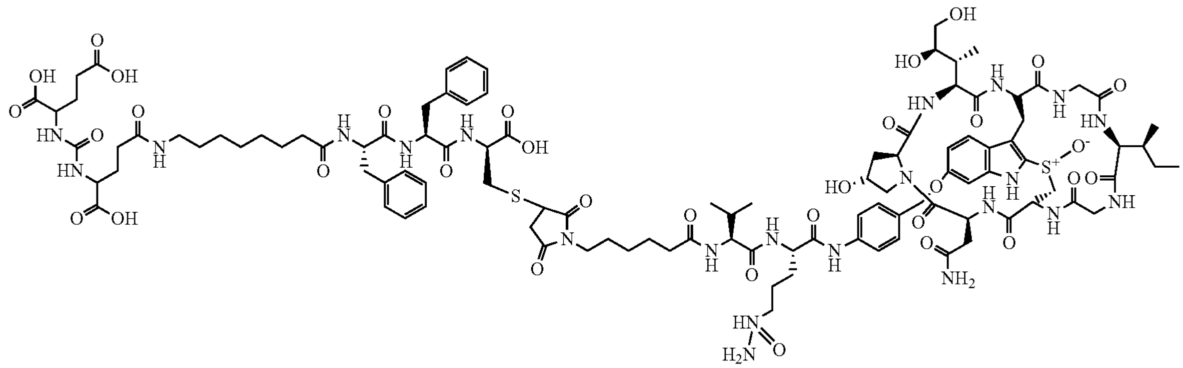
HDP 30.2471
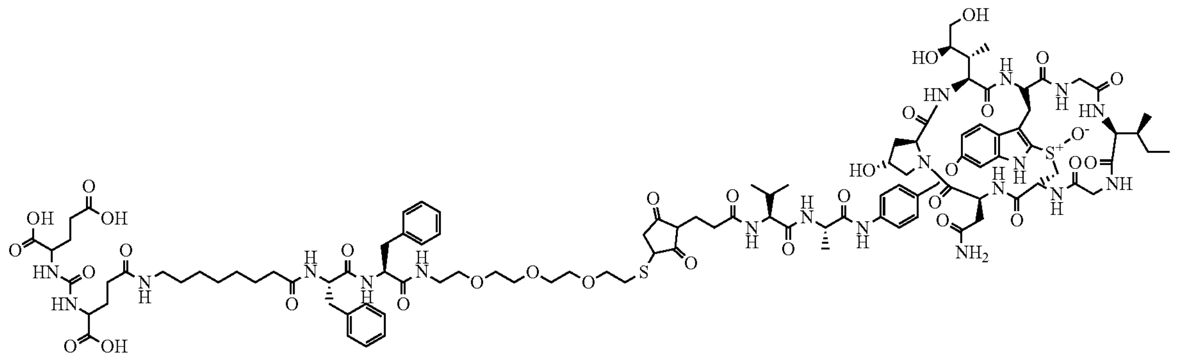
HDP 30.2474
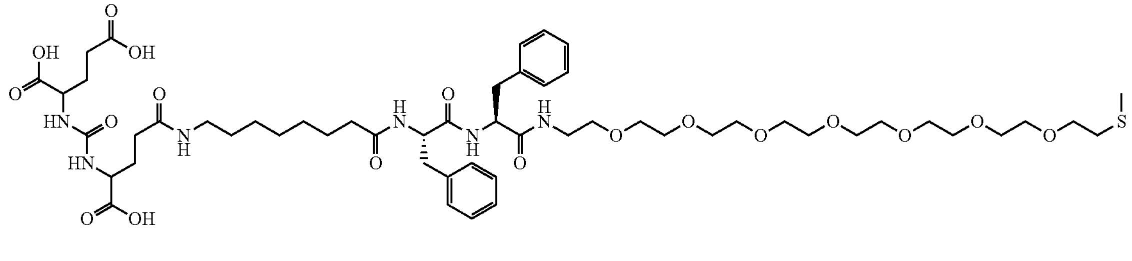

-continued
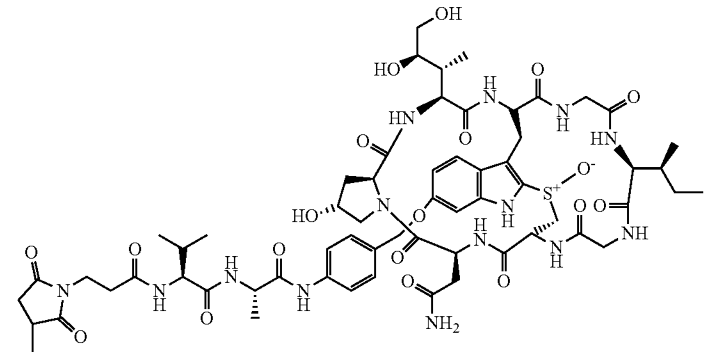
HDP 30.2301
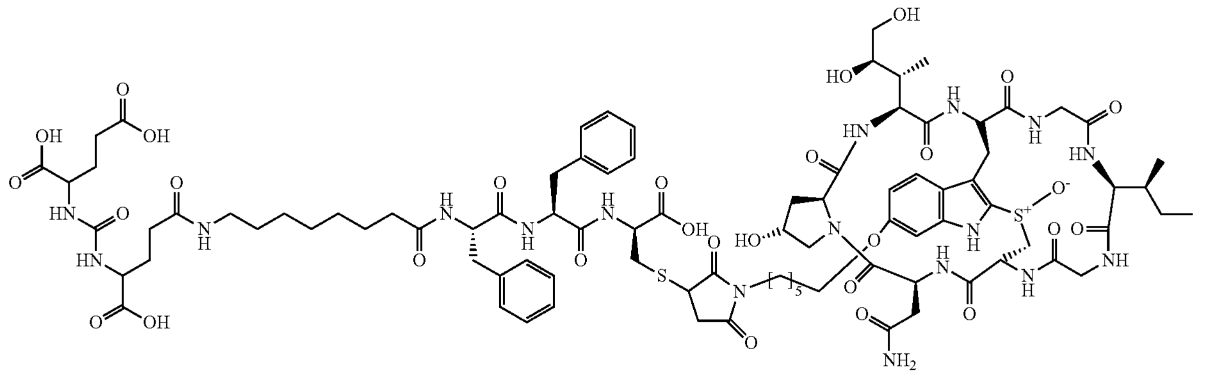
HDP 30.2515
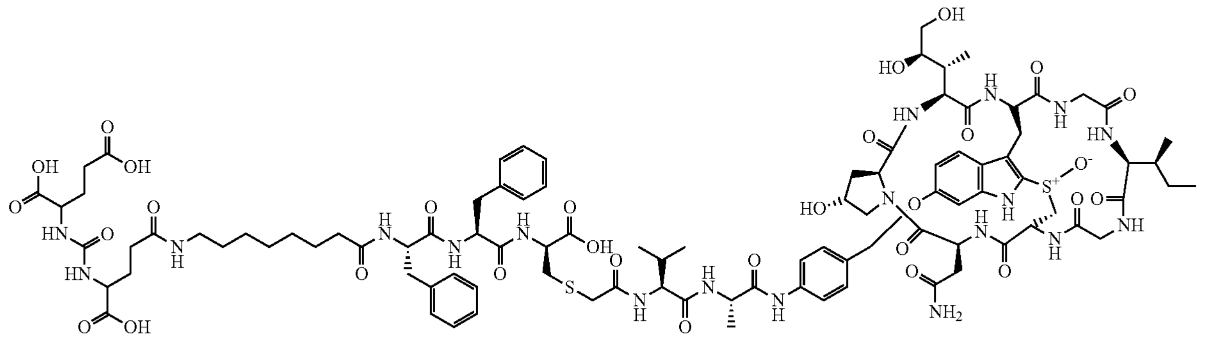
HDP 30.2523
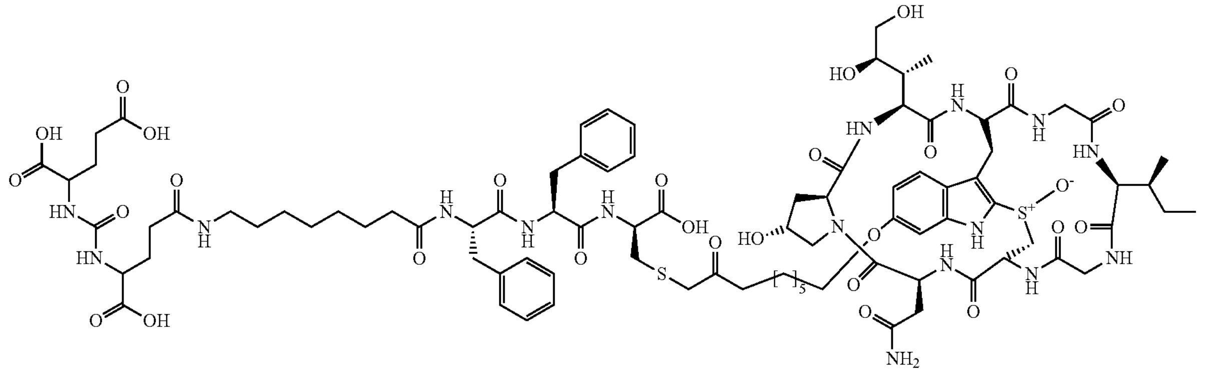

-continued
HDP 30.2594
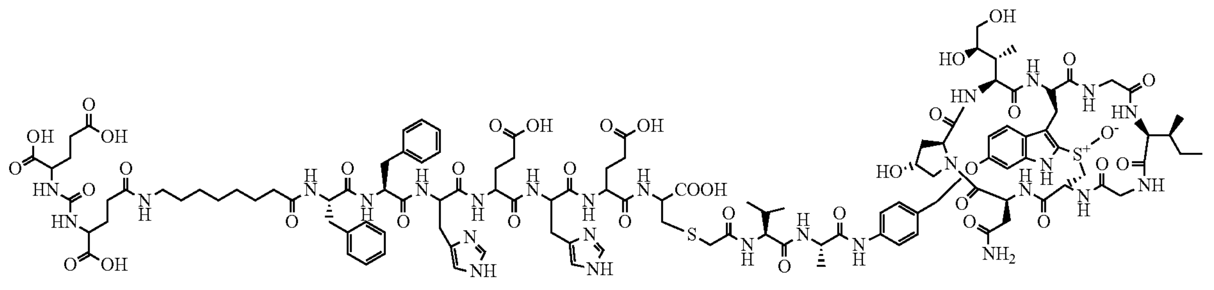
HDP 30.2300
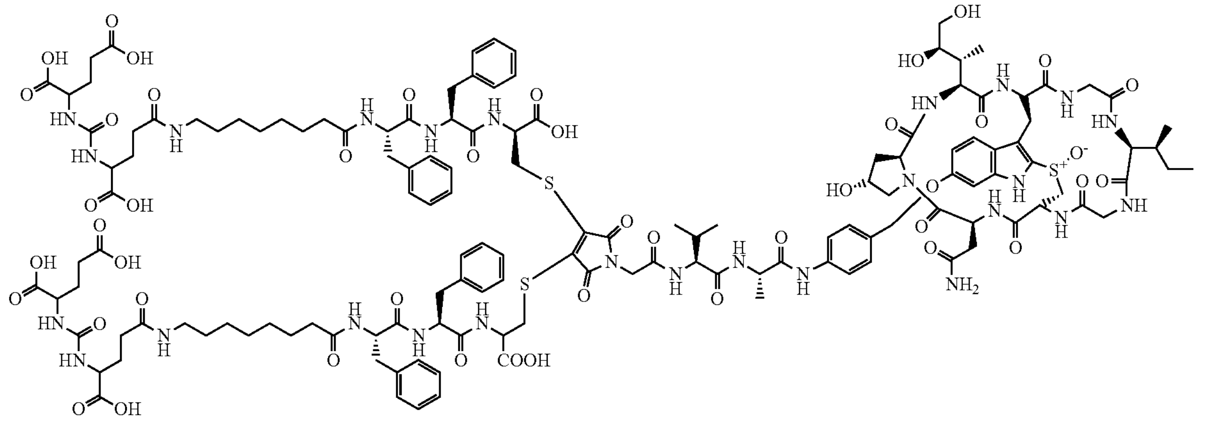
HDP 30.2448
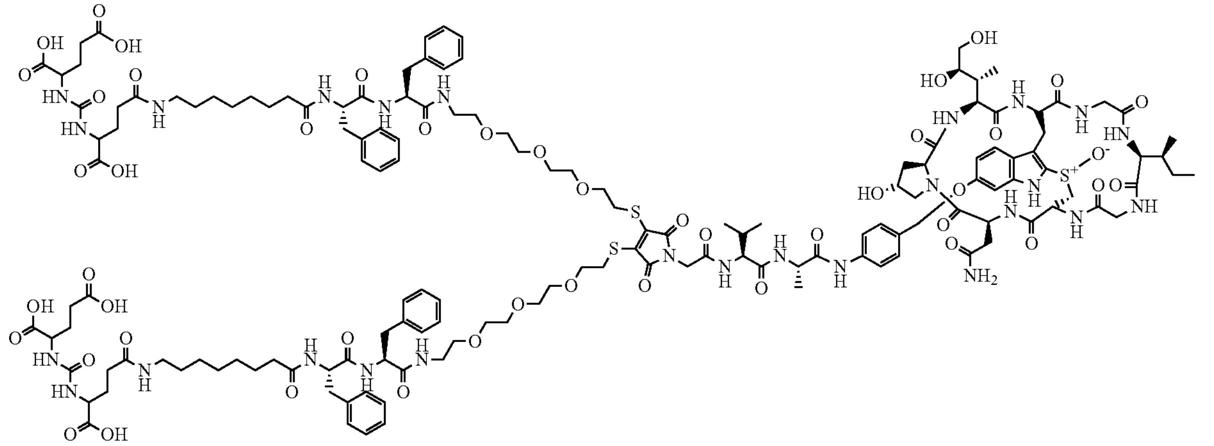
HDP 30.2490
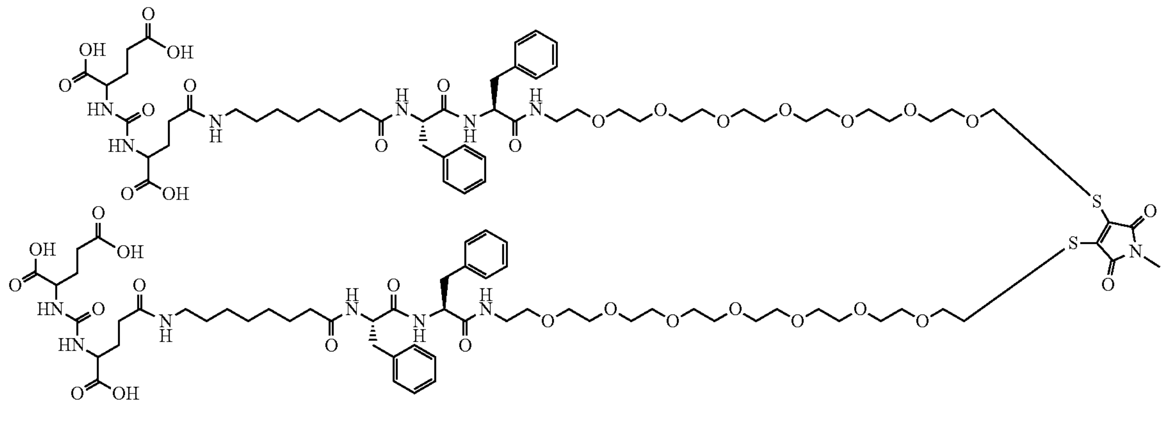

-continued
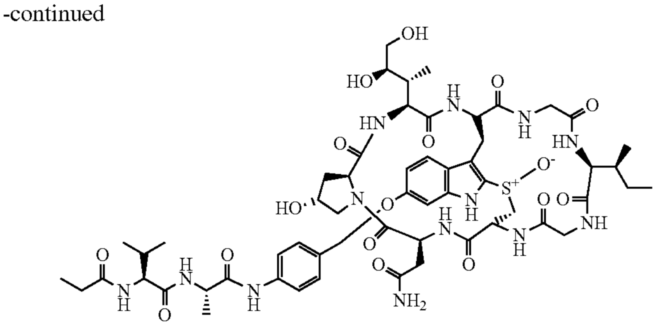
HDP 30.2595
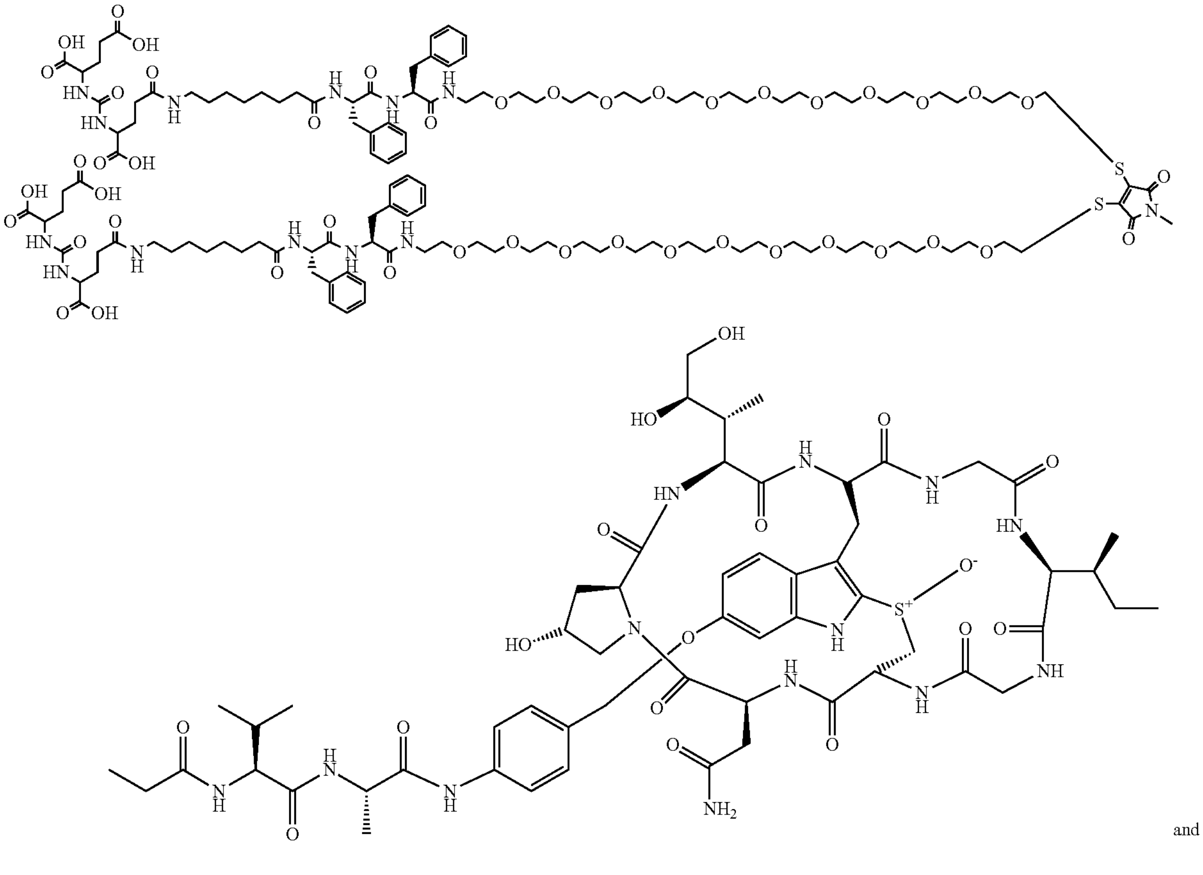
and
HDP 30.2661
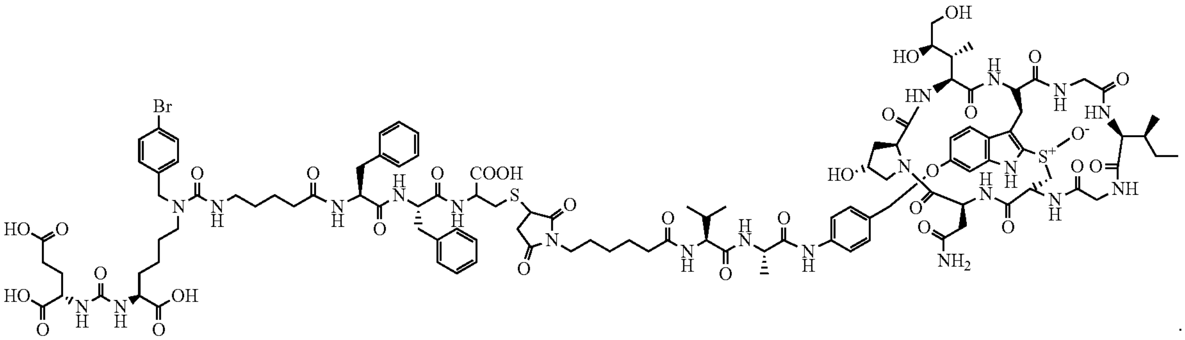
.

In a second aspect, the present invention relates to versions of a conjugate comprising an amatoxin, linked to a PSMA-binding moiety based on 2-[3-(1,3-dicarboxy-propyl)ureido]pentanedioic acid (I) or 6-amino-2-[3-(1,3-dicarboxypropyl)ureido]-hexanoic acid (II), said conjugate having an extended pharmacokinetic half-life.

The main route of clearance from serum for proteins and peptides smaller than approximately 70 kDa is glomerular filtration by the kidney. Various strategies have been developed to extend the pharmacokinetic half-life of small-molecule—as well as protein-based therapeutic agents. For protein-based therapeutics, such strategies have included, but were not limited to, the use of synthetic polymer-based fusions, such as e.g. polyethylene glycol (PEG), and protein fusion constructs. Fusion proteins have been used in the pharmaceutical industry for decades to improve the pharmacokinetic properties of otherwise short-half-life therpeutics (for review see Strohl W. R., 2015, Fusion proteins for half-life extension of biologics as a strategy to make biobetters; *BioDrugs* 29, 215-239). These have included, e.g., the use of constant fragment (Fc) moieties of immunoglobulins (antibodies), serum albumin, carboxy-terminal peptide (CTP), and others for the design of fusion constructs.

Conjugation to antibody Fc (fragment crystallizable) fragments is a common strategy applied to reduce the peptide clearance rates by increasing the size and exploiting the neonatal Fc receptor (FcRn) recycling process by epithelial cells, which is responsible for the long half-life in serum of type G immunoglobulins (IgGs) (Strohl W. R., 2015, *BioDrugs* 29, 215-239).

In particular embodiments according to the present invention, the conjugates as disclosed above are further linked via a trifunctional linker to a half-life extension moiety.

In a particularly preferred embodiment of the present invention, the conjugates as disclosed above are linked via a trifunctional linker to a constant fragment (Fc) moiety of an antibody, preferrably of a human antibody, most preferrably of a human IgG-type antibody.

The inventors of the present invention have found that the pharmacokinetic half-lives of said amatoxin-DUPA conjugates as disclosed above could be significantly extended by connection to a constant fragment (Fc) moiety of an antibody. Surprisingly, said conjugates comprising an amatoxin, a PSMA-binding moiety based on 2-[3-(1,3-dicarboxy-propyl)ureido]pentanedioic acid (I) or 6-amino-2-[3-(1,3- dicarboxypropyl)ureido]-hexanoic acid (II), and a constant fragment (Fc) moiety of an antibody retained their PSMA-binding activity as well as their functional activity towards the amatoxin target RNA polymerase II.

In the context of the present invention, the term "half-life extension moiety", also shorty termed as "extension moiety" (EM), refers to any moiety or component of a conjugate, be it before, during or after incorporation in said conjugate, which serves to increase the plasma half-life of said conjugate and/or to reduce the clearance from the blood plasma over time, including, but not being limited to, peptides, polypeptides, proteins, fusion peptides or fusion proteins, small molecules, natural or synthetic chemical compounds. Said half-life extension moieties can be, for example, immunoglobulin Fc domains or fragments or derivatives thereof, albumin or human serum albumin or fragments or derivatives thereof, transferrin or human transferrin or fragments or derivatives thereof, CTP peptide from human chorionic gonadotropin β-subunit, elastin-like peptide (ELP) repeat sequence, proline-alanine-serine (PAS) polymer, homo amino acid polymer (HAP) such as homopolymer of glycine residues, artificial gelatin-like protein (GLP), non-exact repeat peptide sequence (XTEN), polyethylene glycol (PEG) of various lengths, or fragments or derivatives thereof, or combinations thereof.

In particular embodiments, the present invention relates to a conjugate having the structure VII or VIII

VII

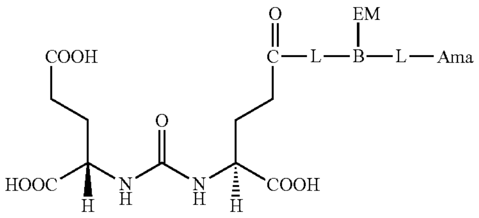

VIII

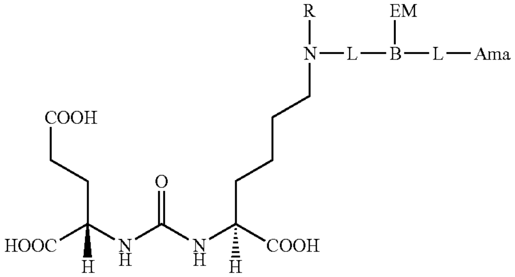

wherein each L is a linker, Ama is an amatoxin, B is a trifunctional linker element, EM is an half-life extension moiety, and R is selected from H, $C_{1-6}$-alkyl and p-bromobenzyl.

In further particular embodiments, the present invention relates to a conjugate having the structure VII or VIII, wherein said half-life extension moiety is comprising an Fc moiety of an antibody, preferrably of a human antibody.

In further particular embodiments, the present invention relates to a conjugate having the structure VII or VIII, wherein the conjugate comprises a 1,2,3-triazole resulting from a reaction of an azide moiety of the trifunctional linker B and an alkyne moiety of said linker L connecting said amatoxin to said trifunctional linker B, and wherein said alkyne moiety is selected from the group consisting of propiolic acid, 3-butynoic acid, 4-pentynoic acid, 5-hexynoic acid, dibenzylcyclooctyne (DiBO), dibenzylazacyclooctynone (DBCO) and bicyclo[6.1.0]non-4-yne (BCN).

In further particular embodiments, the present invention relates to a conjugate having the structure IX

IX

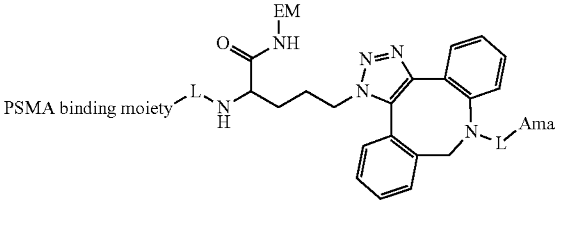

wherein the PSMA-binding moiety is based on 2-[3-(1,3-dicarboxy-propyl)ureido]pentanedioic acid or 6-amino-2-[3-(1,3-dicarboxypropyl)ureido]-hexanoic acid.

In other preferred embodiments, said L-Ama is selected from the following list:
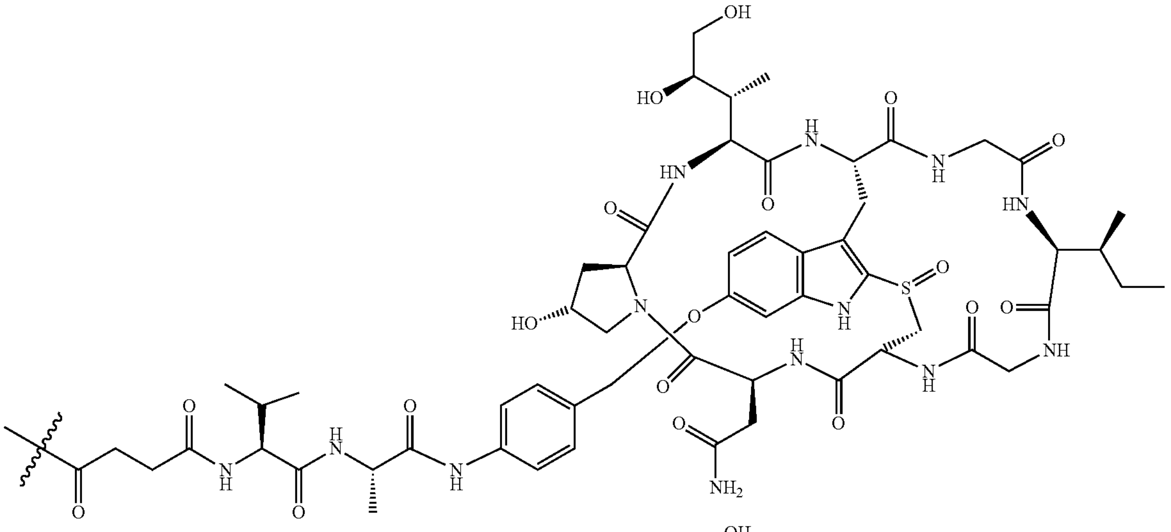
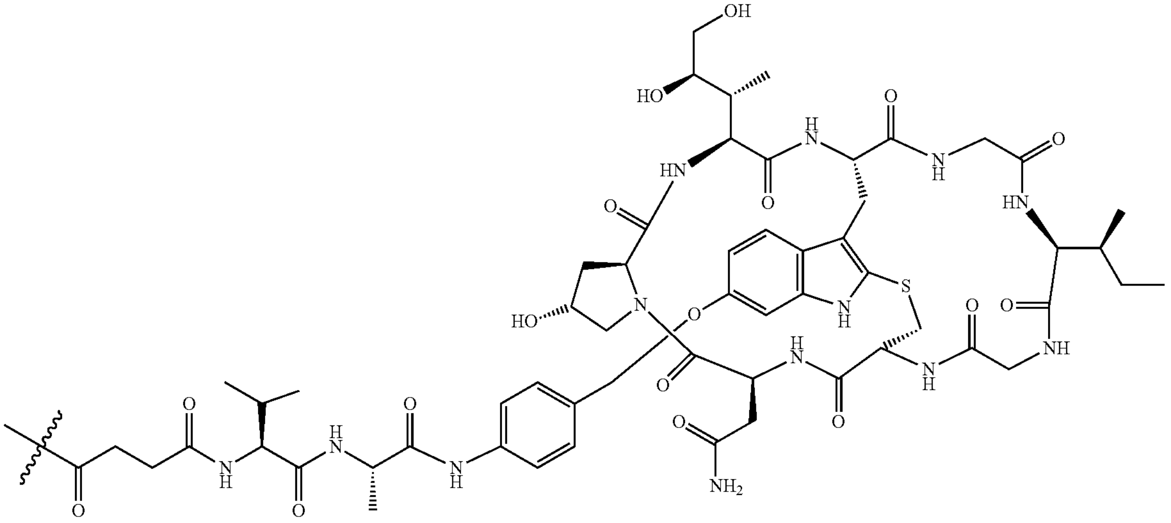
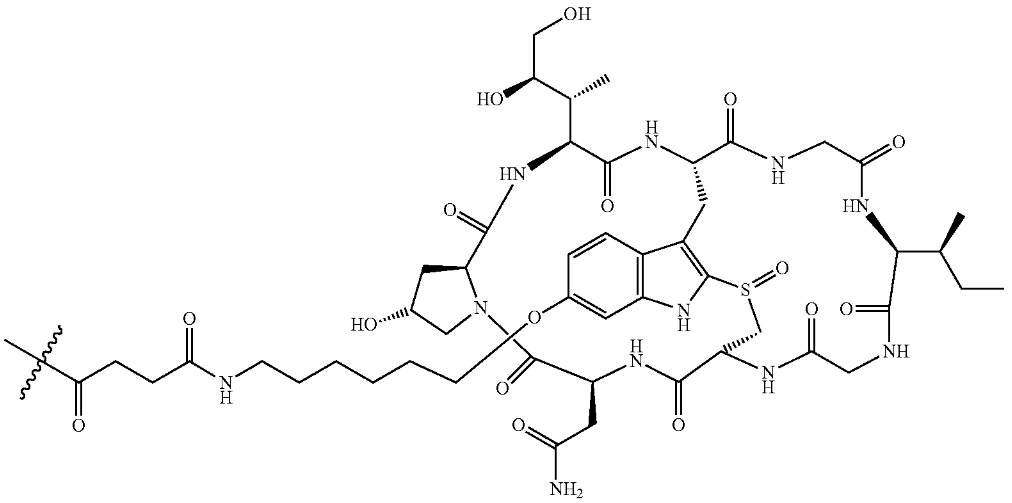

-continued
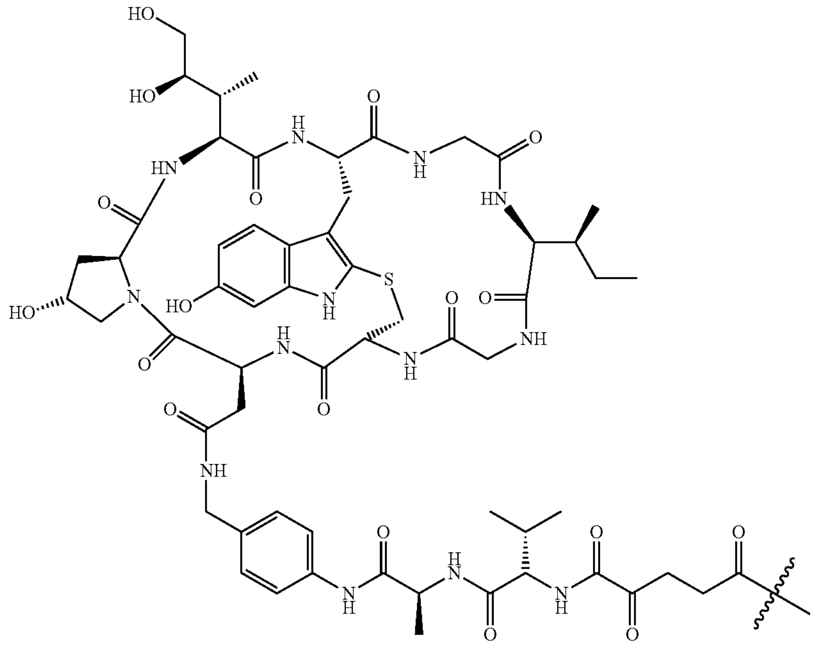
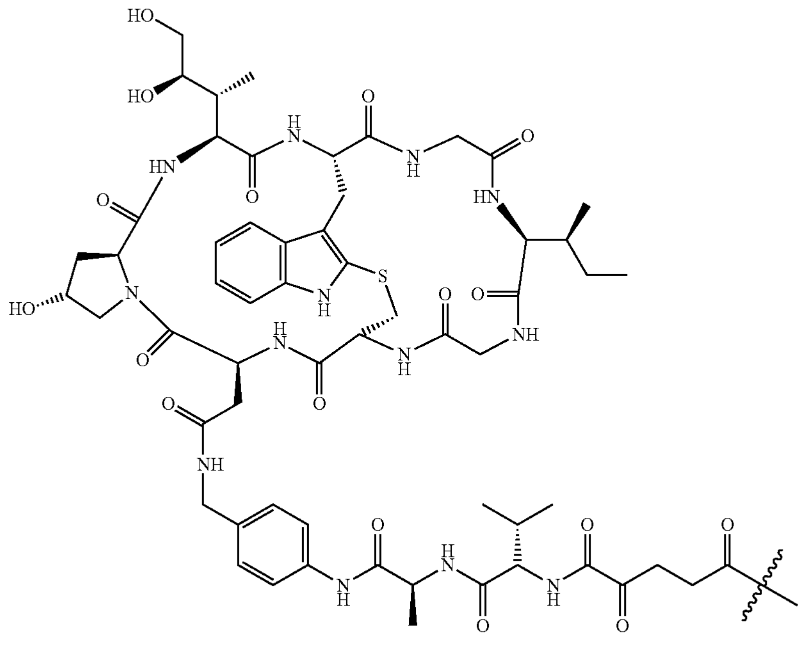

-continued
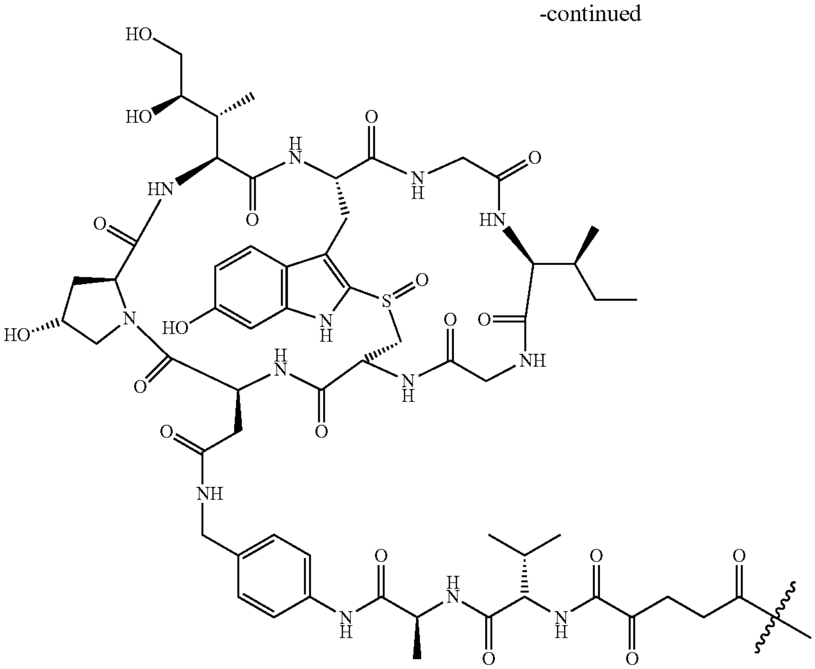
In still further preferred embodiments, the present invention relates to a conjugate selected from the list of

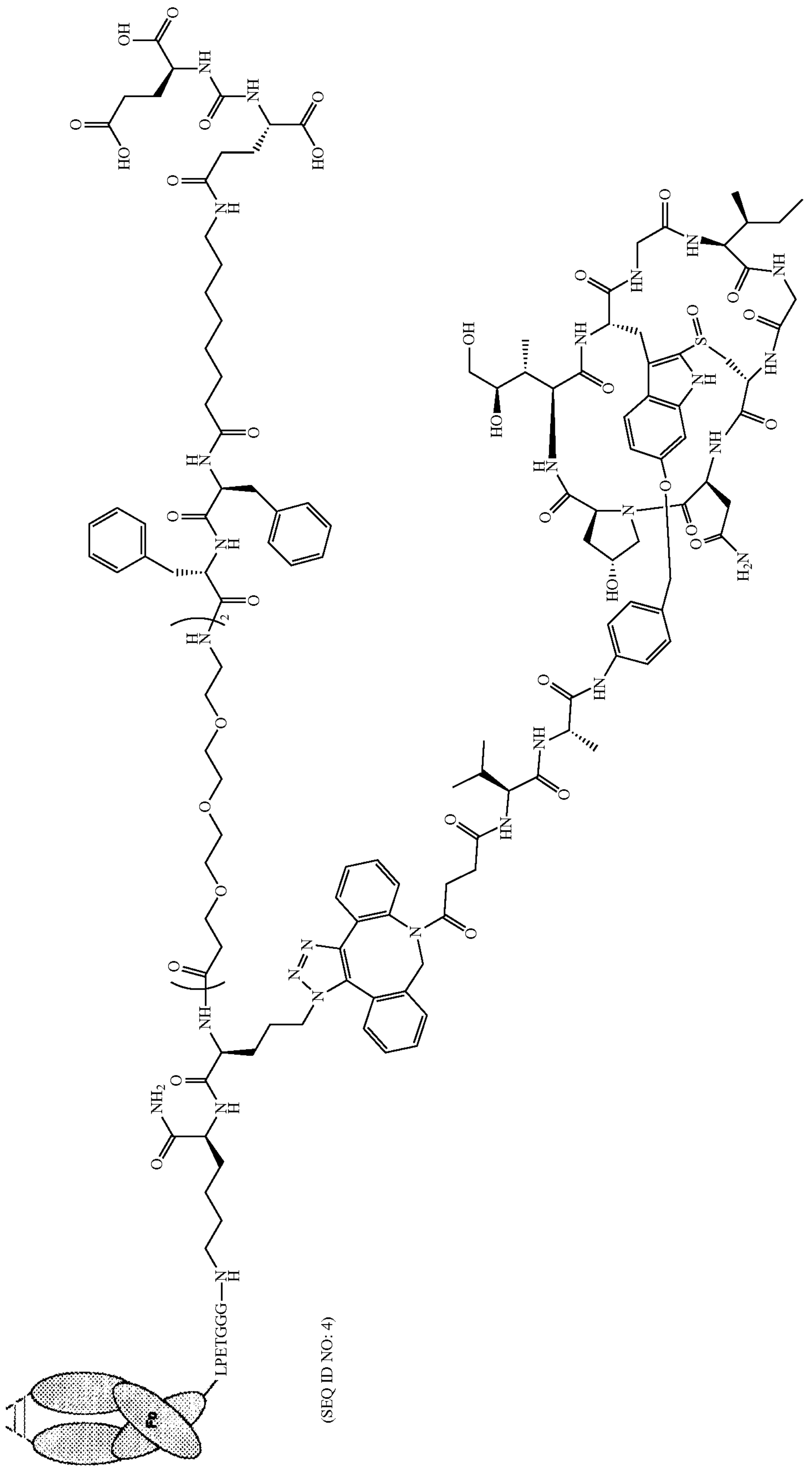
(SEQ ID NO: 4)

-continued
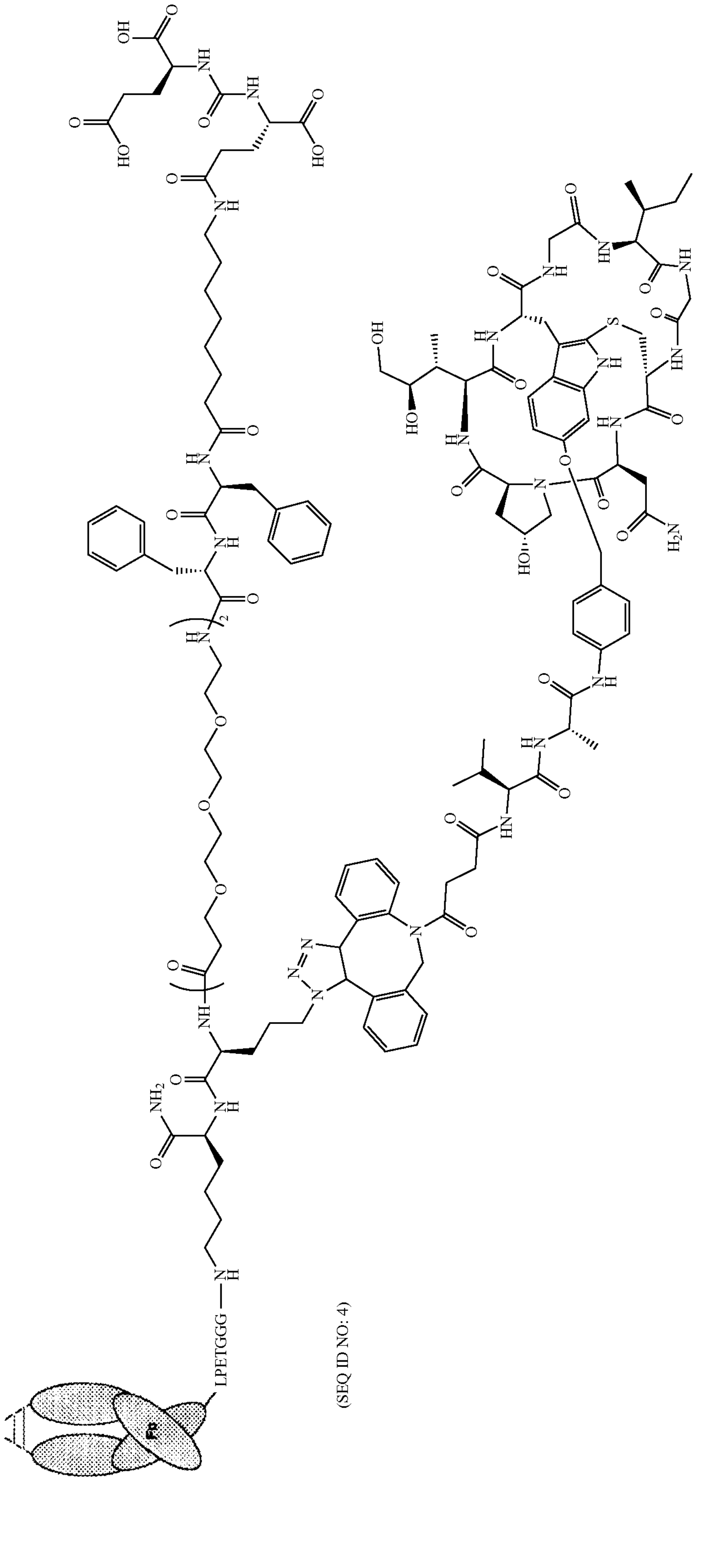
(SEQ ID NO: 4)

-continued
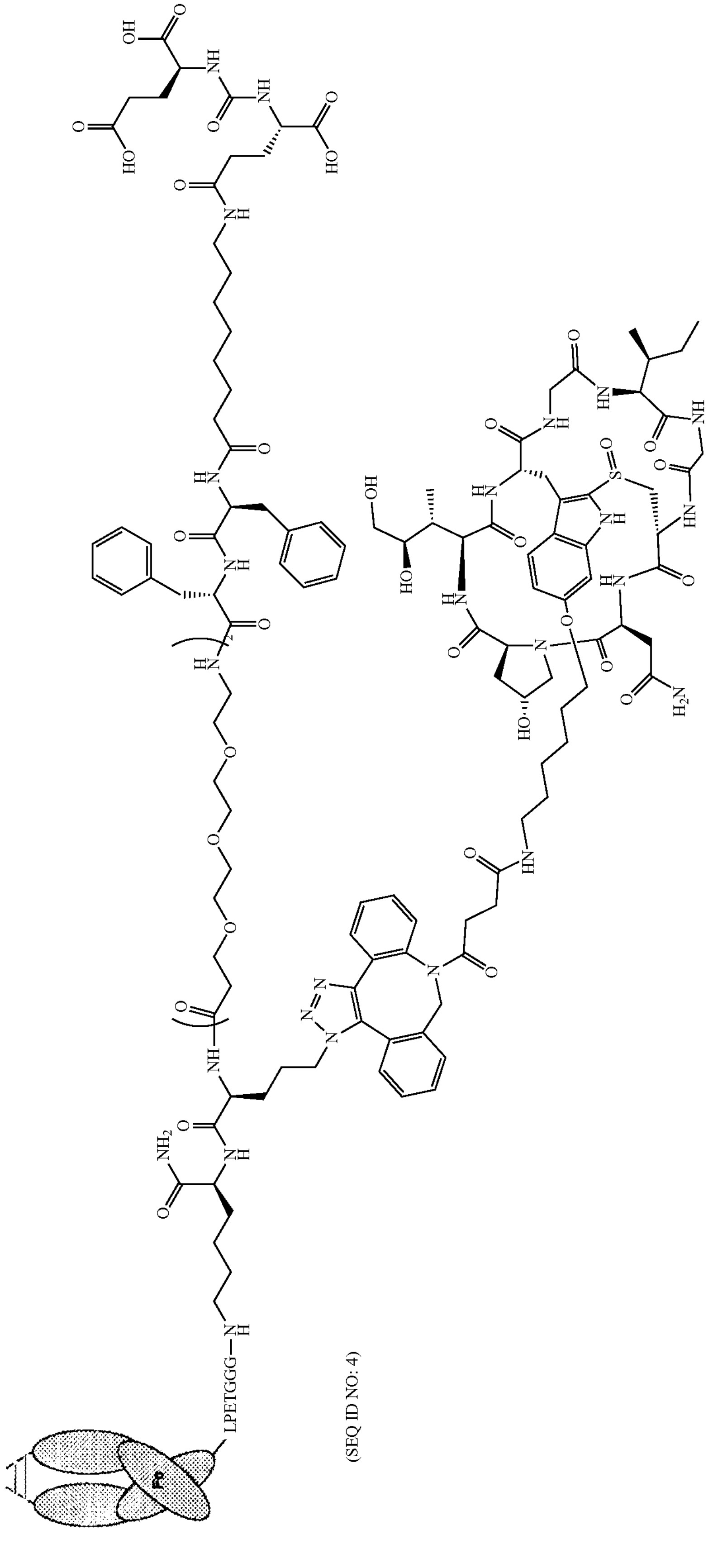
(SEQ ID NO: 4)

-continued
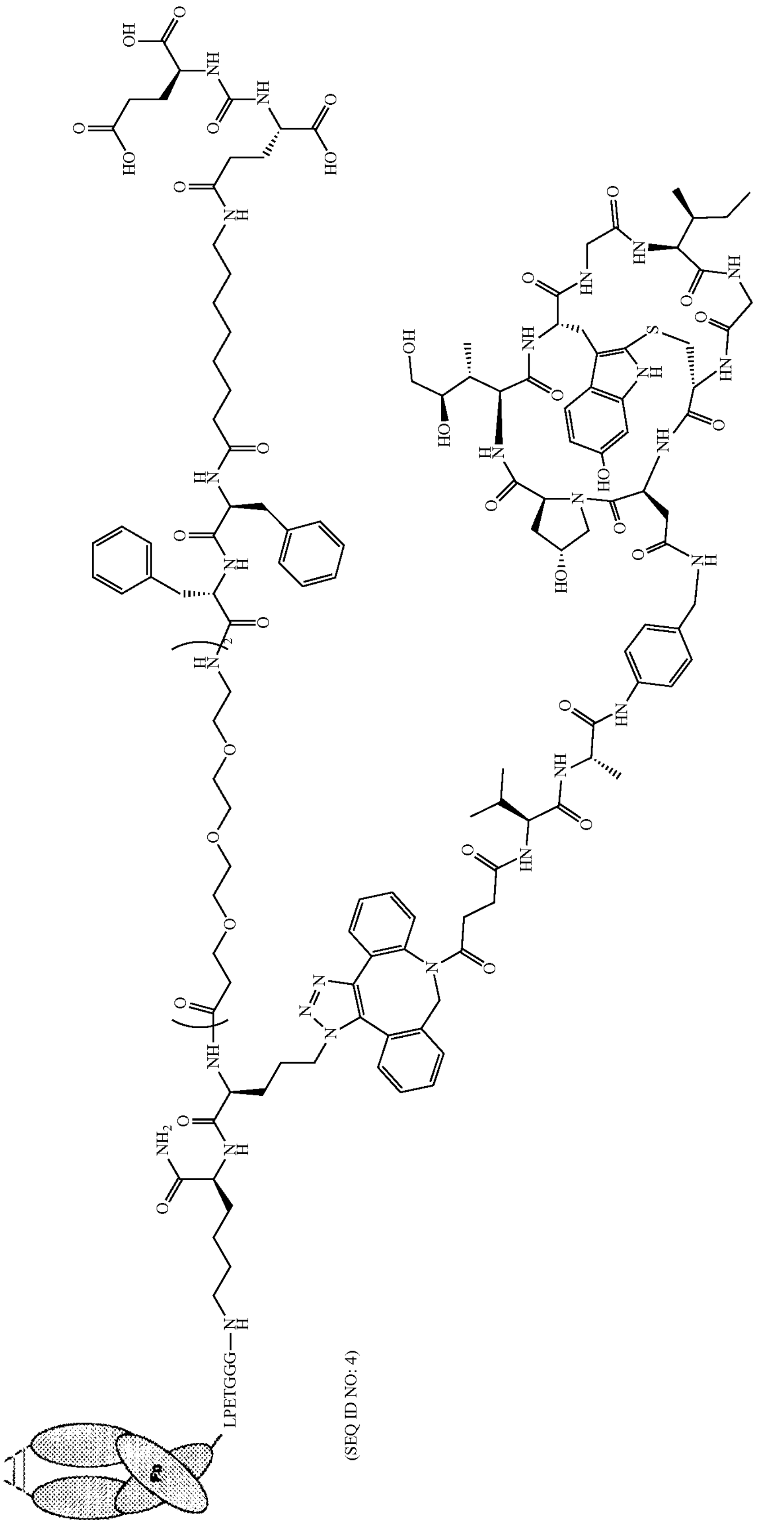
(SEQ ID NO: 4)

-continued
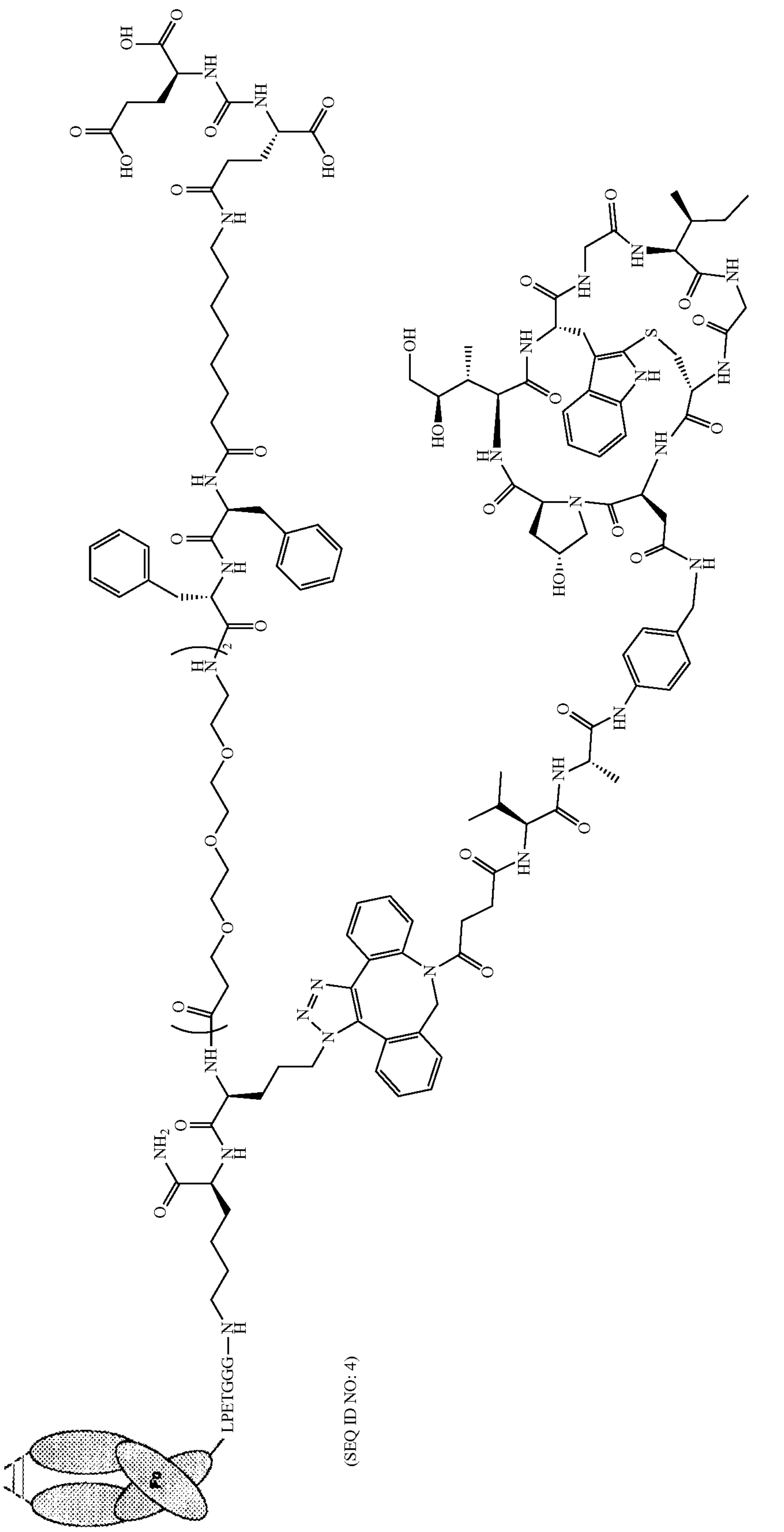
(SEQ ID NO: 4)

In still further preferred embodiments of the present invention, said Fc moiety comprises SEQ ID No. 1.

In a third aspect, the present invention relates to a pharmaceutical composition comprising the conjugate of the present invention.

In a fourth aspect, the present invention relates to a conjugate of the present invention for use in the treatment of cancer in a patient, particularly wherein the cancer is selected from the group consisting of breast cancer, pancreatic cancer, cholangiocarcinoma, colorectal cancer, lung cancer, prostate cancer, ovarian cancer, stomach cancer, kidney cancer, malignant melanoma, leukemia, and malignant lymphoma.

As used herein, "treat", "treating" or "treatment" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, the treatment may comprise administering a conjugate or a pharmaceutical composition according to the present invention to a patient, wherein "administering" includes in vivo administration, as well as administration directly to tissue ex vivo, such as vein grafts.

In particular embodiments, a therapeutically effective amount of the conjugate of the present invention is used.

A "therapeutically effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

In another aspect the present invention relates to pharmaceutical composition comprising an amatoxin according to the present invention, or a conjugate of the present invention of an amatoxin with a target-binding moiety, and further comprising one or more pharmaceutically acceptable diluents, carriers, excipients, fillers, binders, lubricants, glidants, disintegrants, adsorbents; and/or preservatives.

"Pharmaceutically acceptable" means approved by a regulatory agency of the Federal or a state government or listed in the U.S. Pharmacopeia or other generally recognized pharmacopeia for use in animals, and more particularly in humans.

In particular embodiments, the pharmaceutical composition is used in the form of a systemically administered medicament. This includes parenterals, which comprise among others injectables and infusions. Injectables are formulated either in the form of ampoules or as so called ready-for-use injectables, e.g. ready-to-use syringes or single-use syringes and aside from this in puncturable flasks for multiple withdrawal. The administration of injectables can be in the form of subcutaneous (s.c.), intramuscular (i.m.), intravenous (i.v.) or intracutaneous (i.c.) application. In particular, it is possible to produce the respectively suitable injection formulations as a suspension of crystals, solutions, nanoparticular or a colloid dispersed systems like, e.g. hydrosols.

Injectable formulations can further be produced as concentrates, which can be dissolved or dispersed with aqueous isotonic diluents. The infusion can also be prepared in form of isotonic solutions, fatty emulsions, liposomal formulations and micro-emulsions. Similar to injectables, infusion formulations can also be prepared in the form of concentrates for dilution. Injectable formulations can also be applied in the form of permanent infusions both in in-patient and ambulant therapy, e.g. by way of mini-pumps.

It is possible to add to parenteral drug formulations, for example, albumin, plasma, expander, surface-active substances, organic diluents, pH-influencing substances, complexing substances or polymeric substances, in particular as substances to influence the adsorption of the target-binding moiety toxin conjugates of the invention to proteins or polymers or they can also be added with the aim to reduce the adsorption of the target-binding moiety toxin conjugates of the invention to materials like injection instruments or packaging-materials, for example, plastic or glass.

The amatoxins of the present invention comprising a target-binding moiety can be bound to microcarriers or nanoparticles in parenterals like, for example, to finely dispersed particles based on poly(meth)acrylates, polylactates, polyglycolates, polyamino acids or polyether urethanes. Parenteral formulations can also be modified as depot preparations, e.g. based on the "multiple unit principle", if the target-binding moiety toxin conjugates of the invention are introduced in finely dispersed, dispersed and suspended form, respectively, or as a suspension of crystals in the medicament or based on the "single unit principle" if the target-binding moiety toxin conjugate of the invention is enclosed in a formulation, e.g. in a tablet or a rod which is subsequently implanted. These implants or depot medicaments in single unit and multiple unit formulations often consist of so called biodegradable polymers like e.g. polyesters of lactic acid and glycolic acid, polyether urethanes, polyamino acids, poly(meth)acrylates or polysaccharides.

Adjuvants and carriers added during the production of the pharmaceutical compositions of the present invention formulated as parenterals are particularly aqua sterilisata (sterilized water), pH value influencing substances like, e.g. organic or inorganic acids or bases as well as salts thereof, buffering substances for adjusting pH values, substances for isotonization like e.g. sodium chloride, sodium hydrogen carbonate, glucose and fructose, tensides and surfactants, respectively, and emulsifiers like, e.g. partial esters of fatty acids of polyoxyethylene sorbitans (for example, Tween®) or, e.g. fatty acid esters of polyoxyethylenes (for example, Cremophor®), fatty oils like, e.g. peanut oil, soybean oil or castor oil, synthetic esters of fatty acids like, e.g. ethyl oleate, isopropyl myristate and neutral oil (for example, Miglyol®) as well as polymeric adjuvants like, e.g. gelatine, dextran, polyvinylpyrrolidone, additives which increase the solubility of organic solvents like, e.g. propylene glycol, ethanol, N,N-dimethylacetamide, propylene glycol or complex forming substances like, e.g. citrate and urea, preservatives like, e.g. benzoic acid hydroxypropyl ester and methyl ester, benzyl alcohol, antioxidants like e.g. sodium sulfite and stabilizers like e.g. EDTA.

When formulating the pharmaceutical compositions of the present invention as suspensions in a preferred embodiment thickening agents to prevent the setting of the target-binding moiety toxin conjugates of the invention or, tensides and polyelectrolytes to assure the resuspendability of sediments and/or complex forming agents like, for example, EDTA are added. It is also possible to achieve complexes of the active ingredient with various polymers. Examples of such polymers are polyethylene glycol, polystyrene, carboxymethyl cellulose, Pluronics® or polyethylene glycol sorbit fatty acid ester. The target-binding moiety toxin conjugates of the invention can also be incorporated in liquid formulations in the form of inclusion compounds e.g. with cyclodextrins. In particular embodiments dispersing agents can be added as further adjuvants. For the production of lyophilisates scaffolding agents like mannite, dextran, saccharose, human albumin, lactose, PVP or varieties of gelatine can be used.

EXAMPLES

In the following, the invention is explained in more detail by non-limiting examples:

A. Background to Small Molecule Drug Conjugates (SMDCs)

1. Review of Published Information Relating to SMDCs

In order to study the prior art related to SMDCs, the known approaches for addressing the following small molecule targets were studied:

Folate receptor α (FR α)
Cholecystokinin type 2 receptor (CCKBR)
Carbonic anhydrase IX (CAIX)
Integrin
Gondotropin releasing recetor (GnRH)
Prostate Specific Membrane Antigen (PSMA)
Somatostatin Receptor 2 (SSTR2)
Human Epidermal Growth Factor Receptor 2 (HER2)
Bombesin receptor
Gondotropin releasing receptor (GnRH)

In each case data relating to selectivity S ($S=IC_{50\ (receptor\ negative\ cells)}/IC_{50\ (receptor\ positive\ cells)}$) and the targeting index TI ($TI=IC_{50\ (free\ toxin)}/IC_{50\ (conjugate)}$ on receptor positive cell line) were identified. In case where different prior art documents could be found for a given target, the reference with the highest targeting index was chosen. The results of these analyses are summarized in Tables 1 to 5.

In summary, the best described binders with most potent selectivity factors are folic acid and DUPA. However, in many cases, $IC_{50}$ values for receptor negative cell lines are not reported, and the targeting index values for the mainly used toxins (DM1, MMAE, vinblastine, tubulysin, paclitaxel, docetaxel) are rather low.

TABLE 1

Summary of reviewed folate recetor targeted conjugates

| Homing moiety (compound code) | S | TI | Linker | Toxin | Reference |
|---|---|---|---|---|---|
| Folic acid (E072) | >200 | Not available | Disulfide | Mitomycin C | Leamon et al. Synthesis and Biological Evaluation of EC72: A New Folate-Targeted Chemotherapeutic, Bioconjugate Chem., Vol. 16, No. 4, 2005 p.803-811 |
| Folic acid | >100 | 0.5 | Disulfide | Maytansinoid | Ladino et al., Folate-maytansinoids:target-selective drugs of low molecular weight. Int J Cancer. 1997 Dec 10;73(6):859-64. |
| Folic acid | 813 (for KB cells) | 1 | β-galactosidase cleavable self-immolative | MMAE | Papot S. et al., Angew. Int. Ed. Chem. 2012;51:1-6 |
| Folic acid (EC305) | >100 | 0.5 | Disulfide | Tubulisin | Leamon et al., Folate Targeting Enables Durable and Specific Antitumor Responsesfrom a Therapeutically Null Tubulysin B Analogue., Cancer Res 2008; 68: (23).December 1, 2008 |
| Folic acid (EC140) | >90 | 2.19 | Acyl-hydrazone linker | Desacetylvinblastine monohydrazide (DAVLBH) | 1) Leamon et al. Synthesis and Biological Evaluation of EC140: A Novel Folate-Targeted Vinca Alkaloid Conjugate, Bioconjugate Chem. 2006, 17, 1226-1232 2) Leamon et al. Folate-Vinca Alkaloid Conjugates for Cancer Therapy: A Structure-Activity Relationship, Bioconjugate Chem. 2014, 25, 560-568 |
| Folic acid (EC145) | >111 | 2.6 | Disulfide | Desacetylvinblastine monohydrazide (DAVLBH) | 1) Leamon et al. Comparative preclinical activity of the folate-targeted Vinca alkaloid conjugates EC140 and EC145, Int. J. Cancer: 121, 1585-1592 (2007) 2) Leamon et al. Folate-Vinca Alkaloid Conjugates for Cancer Therapy: A Structure-Activity Relationship, Bioconjugate Chem. 2014, 25, 560-568 |

TABLE 2

| Summary of reviewed CCK2R targeted conjugates | | | | | |
|---|---|---|---|---|---|
| Homing moiety (compound code) | S | TI | Linker | Toxin | Reference |
| Non peptidic CCK receptor ligand | — | 0.31 | Hydrazide | Vinblastin | 1) Low P. S. et al Mol. Pharm. 2015; 12:2477-2483. 2) WO2013126797A1 |
| | — | 1.35 | Hydrazide | Tubulysin | 1) Low P. S. et al Mol. Pharm. 2015; 1 2:2477-2483. 2) WO2013126797A1 |

TABLE 3

| Summary of reviewed CAIX targeted conjugates | | | | | |
|---|---|---|---|---|---|
| Homing moiety (compound code) | S | TI | Linker | Toxin | Reference |
| Acetazolamide based ligand | — | 0.33 | Val-arg cleavable self immolative | MMAE | Cazzamalli et al., Linker stability influences the anti-tumor activity of acetazolamide-drug conjugates for the therapy of renal cell carcinoma, J Control Release. 2017 Jan. 28; 246:39-45. |
| | — | 2.62 | Disulfide | Ducarmycin derivative | Krall et al., A Small-Molecule Drug Conjugate for the Treatment of CarbonicAnhydrase IX Expressing Tumors, Angew. Chem. Int. Ed. 2014, 53, 1-6. |
| | — | 0.105 | Disulfide | DM1 | |

TABLE 4

| Summary of reviewed integrin targeted conjugates | | | | | | |
|---|---|---|---|---|---|---|
| Homing moiety (compound code) | S | S | TI | Linker | Toxin | Reference |
| Integrin $\alpha_v$ | RGD-C4 | — | 0.008 | stable | Doxorubicin | Kim J. W. Et al. J Mol Med. 2004; 14(4): 529-535 |
| Integrin $\alpha_v$ | RGD-C4 | — | 0.6 | plasmin-cleavable amide bond | Doxorubicin | de Groot F. M. H. Mol. Cancer Ther. 2002; 1: 901-911. |
| Integrin $\alpha_v\beta_3$ | RGD-C4 (acyclic) | — | 1 | plasmin-cleavable tether | Doxorubicin | Burkhart D. J. et al. Mol Cancer Ther, 2004; 3(12): 1593-1604 |
| Integrin $\alpha_v\beta_3$ | cyclo-RGD | — | 1.37 | Legumain cleavable | Paclitaxel | Pilkington-Miksa M. Bioconjug. Chem. 2012; 23(8): 1610-1622. |
| Integrin $\alpha_v\beta_3$ | Dimeric c[RGDyK] | — | 0.254 | stable | Paclitaxel | Chen X. et al. J Med Chem 2005; 48(4): 1098-106. |
| Integrin $\alpha_v\beta_3$ | Dimeric c[RGDfK] | — | 1 | stable | Paclitaxel | Ryppa C. Int. J. Pharm. 2009; 368(1-2): 89-97. |
| Integrin $\alpha_v\beta_3$ | c[DKP-RGD] | 66.9 | 0.273 | Val-Ala cleavable | Paclitaxel | Gennari C. Chem. Eur. J. 2015; 21(18): 6921-6929 |

TABLE 5

| Summary of reviewed DUPA conjugates | | | | | |
|---|---|---|---|---|---|
| Homing moiety (compound code) | S | TI | Linker | Toxin | Reference |
| DUPA | — | <<0.044 | Glutaric acid linker | Doxorubicin | Kozikowski et al. Chem. Med. Chem. 2006, 1:299-302. |
| DUPA | — | 1.23 | Disulfide | Tubulisin hydrazide | Low P.S. et al. Mol. Pharm. 2009, 6(3): 780-789. |
| Glu-CO-Lys (DUPA analogue) (EC1169) | — | 0.28 | Disulfide | Tubulisin hydrazide | Endocyte Inc. WO2014/078484 A1. |
| DUPA | — | 0.175 | Disulfide | Indotecan | 1) Cushman et al. J. Med. Chem. 2015, 58:3094-3103. 2) WO2015069766 Al. |
| Multimeric DUPA (ca. 8 DUPA/conjugate) | — | 1.38 | Cathepsin B cleavable | Docetaxel | Kopecek J. et al. Drug Target 2013, 21(10):968-980. |
| DUPA | — | 0.74 | Cathepsin B cleavable | TubH-vinca alkaloid | Kularatne et al. J. Med. Chem. 2010, 53(21):7767-7777 |

TABLE 6

| Summary of additional SMDCs | | | | | |
|---|---|---|---|---|---|
| Homing moiety (compound code) | S | TI | Linker | Toxin | Reference |
| Somatostatin Receptor 2 (SSTR2) | | | | | Zhang et al., A Novel Octreotide Modified Lipid Vesicle Improved the Anticancer Efficacy of Doxorubicin in Somatostatin Receptor 2 Positive Tumor Models, Molecular Pharmaceutics VOL. 7, NO. 4, 1159-1168 |
| Gonadotropin-releasing hormone III receptor (GnRHR) | | | | | Szabo I et al., Development of an oxime bond containing daunorubicin-gonadotropin-releasing hormone-III conjugate as a potential anticancer drug, Bioconjug Chem. 2009 Apr; 20(4): 656-65. doi: 10.1021/bc800542u |
| Human epidermal Growth Factro Receptor 2 (HER2) | | | | | Guillemard V et al., HER2-Mediated Internalization of a Targeted Prodrug Cytotoxic Conjugate Is Dependent on the Valency of the Targeting Ligand, DNA AND CELL BIOLOGY Volume 24, Number 6, 2005 |
| Bombesin receptor | | | | | Yang et al. Bombesin Analogue-Mediated Delivery Preferentially Enhances the Cytotoxicity of a Mitochondria-Disrupting Peptide in Tumor Cells., PLOS ONE February 2013; Volume 8; Issue 2 |

2. Generation of Additional Small Molecule-Amatoxin Conjugates

In order to complement the data obtained in the study of the prior art related to SMDCs shown in Example A.1 above, a number of amanitin-based SMDCs were generated. Table 7 shows the results for these constructs.

TABLE 7

| Summary of results obtained with amanitin-based SMDCs | | | | | |
|---|---|---|---|---|---|
| Target | Homing moiety | S | TI | Linker | Toxin |
| Integrin $\alpha_v\beta_3$ | cyclo-RGD | 1.02<br>2.3 | 0.53<br>0.2 | Cleavable<br>stable | α-amanitin |

TABLE 7-continued

| Summary of results obtained with amanitin-based SMDCs | | | | | |
|---|---|---|---|---|---|
| Target | Homing moiety | S | TI | Linker | Toxin |
| Integrin $\alpha_v\beta3$ | RGDfK | —<br>— | 2<br>0.14 | Cleavable<br>stable | |
| GnRH III | GnRH III recognizing peptide | Not available | 0.6<br>0.012 | Cleavable<br>stable | α-amanitin |

B. Synthesis of DUPA-Amatoxin Conjugates

Example 1

(S)-di-tert-butyl 2-(3-((S)-6-amino-1-(tert-butoxy)-1-oxohexan yl)ureido)pentanedioate (HDP 30.1570)

Step 1: (9S,13S)-tri-tert-butyl 3,11-dioxo-1-phenyl-2-oxa-4,10,12-triazapentadecane 9,13,15-tricarboxylate (HDP 30.1567)

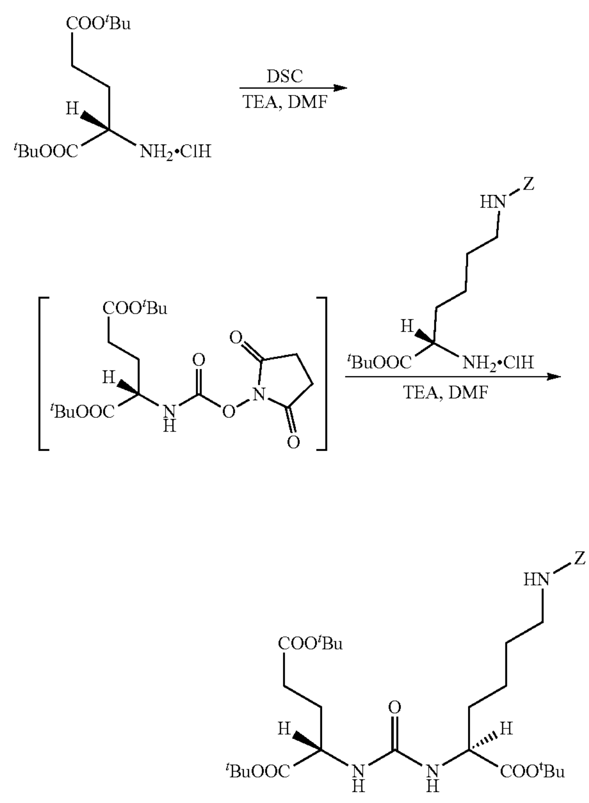

HDP 30.1567

To a solution of disuccinimidyl carbonate (DSC) (1 g, 3.90 mmol) in N,N-dimethylformamide (DMF; 20 ml) α,γ-di-tert-butyl L-glutamate (1.16 g, 3.90 mmol) was added in portions at 0° C. After 50 minutes, triethylamine (TEA; 541 μl, 3.90 mmol) was added. After complete conversion, α-tert-butyl-γ-carboxybenzyl L-lysine (1.46 g, 3.90 mmol) and TEA (1.08 ml, 7.8 mmol) were added at 0° C. The reaction mixture was stirred overnight at room temperature. DMF was removed and the residue taken up with methyl tert-butylether (MTBE; 50 ml). The organic layer was washed with a 15% citric acid solution (2×50 ml), water (2×50 ml), a saturated sodium hydrogen carbonate ($NaHCO_3$) solution (2×50 ml) and water (30 ml) in sequence. The organic layer was dried over magnesium ($MgSO_4$), filtered and concentrated. The resulting yellowish oil was purified by flash chromatography (0-60% gradient of MTBE in hexane) to provide the urea HDP 30.1567 as syrup (2.34 g, 97%).

Step 2: (S)-di-cert-butyl 2-(3-((S)-6-amino-1-(tert-butoxy)-1-oxohexan-yl)ureido)penanedioate (HDP 30.1570)

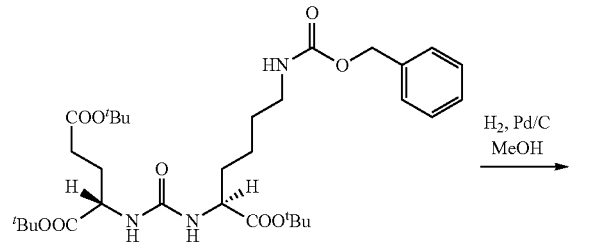

HDP 30.1567

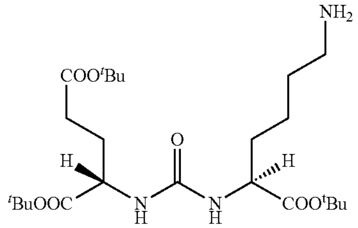

HDP 30.1570

HDP 30.1567 (2.32 g, 3.73 mmol) was hydrogenated at room temperature in MeOH (50 ml) and in presence of Pd—C for 2 h. The mixture was then filtered and washed with MeOH. The solution was concentrated under reduced pressure. The colorless oil was dissolved in tert-butanol ($^{t}$BuOH) (50 ml, pH=8), and 1 M HCl (3.44 ml, 3.44 mmol) was added dropwise. The product was lyophilized overnight to yield HDP 30.1570 as colorless solid (1.84 g, 94%).

MS (ESI+): m/z found: 488.40 calc.: 488.33 $[M+H]^+$; found: 975.36 calc.: 975.66 $[2M+H]^+$; found: 432.29 calc: 432.27 $[MH-CH_2{=}C(CH_3)_2]$+; found: 376.26 calc: 376.21 $[MH-2{\times}CH_2{=}C(CH_3)_2]^{+}$. $^1$H NMR (500 MHz, $CDCl_3$): δ=8.17 (t, J=5.9 Hz, 3H), 6.30 (d, J=7.9 Hz, 1H), 6.11 (d, J=8.3 Hz, 1H), 4.36 (td, J=8.1, 4.7 Hz, 1H), 4.28 (td, J=7.2, 4.3 Hz, 1H), 3.11 (dt, J=11.4, 5.9 Hz, 2H), 2.35 (ddd, J=15.8, 11.8, 6.3 Hz, 2H), 1.95-1.68 (m, 4H), 1.62-1.51 (m, 2H), 1.45 (s, 18H), 1.43 (s, 9H). $^{13}$C NMR (126 MHz, $CDCl_3$): δ=173.42, 172.64, 172.37, 157.54, 82.13, 81.52, 80.47, 53.34, 52.80, 39.42, 31.72, 31.18, 28.30, 28.06, 28.02 (2×), 26.72, 21.81.

Step 3: (S)-di-tert-butyl 2-(3-((S)-1-(tert-butoxy)-6-((((2,5-dioxopyrrolidin yl)oxy)carbonyl)amino)-1-oxohexan-2-yl)ureido)pentanedioate (HDP 30.1579)

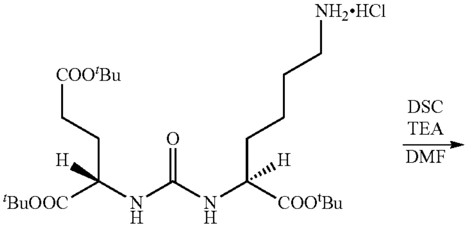

HDP 30.1570

-continued

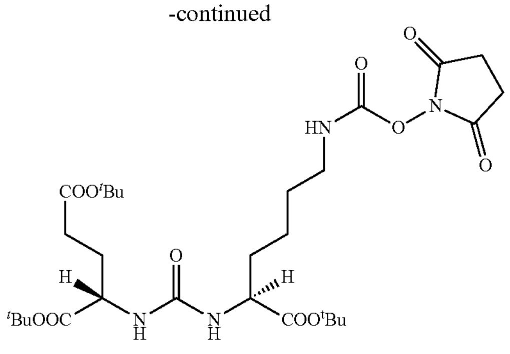

HDP 30.1579

To a solution of DSC (256 mg, 1 mmol) in DMF (10 ml) a solution of HDP 30.1570 (524 mg, 1 mmol) in DMF (10 ml) and TEA (139 μl, 1 mmol) was added dropwise over 10 minutes at 0° C. Reaction mixture was stirred at 0° C. for 1 h. After stirring for 3 h at room temperature, reaction mixture was evaporated under high vacuum. The crude product was purified by flash chromatography (0-50% gradient of acetone in hexane). The pure fractions were combined, evaporated and lyophilized overnight from 1,4-dioxane affording the product as colorless powder (544 mg, 86%).

MS (ESI+): m/z found: 629.26 calc.: 629.34 $[M+H]^+$.

$^1H$ NMR (500 MHz, $CDCl_3$): δ=6.54 (dd, J=6.8, 4.8 Hz, 1H), 5.53 (d, J=8.0 Hz, 1H), 5.43 (d, J=8.3 Hz, 1H), 4:39-4.31 (m, 1H), 4.29 (dt, J=8.3, 4.2 Hz, 1H), 3.27-3.36 (m, 1H), 3.18-3.25 (m, 1H), 2.85 (s, 4H), 2.30 (qdd, J=16.2, 9.5, 6.1 Hz, 2H), 2.04 (ddd, J=14.2, 9.5, 6.3, 4.7 Hz, 1H), 1.86-1.76 (m, 3H), 1.71-1.50 (m, 2H), 1.49-1.32 (m, 29H). $^{13}C$ NMR (126 MHz, $CDCl_3$): δ=172.87, 172.44, 172.36, 170.45, 157.27, 151.84, 81.98, 81.45, 80.45, 53.21, 52.90, 41.35, 31.74, 28.38, 28.05, 27.99, 27.93 2×, 25.50, 21.57.

Example 2

(S)-5-(tert-butoxy)-4-(3-((S)-1,5-di-tert-butoxy-1,5-dioxopentan-2-yl)ureido)-5-oxopentanoic acid (HDP 30.2178)

Step 1: (S)-5-benzyl 1-tert-butyl 2-(3-((S)-1,5-di-tert-butoxy-1,5-dioxopentan yl)ureido)pentanedioate (HDP 30.2175)

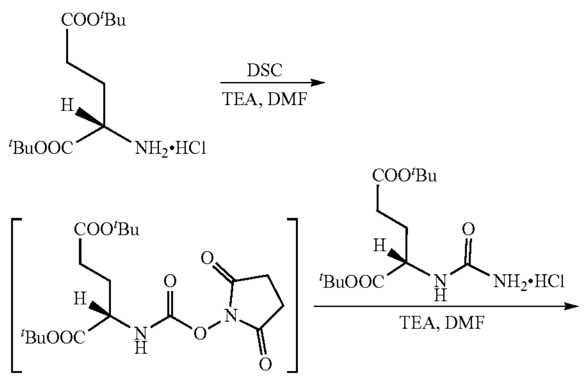

-continued

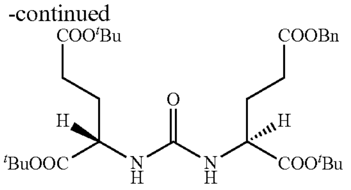

HDP 30.2175

To a solution of DSC (1.73 g, 6.76 mmol) in DMF; 31.6 ml) α,γ-di-tert-butyl L-glutamate (2 g, 6.76 mmol) was added in portions at 0° C. After 50 minutes, TEA (937 μl, 6.76 mmol) was added. After complete conversion, α-tert-butyl-γ-benzyl L-glutamate (2.23 g, 6.76 mmol) and TEA (1.87 ml, 13.52 mmol) were added at 0° C. The reaction mixture was stirred overnight at room temperature. DMF was removed in vacuo and the residue was dissolved in MTBE (100 ml). The organic layer was washed with 15% citric acid solution (2×100 ml), water (2×100 ml), saturated $NaHCO_3$ solution (2×100 ml) and water (80 ml) in sequence. The organic layer was dried over $MgSO_4$, filtered and concentrated. The resulting yellowish oil was purified by chromatography on silica gel column (0-33% gradient of ethyl acetate (EtOAc) in hexane) to provide the urea HDP 30.2175 as colorless syrup (3.02 g, 77%).

MS (ESI+): m/z found: 579.17 calc.: 579.72 $[M+H]^+$; found: 601.35 calc.: 601.70 $[M+Na]^+$; found: 1180.35 calc.: 1180.41 $[2M+Na]^+$.

Step 2: (S)-5-(tert-butoxy)-4-(3-((S)-1,5-di-tert-butoxy-1,5-dioxopentan-2-yl)ureido)-5-oxopentanoic acid (HDP 30.2178)

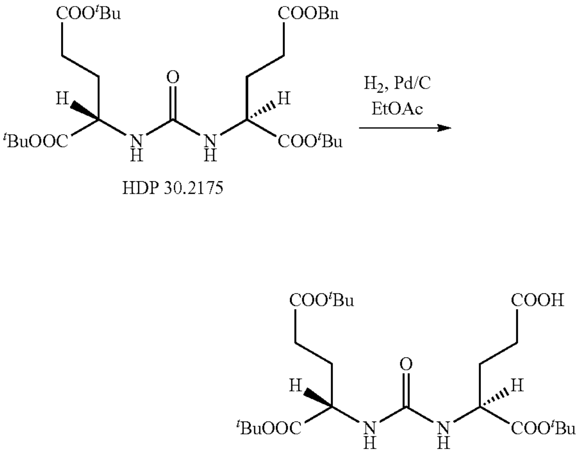

HDP 30.2175

HDP 30.2178

HDP 30.2175 (3.02 g, 5.21 mmol) was hydrogenated at room temperature in ethyl acetate (EtOAc; 27.3 ml) and in presence of Pd—C overnight. The mixture was then filtered and washed with EtOAc. The filtrate was concentrated under reduced pressure to provide the DUPA precursor HDP 30.2178 as clear colorless syrup (2.45 g, 96%).

MS (ESI+): m/z found: 489.20 calc.: 489.59 $[M+H]^+$; found: 978.22 calc.: 978.16 $[2M+Na]^+$.

Example 3

DUPA-Aoc-Phe-Phe-Cys Reagent (HDP 30.2225)

Step 1: ($^{t}$BUO)$_2$DUPA$^{OtBu}$-Aoc-Phe-Phe-Cys$^{Trt}$ Reagent (HDP 30.2185)

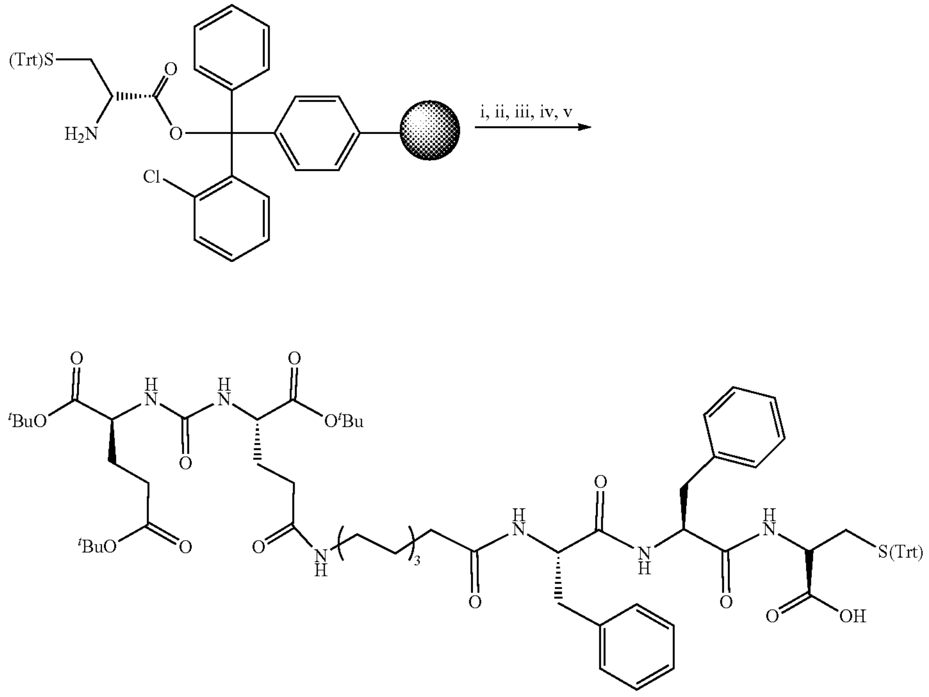

HDP 30.2185

Reagents and conditions. i) a-Fmoc-Phe-OH, 1-hydroxybenzotriazole (HOBt), (2-(1H-benzotriazol-1-yl)-1,1,3,3-tetramethyluronium hexafluorophosphate (H BTU), N,N-diisopropylethylamine (DI PEA), DMF, 60° C., 40 W, 10 min; b) 20% piperidine/DMF, 60° C., 40 W, 3 min; ii) a-Fmoc-Phe-OH, HOBt, HBTU, DIPEA, DMF, 60° C., 40 W, 10 min; b) 20% piperidine/DMF, 60° C., 40 W, 3 min; iii) a-Fmoc-Aoc-OH, HOBt, HBTU, DIPEA, DMF, 60° C., 40 W, 10 min; b-20% piperidine/DMF, 60° C., 40 W, 3 min; iv) HDP 30.2178, HOBt, HBTU, DIPEA, DMF, 60° C., 40 W, 10 min; v) TFE/AcOH/DCM (1:1:8), 23° C., 1 h 30 min.

DUPA-peptide precursor HDP 30.2185 was prepared by microwave-assisted Fmoc-solid phase peptide synthesis starting from H-Cys(Trt)-(2-ClTrt) resin (391 mg, 0.25 mmol) in the conditions described above. The resin-bound peptide was cleaved from the resin by washing with a trifluoroethanol(TFE)/acetic acid(AcOH)/dichloromethane (DCM) (1:1:8) mixture (10 ml, 2 h 30 min). The resin was then washed with fresh TFE/AcOH/DCM (1:1:8) mixture (10 ml, 2 min), DCM (10 ml, 2 min) and MeOH (10 ml, 2 min) in sequence. The filtrates were collected and concentrated in vacuo to afford 214 mg of product (68%).

MS (ESI+): m/z found: 1292.5 calc.: 1292.60 $[M+Na]^+$.

Step 2: DUPA-Aoc-Phe-Phe-Cys Reagent (HDP 30.2225)

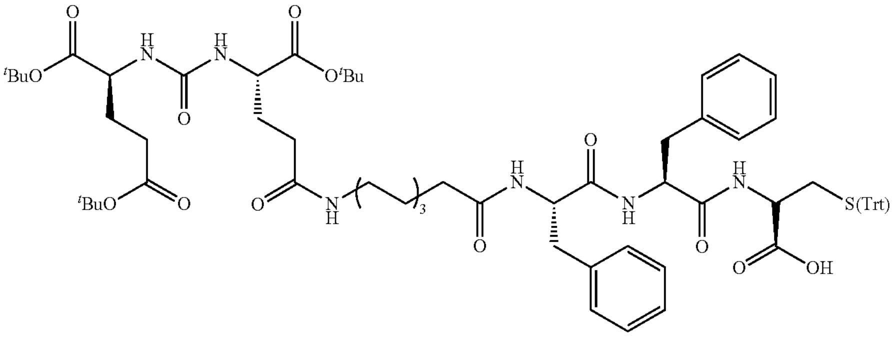

-continued

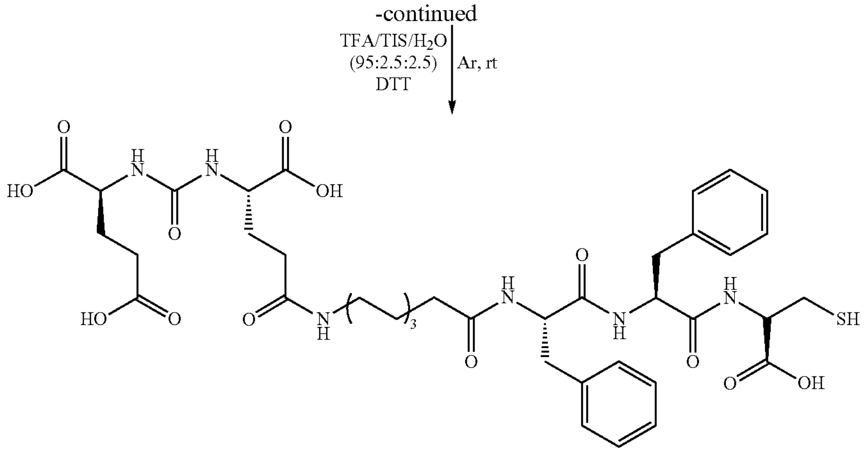

HDP 30.2225
DUPA-Aoc-Phe-Phe-Cys
Aoc = 8-aminocaprylic acid

HDP 30.2185 (109 mg, 85.6 μmol) was treated with a trifluoroacetic acid (TFA)/triisopropylsilane(TIS)/$H_2O$ (95:5:5) cocktail (8 ml) and 1,4-dithiothreitol (DTT) (362 mg) and stirred at room temperature under argon for 1 h and 30 min. Mixture was co-evaporated with toluene (2×8 ml). Addition of cold MTBE (40 ml) caused precipitation of a solid. The precipitate was isolated by centrifugation at 0° C., collected and washed with additional cold MTBE (40 ml), centrifuged at 0° C. and collected. Pellet was dissolved in acetonitrile (ACN)/$H_2O$ (1:1, v:v, 2 ml) and purified in portions by preparative revers-phase high-performance liquid chromatography (RP-HPLC) on a C18 column [λ=210 nm; gradient: 0 min 5% B; 15-18 min 100% B; 18.50-22 min 5% B; A=water with 0.05% TFA, B=acetonitrile]. Tubes containing the target compound were combined, evaporated and lyophilized overnight in tBuOH/$H_2O$ (4:1, v:v, 5 ml) to afford the reagent HDP 30.2225 as white powder (122.9 mg, 85%).

MS (ESI+): m/z found: 859.33 calc.: 859.98 $[M+H]^+$; found: 881.33 calc.: 881.96 $[M+Na]^+$.

Example 4

DUPA-Aoc-Phe-Phe-OSu (HDP 30.2401)

Step 1:$(Bu^tO)_2DUPA^{OtBu}$-Aoc-Phe-Phe-OH Reagent (HDP 30.2393)

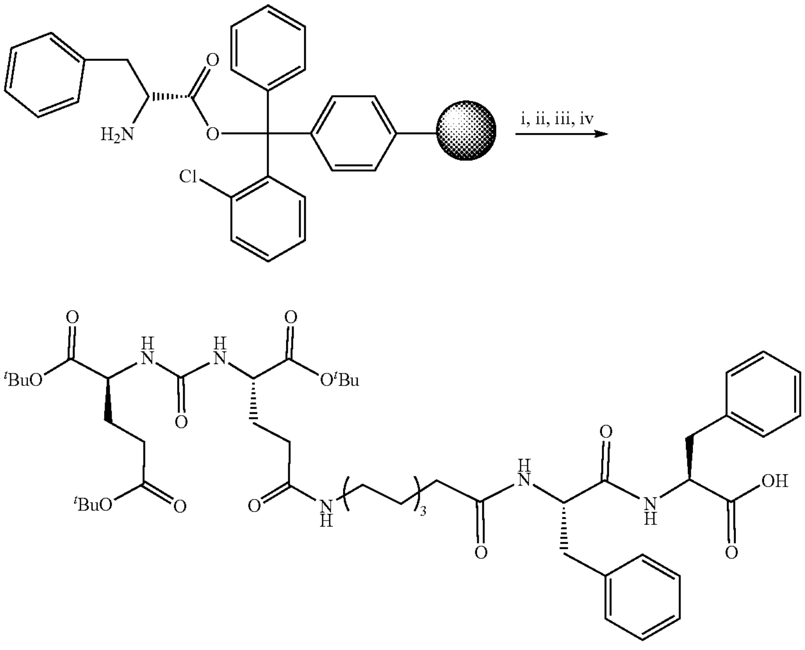

HDP 30.2393
DUPA-Aoc-Phe-Phe

Reagents and conditions. i) a-Fmoc-Phe-OH, HOBt, HBTU, DIPEA, DMF, 60° C., 40 W, 10 min; b) 20% piperidine/DMF, 60° C., 40 W, 3 min; ii) a-Fmoc-Aoc-OH, HOBt, HBTU, DIPEA, DMF, 60° C., 40 W, 10 min; b-20% piperidine/DMF, 60° C., 40 W, 3 min; iii) HDP 30.2178, HOBt, HBTU, DIPEA, DMF, 60° C., 40 W, 10 min; iv) TFE/AcOH/DCM (1:1:8), 23° C., 1 h 30 min.

DUPA-peptide precursor HDP 30.2393 was prepared by microwave-assisted Fmoc-solid phase peptide synthesis starting from H-Phe-(2-ClTrt) resin (417 mg, 0.25 mmol) in the conditions described above. The resin-bound peptide was cleaved from the resin by washing with a TFE/AcOH/DCM (1:1:8) mixture (10 ml, 2 h 30 min). The resin was then washed with fresh TFE/AcOH/DCM (1:1:8) mixture (10 ml, 2 min), DCM (10 ml, 2 min) and MeOH (10 ml, 2 min) in sequence. The filtrates were collected and concentrated in vacuo to afford 131.15 mg of product (57%).

MS (ESI+): m/z found: 924.50 calc.: 924.18 $[M+H]^+$; found: 946.58 calc.: 946.16 $[M+Na]^+$.

Step 2: $(Bu^tO)_2DUPA^{OtBu}$-Aoc-Phe-Phe-OSu Reagent (HDP 30.2401)

HDP 30.2393 (131.01 mg, 0.15 mmol) was dissolved in tetrahydrofuran (THF; 2.5 ml) at room temperature under argon. Dicyclohexylcarbodiimide (DCC; 52.61 mg, 0.26 mmol) and N-hydroxysuccinimide (HOSu; 29.34 mg, 0.26 mmol) dissolved in THF (200 μl each) were added sequentially.

Reaction mixture was stirred at room temperature under argon for 18 hours. DCC was filtered off and washed with a small amount of THF. The solvent was evaporated and the residue redissolved in ACN/MeOH with 0.05% TFA (5:1, 6 ml) and transferred into a 15 ml centrifuge tube, cooled to 0° C. and centrifuged (4500 rpm, 3 min). Solid residue was discarded and supernatant collected, evaporated under reduced pressure and lyophilized in $^t$BuOH with 0.05% TFA (5 ml) overnight to afford 147.77 mg (97%) of HDP 30.2401 as white powder.

MS(ESI+): m/z found: 1021.80, calc.: 1022.24 $[M+H]^+$.

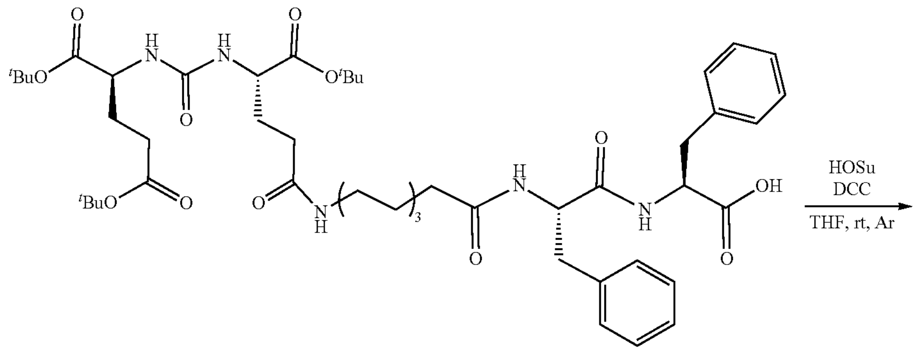

HDP 30.2393

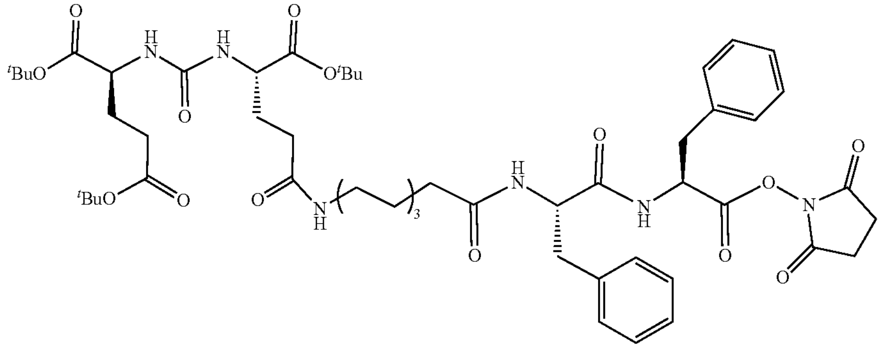

HDP 30.2401

Example 5

DUPA-Aoc-Phe-Phe-(His-Glu)$_2$-Cys Reagent (HDP 30.2579)

Step 1: ($^t$BuO)$_2$DUPA$^{OtBu}$-Aoc-Phe-Phe-(His$^{Trt}$-Glu$^{OtBu}$)$_2$-Cys$^{Trt}$ Reagent (HDP 30.2557)

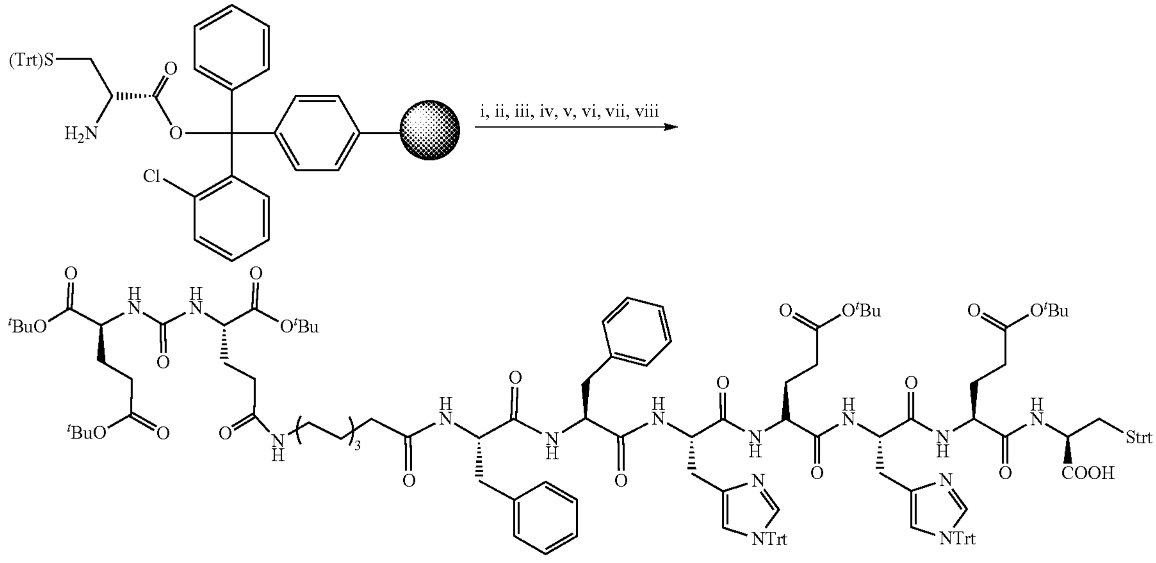

HDP 30.2557

Reagents and conditions. i) a-Fmoc-Glu(O$^t$Bu)-OH, HOBt, HBTU, DIPEA, DMF, 60° C., 40 W, 10 min; b) 20% piperidine/DMF, 60° C., 40 W, 3 min; ii) a-Fmoc-His(Trt)-OH, HOBt, HBTU, DIPEA, DMF, 60° C., 40 W, 10 min; b) 20% piperidine/DMF, 60° C., 40 W, 3 min; iii) a-Fmoc-Glu (O$^t$Bu)-OH, HOBt, HBTU, DIPEA, DMF, 60° C., 40 W, 10 min; b) 20% piperidine/DMF, 60° C., 40 W, 3 min; iv) a-Fmoc-His(Trt)-OH, HOBt, HBTU, DIPEA, DMF, 60° C., 40 W, 10 min; b) 20% piperidine/DMF, 60° C., 40 W, 3 min; v) a-Fmoc-Phe-OH, HOBt, HBTU, DIPEA, DMF, 60° C., 40 W, 10 min; b) 20% piperidine/DMF, 60° C., 40 W, 3 min; vi) a-Fmoc-Phe-OH, HOBt, HBTU, DIPEA, DMF, 60° C., 40 W, 10 min; b) 20% piperidine/DMF, 60° C., 40 W, 3 min; vii) a-Fmoc-Aoc-OH, HOBt, HBTU, DIPEA, DMF, 60° C., 40 W, 10 min; b-20% piperidine/DMF, 60° C., 40 W, 3 min; viii) HDP 30.2178, HOBt, HBTU, DIPEA, DMF, 60° C., 40 W, 10 min; ix) TFE/AcOH/DCM (1:1:8), 23° C., 1 h 30 min.

DUPA-peptide precursor HDP 30.2557 was prepared by microwave-assisted Fmoc-solid phase peptide synthesis starting from H-Cys-(2-ClTrt) resin (391 mg, 0.25 mmol) in the conditions described above. The resin-bound peptide was cleaved from the resin by washing with a trifluoroethanol(TFE)/acetic acid(AcOH)/dichloromethane(DCM) (1:1:8) mixture (10 ml, 2 h 30 min). The resin was then washed with fresh TFE/AcOH/DCM (1:1:8) mixture (10 ml, 2 min), DCM (10 ml, 2 min) and MeOH (10 ml, 2 min) in sequence. The filtrates were collected and concentrated in vacuo to afford 284 mg of product (47%).

MS (ESI−): m/z found: 2397.50 calc.: 2397.99 [M−H]$^-$.

Step 2: DUPA-Aoc-Phe-Phe-(His-Glu)$_2$-Cys Reagent (HDP 30.2579)

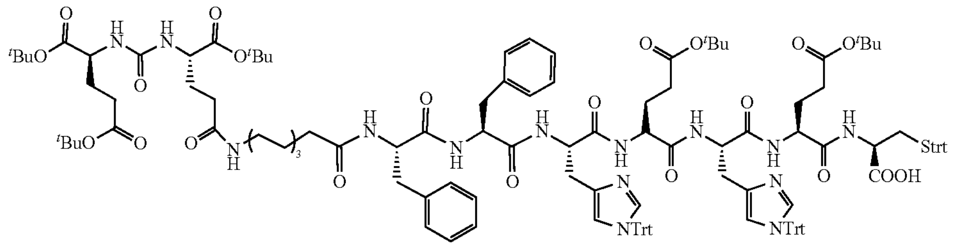

HDP 30.2557

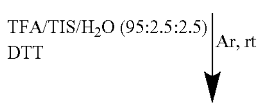

-continued

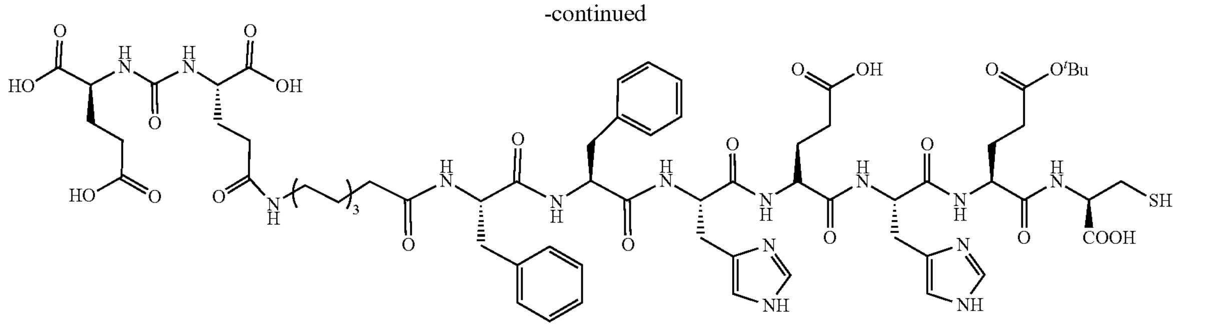

HDP 30.2579
DUPA-Aoc-Phe-Phe-(His-Glu)2-Cys

HDP 30.2557 (284 mg, 0.118 mmol) was treated with a TFA/TIS/$H_2O$ (95:2.5:2.5) cocktail (6 ml) and DTT (150 mg) and stirred at room temperature under argon for 1 h and 30 min. Mixture was co-evaporated with toluene (2×6 ml). Addition of cold MTBE (40 ml) caused precipitation of a solid. The precipitate was isolated by centrifugation at 0° C., collected and washed with additional cold MTBE (40 ml), centrifuged at 0° C. and collected. Pellet was dissolved in ACN/$H_2O$ (9:1, v:v, 1.5 ml) and purified in portions by preparative RP-HPLC on a C18 column [λ=246 nm; gradient: 0 min 5% B; 15-18 min 100% B; 18.50-22 min 5% B; A=water with 0.05% TFA, B=acetonitrile]. Fractions containing the product were combined, evaporated and lyophilized in tBuOH/$H_2O$ (4:1, v:v, 5 ml) overnight to afford the DUPA-peptide reagent HDP 30.2579 as white solid (115.38 mg, 70%).

MS (ESI+): m/z found: 1391.50 calc.: 1391.50 $[M+H]^+$; found: 696.42 calc.: 696.76 $[M+Na]^{2+}$.

Example 6

1,1,1-triphenyl-5,8,11-trioxa-2-thiatridecan-13-amine (HDP 30.2383)

Step 1: 1-bromo-2-(2-(2-(2-bromoethoxy)ethoxy)ethoxy)ethane (HDP 30.0381)

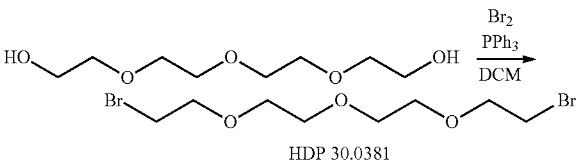

HDP 30.0381

Triphenylphosphine ($Ph_3P$; 0.5 g, 230.8 mmol) was dissolved in dry DCM (190 ml) and mixture was cooled to 0° C. Bromine (11.8 ml, 230.8 mmol) was added dropwise. After 5 minutes, tetraethylene glycol (20.0 ml, 115.4 mmol) dissolved in DCM (11.8 ml) was added dropwise and reaction mixture was thawed to room temperature and stirred for 74 hours. Reaction mixture was cooled to 0° C. and diluted with a saturated $NaHCO_3$ solution (400 ml) to pH 7. A 10% sodium thiosulfate ($Na_2S_2O_3$) solution (20 ml) was added and phases were separated. Organic phase was washed with a saturated sodium chloride (NaCl) solution (100 ml), dried over $MgSO_4$ and evaporated under reduced pressure. The residue was taken up with n-hexane (400 ml) and shaked for 30 minutes. Crystals were filtered off, taken up with n-hexane (2×50 ml), sonicated and filtered off.

The filtrates were collected, evaporated and distilled (140° C., 0.0062 mbar) to achieve 34.70 g (94%) of HDP 30.0381 as colorless oil.

Step 2: 1-azido-2-(2-(2-(2-bromoethoxy)ethoxy)ethoxy)ethane (HDP 30.0388)

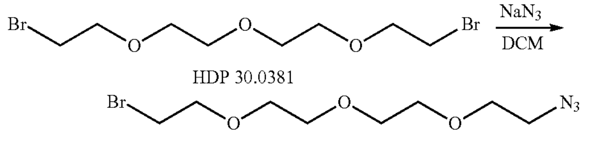

HDP 30.0388

HDP 30.0381 (4.8 g, 15.0 mmol) was dissolved in absolute DMF (30 ml). $NaN_3$ (975 mg, 15.0 mmol) was added and the reaction mixture was stirred at room temperature under argon for 21 hours and used directly in step 3.

Step 3: 13-azido-1,1,1-triphenyl-5,8,11-trioxa-2-thiatridecane (HDP 30.2382)

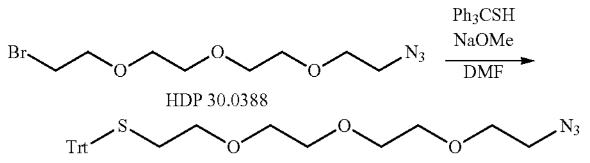

HDP 30.2382

Triphenylmethanethiol (4.17 g, 15.0 mmol) was dissolved in DMF (30 ml) and cooled to 0° C. Sodium methanolate (NaOMe; 2.78 ml, 15.0 mmol, 30% solution in MeOH) was added. After 2 minutes, the reaction mixture HDP 30.0388 was added and reaction was thawed to room temperature and stirred for 1 hour and 30 minutes. DMF was evaporated and residue was taken up with EtOAc (100 ml) and washed with a saturated ammonium chloride ($NH_4Cl$) solution (100 ml), a saturated $NaHCO_3$ solution (100 ml), $H_2O$ (100 ml) and a saturated NaCl solution (100 ml) in sequence. Organic phase was dried over $MgSO_4$ and evaporated. The crude product was purified on silica gel column (330 g, gradient: 0-20% of MTBE in toluene, λ=285 nm). Fractions containing the product were collected and evaporated to 3.12 g of HDP 30.2382.

Step 4: 1,1,1-triphenyl-5,8,11-trioxa-2-thiatridecan-13-amine (HDP 30.2383)

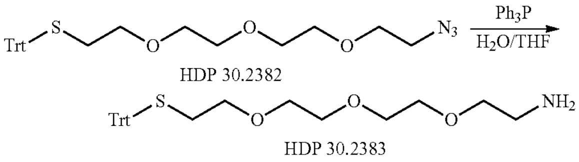

HDP 30.2382 (478 mg, 1 mmol) was dissolved in THF (20 ml). Triphenylphosphine (525 mg, 2 mmol) and $H_2O$ (2 ml) were added in sequence. Reaction mixture was stirred at room temperature for 42 hours. After evaporation, crude product was purified on silica gel column (40 g, gradient: 0-100% of DCM/MTBE/MeOH (6:3:1, v:v:v) with 1% TFA in DCM with 1% TFA, λ=235 nm). Fractions containing the product were collected and evaporated to 354 mg (77%) of HDP 30.2383 as yellowish oil.

$^1H$ NMR (500 MHz, $CDCl_3$): δ=7.46-7.37 (m, 6H), 7.32-7.16 (m, 9H), 3.65-3.53 (m, 6H), 3.51-3.40 (m, 4H), 3.31 (t, J=6.9 Hz, 2H), 2.84 (t, J=5.2 Hz, 2H), 2.43 (t, J=6.9 Hz, 2H), 1.47 (bs, 2H). $^{13}C$ NMR (126 MHz, $CDCl_3$): δ=144.78, 129.57, 127.81, 126.58, 73.38, 70.55, 70.43, 70.24, 69.57, 66.55, 41.75, 31.63.

Example 7

1,1,1-triphenyl-5,8,11,14,17,20,23-heptaoxa-2-thia-pentacosan-25-amine (HDP 30.2407)

Step 1: 1,23-dibromo-3,6,9,12,15,18,21-heptaoxatricosane (HDP 30.2397)

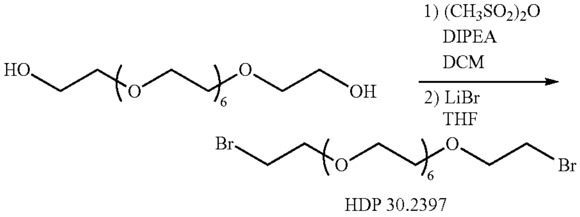

Methanesulfonic anhydride (4.7 g, 27.0 mmol) was dissolved in absolute DCM (80 ml) under argon and cooled to 0° C. Octaethylene glycol (5.0 g, 13.5 mmol), dissolved in DCM (20 ml), was added. DIPEA (9.18 ml, 54 mmol) was added undiluted at 0° C. Reaction mixture was stirred at 0° C. for 5 minutes and then thawed to room temperature. After the complete conversion of starting material (4 h), lithium bromide (LiBr; 11.72 g, 135.0 mmol) in THF (100 ml) was added and reaction mixture was heated under reflux (60° C.) for 30 minutes. After 6 hours, mixture was cooled down and evaporated in vacuo. Residue was taken up in $H_2O$ (100 ml) and extracted with DCM (2×100 ml). Combined organic phases were washed with a saturated NaCl solution (100 ml), dried over $MgSO_4$ and evaporated to 5.78 g (86%) of HDP 30.2397 as orange oil, which was used for the subsequent step without purification.

Step 2: 1-azido-23-bromo-3,6,9,12,15,18,21-heptaoxatricosane (HDP 30.2402)

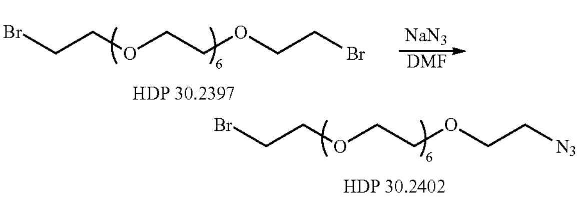

HDP 30.2402 was prepared as described herein in Example 6, Step 2.

Step 3: 25-azido-1,1,1-triphenyl-5,8,11,14,17,20,23-heptaoxa-2-thiapentacosane (HDP 30.2403)

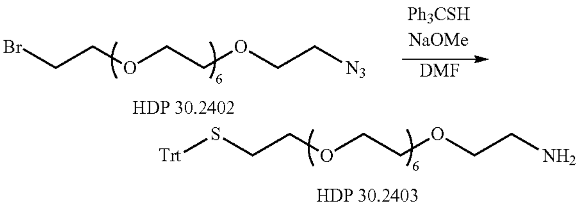

HDP 30.2403 was prepared as described herein in the Example 6, Step 3, affording 1.93 g (51%) of product.

MS(ESI+): m/z found: 676.42 calc.: 676.30 $[M+H]^+$.

Step 4: 1,1,1-triphenyl-5,8,11,14,17,20,23-heptaoxa-2-thiapentacosan-25-amine (HDP 30.2407)

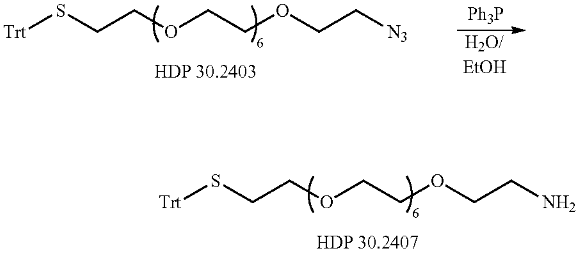

HDP 30.2403 (654 mg, 1 mmol) was dissolved in THF (20 ml) and triphenylphosphine (525 mg, 2 mmol) was added. After the complete dissolution of triphenylphosphine, $H_2O$ (2 ml) was added and reaction mixture was stirred at room temperature with open tap overnight.

After evaporation, product was purified on silica gel column (40 g, eluent: 0-100% of DCM/MeOH (4:1, v:v) with 1% TFA in DCM with 1% TFA, λ=235 nm).

Fractions corresponding to the product were combined and evaporated. Residue was redissolved in cyclohexane (10 ml) and DCM (2 ml) and precipitate was filtered off. Filtrate was evaporated and lyophilized to yield 622.7 mg (99%) of HDP 30.2407 as yellowish oil.

MS(ESI+): m/z found: 628.42 calc.: 628.33 $[M+H]^+$.

Example 8

1,1,1-triphenyl-5,8,11,14,17,20,23,26,29,32,35-undecaoxa-2-thiaheptatriacontan-37-amine (HDP 30.2585)

Step 1: 1,35-dibromo-3,6,9,12,15,18,21,24,27,30,33-undecaoxapentatriacontane (HDP 30.2564)

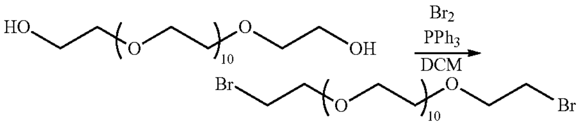

HDP 30.2564

HDP 30.2564 was prepared as described herein in Example 6, Step 1, affording 1.74 g (57%) of product as yellowish oil.

MS(ESI+): m/z found: 673.17 calc.: 673.46 $[M+H]^+$; found: 690.25 calc: 690.47 $[M+NH_4]$+.

Step 2: 1-azido-35-bromo-3,6,9,12,15,18,21,24,27,30,33-undecaoxapentatriacontane (HDP 30.2575)

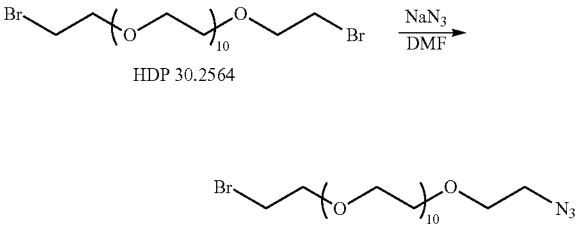

HDP 30.2564

HDP 30.2575

HDP 30.2575 was prepared as described in Example 6, Step 2.

Step 3: 37-azido-1,1,1-triphenyl-5,8,11,14,17,20,23,26,29,32,35-undecaoxa thiaheptatriacontane (HDP 30.2576)

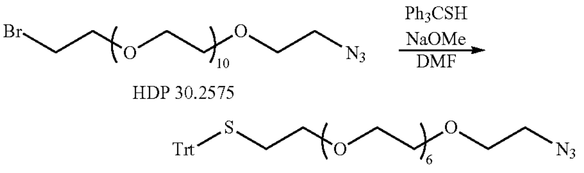

HDP 30.2575

HDP 30.2576

HDP 30.2576 was prepared as described herein in Example 5, Step 3, affording 1.94 g of material (90%).

Step 4: 1,1,1-triphenyl-5,8,11,14,17,20,23,26,29,32,35-undecaoxa-2-thiaheptatriacontan-37-amine (HDP 30.2581)

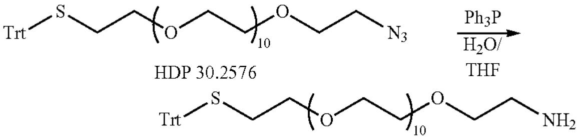

HDP 30.2576

HDP 30.2581

HDP 30.2581 was prepared as described herein in Example 5, Step 4, yielding 627 mg (22%) of product as yellowish oil.

MS(ESI+): m/z found: 804.50 calc.: 804.08 $[M+H]^+$; found: 826.42 calc.: 826.06 $[M+Na]^+$.

Example 9

DUPA-Aoc-Phe-Phe-$PEG_4$-SH Reagent (HDP 30.2439)

Step 1: $(Bu^tO)_2DUPA^{OtBu}$-Aoc-Phe-Phe-$PEG_4$-S (Trt) Reagent (HDP 30.2409)

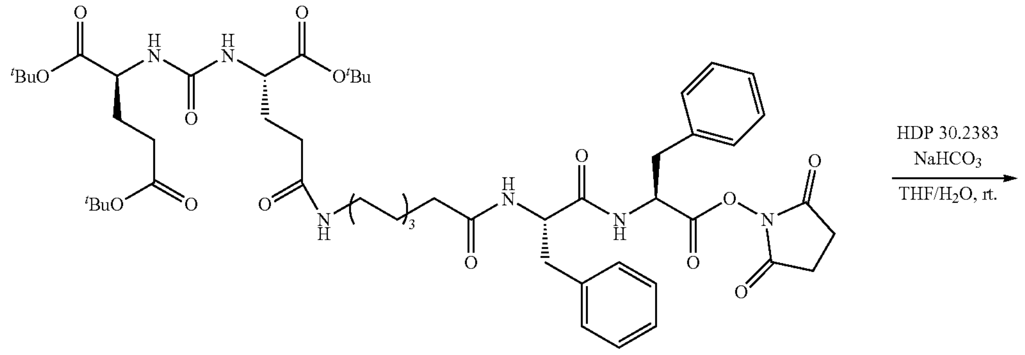

HDP 30.2401

-continued

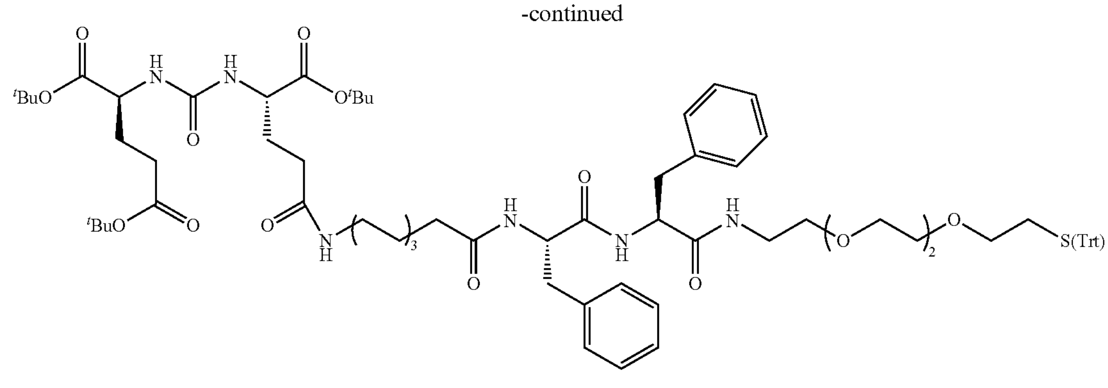

HDP 30.2409

HDP 30.2401 (20 mg, 0.020 mmol) was dissolved in THF (237 μl), HDP 30.2383 (9.29 mg, 0.021 mmol) and $NaHCO_3$ (1.81 mg, 0.022 mmol) were dissolved in $H_2O$ (158 μl) and added to the HDP 30.2401 solution. The reaction mixture was stirred at room temperature for 1 hour. Reaction was acidified with 0.2 M citric acid solution (237 μl). EtOAc (237 μl) was added and organic compound extracted (×2). Combined aqueous phase were acidified to pH=3 with citric acid and extracted with EtOAc (3×237 μl). Organic phase was washed with $H_2O$, NaCl saturated solution, dried over $MgSO_4$ and evaporated under reduced pressure and lyophilized to 15.8 mg (59%) of HDP 30.2409 as white solid.

MS (ESI+): m/z found: 1379.75 calc.: 1380.76 $[M+Na]^+$.

Step 2: DUPA-Aoc-Phe-Phe-$PEG_4$-SH Reagent (HDP 30.2439)

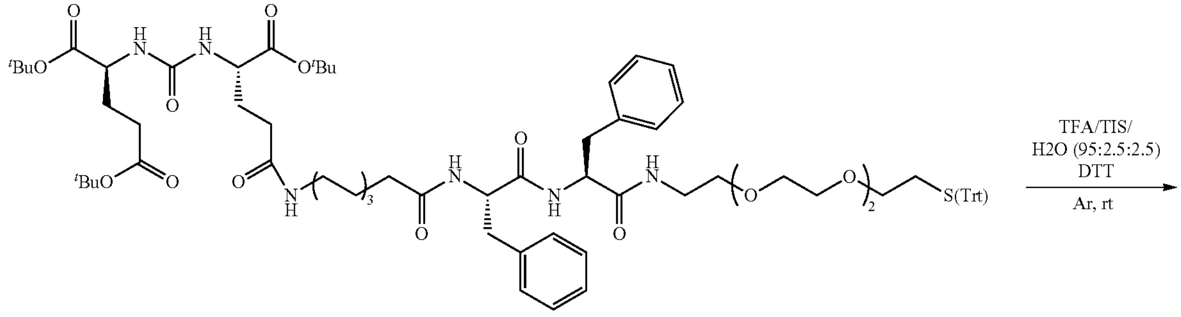

HDP 30.2409

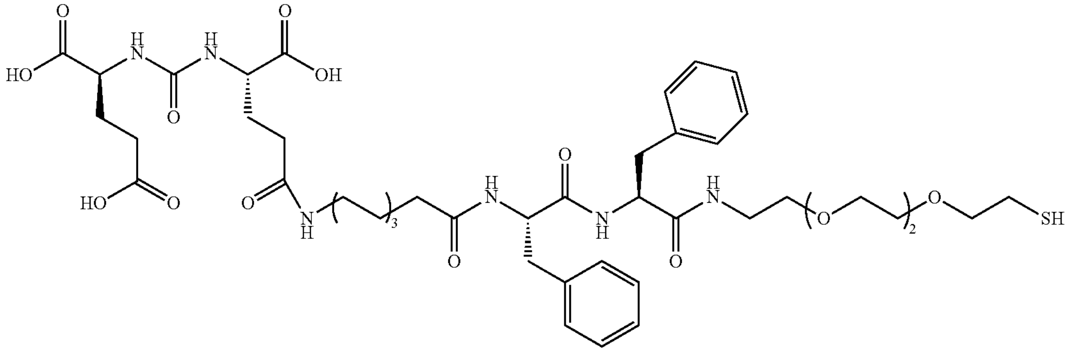

HDP 30.2439

HDP 30.2409 (15.8 mg, 11.6 μmol) was treated with a TFA/TIS/$H_2O$ (95:2.5:2.5) cocktail (2 ml) and stirred at room temperature under argon for 1 h and 30 min. Mixture was co-evaporated with toluene (2×2 ml). Addition of cold MTBE (10 ml) caused precipitation of a solid. The mixture was centrifuged at 0° C. and the precipitate was collected. The precipitate was washed with additional cold MTBE (10 ml), centrifuged at 0° C., collected and lyophilized overnight to afford the reagent HDP 30.2439 as white powder (6.7 mg, 61%).

MS (ESI+): m/z found: 947.50 calc.: 948.21 $[M+H]^+$; found: 969.50 calc.: 970.11 $[M+Na]^+$.

Example 10

DUPA-Aoc-Phe-Phe-$PEG_8$-SH Reagent (HDP 30.2466)

Step 1: $(Bu^tO)_2DUPA^{OtBu}$-Aoc-Phe-Phe-$PEG_8$-S(Trt) Reagent (HDP 30.2461)

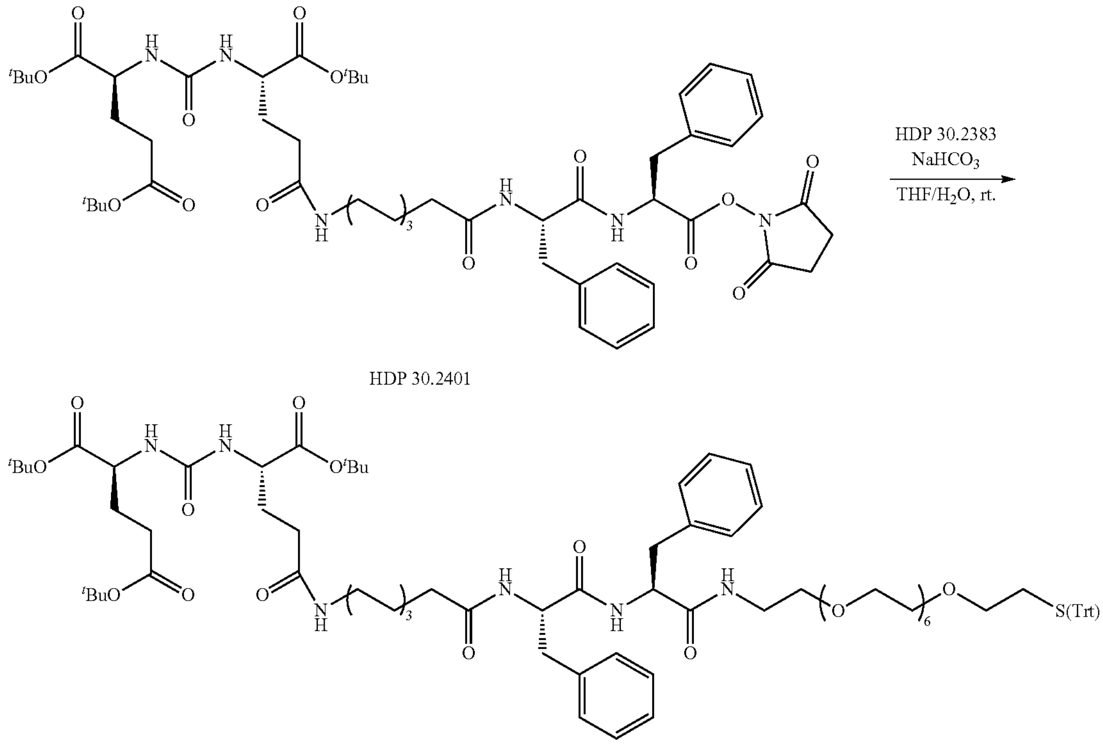

HDP 30.2401

HDP 30.2461

HDP 30.2401 (78.0 mg, 0.077 mmol) was dissolved in THF (0.93 ml), HDP 30.2407 (50.8 mg, 0.081 mmol) and $NaHCO_3$ (7.12 mg, 0.085 mmol) were dissolved in $H_2O$ (0.62 ml) and added to the HDP 30.2401 solution. The reaction mixture was stirred at room temperature for 8 hours. Reaction was evaporated under reduced pressure and residue redissolved in ACN/$H_2O$ (9:1, v:v, 500 μl) and purified in two portions on preparative HPLC on a C18 column [λ=210 nm; gradient: 0-1 min 5% B; 1-14 min 54% B; 14-26 min 100% B; 26-30 min 100% B; 30-35 min 5% B; A=water with 0.05% TFA; B=acetonitrile]. Fractions containing the product were combined, evaporated and lyophilized to 46.38 mg (40%) of HDP 30.2461 as white solid.

MS (ESI+): m/z found: 1555.75 calc.: 1556.98 $[M+Na]^+$; found: 786.92 calc.: 787.05 $[M+H+K]^{2+}$.

Step 2: DUPA-Aoc-Phe-Phe-$PEG_8$-SH Reagent (HDP 30.2466)

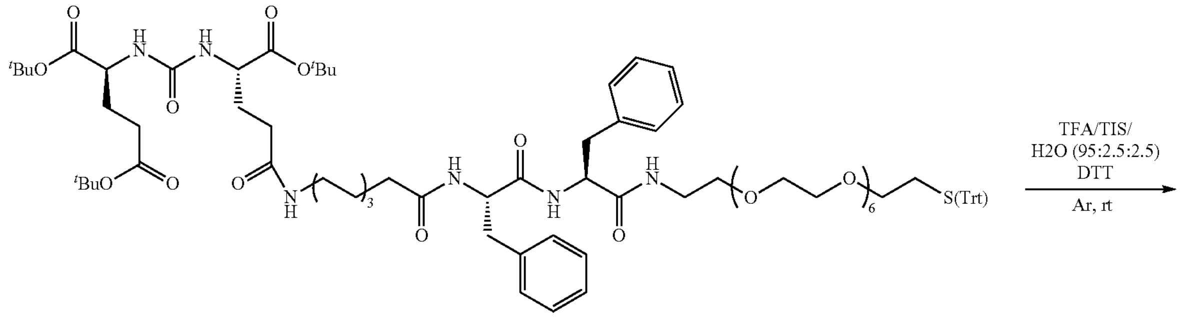

HDP 30.2461

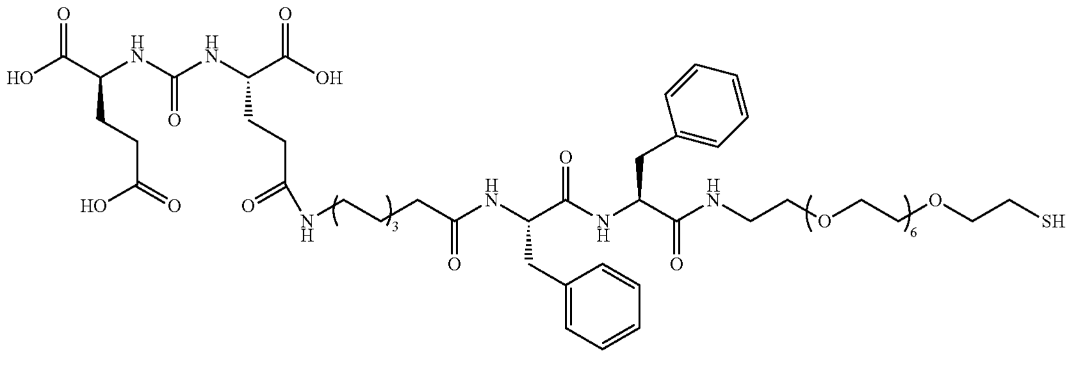

HDP 30.2466

HDP 30.2461 (46 mg, 30.0 μmol) was treated with a TFA/TIS/$H_2O$ (95:5:5, 5 ml)/DTT (260 mg) cocktail and stirred at room temperature under argon for 1 h and 30 min. Mixture was co-evaporated with toluene (2×5 ml). Residue, dissolved in MeOH (200 μl), was dripped in cold MTBE (13 ml) which caused the precipitation of a solid. The mixture was centrifuged at 0° C. and the precipitate was collected and washed with additional cold MTBE (13 ml), centrifuged at 0° C. and collected. Pellet was dissolved in ACN/$H_2O$ (5:5, v:v, 200 μl) and purified on preparative HPLC on a C18 column [λ=210 nm; gradient: 0-1 min 5% B; 1-14 min 54% B; 14-26 min 100% B; 26-30 min 100% B; 30-35 min 5% B; A=water with 0.05% TFA; B=acetonitrile]. Fractions containing the product were combined, evaporated and lyophilized to 18.1 mg (54%) of HDP 30.2466 as white solid.

MS (ESI+): m/z found: 1145.50 calc.: 1146.33 $[M+Na]^+$; found: 573.33 calc.: 573.67 $[M+H+Na]^{2+}$.

Example 11

DUPA-Aoc-Phe-Phe-$PEG_{12}$-SH Reagent (HDP 30.2585) (HDP 30.2585)

Step 1: $(Bu^tO)_2DUPA^{OtBu}$-Aoc-Phe-Phe-$PEG_{12}$-S (Trt) Reagent (HDP 30.2584)

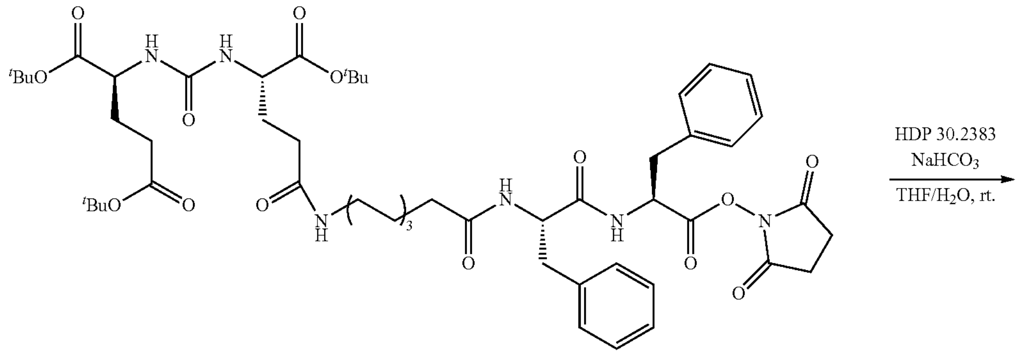

HDP 30.2401

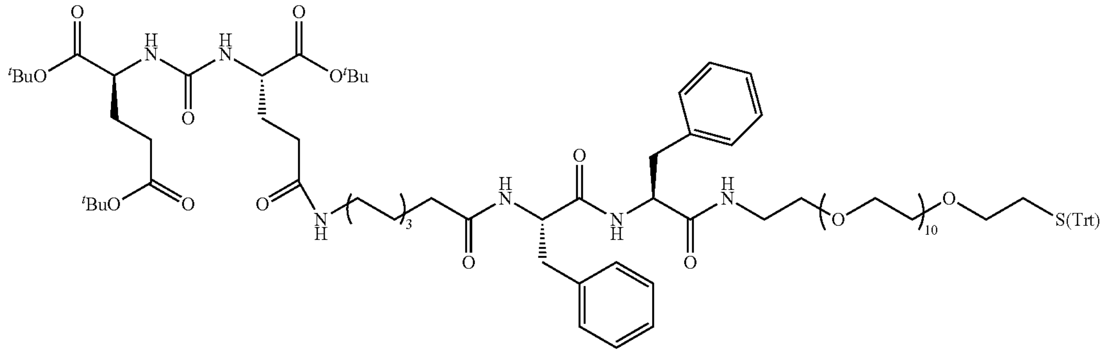

HDP 30.2584

HDP 30.2401 (50.0 mg, 0.045 mmol) was dissolved in THF (545 μl), HDP 30.2581 (41.3 mg, 0.051 mmol) and $NaHCO_3$ solution (4.16 mg, 0.050 mmol) were dissolved in $H_2O$ (362 μl) and added to the HDP 30.2401 solution. The reaction mixture was stirred at room temperature for 2 hours. Reaction was evaporated under reduced pressure and residue redissolved in $ACN/H_2O$ (1:1, v:v, 400 μl) and purified on preparative HPLC on a C18 column [λ=210 nm; gradient: 0 5% B; 15 min 100% B; 18 min 100% B; 18.5 min 5% B; 22 min 5% B; A=water with 0.05% TFA; B=acetonitrile]. Fraction containing the product was evaporated and lyophilized to 43.75 mg (57%) of HDP 30.2584 as white lyophilized powder.

MS (ESI+): m/z found: 1707.67 calc.: 1707.93 $[M-H]^-$; found: 1754.50 calc.: 1753.94 $[M+HCOOH-H]^-$.

Step 2: DUPA-Aoc-Phe-Phe-$PEG_{12}$-SH Reagent (HDP 30.2585)

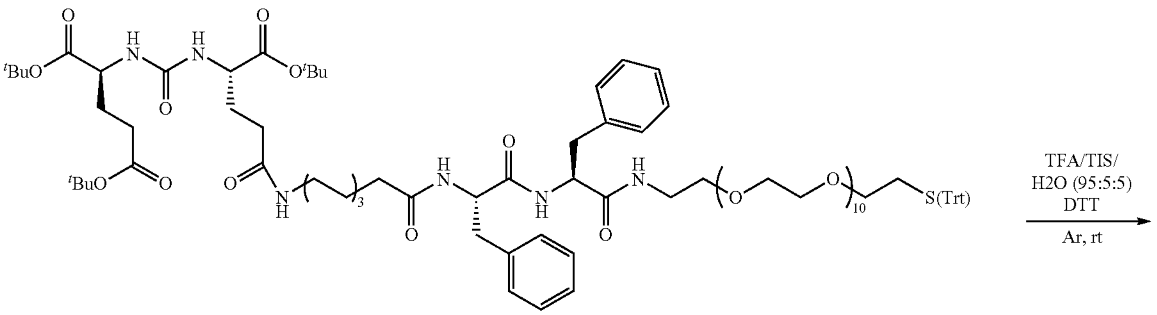

HDP 30.2584

-continued

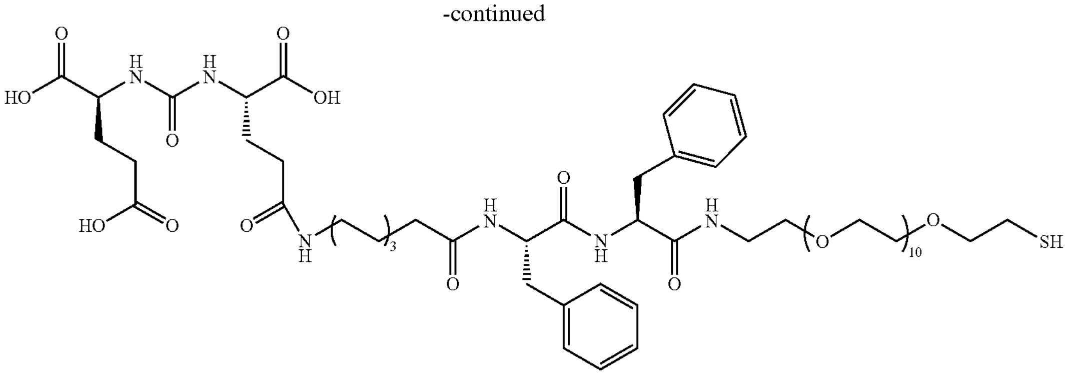

HDP 30.2585

HDP 30.2584 (43.18 mg, 43.0 μmol) was treated with a TFA/TIS/$H_2O$ (95:5:5, 6 ml)/DTT (120 mg) cocktail and stirred at room temperature under argon for 1 h and 30 min. Mixture was co-evaporated with toluene (2×6 ml). Residue, dissolved in ACN (200 μl) was dripped in cold MTBE (40 ml) which caused the precipitation of a solid. The mixture was centrifuged at 0° C. and the precipitate was collected. The precipitate was washed with additional cold MTBE (40 ml), centrifuged at 0° C. and collected. Pellet was dissolved in ACN/$H_2O$ (8:2, v:v, 200 μl) and purified by preparative HPLC on a C18 column [λ=210 nm; gradient: 0-1 min 5% B; 1-14 min 54% B; 14-26 min 100% B; 26-30 min 100% B; 30-35 min 5% B; A=water with 0.05% TFA; B=acetonitrile]. Fractions containing the product were combined, evaporated and lyophilized to 18.2 mg (55%) of HDP 30.2585 as white solid.

MS (ESI+): m/z found: 1299.58 calc.: 1300.30 $[M+H]^+$; found: 1316.42 calc.: 1316.58 $[M+NH_4]^+$; found: 1321.58 calc.: 1322.54 $[M+Na]^+$; found 1337.50 calc.: 1338.65 $[M+K]^+$; found: 658.92 calc.: 658.90 $[M+H+NH_4]^{2+}$.

Example 12

DUPA-Aoc-Phe-Phe-N-(1-amido-2-mercapto)butane Reagent (HDP 30.2614)

Step 1: ($^t$BuO)$_2$DUPA$^{tBu}$-Aoc-Phe-Phe-N-(1-amido-2-(S-tritylthio)butane Reagent (HDP 30.2612)

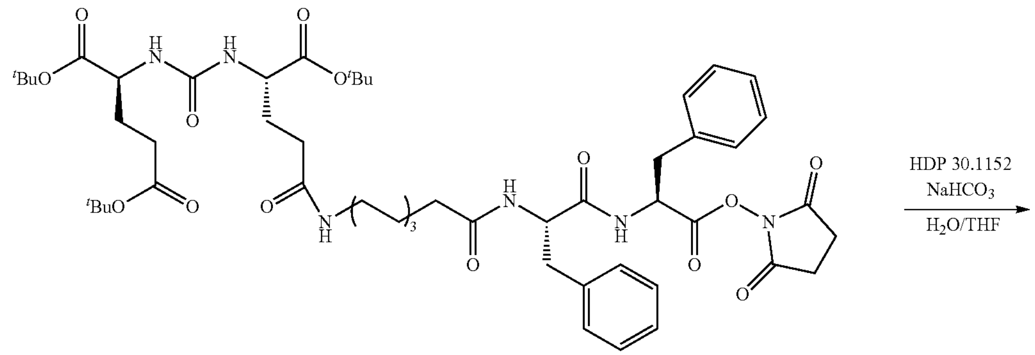

HDP 30.2401

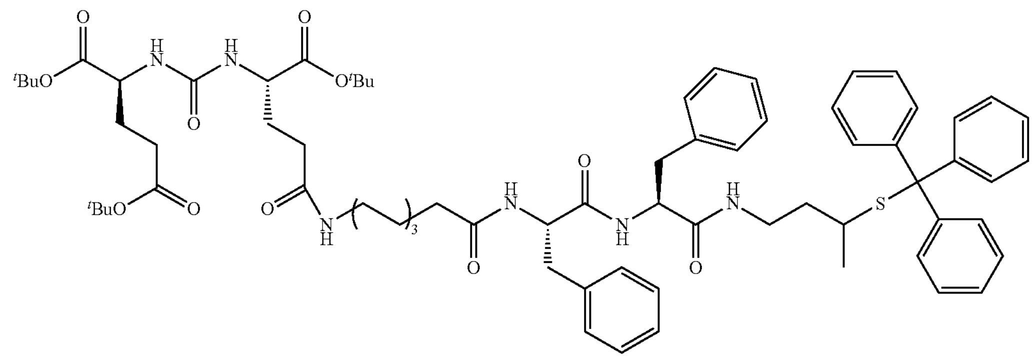

HDP 30.2612

HDP 30.2612 was prepared as described herein in example 9, step 1 with 3-tritylsulfanyl-butylamine as amine compound, yielding 30.29 mg (56%) of product.

MS(ESI+): m/z found: 1253.50 calc.: 1254.68 $[M+H]^+$.

Step 2: DUPA-Aoc-Phe-Phe-N-(1-amido-2-mercapto)butane Reagent (HDP 30.2614)

The resulted precipitate was filtered off and re-crystallized from MeOH to yield 6.62 g (83%) crystals (m.p.: 137° C.).

$^1H$ NMR (500 MHz, $CDCl_3$): δ(ppm)=8.68 (broad singlet, 1H), 6.31 (singlet, J, 2H), 2.88 (singlet, 2H), 1.73 (singlet, 6H). $^{13}C$ NMR (100 MHz, $CDCl_3$): δ(ppm)=175.04, 140.82, 87.68, 53.77, 15.76.

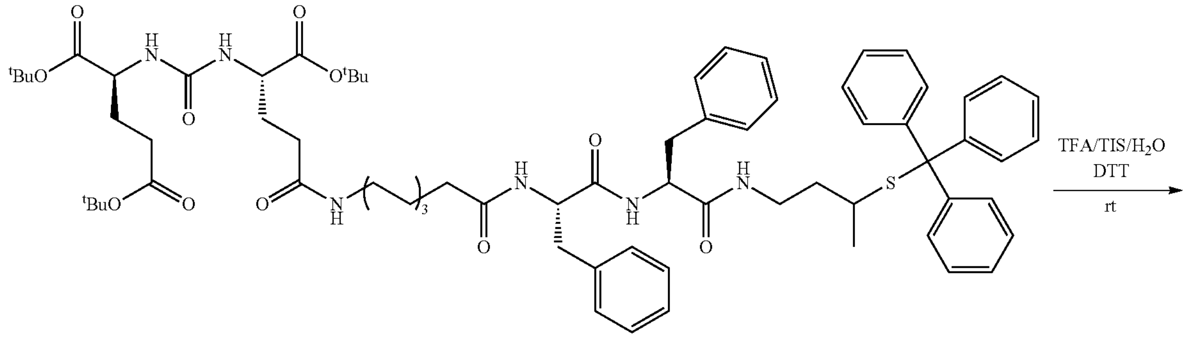

HDP 30.2612

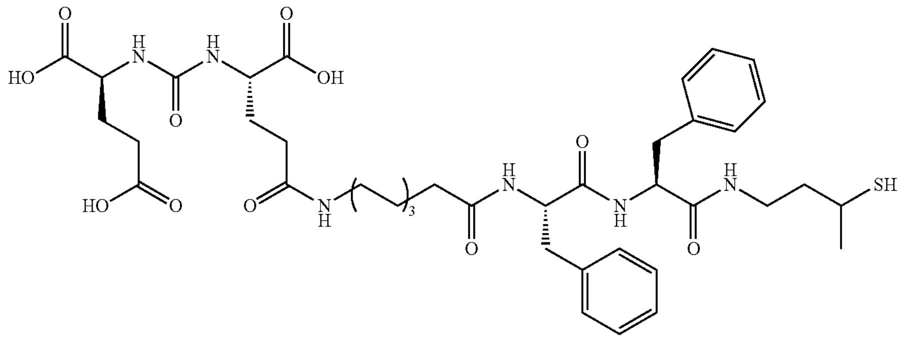

HDP 30.2614

HDP 30.2614 was prepared as described herein in example 9, step 2, affording 6.10 mg (30%) of product as white powder.

MS(ESI−): m/z found: 841.33 calc.: 842.01 $[M-H]^-$; found: 863.33 calc.: 864.17 $[(M-2H)+Na]^-$.

Example 13

6'(6-N-maleimido-hexyl)-α-amanitin (HDP 30.0880)

Step 1: 1,7-dimethyl-10-oxa-4-azatricyclo[5.2.1.0$^{2,6}$]dec-8-en-3,5-dione,exo isomer (HDP 30.0891)

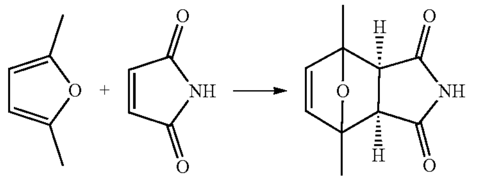

4.00 g (41.2 mmol) 2,5-dimethyl furan and 5.93 g (61.7 mmol, 1.5 eq.) maleimide were dissolved in 30 ml diethyl ether ($Et_2O$) and heated to 90° C. in a Parr reactor for 12 h.

Step 2: 4-(6-Bromohexyl)-1,7-dimethyl-10-oxa-4-azatricyclo[5.2.1.0$^{2,6}$]dec-8-en-3,5-dione, exo isomer (HDP 30.0916)

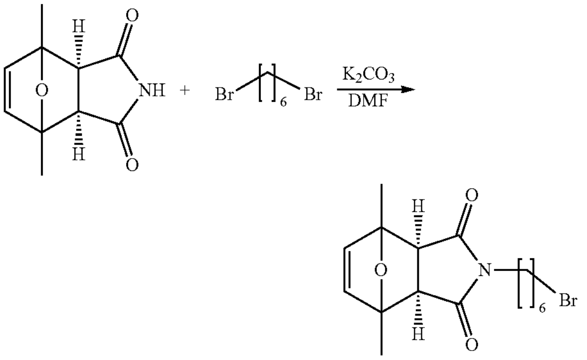

386 mg (2 mmol) HDP 30.0891 and 1.952 g (8 mmol) 1,6-dibromohexane were dissolved in 20 ml DMF, 276 mg (2 mmol) potassium carbonate were added and the suspension was heated to 50° C. for 3 h. Subsequently the DMF was evaporated, the residue was taken up with 100 ml of DCM. The inorganic salts were removed by filtration, diatomaceous earth (3 g) was added to the filtrate and the solvent removed under vacuum. The residue was purified by silica gel chromatography eluting with a gradient n-hexane—ethyl acetate to result HDP 30.0916 (483 mg) as waxy crystals in 68% yield.

$^{1}$H NMR (500 MHz, $CDCl_3$): δ(ppm)=6.31 (s, 2H), 3.48 (t, J=7.2 Hz, 2H), 3.39 (t, J=6.8 Hz, 2H), 2.81 (s, 1H), 1.90-1.77 (m, 2H), 1.70 (s, 5H), 1.64-1.52 (m, 2H), 1.44 (dddd, J=9.2, 7.4, 6.5, 5.4 Hz, 2H), 1.35-1.23 (m, 2H).

$^{13}$C NMR (126 MHz, $CDCl_3$): δ(ppm)=174.81, 140.81, 87.52, 52.33, 38.42, 33.65, 32.50, 27.54, 27.33, 25.64, 15.87.

Step 3: 6''-(6-(1,7-dimethyl-10-oxa-4-azatricyclo [5.2.1.0$^{2,6}$]dec-8-en-3,5-dione-4-yl-hexyl)-α-amanitin (HDP 30.0903)

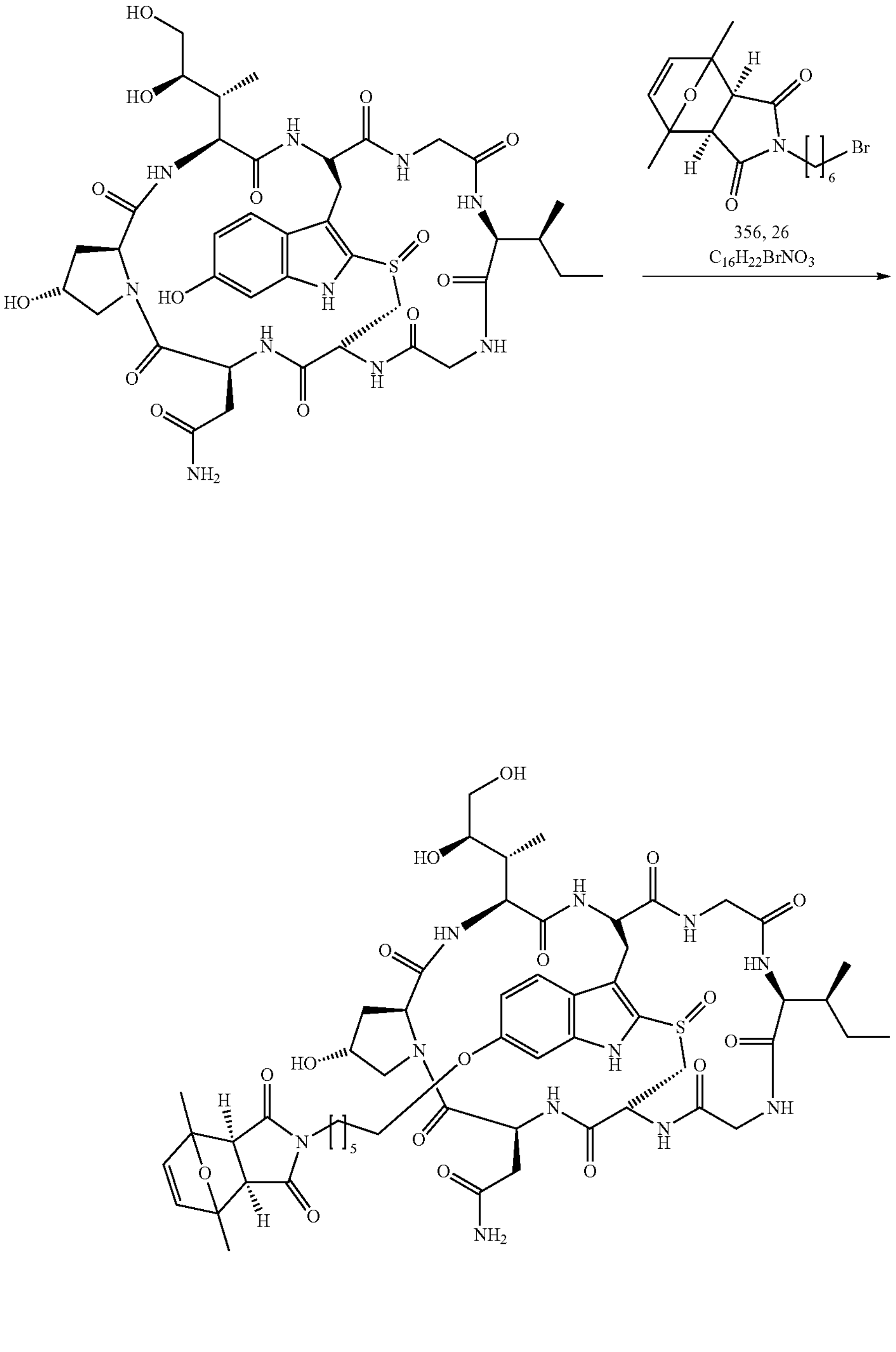

Under argon and at room temperature 34.5 mg (37.5 μmol) of vacuum dried α-amanitin were dissolved in 1000 μl dry dimethyl sulfoxide (DMSO). HDP 30.0916 (106.8 mg, 8 equivalents) and 1M sodium hydroxide (41.2 μl, 1.1 eq.) were added. After 3 h at room temperature the reaction mixture was acidified to pH=5 with 41.2 μl of a 1 M AcOH solution in DMSO. The solvent was removed in vacuo and the residue was purified by preparative RP-HPLC on a C18 column with a gradient from 5-100% MeOH. The fractions containing product were evaporated to 27.2 mg (59%) of HDP 30.0903 as a colorless solid.

MS (ESI+): m/z found: 1194.17 calc.: 1195.35 $[M+H]^+$; found: 1216.10 calc.: 1217.33 [M+Na]'".

Step 4: 6'-(6-N-Maleimido-hexyl)-α-amanitin (HDP 30.0880)

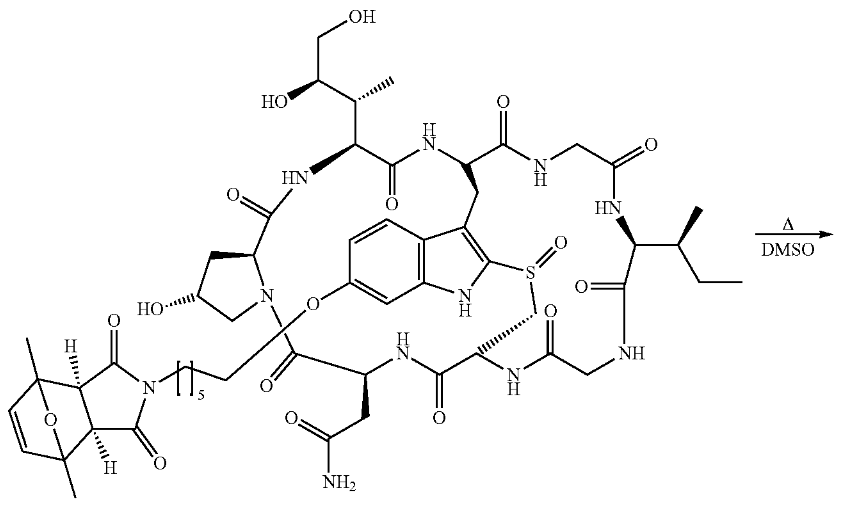

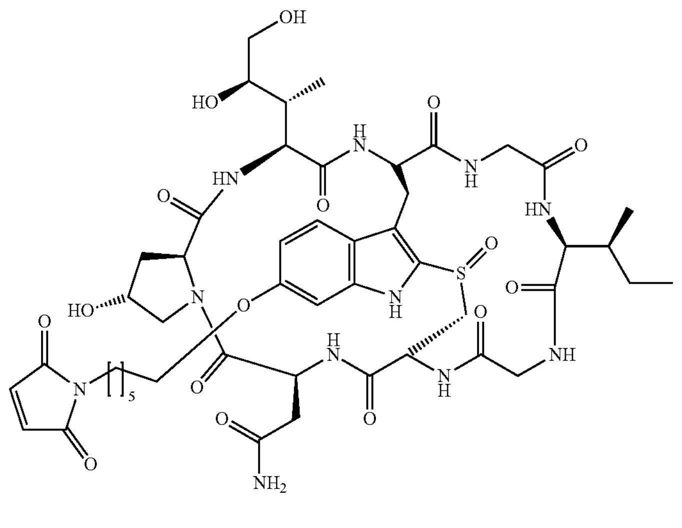

HDP 30.0903 (27.2 mg, 22.7 μmol) was dissolved in 3000 μl of dry DMSO. The reaction mixture was heated to 100° C. and stirred for 1.5 h. After cooling to 40° C., DMSO was removed in vacuo and the residue purified by preparative HPLC with the above mentioned method. The fraction with the retention time of 17.3-18.1 min were collected and the solvents evaporated. The residue was lyophilized from 3 ml tBuOH to provide 23.6 mg (94%) of HDP 30.0880 as off-white powder.

MS (ESI+): m/z found: 1098.29 calc.:1099.22 $[M+H]^+$; found: 1120.36 calc.: 1121.20 $[M+Na]^+$.

Example 14

6'-O-[3-(5-Nitro-pyridine-2-yldisulfanyl)propyl)]-α-amanitin (HDP 30.0951)

Step 1: 6'-O-(3-S-tritylsulfanyl-propyl)-α-amanitin (HDP 30.0517)

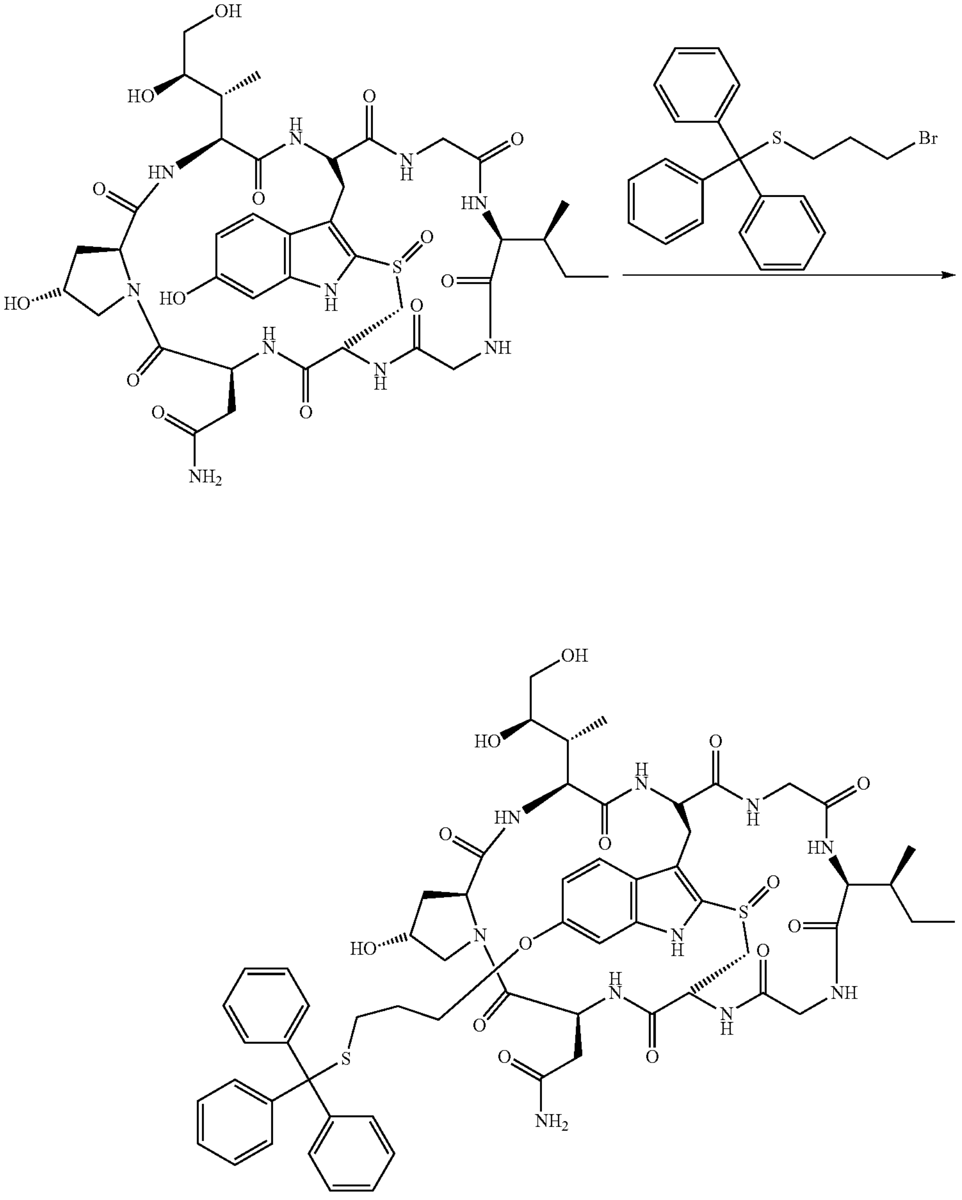

Under argon 46 mg (50 μmol) of vacuum dried α-amanitin was dissolved in 2500 μl in dry DMSO. 3-(S-trityl)-mercaptopropyl-1-bromide (159 mg, 8 eq.) was added, followed by 60 μl of a 1M sodium hydroxide (NaOH) solution. After 1.5 h at room temperature the reaction mixture was acidified to pH=5 with 50 μl 1M AcOH in DMSO and the solvent was evaporated. The residue was dissolved in 200 μl of MeOH and added dropwise to a centrifugation tube filled with 10 ml of MTBE. The resulted precipitate was cooled to 0° C. for 10 min and isolated by centrifugation (4000×g) and washed with 10 ml MTBE subsequently. The supernatants were discarded and the pellet dissolved in 750 μl of MeOH and purified in 3 portions on preparative HPLC on a C18 column (250×21.2 mm, Luna RP-18, 10 μm, 100 Å) [gradient: 0 min 5% B; 5 min 5% B 20 min 100% B; 25 min 100% B; 27 min 5% B, 35 min 5% B; Flow 30 ml/min]. The fractions with a retention time of 21.1-21.8 min were collected and the solvents evaporated to 36.5 mg (59%) of HDP 30.0517 as a colorless solid.

MS (ESI+): m/z found: 1234.8 calc.:1236.45 $[M+H]^+$; found: 1257.3 calc.: 1258.45 $[M+Na]^+$.

Step 2: 6'-O-[3-(5-nitro-pyridine-2-yldisulfanyl) propyl)]-α-amanitin (HDP 30.0951)

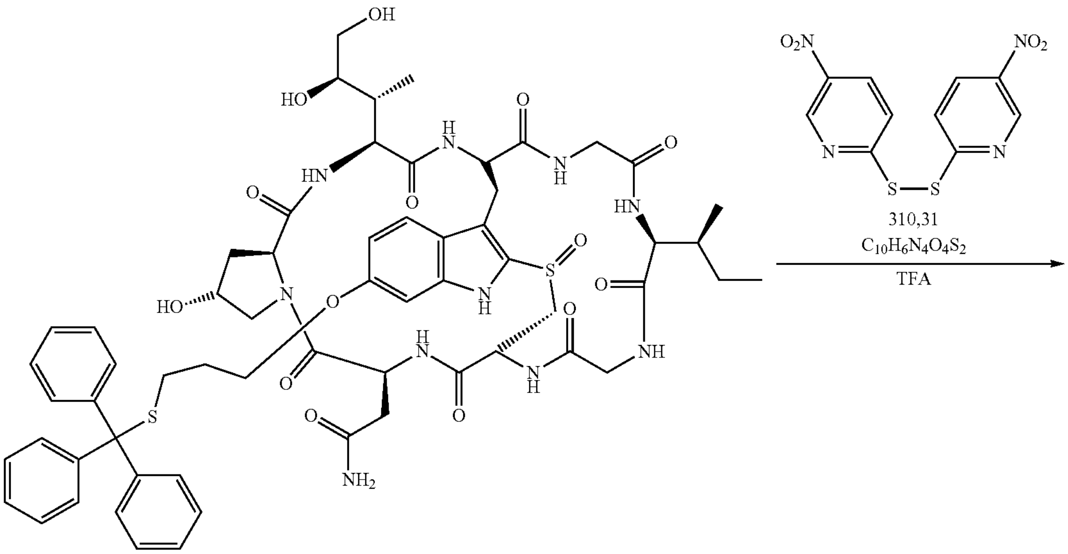

1235,46
$C_{61}H_{74}N_{10}O_{14}S_2$
HDP 30.0517

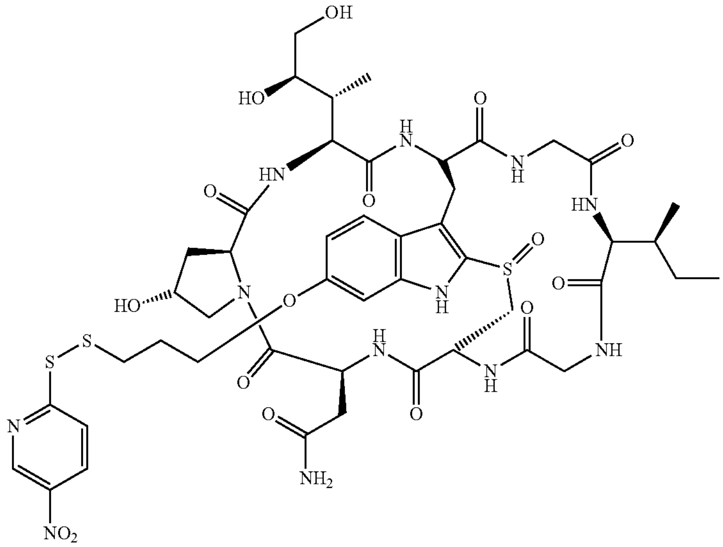

1147,28
$C_{47}H_{62}N_{12}O_{16}S_3$
HDP 30.0951

To step 1 product (5.00 mg, 4.05 μmol) 2,2'-dithiobis(5-nitropyridine) (DTNP) (6.28 mg, 5 eq.), dissolved in 200 μl TFA, was added. After 4 min, the volatiles were distilled off and the residue was co-evaporated with 1000 μl MeOH. The crude product was purified by RP-HPLC as in the step 1. The fractions with a retention time of 18.46-19.28 min were collected and the solvents evaporated. The residue was lyophilized from 2 ml $^t$BuOH to 2.99 mg (64%) of HDP 30.0951 as a slight yellowish solid.

MS (ESI$^+$): m/z found: 1146.97 calc.:1148.29 $[M+H]^+$; found: 1169.17 calc.:1170.27 $[M+Na]^+$.

Example 15

6'-O-[3-(5-nitro-pyridine-2-yldisulfanyl)butyl)]-α-amanitin (HDP 30.2587)

Step 1: 6'-O-(3-S-tritylsulfanyl-butyl)-α-amanitin (HDP 30.1168)

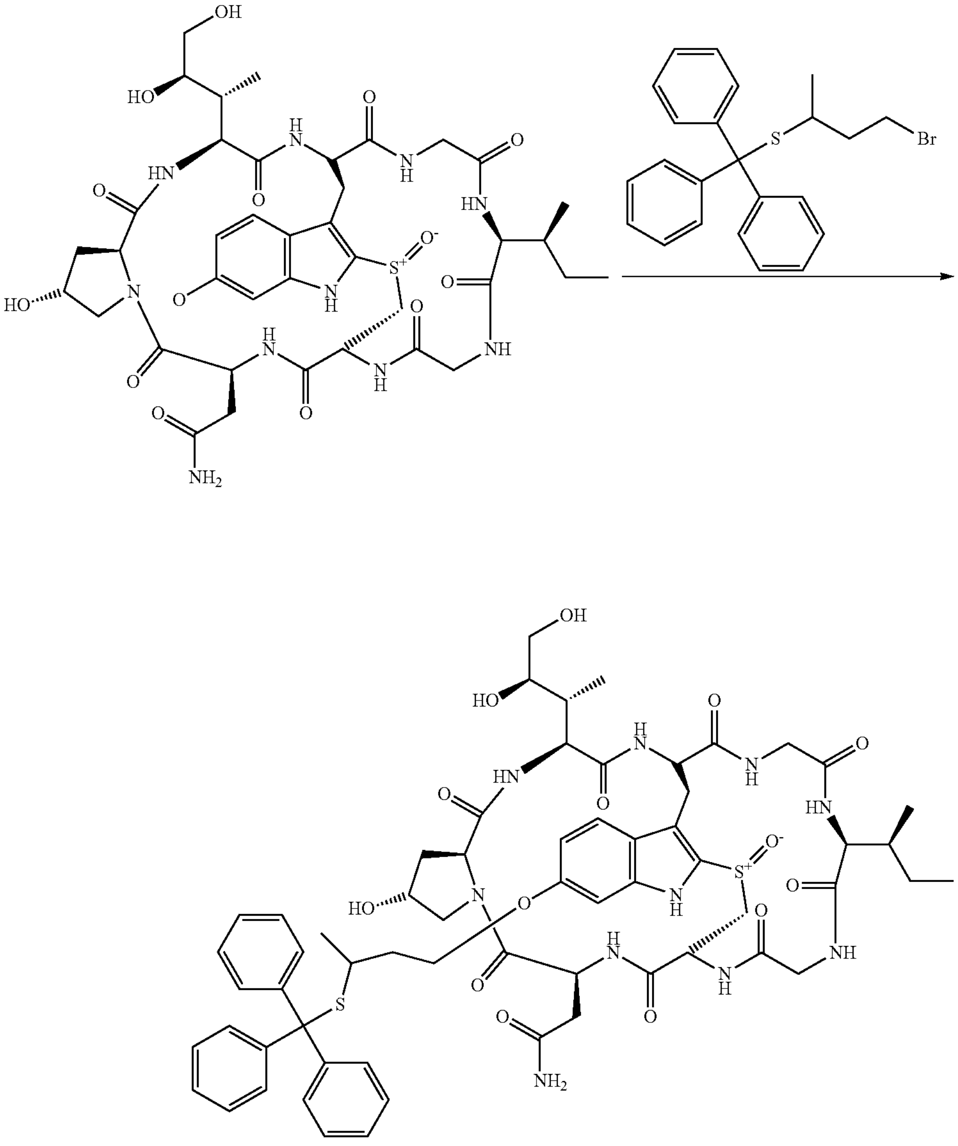

HDP 30.1168

Under argon 38 mg (41.3 μmol) of vacuum dried α-amanitin was dissolved in dry DMSO (1150 μl). 1-bromo-3-tritylsulfanyl-butane (68.1 mg, 4 eq.) was added, followed by a 2M lithium hydroxide (LiOH) solution (25 μl, 1.2 eq). After 26 h at room temperature the reaction mixture was acidified with 1M AcOH in DMSO (50 μl, 1.2 eq) and the solvent was evaporated. The residue was dissolved in 400 μl of MeOH and added dropwise to a centrifugation tube filled with 10 ml of MTBE. The resulted precipitate was cooled to 0° C. for 10 min and isolated by centrifugation (4000×g) and washed with 10 ml MTBE subsequently. The supernatants were discarded and the pellet dissolved in 800 μl of MeOH and purified in 2 portions on preparative HPLC on a C18 column (250×21.2 mm, Luna RP-18, 10 μm, 100 Å) [λ=305 nm; gradient: 0 min 5% B; 15 min 100% B 18 min 100% B; 18.5 min 5% B; 22 min 5% B; A=water with 0.05% TFA, B=methanol with 0.05% TFA; Flow 30 ml/min;]. The fractions corresponding to the product were collected and the solvents evaporated to 31.3 mg (61%) of HDP 30.1168 as a colorless solid.

MS (ESI+): m/z found: 1271.42 calc.:1272.49 $[M+Na]^+$.

Step 2: 6'-O-[3-(5-nitro-pyridine-2-yldisulfanyl) butyl)]-α-amanitin (HDP 30.2587)

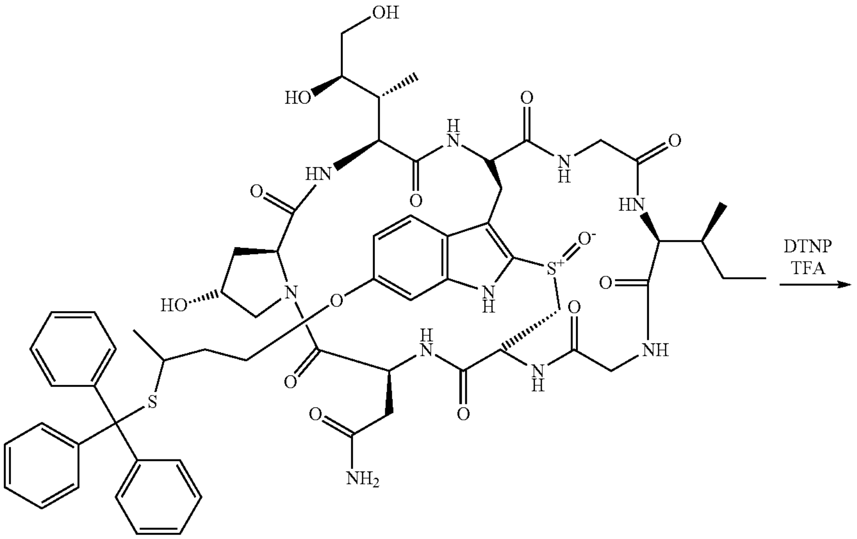

HDP 30.1168

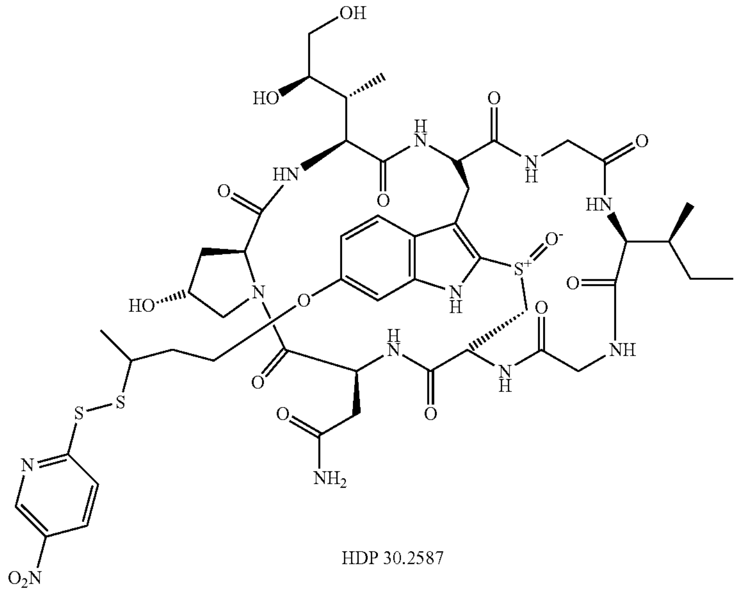

HDP 30.2587

To HDP 30.1168 (31.17 mg, 2.6 μmol) 2,2'-dithiobis(5-nitropyridine) (DTNP) 0.5 M solution in TFA (260 μl, 5.0 eq) was added and mixture was vortexed at room temperature. After 4 min, reaction mixture was dripped into 10 ml of cold MTBE/n-hexane (1:1) mixture. The precipitate was cooled to 0° C. for 10 minutes and isolated by centrifugation at 0° C. The supernatants were discarded and the pellet dissolved in 400 μl of MeOH and purified in two steps as in the conditions described in step 1. The fractions with a retention time of 18.46-19.28 min were collected and the solvents evaporated. The residue was lyophilized from tBuOH/$H_2O$ (4:1, 10 ml) to 17.92 mg (59%) of HDP 30.2587 as a yellowish powder.

MS ($ESI^+$): m/z found: 1183.33 calc.: 1183.36 $[M+Na]^+$.

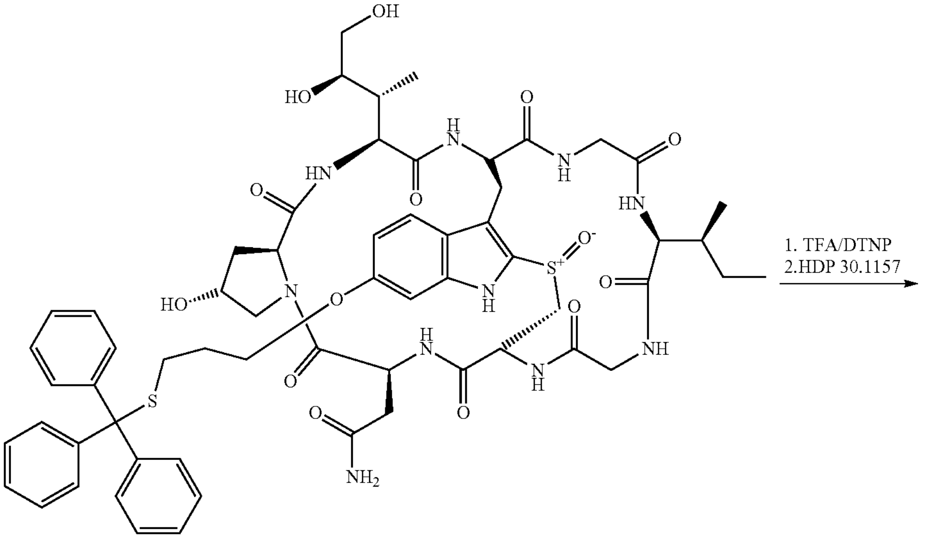

HDP 30.0951

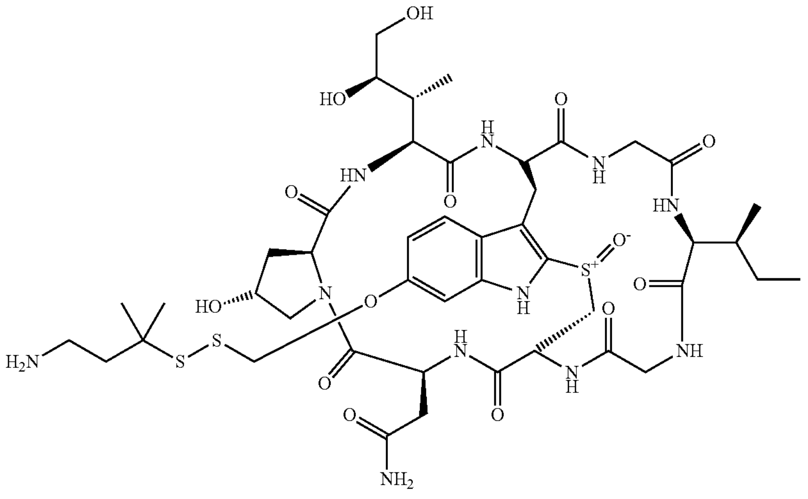

HDP 30.1172

HDP 30.0951 (10.0 mg, 8.09 μmol) was weighted into a 15 ml centrifuge tube and dissolved in 0.5 M DTNP solution in TFA (80.94 μl, 5 eq). Reaction mixture was stirred at room temperature for 4 minutes. Reaction mixture was then diluted with MTBE/n-hexane (1:1, 10 ml). The precipitate was cooled to 0° C. for 10 minutes, isolated by centrifugation (4000×g) and washed with MTBE (10 ml) subsequently. The supernatants were discarded and the pellet dissolved in 500 μl of MeOH. 4-amino-2-methylbutane-2-thiol HDP 30.1157 (17 mg, 9 eq) was added. After 1 h, the mixture was triturated with MTBE with 0.05% TFA (10 ml), the ether decanted and replaced with fresh MTBE with 0.05% TFA (10 ml). The obtained precipitate was dissolved in MeOH (200 μl) and purified on preparative HPLC on a C18 column (250×21.2 mm, Luna RP-18, 10 μm, 100 Å) [λ=305 nm; gradient: 0-5 min 5% B; 20-25 min 100% B; 27-35 min 5% B; A=water with 0.05% TFA; B=methanol with 0.05% TFA]. The fractions corresponding to the product were collected and the solvents evaporated to 8.05 mg (81%) of HDP 30.1172 as a white powder.

MS (ESI+): m/z found: 1110.39 calcd.: 1110.44 $[M+H]^+$.

Example 17

6'-O-(6-aminohexyl)-α-amanitin (HDP 30.0134)

Step 1: 6'-O-(6-Boc-aminohexyl)-α-amanitin (HDP 30.0132)

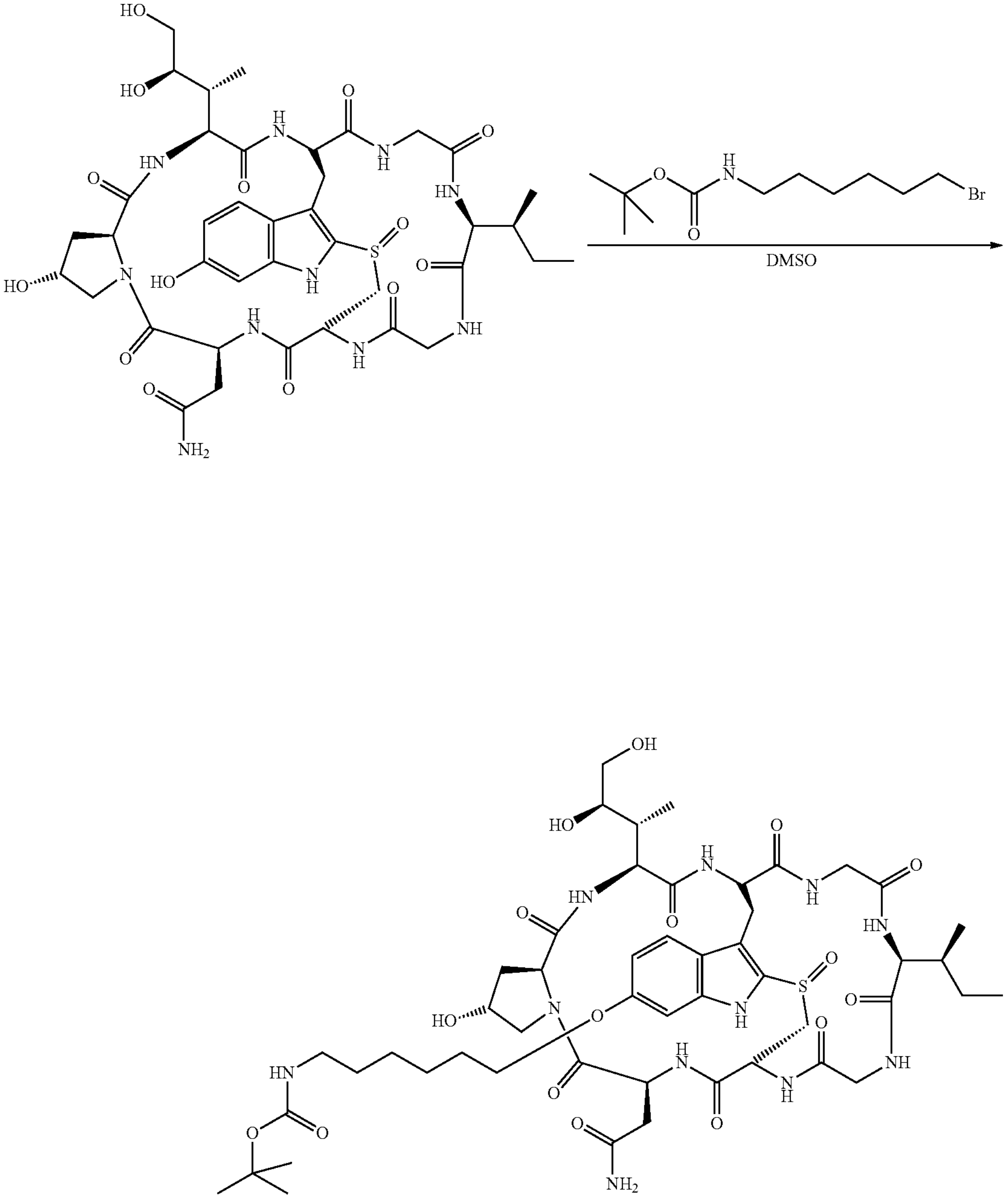

HDP 30.0132

A solution of α-amanitin (105 mg, 114 μmol) and 6-(Boc-amino)hexyl bromide (128 mg, 457 μmol) in DMSO (3.5 mL) was treated with a 2 M LiOH solution (68.6 μl, 137.1 μmol) under argon atmosphere. After stirring at ambient temperature for 40 min, the reaction mixture was acidified by addition of AcOH (7.84 μl) and then the mixture was added drop wise to a flask containing MTBE (40 mL) in order to precipitate the desired ether intermediate. The supernatant was decanted and discarded. The precipitate was purified by preparative RP-HPLC [λ=305 nm; gradient: 0-5 min 5% B; 20-25 min 100% B; 27-35 min 5% B; A=water; B=methanol] to provide HDP 30.0132 (84.37 mg, 66%) as a white powder.

MS (ESI+): m/z found: 1118.5 calc.: 1119.29 $[M+H]^+$.

Step 2: 6'-O-(6-aminohexyl)-α-amanitin (HDP 30.0134)

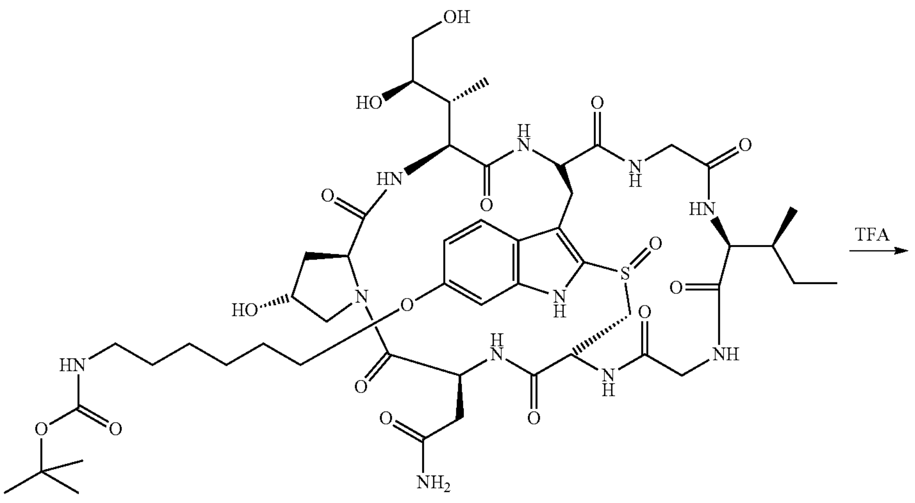

HDP 30.0132

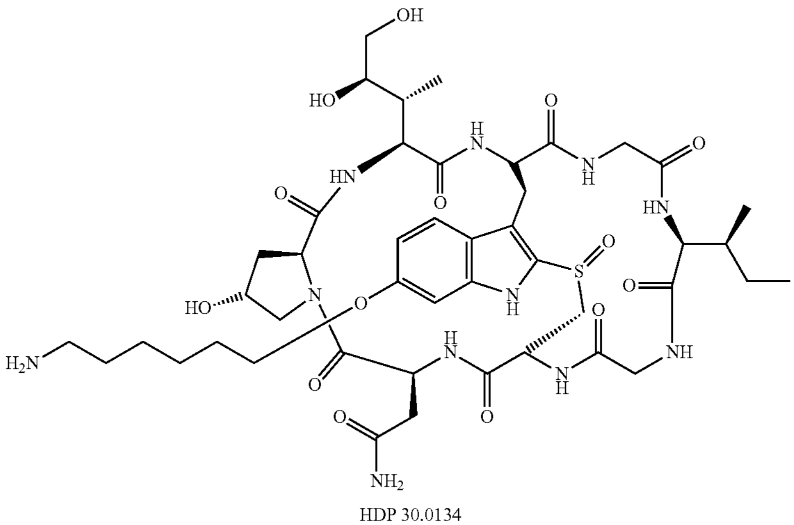

HDP 30.0134

To HDP 30.0132 (152 mg, 136 μmol) TFA (5 mL) was added and the reaction mixture was stirred for 2 min at ambient temperature. The reaction mixture was concentrated under reduced pressure, and the crude product was purified by preparative RP-HPLC [λ=305 nm; gradient: 0 min 5% B; 0-1 min 30% B; 1-10 min 39% B; 10-13 min 100% B; 13-18 min 5% B; A=water with 0.05% TFA; B=methanol with 0.05% TFA]. The fractions containing the product were combined, concentrated and lyophilized to yield the derivative HDP 30.0134 (118.67 mg, 86%)

MS (ESI+): m/z found: 1018.5 calc.: 1019.17 $[M+H]^+$.

Example 18

6'-[H-Val-Ala-PAB]-α-amantin (HDP 30.1702)

Dipeptide p-aminobenzylbromides were synthesized from the corresponding benzylacohols by adaption of the methods disclosed by Jeffrey et al. in *J. Med. Chem.* 2005, 48, 1344-1358. The general procedure is exemplified by the following scheme:

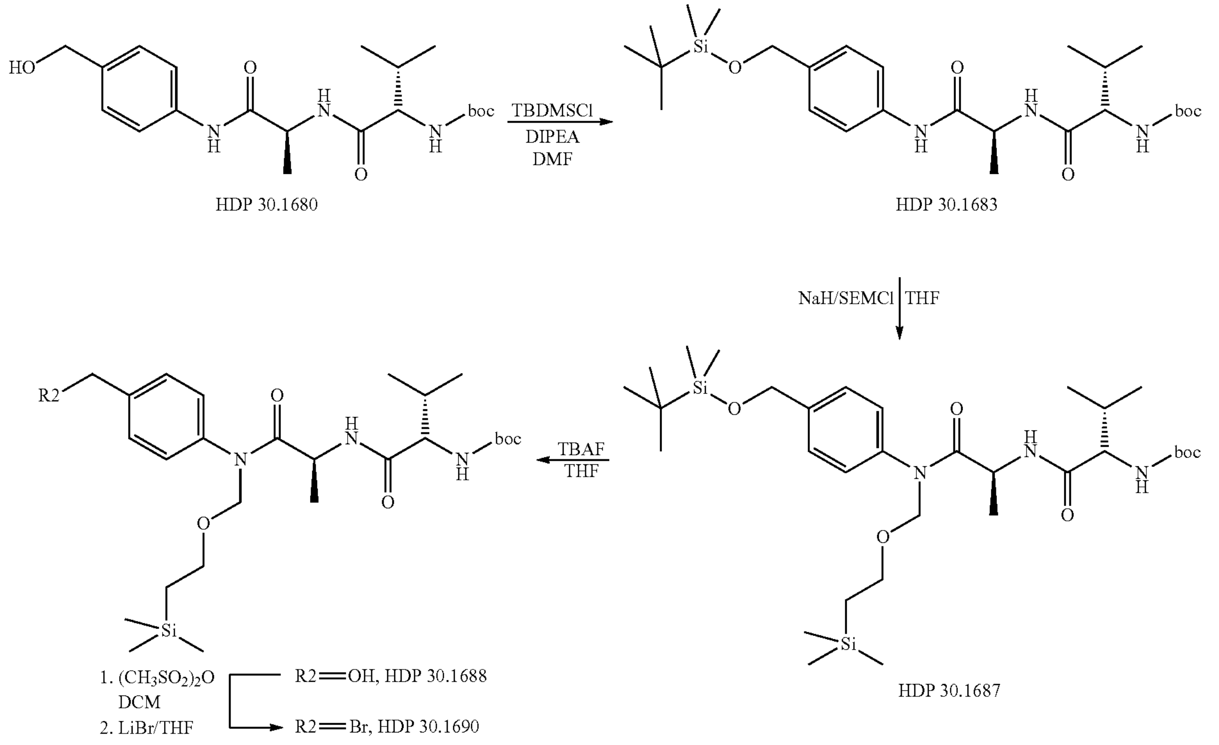

Step 1: Boc-Val-Ala-PAB-OTBDMS (HDP 30.1683)

Boc-Val-Ala-PAB-OH (HDP 30.1680, 8.28 g, 21.04 mmol) was dissolved in DMF (50 ml), and DIPEA (8.61 ml, 52.61 mmol) and tert-butyldimethyl-chlorosilane (TBDMSCl) (10.99 ml, 31.56 mmol) were added. After 30 min, DMF was evaporated and the residue was dissolved in 200 ml of EtOAc, and washed with 100 ml 0.2M citric acid solution, water, saturated $NaHCO_3$, saturated NaCl solution, dried over $MgSO_4$, and concentrated under reduced pressure. The crude product was purified by flash chromatography with a gradient of 0 to 100% MTBE in hexane. Pure fractions were combined and evaporated to 9.12 g (85%) of product as solid.

MS (ESI+): m/z found: 508.09 calc.: 508.32 $[M+H]^+$; found: 530.29 calc.: 530.30 $[M+Na]^+$; found: 376.22 calc.: 376.22 $[MH+{}^tBDMSO]^+$; found: 320.22 calc.: 320.16 $[MH+{}^tBDMSO-C_4H_4]^+$; found: ca. 1015 calc.: 1015.63 $[2M_+H]^+$; found: 1037.21 calc.:1037.62$[2M+Na]^+$.

$^1H$ NMR (500 MHz, $CDCl_3$): δ(ppm)=8.74-8.70 (m, 1H), 7.51 (d, J=8.5 Hz, 2H), 7.24 (d, J=8.4 Hz, 2H), 6.90 (d, J=7.5 Hz, 1H), 5.12 (d, J=7.8 Hz, 1H), 4.73-4.64 (m, 3H), 4.00 (s, 1H), 2.15 (dq, J=13.4, 6.7 Hz, 1H), 1:45 (d, J=7.0 Hz, 3H), 1.43 (s, 9H), 0.96 (d, J=6.9 Hz, 3H), 0.94-0.90 (m, 12H), 0:07 (s, 6H). $^{13}C$ NMR (126 MHz, $CDCl_3$): δ(ppm)=172.24, 170.17, 156.28, 137.53, 136.77, 126.81, 119.98, 80.60, 64.80, 60.31, 49.77, 30.84, 28.43, 26.08, 19:44, 18:55, 17.89, 17.78, −5.07.

Step 2: Boc-Val-Ala(SEM)-PAB-OTBDMS (HDP 30.1687)

To a solution of step 1 product (9.12 g, 17.96 mmol) in THF (100 mL) lithium bis(trimethylsilyl) amide (LiHMDS) (26.94 ml, 1M solution in THF) was added at 0° C. After 10 min, neat 2-(trimethylsilyl)-ethoxymethyl chloride (SEMCl) (6.36 ml, 35.92 mmol) was added at 0° C., and the reaction mixture was stirred for 1 h at room temperature. After conversion, 200 ml of sodium citrate buffer (pH=6.40) were added and the product was extracted with EtOAc (2×50 ml). The organic layers were combined and washed with 200 ml of sodium citrate buffer (pH=4.76), 100 ml of saturated $NaHCO_3$ solution and 100 ml of NaCl solution, dried over $MgSO_4$ and concentrated. The crude product was purified by flash chromatography with a gradient of 0 to 50% of MTBE in hexane, affording the pure product (7.51 g, 66%) as white foam.

MS (ESI+): m/z found: 638.03 calc.: 638.40 $[M+H]^+$; found: 660.47 calc.: 660.3 $[M+Na]^+$.

$^1H$ NMR (500 MHz, $CDCl_3$): δ=7.40 (d, J=8.1 Hz, 2H), 7.25 (d, J=8.0 Hz, 2H), 6:53 (d, J=7.4 Hz, 1H), 5.14 (d, J=10.0 Hz, 1H), 5.05 (d, J=9.0 Hz, 1H), 4.97 (d, J=10.0 Hz, 1H), 4.76 (s, 2H), 4.54 (p, J=6.9 Hz, 1H), 3.93 (t, J=7.6 Hz, 1H), 3.63 (dd, J=9.6, 7.3 Hz, 2H), 2.10 (h, J=6.7 Hz, 1H), 1.43 (s, 9H), 1.16 (d, J=6.9 Hz, 3H), 0.98-0.92 (m, 14H), 0.90 (d, J=6.8 Hz, 3H), 0:12 (d, J=1.4 Hz, 6H), 0.00 (s, 9H).

Step 3: Boc-Val-Ala(SEM)-PAB-OH (HDP 30.1688)

To a solution of step 2 product (7.51 g, 11.96 mmol) in THF (200 mL) was added n-tetrabutylammonium fluoride (TBAF) (14.35 ml, 1 M solution in THF, 14.35 mmol). After 20 min, diatomaceous earth (20 g) was added to the reaction mixture and the volatiles were removed under reduced pressure. The remaining solids were applied on top of a silica gel column and eluted with a gradient of 0 to 50% acetone in hexane. Pure fractions were combined and evaporated to yield the product (6.16 g, 100%) as white foam.

MS (ESI+): m/z found: 524.09 calc.: 524.32 $[M+H]^+$; found: 546.46 calc.: 546.30 $[M+Na]^+$; found: 562.41 calc.: 562.2 $[M+K]^+$; found: 271.07 calc.: 271.17 $[M-C_{13}H_{22}NO_2Si]^+$.

Step 4: Boc-Val-Ala(SEM)-PAB-Br (HDP 30.1690)

To a solution of step 3 product (4.73 g, 9.03 mmol) in DCM (100 mL) was added methanesulfonic anhydride (1.89 g, 1M solution in DCM, 10.84 mmol) followed by DIPEA (3.69 ml, 21.47 mmol) at 0° C. under argon. After 35 min, lithium bromide (LiBr) (3.92 g, solution in THF, 45.16 mmol) was added at 0° C. After 10 min, the reaction mixture was stirred at room temperature for 3 h. 200 ml of sodium citrate buffer (pH=6.40) were added and the mixture was diluted with 200 ml of MTBE. The organic layer was washed with 200 ml of sodium citrate buffer (pH=4.76), 200 ml of saturated $NaHCO_3$ solution and 200 ml of NaCl solution in sequence. Organic layers were combined and dried over $MgSO_4$, concentrated and purified on silica column with a gradient of 0 to 100% MTBE in hexane. Fractions containing the product were combined and evaporated under reduced pressure and lyophilized affording the pure product (5.96 g, 93%).

MS (ESI+): m/z found: ca. 586/approx 588 calc.: 586.23/588.23 $[M+H]^+$; found: ca.608/610.28 calc.: 608.21/610.21 $[M+Na]^+$.

Step 5: 6'-[Boc-Val-Ala(SEM)-PAB]-α-amanitin (HDP 30.1698)

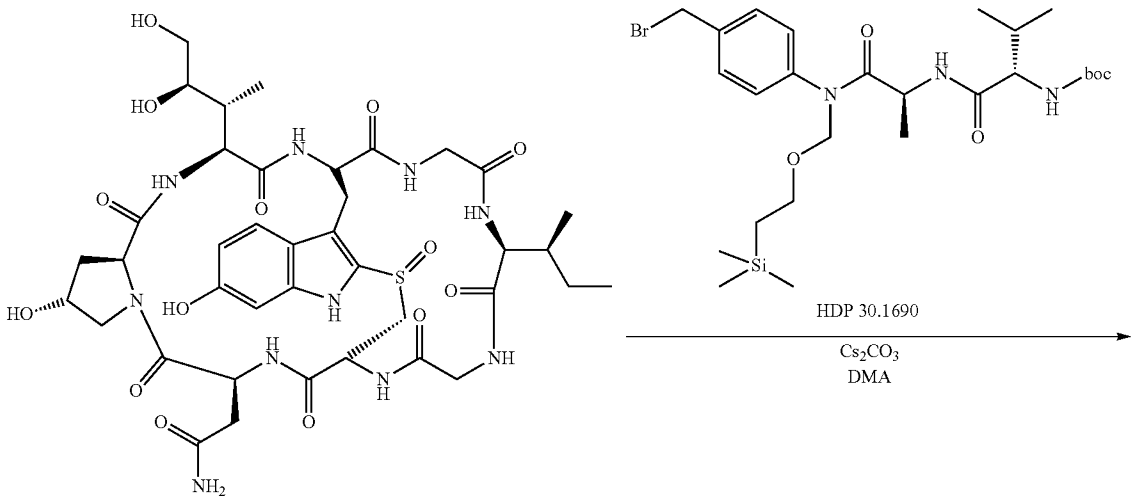

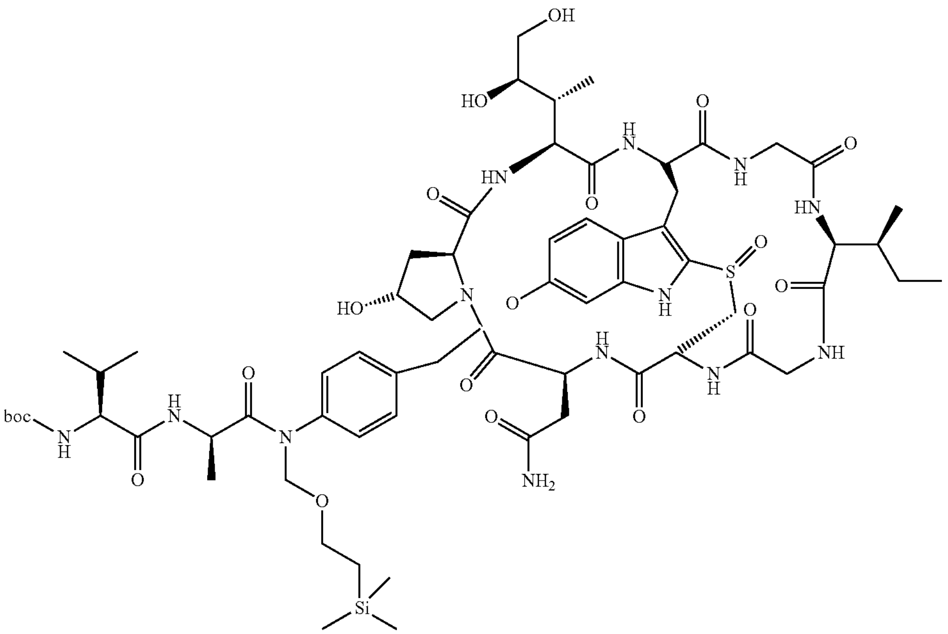

HDP 30.1698

Under argon and at room temperature 57 mg (62.02 μmol) of vacuum dried α-amanitin were dissolved in 3000 μl dry dimethyl acetamide (DMA). Step 4 product (145.5 mg, 248.1 μmol) and 0.2M cesium carbonate ($Cs_2CO_3$) (372.2 μl, 74.43 μmol) were added. After 4 h at room temperature the reaction mixture was acidified to pH=5 with 10 μl of AcOH. The solvent was removed in vacuo and the residue was purified by preparative HPLC on a C18 column [λ=305 nm; gradient: 0-5 min 5% B; 20-25 min 100% B; 27-35 min 5% B; A=water; B=methanol]. The fractions containing the product were evaporated to 54.46 mg (62%) of HDP 30.1698.

MS (ESI+): m/z found: 1425.23 calc.: 1424.6

Step 6: 6'-[H-Val-Ala-PAB]-α-amanitin (HDP 30.1702)

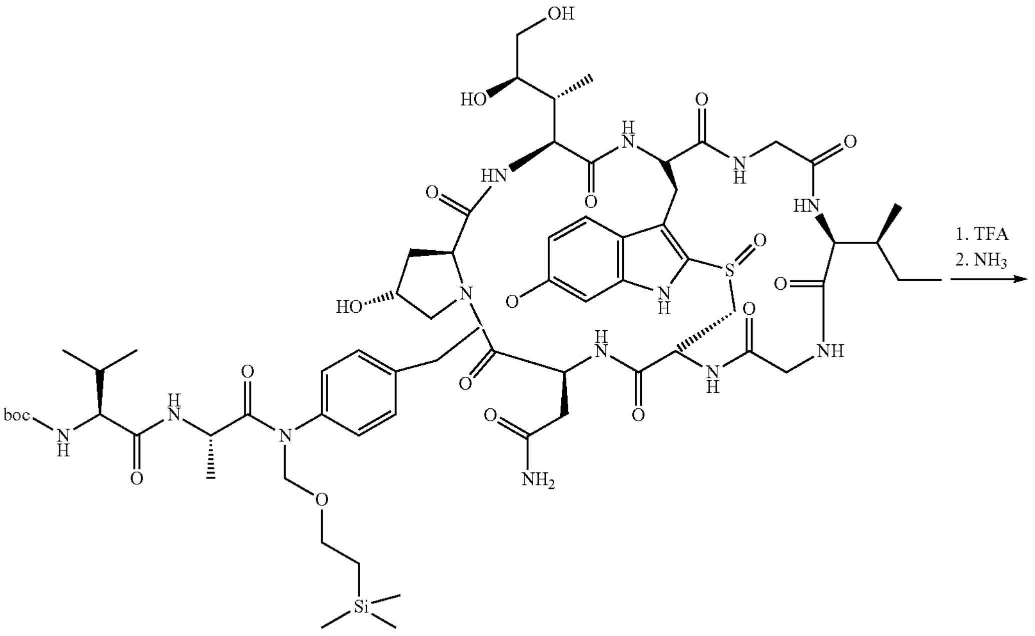

HDP 30.1697

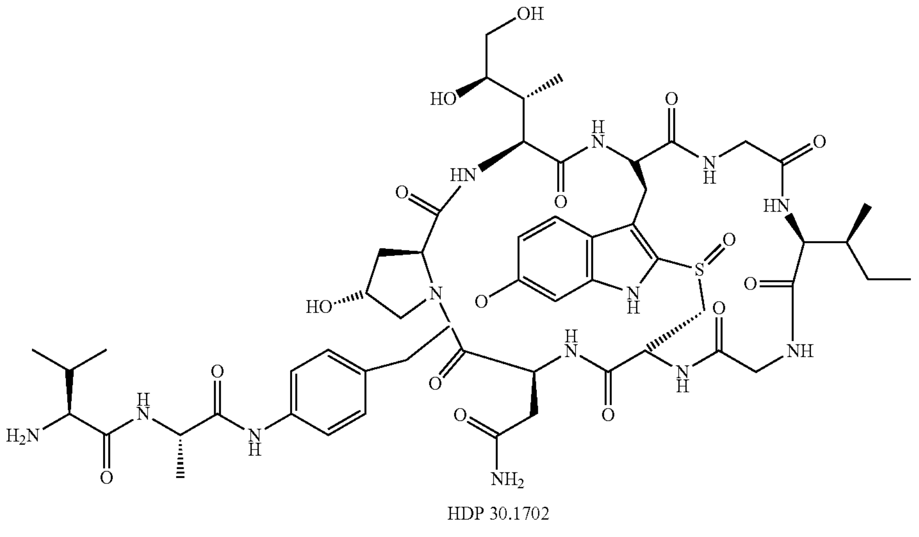

HDP 30.1702

The Boc- and SEM-protected step 5 product (134.29 mg, 94.25 μmol) was dissolved in 5 ml of TFA. After 2 min the mixture was evaporated to dryness at room temperature, redissolved in 5 ml of water, and adjusted to pH 10 with 3.2% ammonia added dropwise. The resulted suspension was freeze-dried, applied to RP18-HPLC [λ=305 nm; gradient: 0-2 min 5% B; 2-10 min 20% B; 10-10.5 min 25% B; 10.5-13 min 100% B; 13-14 min 5% B; A=water with 0.05% TFA; B=acetonitrile] and the pure fractions were evaporated and lyophilized to 68.59 mg (55%) of colorless powder.

MS (ESI+): m/z found: 1194.8 calc.: 1194.53 $[M+H]^+$; found: 1217.8 calc.: 1216.51 $[M+Na]^+$.

Example 19

6'-[(6-maleidohexanamido]-Val-Cit-PAB)-α-amantin (HDP 30.1919)

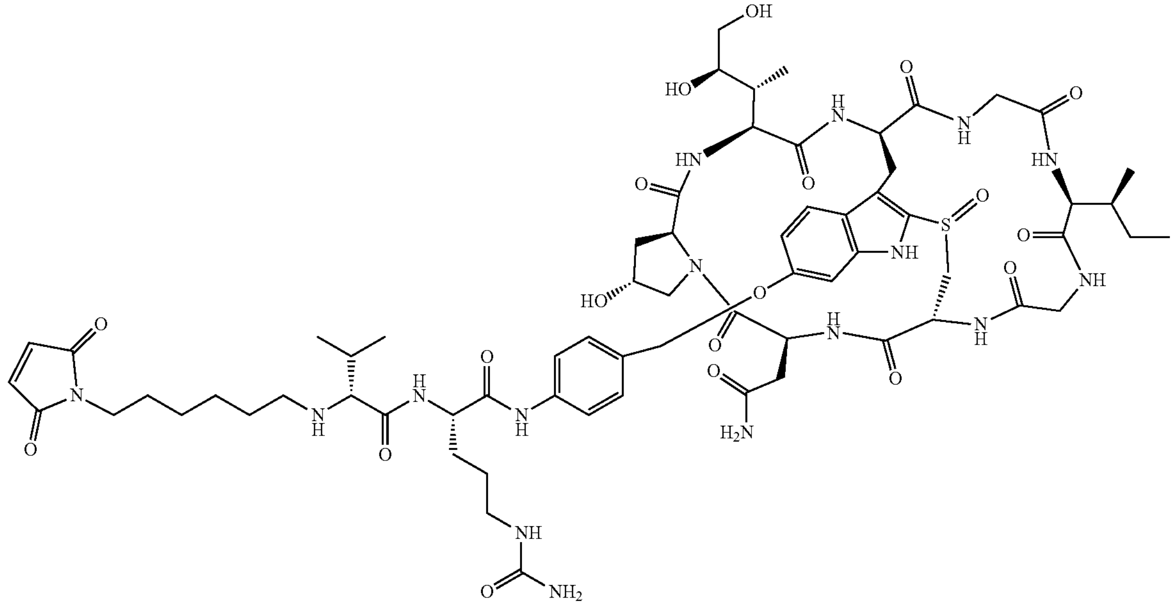

HDP 30.1919

By repeating the methods of example 18 steps 1-6 with Boc-Val-Cit-PAB-OH as starting material and by applying the procedure reported in example 25 the title substance was obtained as colorless powder:

MS (ESI+): m/z found: 1473.60; calc.: 1473.65 $[MH]^+$

Example 20
6'-[H-Val-Ala-(N-methyl)-PAB]-α-amanitin (HDP 30.1584)
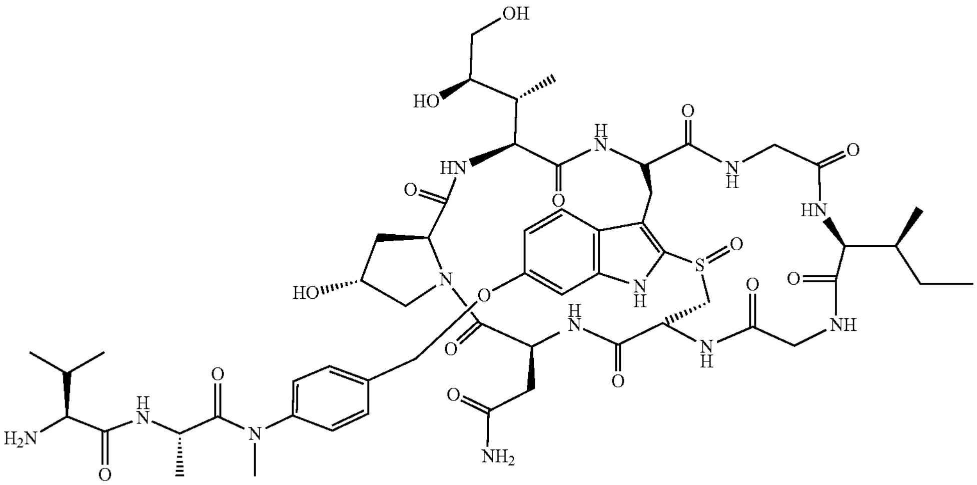
HDP 30.1584
By repeating the methods of example 17 steps 1-6 with Boc-Val-Ala-(N-methyl)-PAB-OH as starting material the title substance was received as colorless powder:
MS (ESI+): m/z found: 1208.59 calc.:1208.54 $[M+H]^+$; found: 1230.61 calc.:1230.52 $[M+Na]^+$.
Example 21
6'[(2-Bromo-acetamido)-Val-Ala-PAB]-α-amantin (HDP 30.1704)
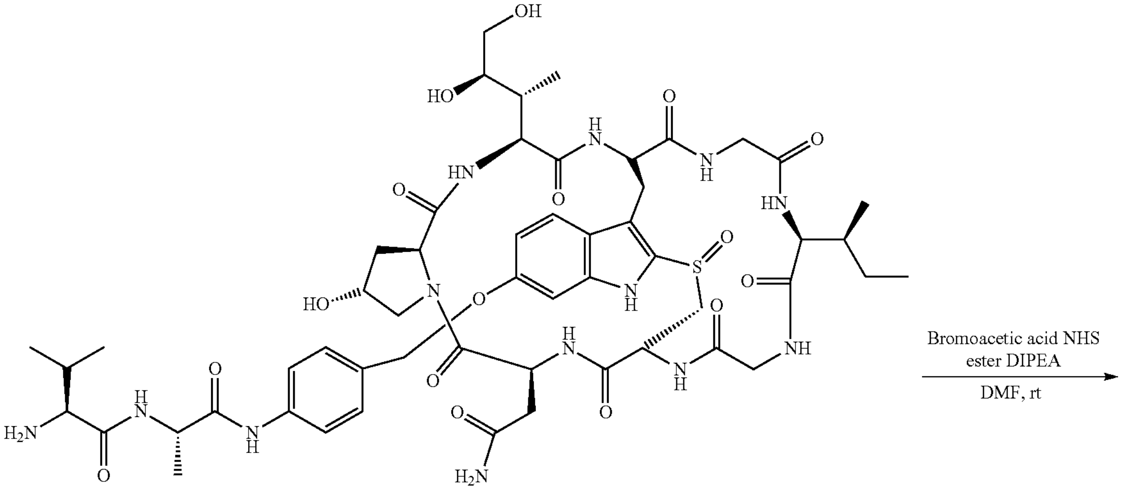
HDP 30.1702

-continued

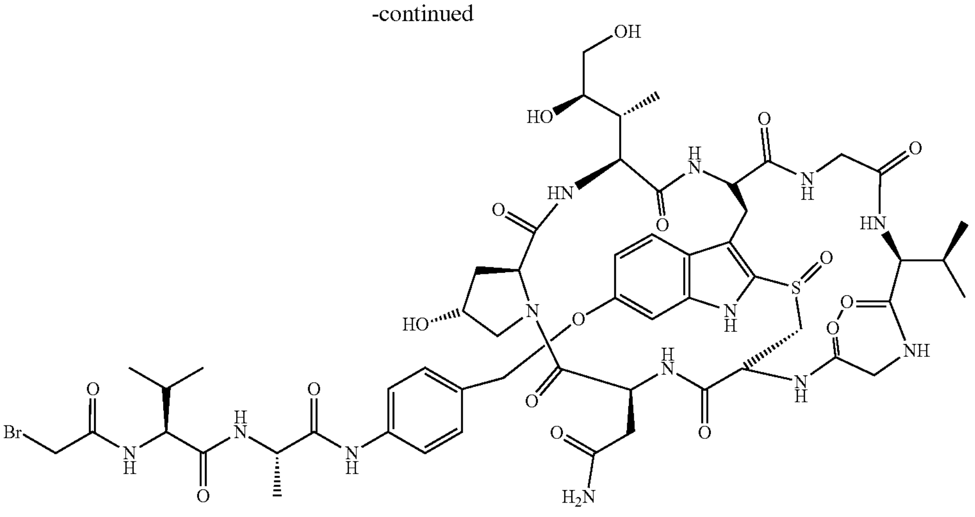

HDP 30.1704

HDP 30.1702 (15 mg, 11.5 μmol) was dissolved in dry DMF (457.26 μl). 0.1 M solution of bromoacetic acid N-hydroxysuccinimide ester (229.2 μl, 22.9 μmol, 2.0 eq) and 0.1 M solution of DIPEA (458.4 μl, 45.84 μmol, 4.0 eq) were added and reaction mixture was stirred at room temperature. After 1 hour, reaction mixture was diluted with MTBE (40 ml). The precipitate was cooled to 0° C. for 10 minutes, isolated by centrifugation (4000×g) and washed with MTBE (40 ml) subsequently. The supernatants were discarded. The pellet was dried, redissolved in MeOH (200 μl) and purified by preparative RP-HPLC on a C18 column [λ=305 nm; gradient: 0-5 min 5% B; 20-25 min 100% B; 27-35 min 5% B; A=water with 0.05% TFA; B=methanol with 0.05% TFA] to afford 6.26 mg (42%) of product as white powder after lyophilization.

MS(ESI+): m/z found: 1338.33, calc.: 1338.27 $[M+Na]^+$.

Example 22

6'-O-[6-(2-Bromoacetamido)hexyl]-α-amanitin (HDP 30.1619)

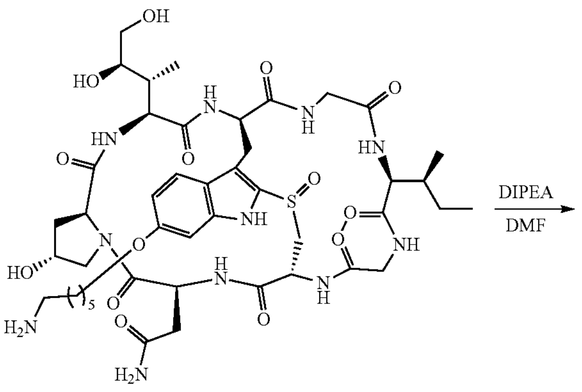

HDP 30.0134

-continued

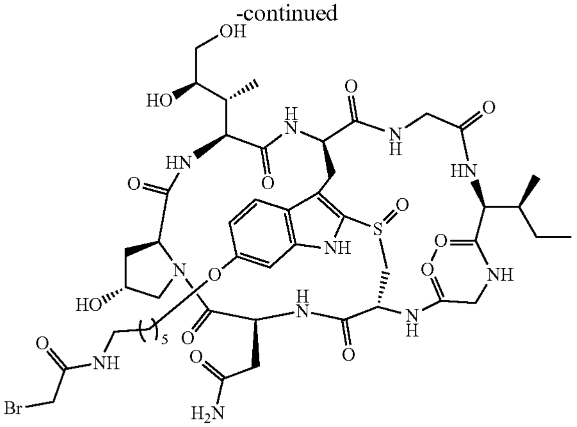

HDP 30.1619

HDP 30.1619 was prepared by using the procedure described herein in Example 21, starting from HDP 30.0134 as amanitin precursor. The product was isolated as white powder (12.34 mg, 83%).

MS(ESI+): m/z found: 1162.42, calc.: 1162.09 $[M+Na]^+$.

Example 23

6'-[(3,4-bis(phenylthio)-3-maleidopropanamido)-Val-Ala-PAB)-α-amantin (HDP 30.1751)

Step 1: 3,4-Dibromo-2,5-dioxo-2,5-dihydro-pyrrole-1-carboxylic acid methyl ester (HDP 30.1621)

3,4-dibromo-N-methyl ester maleimide was synthetized from the corresponding 3,4-dibromomaleimide by adapting the procedure disclosed by Castañeda et al. in *Tetrahedron Lett.* 2013, 54, 3493-3495.

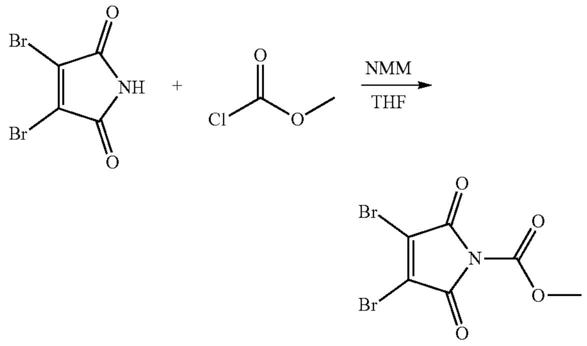

HDP 30.1621

3,4-dibromomaleimide (5 g, 19.92 mmol) was dissolved in THF (175 ml). N-methylmorpholine (2.16 ml, 19.92 mmol) and methyl chloroformate (1.51 ml, 19.92 mmol) were added at room temperature under argon. The reaction mixture was stirred at room temperature under argon for 20 min, then diluted with DCM (200 ml). The organic layer was washed with water (200 ml), dried over $MgSO_4$, concentrated and lyophilized to yield 6.15 g (100%) of product.

$^1H$ NMR (500 MHz, $CDCl_3$): δ=4.01 (s, 3H). $^{13}C$ NMR (126 MHz, $CDCl_3$): 5=159.23, 146.91, 131.41, 54.79.

Step 2: 3,4-Dibromo-2,5-dioxo-2,5-dihydro-pyrrol-1-yl)-acetic acid tert-butyl ester (HDP 30.1732)

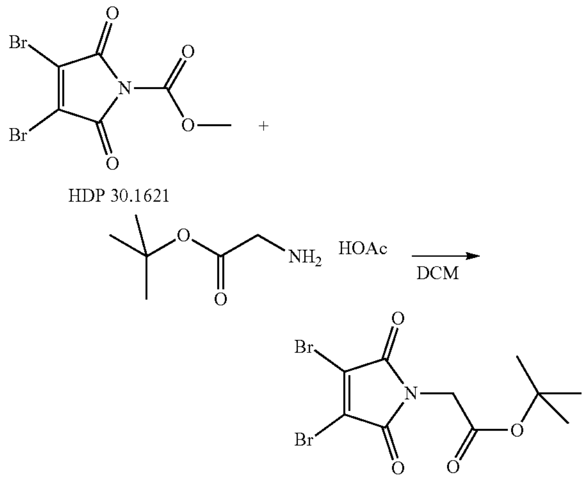

HDP 30.1732

HDP 30.1621 (2.23 g, 7.13 mmol) was dissolved in DCM and tert-butyl glycine monoacetate (1.36 g, 7.13 mmol) was added. The reaction mixture was stirred at room temperature for 1 h and 30 min. After that, the mixture was evaporated and the residue redissolved in DCM. Diatomaceous earth (25 g) was added and volatiles were removed under reduced pressure. The residue was purified on silica gel column with a gradient of 0 to 50% MTBE in hexane. The fractions containing the product were combined and concentrated to afford 2.31 g (88%) of HDP 30.1732 as white crystals.

$^1H$ NMR (500 MHz, $CDCl_3$): δ=4.25 (s, 2H), 1.46 (s, 9H). $^{13}C$ NMR (126 MHz, $CDCl_3$): δ 165.45, 163.32, 129.73, 83.44, 40.85, 27.93.

Step 3: [2,5-Dioxo-3-phenylsulfanyl-4-(1-vinyl-penta-1,3-dienylsulfanyl)-2,5-dihydro-pyrrol-1-yl]-acetic acid tert-butyl ester (HDP 30.1660)

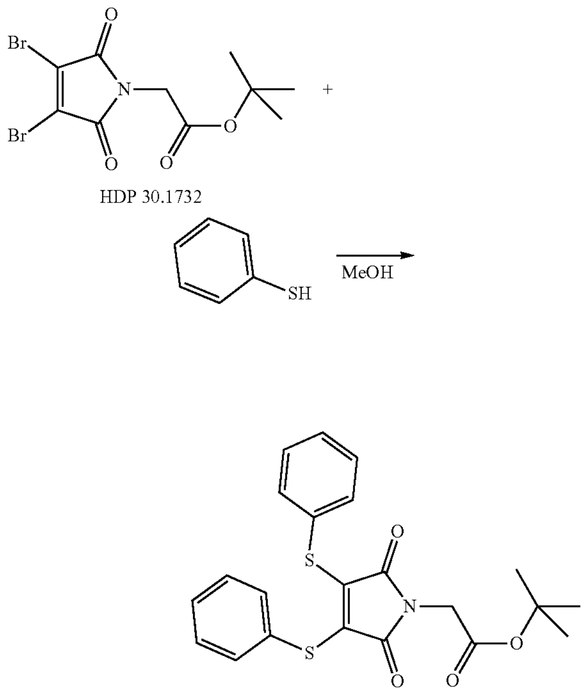

HDP 30.1660

2.31 g (6.26 mmol) of HDP 30.1732 were dissolved in MeOH (50 ml). Sodium acetate (NaOAc) (1.18 g, 14.40 mmol) and thiophenol (PhSH) (1.47 ml, 14.40 mmol) were added at room temperature. After 2 h, diatomaceous earth (12 g) was added to the reaction mixture and volatiles were removed under reduced pressure. The residue was purified on silica gel column with a gradient of 0 to 20% MTBE in hexane. The fractions corresponding to the product were combined and concentrated to yield 2.55 g (95%) of target material as yellow oil.

MS (ESI+): m/z found: 450.07 calc.: 450.08 $[M+Na]^+$; found: 372.09 calc.: 372.04 $[MH-C_4H_8]^+$.

Step 4: (2,5-Dioxo-3,4-bis-phenylsulfanyl-2,5-dihydro-pyrrol-1-yl)-acetic acid (HDP 30.1730)

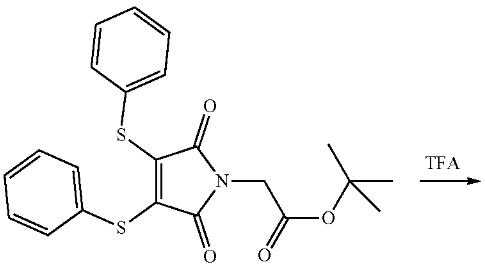

HDP 30.1660

-continued

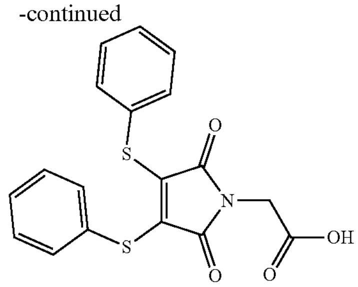

HDP 30.1730

-continued

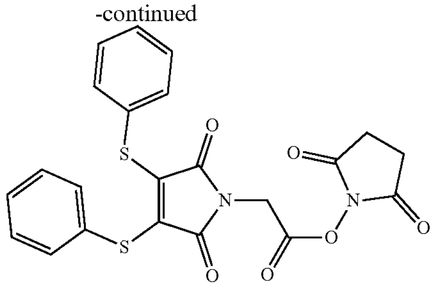

HDP 30.1746

HDP 30.1660 (2.55 g, 5.96 mmol) was dissolved in TFA (30 ml) and stirred at room temperature for 5 min. After that, TFA was co-evaporated with toluene (2×30 ml) in vacuo, affording HDP 30.1730 (2.78 g) as orange oil, which was used in the next reaction without further purification.

MS (ESI+): m/z found: 372.16 calc.: 372.04 $[M+H]^+$; found: 326.24 calc.: 326.03 $[MH-HCO_2]^+$.

Step 4: 2,5-dioxopyrrolidin-1-yl 2-(2,5-dioxo-3,4-bis(phenylthio)-2,5-dihydro-1H-pyrrol-1-yl)acetate (HDP 30.1746)

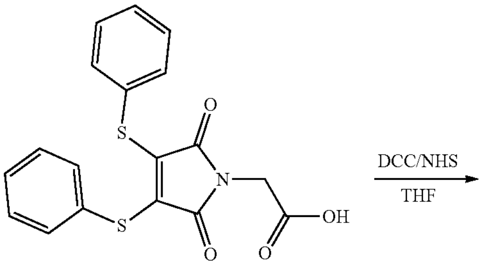

HDP 30.1730

HDP 30.1730 (2.78 g,max. 6.26 mmol) was dissolved in THF (60 ml). and HOSu (793 mg, 6.56 mmol) was added. DCC (1.42 g, 6.89 mmol), dissolved in 28 ml THF was added. After 22 h of stirring at room temperature, the dicyclohexylurea (DCU) was filtered off and the filtrate was evaporated. The residue was redissolved in DCM (60 ml) and additional DCU was filtered off with suction . . . The residue was purified on silica gel column with a gradient of 0 to 20% MTBE in DCM. The fraction containing the product was evaporated, affording the compound (2.12 g, 72%) as orange solid.

$^1H$ NMR (500 MHz, $CDCl_3$): δ=7.33-7.20 (m, 10H), 4.58 (s, 2H), 2.81 (s, 4H). $^{13}C$ NMR (126 MHz, $CDCl_3$): δ=167.89, 164.83, 162.89, 136.03, 131.87, 128.83, 128.40, 128.35, 36.91, 25.27.

Step 5 6'-[(3,4-Bis(phenylthio)-3-maleido-ethan-amido)-Val-Ala-PAB]-α-amantin (HDP 30.1751)

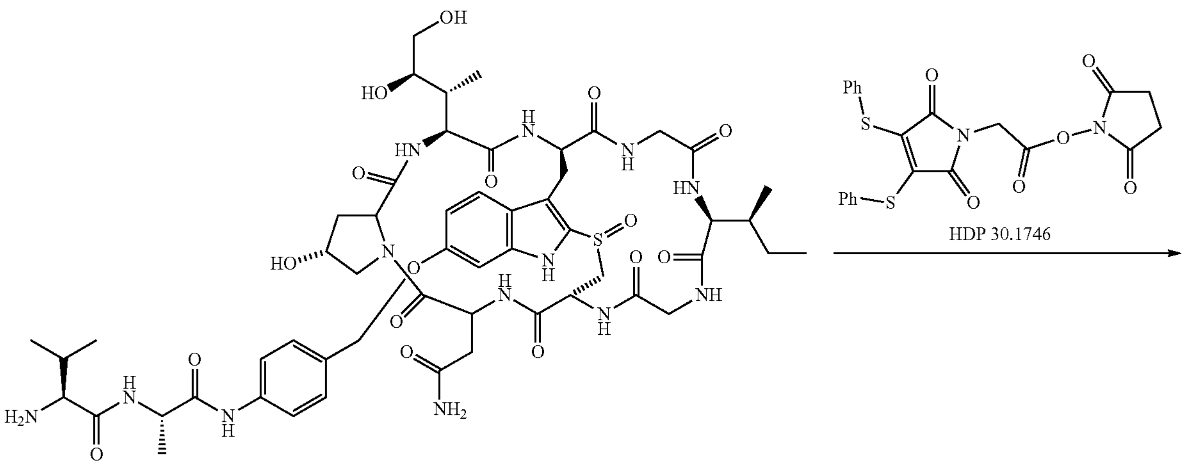

-continued

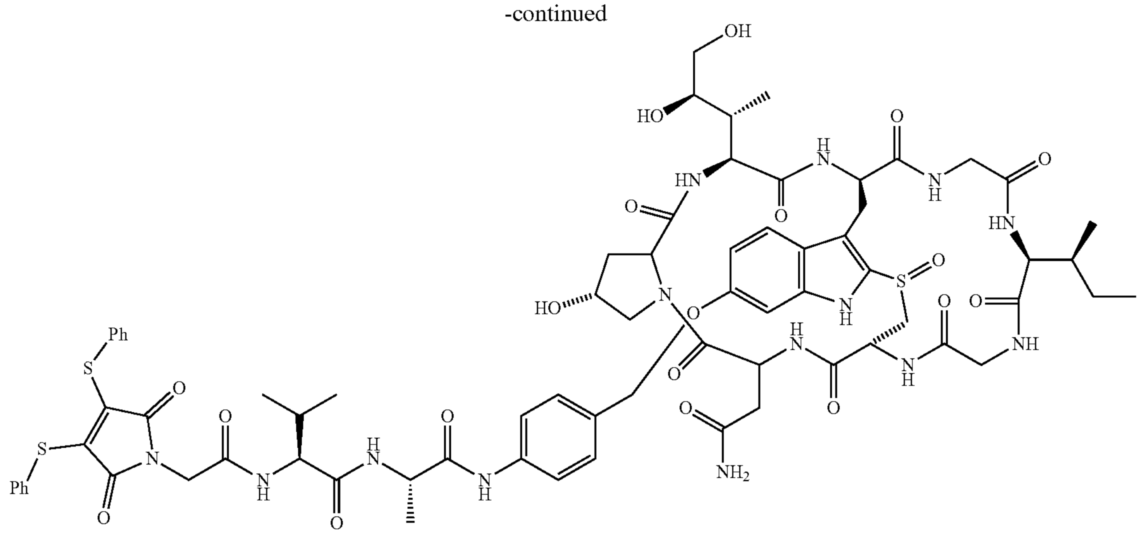

HDP 30.1751

To HDP 30.1702 (15.00 mg, 11.46 μmol) dissolved in 2 ml of dry DMF were added subsequently 1.72 ml (34.39 μmol) of HDP 30.1746 solution (20 mM in DMF) and DIPEA (5.85 μl, 34.39 μmol). After 2 h at room temperature under argon, mixture was evaporated in vacuo, and the residue was dissolved in MeOH (200 μl) and dripped into 10 ml of cold MTBE, and centrifuged at 0° C. The precipitate was collected, washed with additional 10 ml of MTBE and centrifuged again. The crude product was dried and then purified by preparative RP-HPLC [λ=305 nm; gradient: 0 min 5% B; 0-1 min 30% B; 1-10 min 39% B; 10-13 min 100% B; 13-18 min 5% B; A=water; B=methanol]. The fractions containing the product were concentrated and lyophilized to 9.27 mg (52%) of product as white powder.

MS (ESI+): m/z found: 796.63 calc.: 796.26 $[M+2Na]^{2+}$

Example 24

6'-[(3-maleimidopropanamido)-Val-Ala-PAB]-α-amantin (HDP 30.1699)

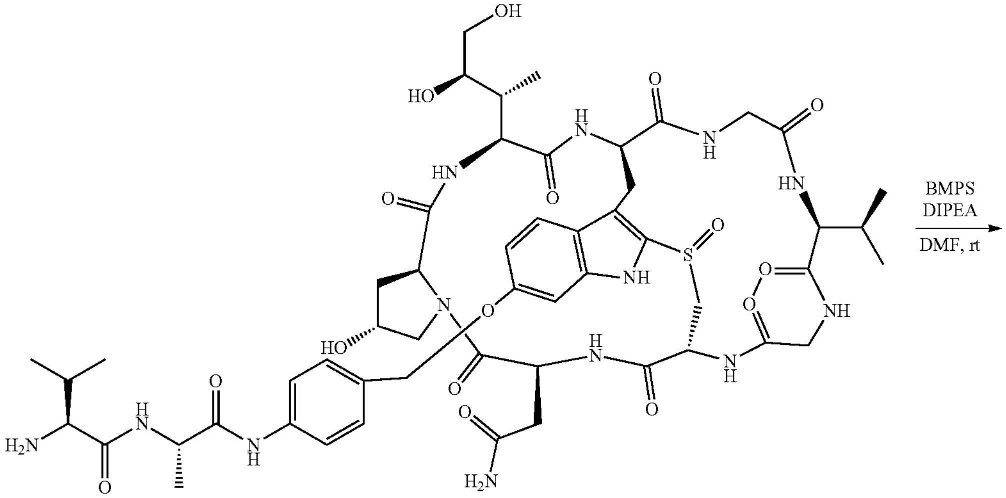

HDP 30.1702

-continued

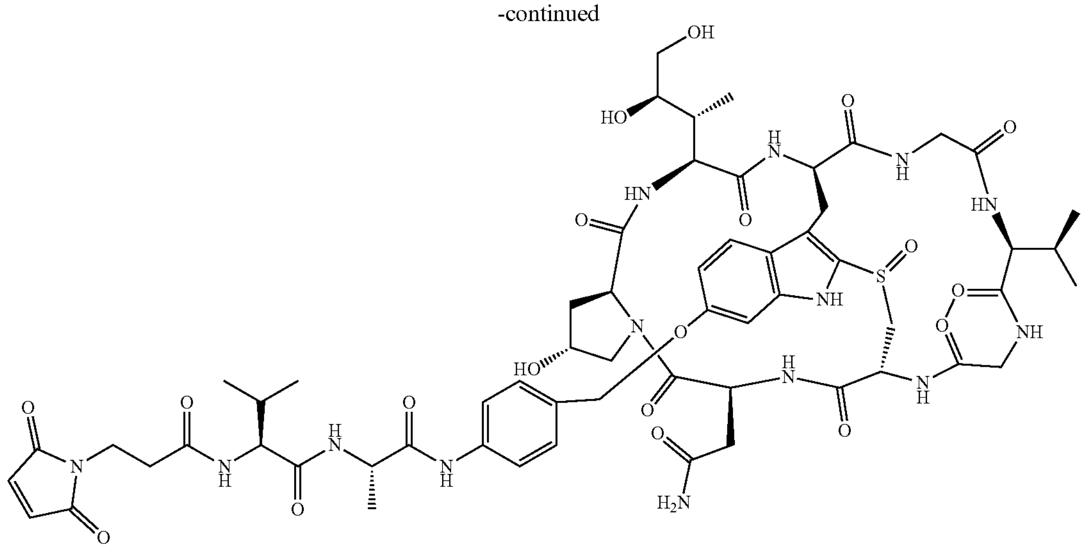

HDP 30.1699

HDP 30.1702 (17.09 mg, 14.3 μmol) was dissolved in dry DMF (350 μl). 3-(maleimido)propanoic acid N-hydroxysuccinimide ester (BMPS) (7.62 mg, 28.6 μmol, 2.0 eq) dissolved in DMF (350 μl), and undiluted DIPEA (9.79 μl, 57.2 μmol, 4.0 eq) were added. After 1 h and 30 minutes of stirring at room temperature under argon, mixture was dripped into 40 ml of cold MTBE and centrifuged at 0° C. The precipitate was collected and washed with 40 ml of MTBE and centrifuged again. The crude product was dried and purified by RP18-HPLC [λ=305 nm; gradient: 0-5 min 5% B; 20-25 min 100% B; 27-35 min 5% B; A=water with 0.05% TFA; B=methanol with 0.05% TFA]. The pure fractions were lyophilized to yield 12.51 mg (65%) of title product 6'-[(3-maleidopropanamido)-Val-Ala-PAB]-α-amanitin as white powder.

MS (ESI+): m/z found: 1367.50 calc.: 1368.45 $[M+Na]^+$.

Example 25

6'-[(6-maleimidohexanamido)-Val-Ala-PAB]-α-amantin (HDP 30.2254)

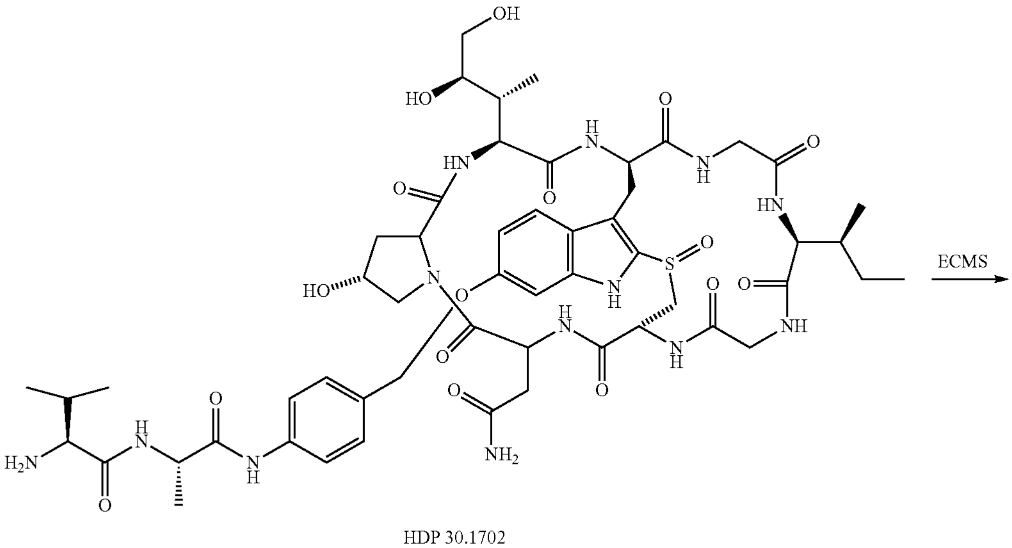

HDP 30.1702

-continued

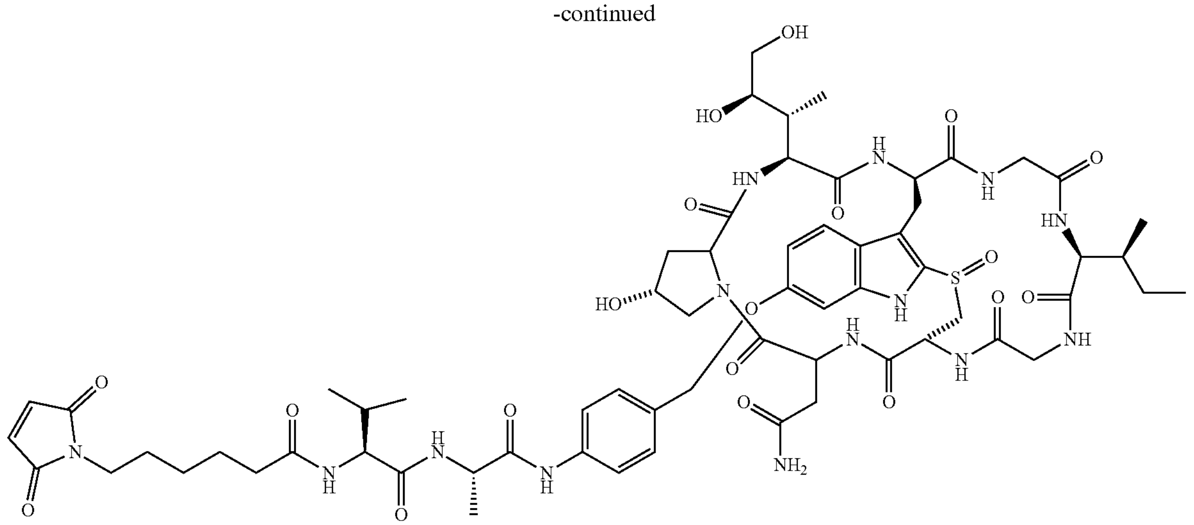

HDP 30.2254

HDP 30.1702 (23.49 mg, 17.9 μmol) was dissolved in dry DMF (400 μl). 6-(maleimido)hexanoic acid N-hydroxysuccinimide ester (ECMS) (11.07 mg, 35.9 μmol) dissolved in DMF (562 μl), and DIPEA (12.21 μl, 7.16 μmol) were added. After 2 h at room temperature under argon, mixture is dripped into 40 ml of cold MTBE and centrifuged at 0° C. The precipitate was collected and washed with 40 ml of MTBE and centrifuged again. The crude product was dried and purified by RP18-HPLC [λ=305 nm; gradient: 0-5 min 5% B; 20-25 min 100% B; 27-35 min 5% B; A=water with 0.05% TFA; B=methanol with 0.05% TFA]. The pure fractions were lyophilized to yield 21.03 mg (86%) of title product 6'-[(6-Maleidohexanamido)-Val-Ala-PAB]-α-amanitin as white powder.

MS (ESI+): m/z found: 1145.7 calc.: 1144.99 $[M+Na]^+$.

Example 26

6'-O-[6-((Glu-ureido-Lys)-ureido)-hexyl]-α-amanitin (HDP 30.1585)

Step 1: 6'-O-[6-((Glu($^t$BuO)$_3$-ureido-Lys)-ureido)-hexyl]-α-amanitin (HDP 30.1581)

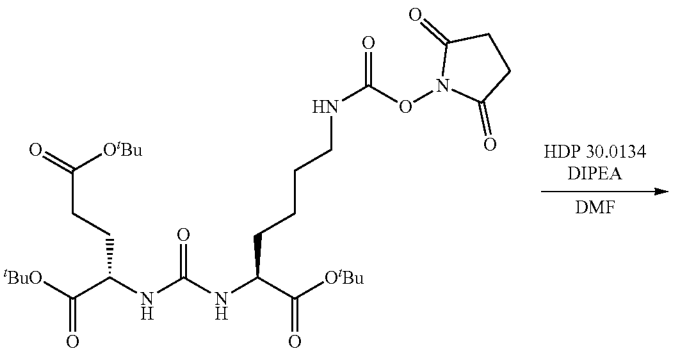

HDP 30.1579

-continued

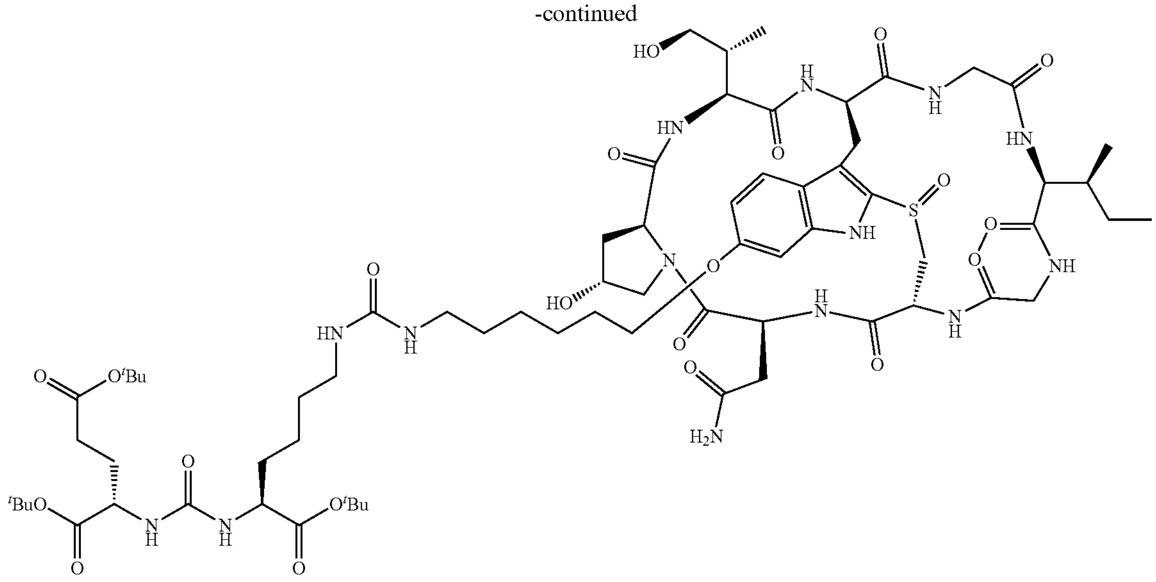

HDP 30.1581

To a solution of 6"-O—(-6-aminohexyl)-α-amanitin (HDP 30.0134, synthesized as disclosed in EP 2621536), (11.32 mg, 10 mmol) in DMF (1 ml) a solution of HDP 30.1579 (12.57 mg, 20 mmol) in DMF (1 ml) was added, while DIPEA (5.10 μl, 30 mmol) was added neat. After 17 h, water (100 μl) was added and the mixture was concentrated under high vacuum. The crude product was purified by preparative RP-HPLC [λ=305 nm; gradient: 0-5 min 5% B; 20-25 min 100% B; 27-35 min 5% B; A=water; B=methanol]. Pure fractions were combined, concentrated and lyophilized for 24 h affording the conjugate HDP 30.1581 (13.38 mg, 87%) as colorless residue.

MS (ESI+): m/z found: 1531.61 calc.: 1531.77 $[M+H]^+$; found: 1553.79 calc.: 1553.75 $[M+Na]^+$; found: 1475.56 calc.: 1475.71 $[MH-^tBu]^+$; found: 1419.53 calc.: 1419.65 $[MH-2\bullet^tBu]^+$; found: 1363.54 calc.: 1363.58 $[MH-3\bullet^tBu]^+$.

Step 2: 6'-O-[6-((Glu-ureido-Lys)-ureido)-hexyl]α-amanitin (HDP 30.1585)

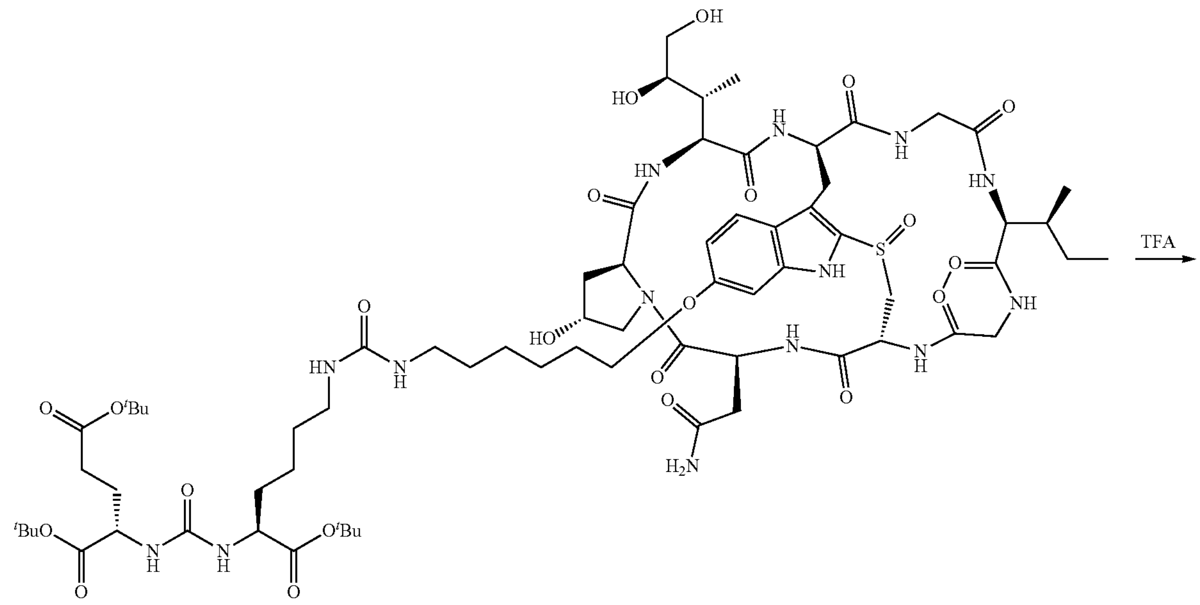

HDP 30.1581

-continued

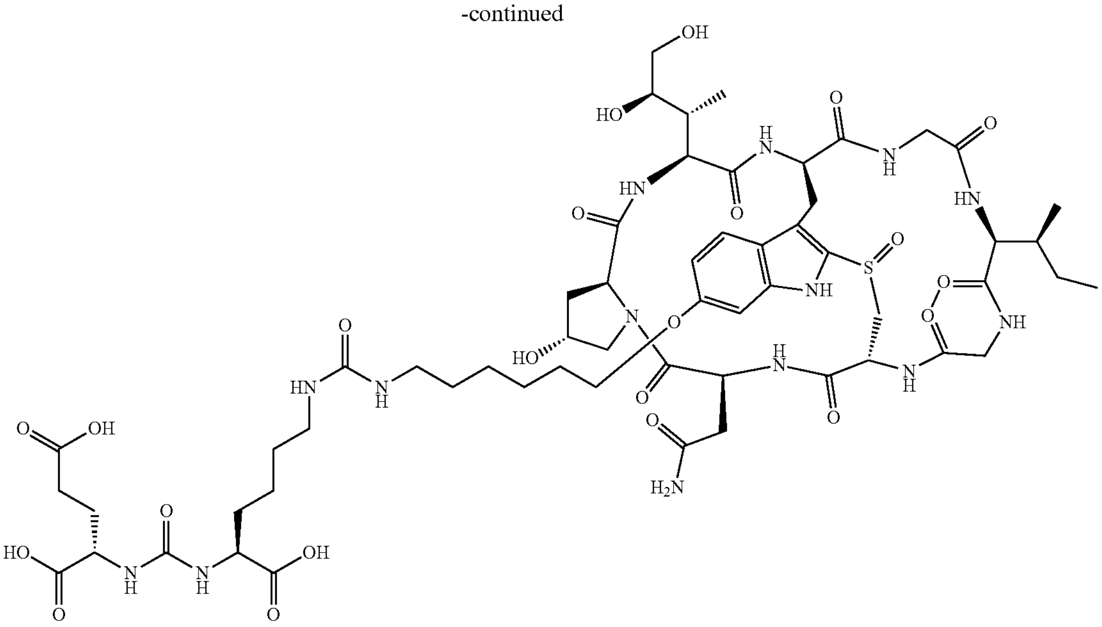

HDP 30.1585

HDP 30.1581 (13.38 mg, 8.73 μmol) was dissolved in TFA (1 ml) and the mixture was stirred at room temperature for 2 min and then concentrated under reduced pressure. The residue was dissolved again in TFA (1 ml) and the mixture was stirred at room temperature for 5 min and then concentrated under reduced pressure. The crude product was purified by preparative RP-HPLC [λ=305 nm; gradient: 0-5 min 5% B; 20-25 min 100% B; 27-35 min 5% B; A=water with 0.05% TFA; B=methanol with 0.05% TFA]. Pure fractions were combined, concentrated and lyophilized for 24 h to yield the product HDP 30.1585 (6.82 mg, 57%) as colorless solid.

MS (ESI+) found: 1363.56 calc.: 1363.58 $[M+H]^+$; found: 1385.59 calc.: 1385.57 $[M+Na]^+$.

Example 27

6'-O-[-((Glu-ureido-Lys)-ureido-Val-Ala-(N-methyl) PAB]-α-amanitin (HDP 30.1592)

Step 1: 6'-O-[(Glu($^t$BuO)$_3$-ureido-Lys)-ureido-Val-Ala-(N-methyl)PAB]-α-amanitin (HDP 30.1588)

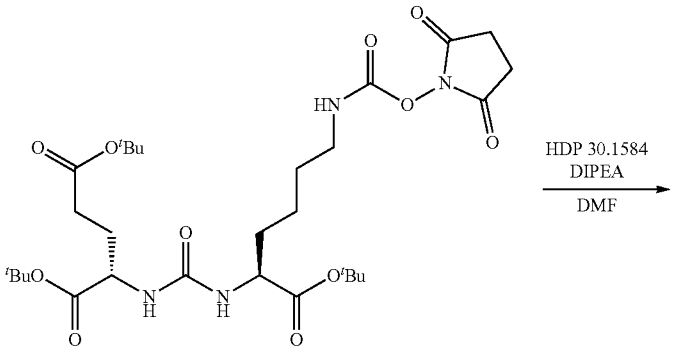

HDP 30.1579

-continued

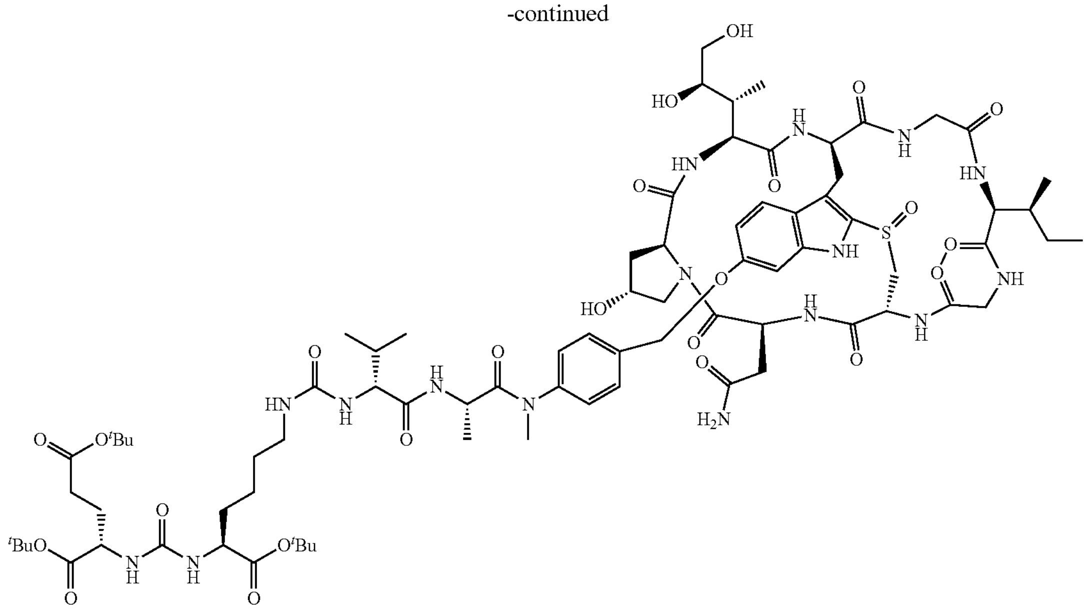

HDP 30.1588

To a solution of HDP 30.1584 (7.68 mg, 5.81 mmol) in DMF (1 ml) a solution of HDP 30.1579 (7.30 mg, 11.61 mmol) in DMF (1 ml) was added, while DIPEA (3.95 μl, 23.23 mmol) was added neat. After 22 h, $H_2O$ (100 μl) was added and the mixture was concentrated under high vacuum. The crude product was purified by preparative RP-HPLC [λ=305 nm; gradient: 0-5 min 5% B; 20-25 min 100% B; 27-35 min 5% B; A=water; B=methanol]. Pure fractions were combined, concentrated and lyophilized for 24 h affording the conjugate HDP 30.1588 (8.42 mg, 84%) as colorless residue.

MS (ESI+): m/z found: ca. 1721 calc.: 1721.85 $[M+H]^+$; found: 1743.72 calc.: 1743.83 $[M+Na]^+$; found: 1665.52 calc.: 1665.78 $[MH-{}^tBu]^+$.

Step 2: 6'-O-[-((Glu-ureido-Lys)-ureido-Val-Ala-(N-methyl)PAB]-α-amanitin (HDP 30.1592)

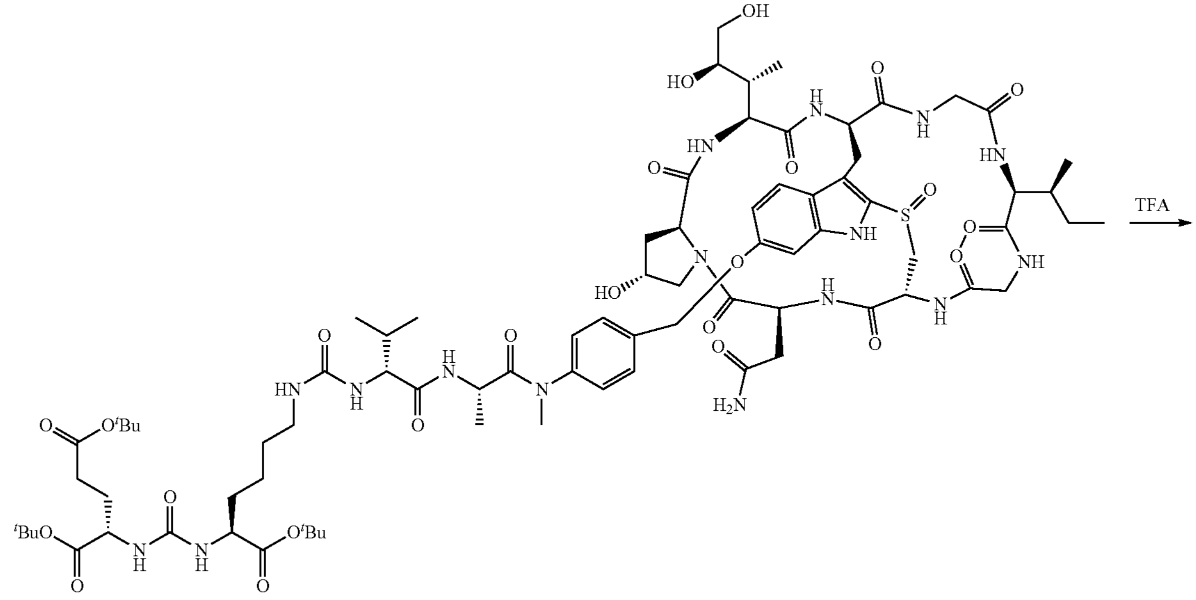

HDP 30.1588

-continued

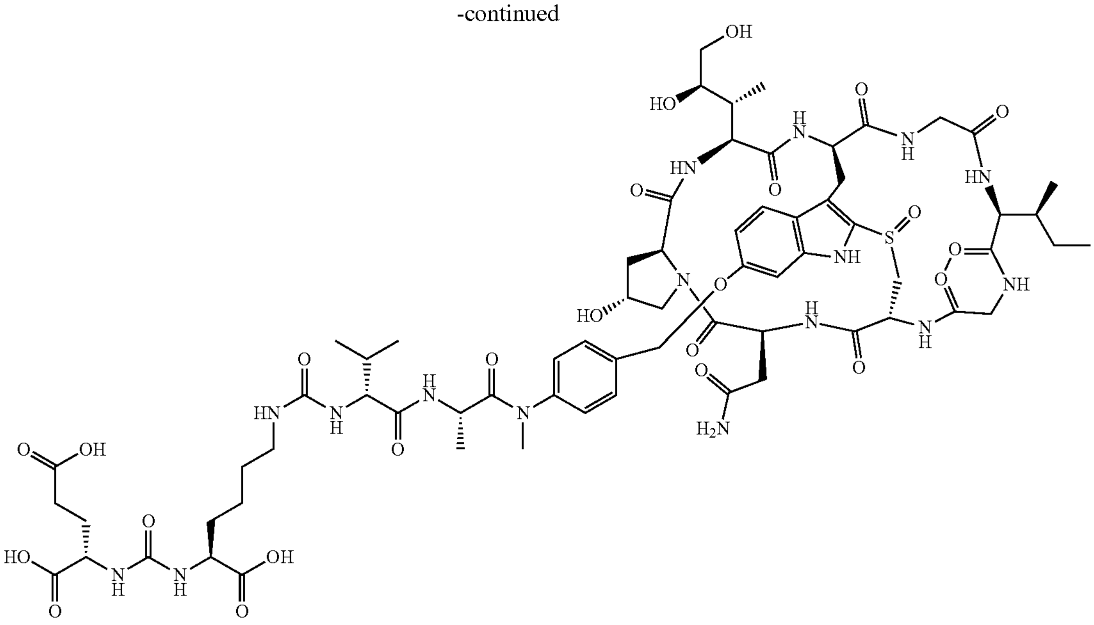

HDP 30.1592

HDP 30.1588 (8.42 mg, 4.89 μl) was dissolved in TFA (1 ml) and the mixture was stirred at room temperature for 2 min and then evaporated under reduced pressure. The residue was dissolved again in TFA (1 ml) and the mixture was stirred at room temperature for 5 min and then concentrated under vacuum. The crude product was purified by preparative RP-HPLC [λ=305 nm; gradient: 0-5 min 5% B; 20-25 min 100% B; 27-35 min 5% B; A=water with 0.05% TFA; B=methanol with 0.05% TFA]. Pure fractions were combined, concentrated and lyophilized for 24 h to yield the product HDP 30.1592 (4.37 mg, 58%) as colorless solid.

MS (ESI+): m/z found: 1553.49 calc.: 1553.66 $[M+H]^+$; found: 1575.56 calc.: 1575.64 $[M+Na]^+$; found: 1535.85 calc.: 1535.65 $[MH-H_2O]^+$.

Example 28

6'-O-[3-(DUPA-Aoc-Phe-Phe-Cys)-dithiapropyl]-α-amanitin (HDP 30.2246)

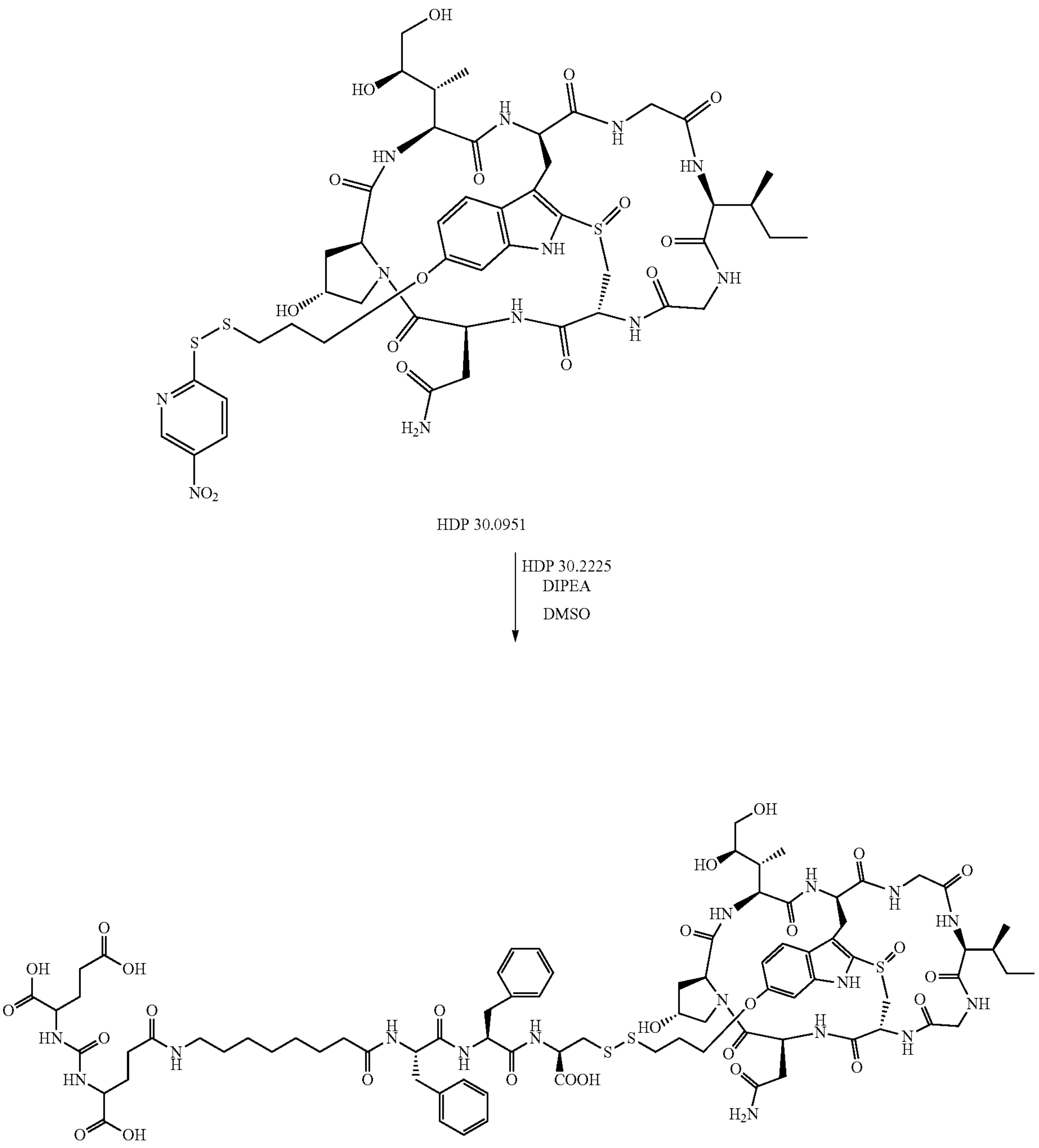

HDP 30.0951

HDP 30.2246

To a solution of HDP 30.2225 (13.4 mg, 15.6 μmol) in DMSO (1.5 ml) a solution of HDP 30.0951 (17.9 mg, 15.6 μmol) in DMSO (1.6 ml) was added at room temperature under argon. DIPEA (5.15 μl, 3.0 μmol) was added undiluted. The reaction mixture was stirred at room temperature for 3 h and 20 min. The orange crude product was purified by preparative RP-HPLC [λ=305 nm; gradient: 0-1 min 5% B; 1-14 min 54% B; 14-16 min 60.6% B; 16-23 min 100% B; 23-26 min 5% B; A=water with 0.05% TFA; B=acetonitrile]. The fractions containing the product were combined, concentrated and lyophilized for 24 h affording the compound HDP 30.2246 (11.36 mg, 40%) as white solid.

MS (ESI+): m/z found: 947.5 calc.: 948.0 $[M+2Na]^{2+}$ found: 1872.4 calc.: 1873.1 $[M+Na]^{+}$.

Example 29

6"-O-[3-(DUPA-Aoc-Phe-Phe-Cys-disulfanyl) butyl)]-α-amanitin (HDP 30.2589)

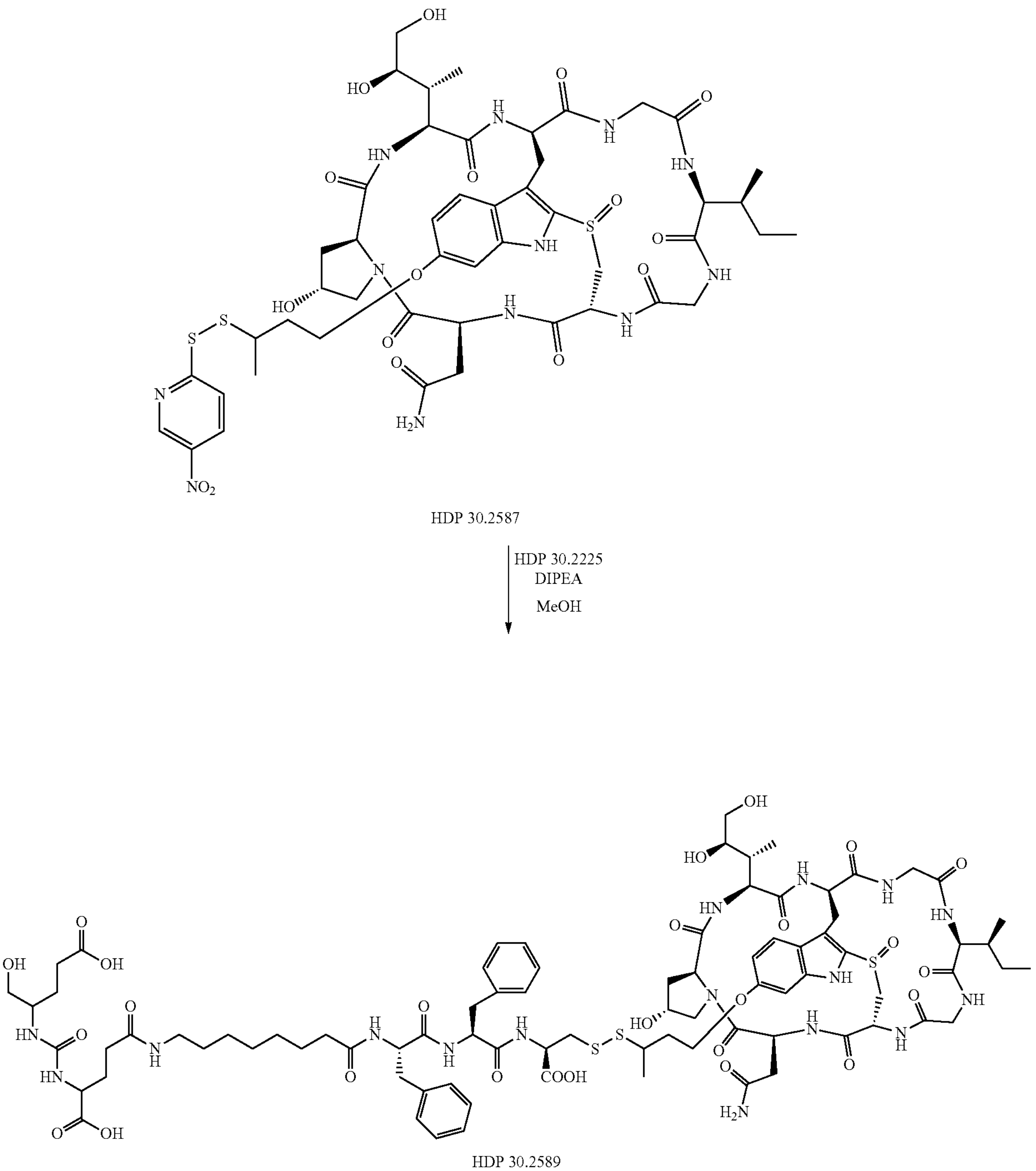

HDP 30.2587

HDP 30.2589

To a solution of HDP 30.2225 (2.27 mg, 2.6 μmol) in MeOH (135 μl) a solution of HDP 30.2587 (3.07 mg, 2.6 μmol) in MeOH (280 μl) was added at room temperature under argon. DIPEA (0.9 μl, 5.2 μmol) was added undiluted. The reaction mixture was stirred at room temperature for 24 hours and solvent was then evaporated. The residue was dissolved in MeOH (200 μl) and purified by preparative RP-HPLC [λ=305 nm; gradient: 0 min 5% B; 15 min 100% B; 18 min 100% B; 18.50 min 100% B; 22 min 5% B; A=water with 0.05% TFA; B=acetonitrile]. The fraction containing the product was concentrated and lyophilized for 24 h affording the compound HDP 30.2589 (2.79 mg, 58%) as white solid.

MS (ESI−): m/z found: 1862.58 calc.: 1861.71 [M−H]$^-$.

Example 30

6'-O-[3-(DUPA-Aoc-Phe-Phe-(4-amido-2-methylbutan-2-yl)disulfanyl)-propyl]-α-amanitin (HDP 30.2609)

Step 1: 6"—O-[3-(($Bu^tO)_2DUPA^{OtBu}$-Aoc-Phe-Phe-(4-amido-2-methylbutan-2-yl)-disulfanyl)-propyl]-α-amanitin (HDP 30.2606)

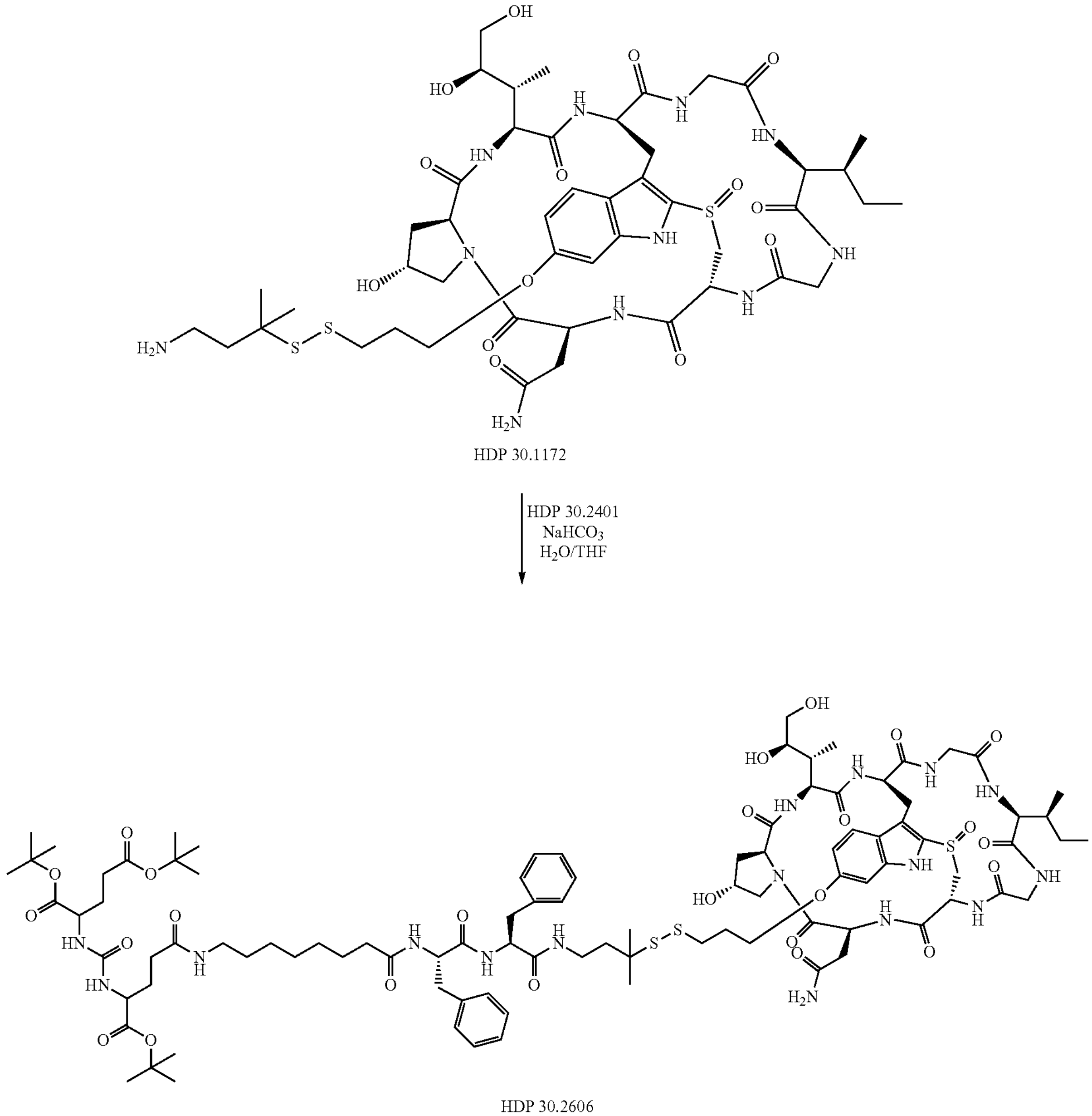

HDP 30.1172 (5.07 mg, 4.6 μmol) and $NaHCO_3$ (0.92 mg, 10.9 μmol) were dissolved in $H_2O$/THF mixture (20:80, 248 μl) and HDP 30.2401 (5.13 mg, 5.03 μmol) was added. The reaction mixture was stirred at room temperature for 3 hours and solvent was then evaporated. The residue was dissolved in MeOH (200 μl) and purified by preparative RP-HPLC [λ=305 nm; gradient: 0-5 min 5% B; 20-25 min 100% B; 27-35 min 5% B; A=water with 0.05% TFA; B=methanol with 0.05% TFA]. The fraction containing the product was concentrated and lyophilized for 24 h affording the compound HDP 30.2606 (6.38 mg, 75%) as white solid.

MS (ESI−): m/z found: 1031.00 calc.: 1031.23 $[M+2Na]^{2+}$.

Step 2: 6'-O-[3-(DUPA-Aoc-Phe-Phe-(4-amido-2-methylbutan-2-yl)disulfanyl)-propyl]-α-amanitin (HDP 30.2609)

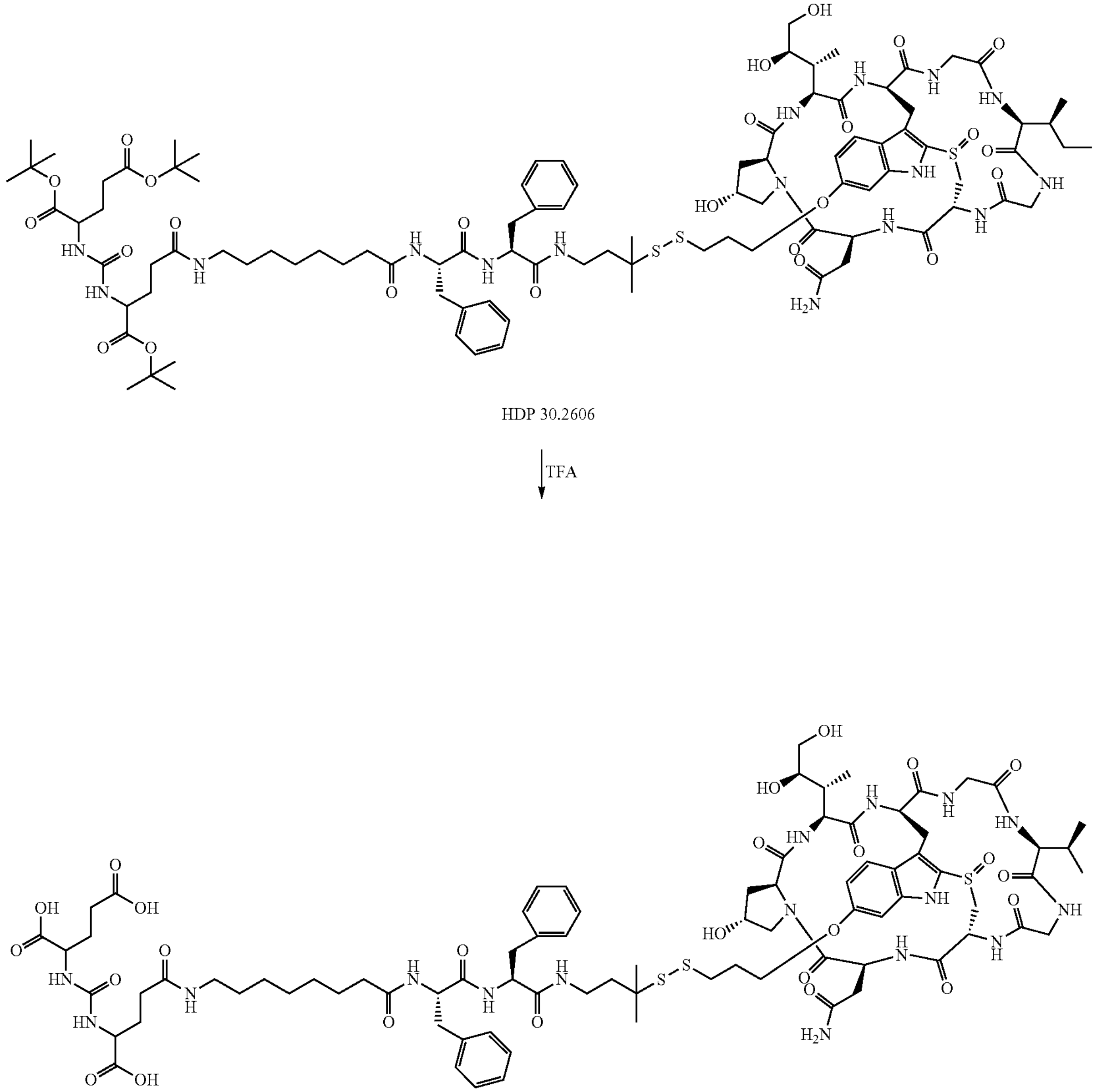

HDP 30.2606

HDP 30.2609

HDP 30.2606 (6.10 mg, 3.0 μmol) was dissolved in TFA (1 ml) and shaked at room temperature for 2 minutes. TFA was then evaporated and residue dissolved in TFA (1 ml) and shaked at room temperature for additional 5 minutes (×2). TFA was finally co-evaporated with toluene (2×1 ml).

Sample was dissolved in ACN/$H_2O$ (8:2, 200 μl) and purified by preparative RP-HPLC on C18 column [λ=305 nm; gradient: 0 min 5% B; 15 min 100% B; 18 min 100% B; 18.50 min 100% B; 22 min 5% B; A=water with 0.05% TFA; B=acetonitrile]. Fraction containing the product was evaporated and lyophilized to 1.1 mg (20%) of HDP 30.2609 as white powder.

MS(ESI−): m/z found: 1846.67 calc.: 1847.15 $[M-H]^-$; found: 922.44 calc.: 923.07 $[M-2H]^{2-}$.

Example 31

6"-O-[3-DUPA-Aoc-Phe-Phe-(4-amido-butan-2-yl) disulfanyl)-propyl]-α-amanitin (HDP 30.2618)

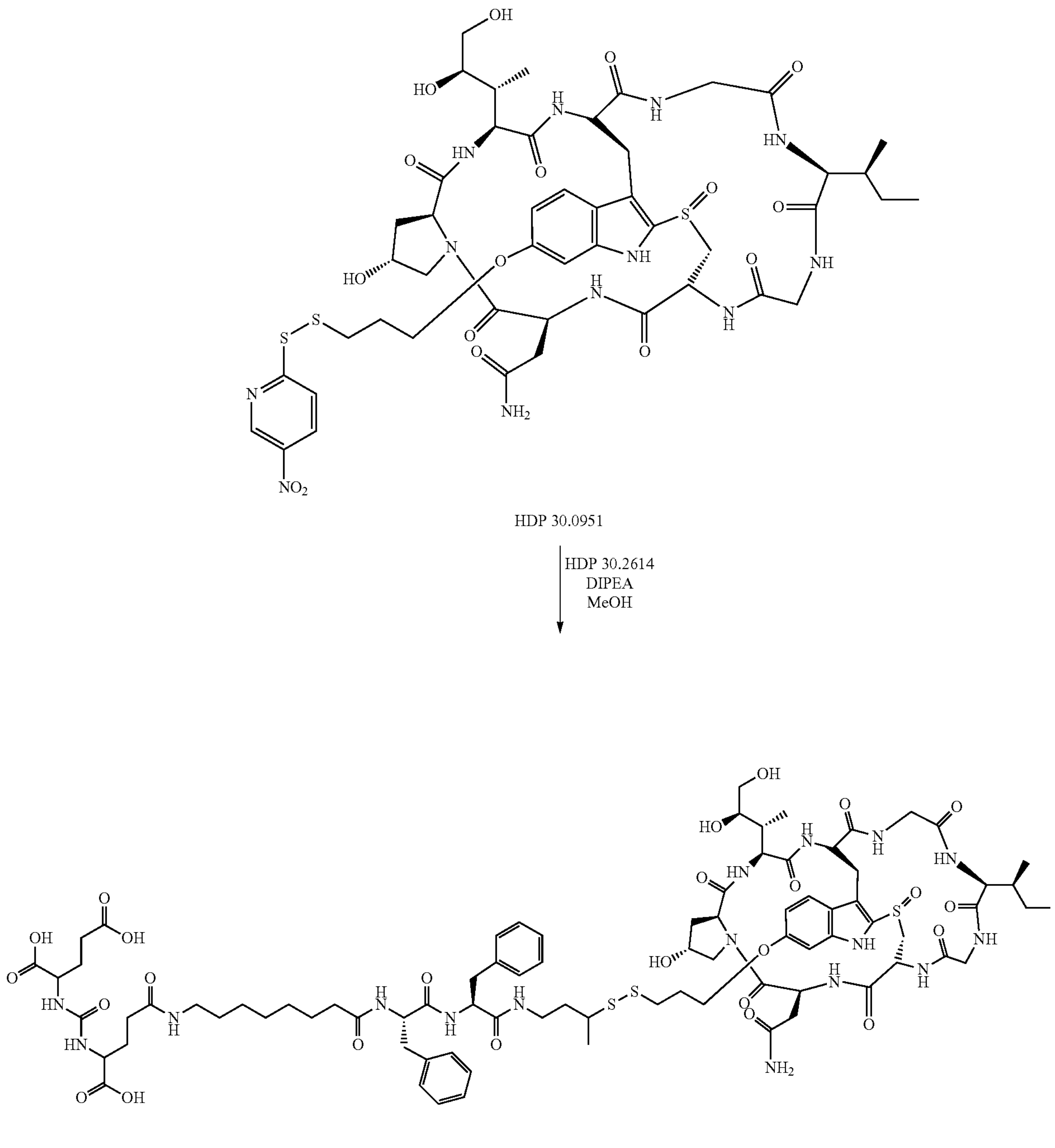

HDP 30.2618

To a solution of HDP 30.2614 (4.64 mg, 5.5 μmol) in MeOH (423 μl) HDP 30.0951 (6.31 mg, 5.5 μmol) was added at room temperature under argon. DIPEA (1.88 μl, 11 μmol) was added undiluted and reaction mixture turned strong yellow. The reaction mixture was stirred at room temperature for 30 minutes and solvent was then evaporated. The residue was dissolved in MeOH (200 μl) and purified by preparative RP-HPLC [λ=305 nm; gradient: 0-1 min 5% B; 1-14 min 54% B; 14-16 min 61% B; 16-19 min 100% B; 19-22 min 100% B; 22-25 min 5% B A=water with 0.05% TFA; B=acetonitrile]. The fraction containing the product was concentrated and lyophilized for 24 h affording the compound HDP 30.2618 (4.69 mg, 47%) as white solid.

MS (ESI−): m/z found: 1832.58 calc.: 1833.12 $[M-H]^-$; found: 915.83 calc.: 916.05 $[M-2H]^{2-}$.

Example 32
6"-O-[3-DUPA-Aoc-Phe-Phe-(4-amido-butan-2-yl) disulfanyl)-butyl]-α-amanitin (HDP 30.2619)
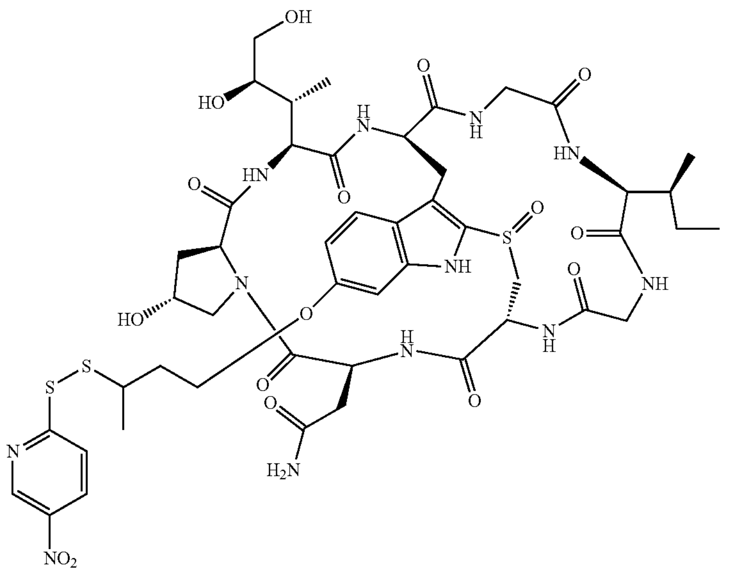
HDP 30.2587
HDP 30.2614
DIPEA
MeOH
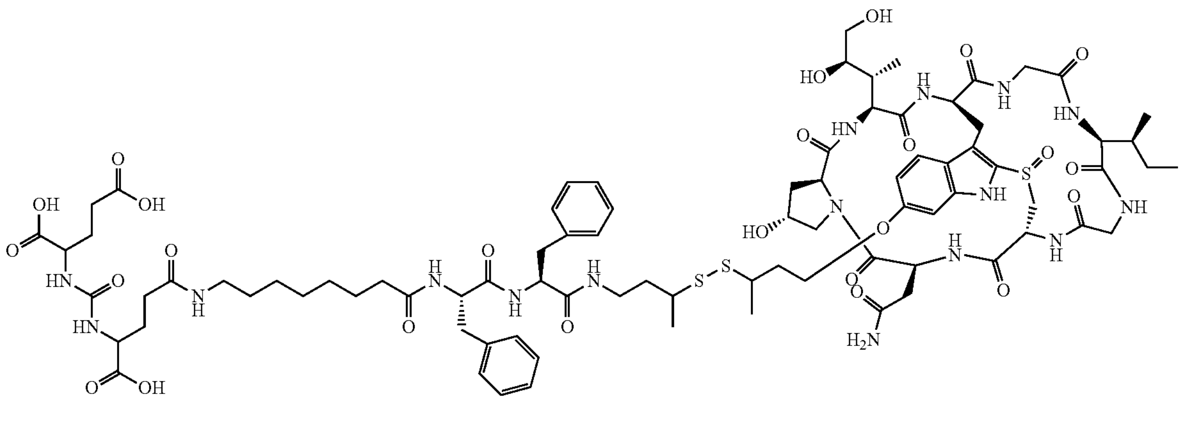
HDP 30.2619
HDP 30.2619 was prepared as described herein in example 29, by using HDP 30.2587 and HDP 30.2614 as precursors, affording 2.9 mg (60%) of the final conjugate as white powder.
MS(ESI−): m/z found: 1846.67 calc.: 1847.15 $[M-H]^-$; found: 922.92 calc.: 923.07 $[M-2H]^{2-}$.

Example 33

6'-O-[6-(3-(((DUPA-Aoc-Phe-Phe-Cys)-sulfanyl)-2,5-dioxopyrrolidin-1-yl)-hexanamido)-Val-Ala-PAB]-α-amantin (HDP 30.2284)

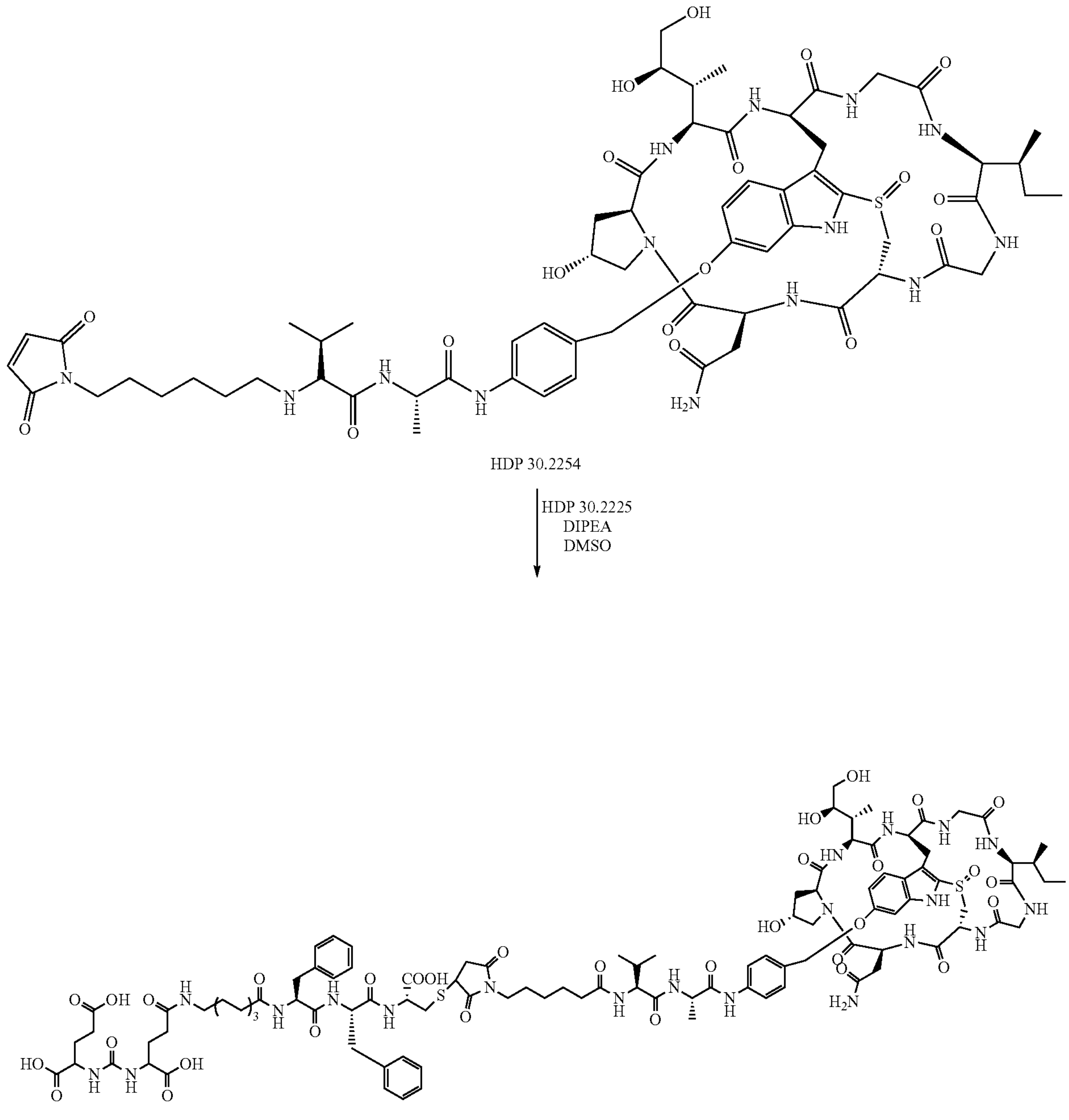

HDP 30.2254

HDP 30.2284

To a solution of HDP 30.2225 (12.97 mg, 15.1 μmol) in DMSO (1 ml) a solution of HDP 30.2254 (21.03 mg, 15.1 μmol) in DMSO (2 ml) was added at room temperature under argon. DIPEA (5.15 μl, 3.0 μmol) was added undiluted. The reaction mixture was stirred at room temperature for 20 h. The reaction mixture was injected into preparative RP-HPLC [λ=305 nm; gradient: 0-5 min 5% B; 20-25 min 100% B; 27-35 min 5% B; A=water with 0.05% TFA; B=methanol with 0.05% TFA]. The fractions containing the product were combined, concentrated and lyophilized for 24 h affording the compound HDP 30.2284 (14.53 mg, 43%) as white solid.

MS (ESI+): m/z found: 1146.5 calc.: 1146.2 $[M+2Na]^{2+}$.

Example 34

6'-O-[3-(3-(((DUPA-Aoc-Phe-Phe-PEG$_n$-sulfanyl)-2,5-dioxopyrrolidin-1-yl)-propanamido)-Val-Ala-PAB]-α-amantin

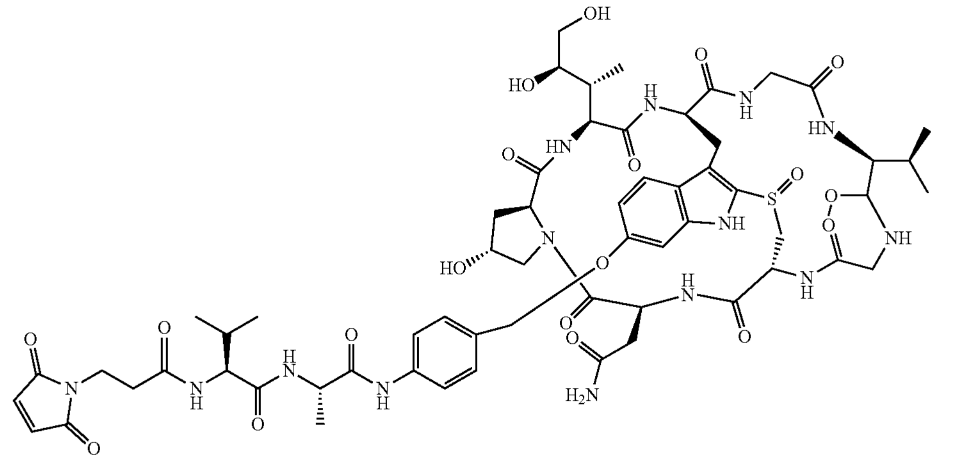

HDP 30.1899

DUPA-Aoc-Phe-Phe-PEG$_n$-SH
DIPEA
DMSO, Ar, rt
n = 4 HDP 30.2439
n = 8 HDP 30.2466
n = 12 HDP 30.2585

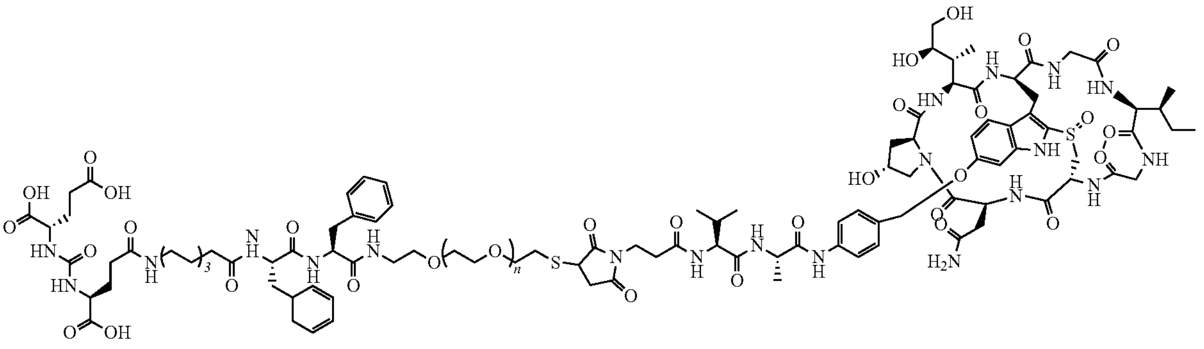

n = 4 HDP 30.2471
n = 8 HDP 30.2474
n = 12 HDP 30.2680

HDP 30.1699 (5.24 mg, 3.9 μmol) was dissolved in DMSO (520 μl). HDP 30.2439 (5.7 mg, 3.9 μmol, 1.0 eq), dissolved in DMSO (260 μl), and DIPEA (1.33 μl, 7.8 μmol, 2.0 eq) were added sequentially. Reaction mixture was stirred at room temperature under argon for 24 hours and the product was then purified by preparative RP-HPLC [λ=305 nm; gradient: 0-1 min 5% B; 14 min 54% B; 18 min 69% B; 19-20 min 100%; 21-22 min 5% B; A=water with 0.05% TFA, B=acetonitrile] to provide 3.54 mg (43%) of product HDP 30.2471 as white powder.

MS(ESI−) m/z=$[M-H]^-$ found: 2290.92, calc.: 2291.58; $[M-2H]^{2-}$ found: 1144.92, calc.: 1145.29.

HDP 30.2474 and HDP 30.2680 were prepared as described above starting from HDP 30.2466 and HDP 30.2585, respectively, as precursors. The synthesis yielded 2.95 mg (41%) of HDP 30.2474 and 1.08 mg (20%) of HDP 30.2680.

HDP 30.2474- MS(ESI+): m/z found: 1254.80 calc.: 1254.39 $[M+H+K]^{2+}$; found: 843.75 calc.: 845.92 $[M+3Na]^{3+}$.

HDP 30.2680- MS(ESI−): m/z found: 2643.33 calc.: 2644.01 $[M-H]^-$; found: 2703.42 calc.: 2704.06 $[M-AcOH-H]^-$; found: 1321.25 calc.: 1321.5 $[M-2H]^{2-}$; found: 1377.85 calc.: 1378.51 $[M+TFA-2H]^{2-}$; found: 1434.42 calc.: 1435.52 $[M+2TFA-2H]^{2-}$.

Example 35

6'-O-[(3,4-Bis-(((DUPA-Aoc-Phe-Phe-Cys)-sulfanyl)-2,5-dioxopyrrolidin-1-yl)-acetamido)-Val-Ala-PAB]-α-amantin (HDP 30.2300)

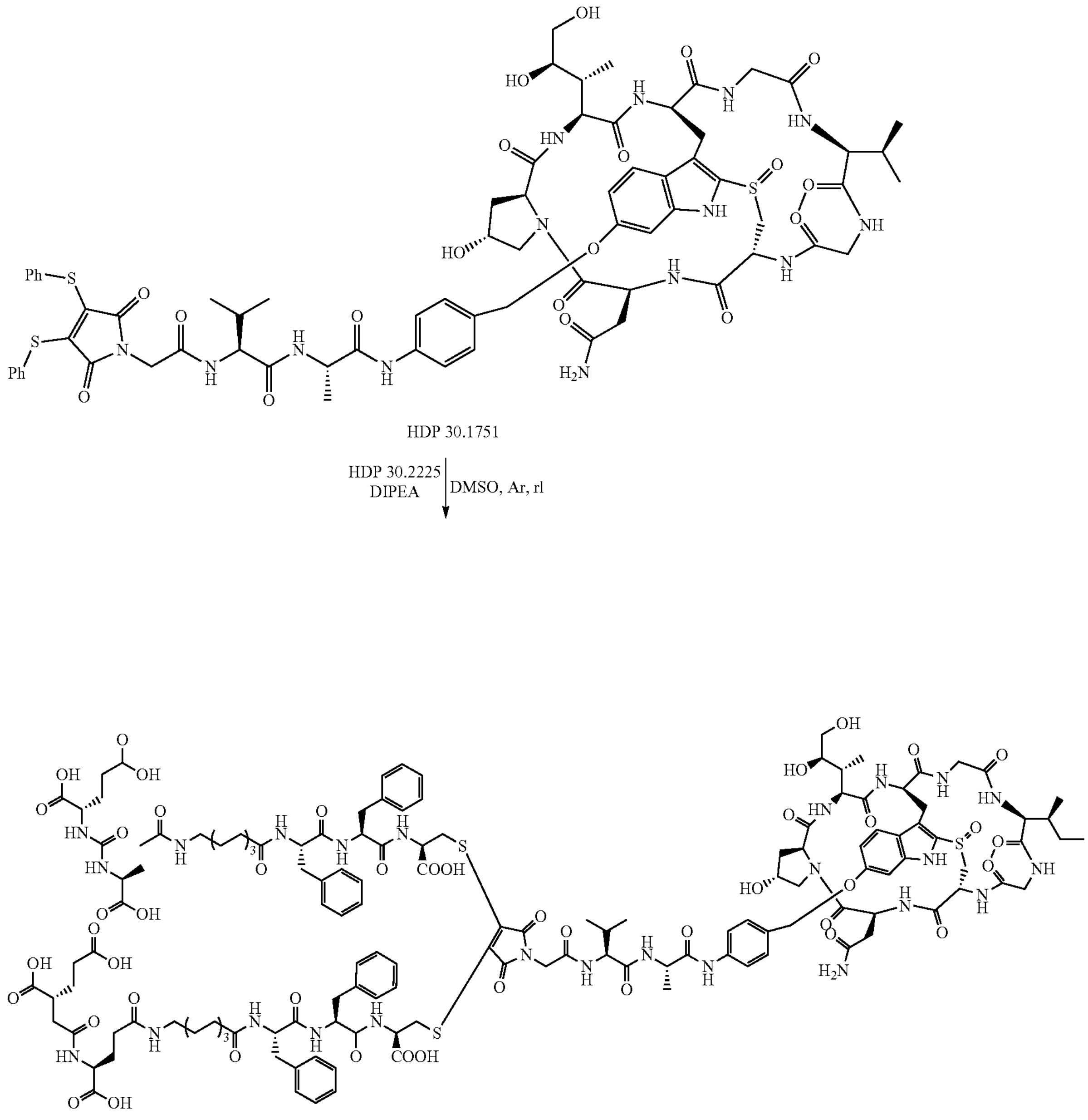

HDP 30.2300

To a solution of HDP 30.1751 (21 mg, 14 μmol) in DMSO (5.6 ml) a solution of HDP 30.2225 (23.2 mg, 27 μmol) was added at room temperature under argon. DIPEA (13.82 μl, 81 μmol) were added undiluted. The reaction mixture was stirred at room temperature for 49 h. The reaction mixture was injected into preparative RP-HPLC [λ=305 nm; gradient: 0-5 min 5% B; 20-25 min 100% B; 27-35 min 5% B; A=water with 0.05% TFA; B=methanol with 0.05% TFA]. The fractions containing the product were combined, concentrated and lyophilized for 24 h affording the compound HDP 30.2300 (4.0 mg, 10%) as white solid.

MS (ESI+): m/z found: 1522.60 calc.: 1522.61 $[M+2H]^{2+}$; found: 1015.40 calc.: 1015.40 $[M+3H]^{3+}$.

Example 36

6'-O-[(3,4-(((DUPA-Aoc-Phe-Phe-PEG$_n$)-sulfanyl)-2,5-dioxopyrrolidin-1-yl)-propanamido)-Val-Ala-PAB]-α-amantin

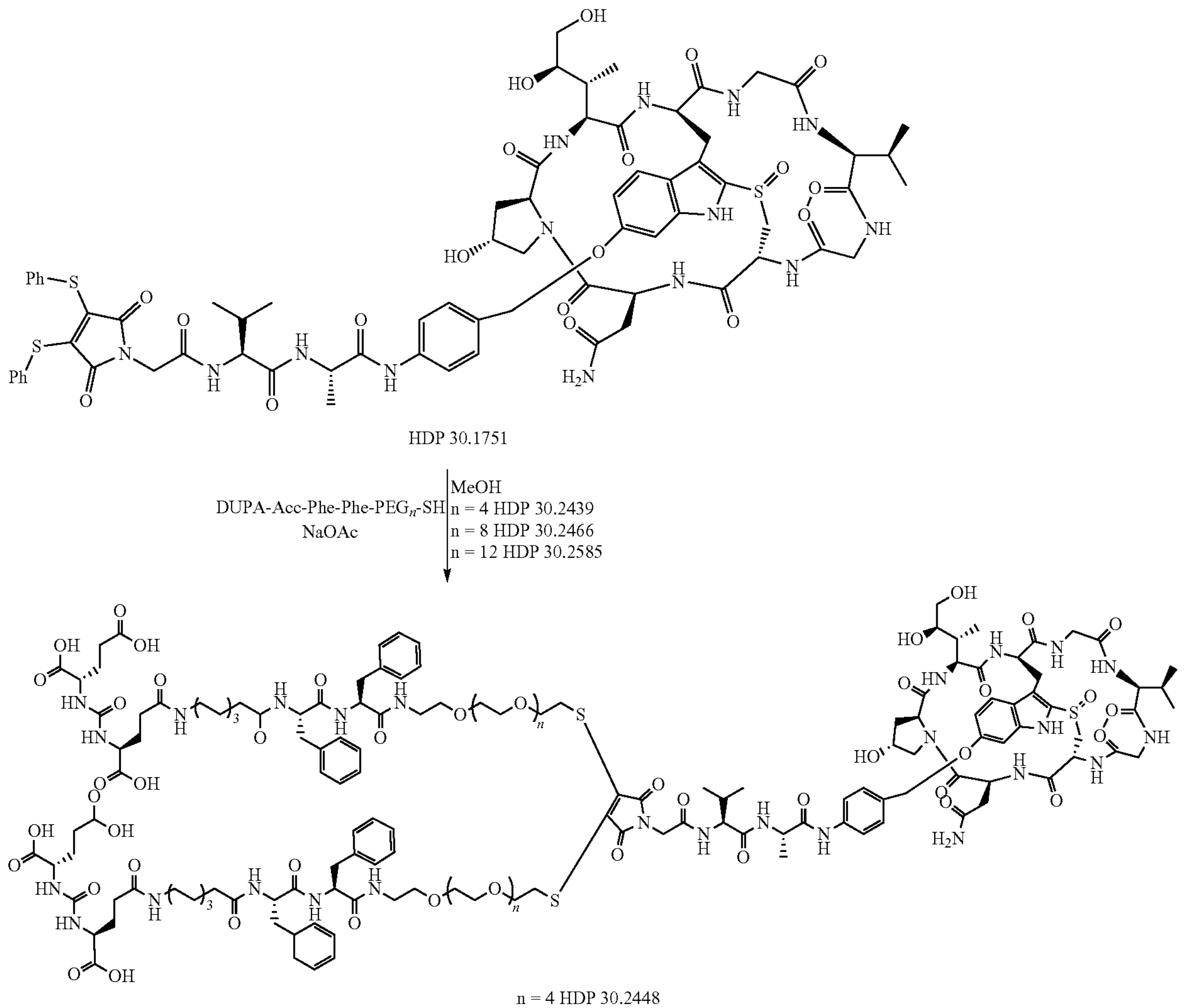

n = 4 HDP 30.2448
n = 8 HDP 30.2490
n = 12 HDP 30.2595

HDP 30.1751 (2.41 mg, 1.62 μmol, 1.0 eq) was dissolved in MeOH (347 μl). A 0.03 M solution of HDP 30.2585 in MeOH (230 μl, 7.29 μmol, 4.5 eq) and a 0.1 M solution of NaOAc in MeOH (140 μl, 12.64 μmol, 7.8 eq) were added sequentially and mixture was stirred at room temperature under argon for 20 hours.

Mixture was evaporated under reduced pressure and residue dissolved in ACN/$H_2O$ (1:1, 200 μl) and purified by preparative RP-HPLC on a C18 column [λ=210 nm; gradient: 0-1 min 5%-30% B; 1-18 min 50% B; 18-20 min 100% B; 20-22 min 100% B; 22-23 min 5% B; 23-25 min 5% B; A=water with 0.05% TFA, B=acetonitrile]. Fraction corresponding to the product was collected, evaporated and lyophilized ($^t$BuOH/$H_2O$, 4:1, 3 ml) to 3.12 mg (49%) of HDP 30.2595 as yellowish powder.

MS(ESI−): m/z found: 1961.83, calc.: 1962.25 $[M-2H]^{2-}$; found: 1307.58, calc.: 1307.83$[M-3H]^{3-}$; found: 980.42, calc.: 980.62 $[M-4H]^{4-}$.

HDP 30.2490 and HDP 30.2595 were prepared as described above starting from HDP 30.2466 and HDP 30.2585, respectively, as precursors. The synthesis yielded 1.86 mg (37%) of HDP 30.2490 and 3.12 mg (49%) of HDP 30.2595 as yellowish powders.

HDP 30.2490- MS(ESI−): m/z found: 1785.75 calc.: 1786.03 $[M-2H]^{2-}$; found: 1190.17 calc.: 1190.35 $[M-3H]^{3-}$; found: 892.42 calc.: 892.51 $[M-4H]^{4-}$.

HDP 30.2595- MS(ESI−): m/z found: 1961.83 calc.: 1962.25 $[M-2H]^{2-}$; found: 1307.58 calc.: 1307.83 $[M-3H]^{3-}$; found: 980.42 calc.: 980.62 $[M-4H]^{4-}$.

Example 37

6'-O-[6-(((DUPA-Aoc-Phe-Phe-Cys)-sulfanyl)-2,5-dioxopyrrolidin-1-yl)-hexyl]-α-amantin (HDP 30.2301)

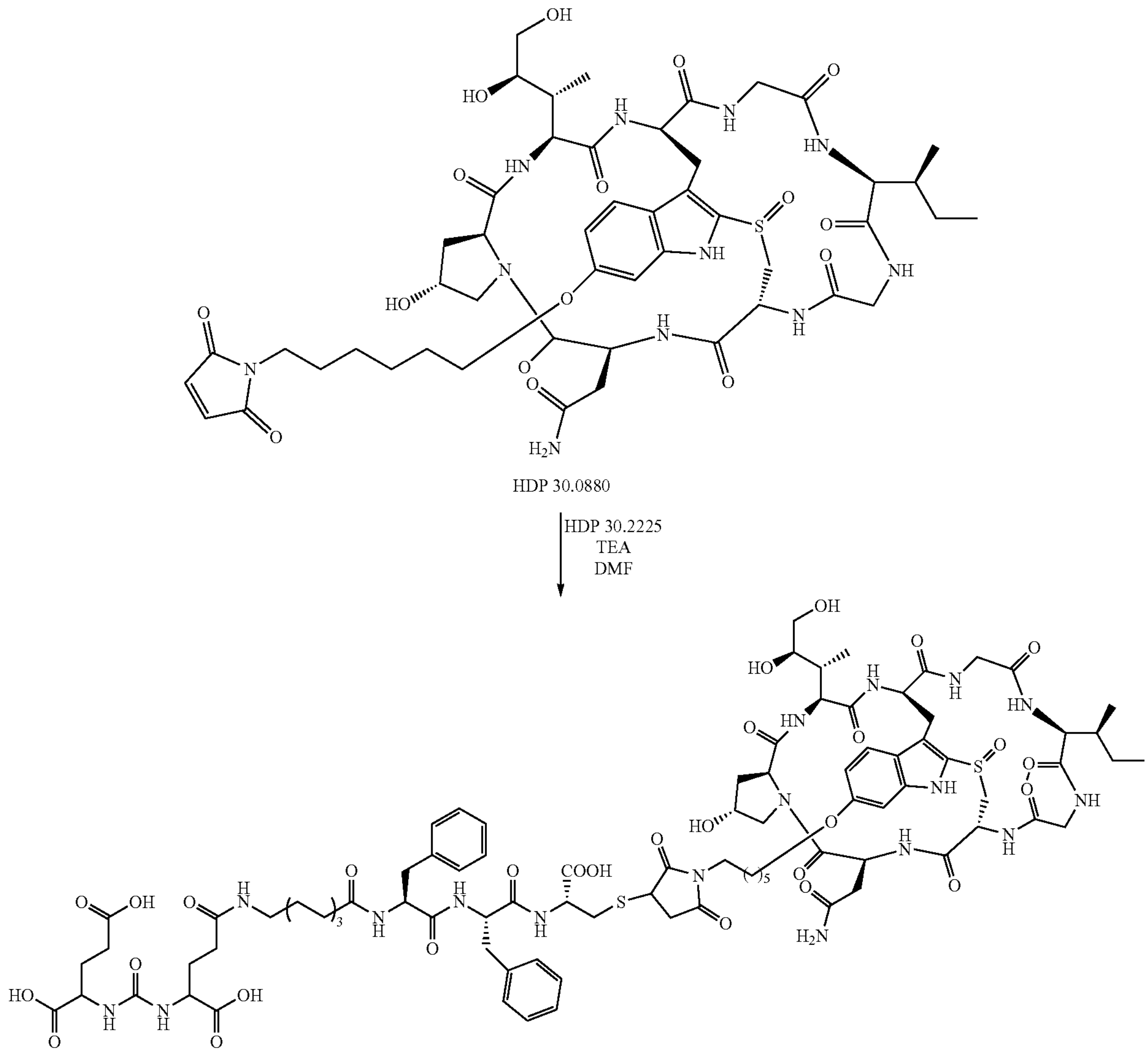

HDP 30.0880

HDP 30.2301

To a solution of HDP 30.0880 (20.48 mg, 18.6 μmol) in DMF (0.5 ml) a solution of HDP 30.2225 (16.0 mg, 18.6 μmol) in DMF (0.5 ml) was added at room temperature under argon. TEA (5.18 μl, 37.2 μmol) was added undiluted. The reaction mixture was stirred at room temperature for 4 days. The reaction mixture was injected into preparative RP-HPLC [λ=268 nm; gradient: 0-1 min 5% B; 1-14 min 54% B; 14-26 min 100% B; 26-30 min 100% B; 30-35 min 5% B; A=water with 0.05% TFA; B=acetonitrile]. The fractions containing the product were combined, concentrated and lyophilized for 24 h affording the compound HDP 30.2301 (6.03 mg, 17%) as white solid.

MS (ESI+): m/z found: 979.42 calc.: 979.60 $[M+2Na]^{2+}$.

Example 38

6'-O-[3-(3-(((DUPA-Aoc-Phe-Phe-Cys)-sulfanyl)-2,5-dioxopyrrolidin-1-yl)-propanamido)-Val-Ala-PAB]-α-amantin (HDP 30.2535)

By using the same procedure reported herein in example 33, the desired compound was obtained as white powder (2.84 mg, 43%).

MS(ESI−): m/z found: 2203.08 calc.: 2203.43 $[M-H]^{-}$; found: 1101.00 calc.: 1101.21 $[M-2H]^{2-}$.

Example 39
6'-O-[6-(3-(((DUPA-Aoc-Phe-Phe-Cys)-sulfanyl)-2,5-dioxopyrrolidin-1-yl)-hexanamido)-Val-Cit-PAI3]-α-amantin (HDP 30.2537)
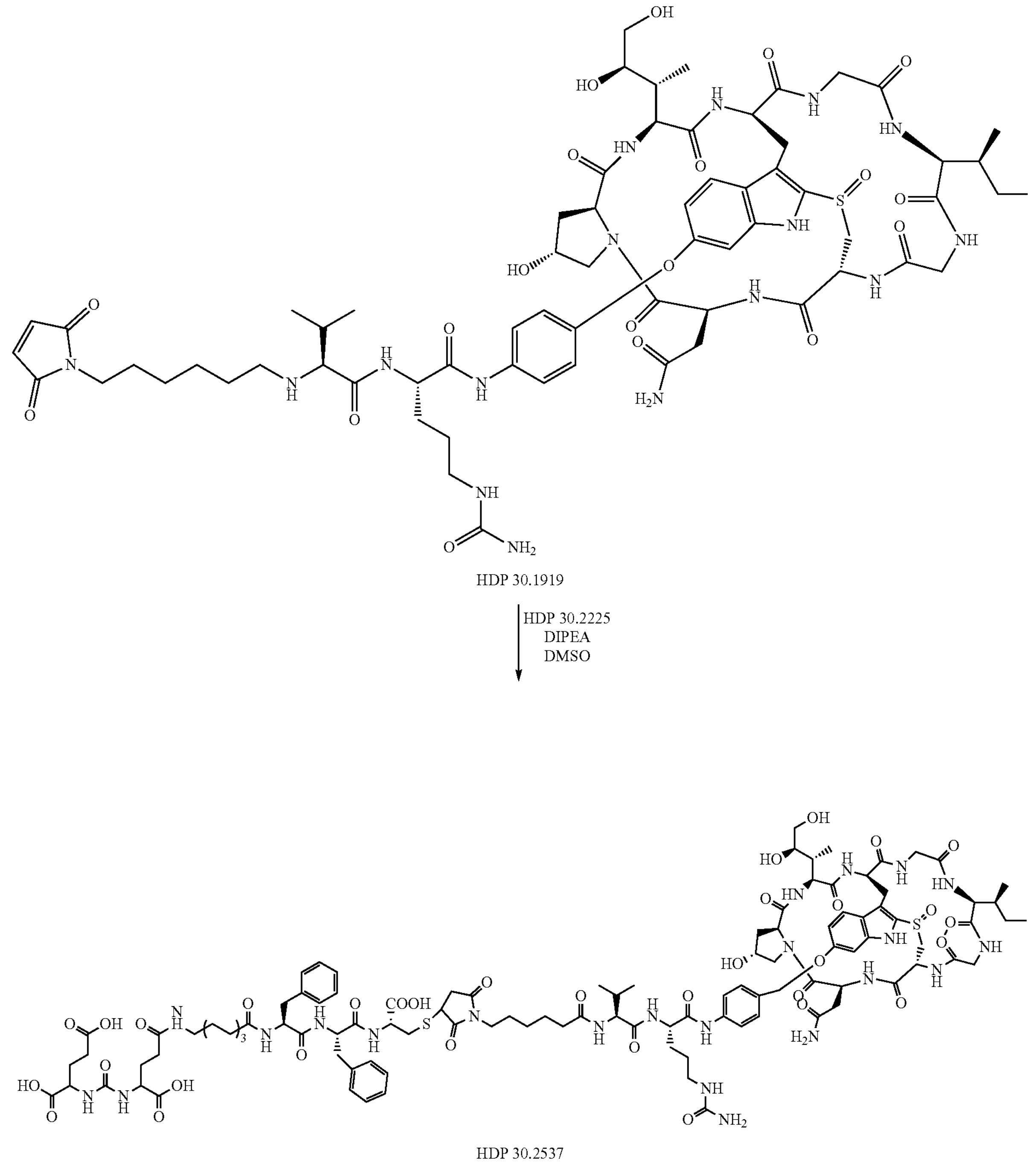
By using the same procedure reported herein in example 33, the desired compound was obtained as white powder (6.42 mg, 83%).
MS(ESI−): m/z found: 2331.00 calc.: 2331.60 $[M-H]^-$; found: 1164.92 calc.: 1165.30 $[M-2H]^{2-}$.

Example 40

6'-O-[2-((DUPA-Aoc-Phe-Phe-Cys)-sulfanyl)-acetamido-Val-Ala-PAB]-α-amantin (HDP 30.2515)

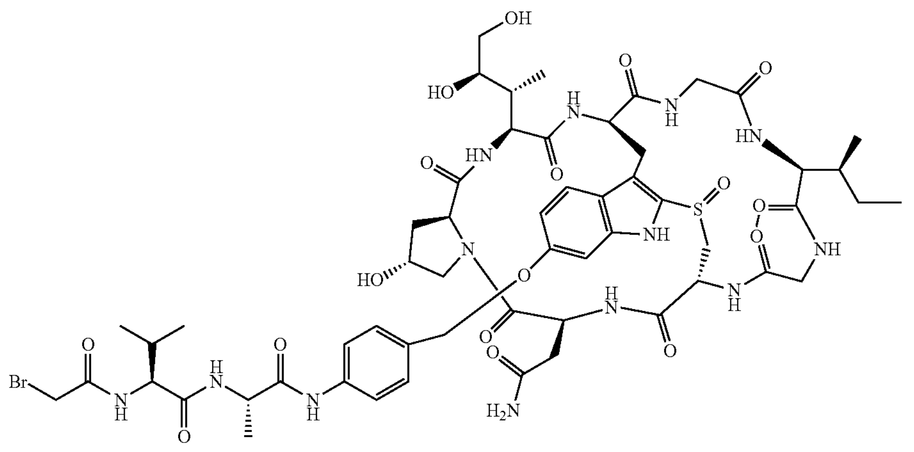

HDP 30.1704

HDP 30.2225
Na2CO3/NAHCO3 100 mM, pH = 9.3
ACN/$H_2O$ (1:1, v:v)

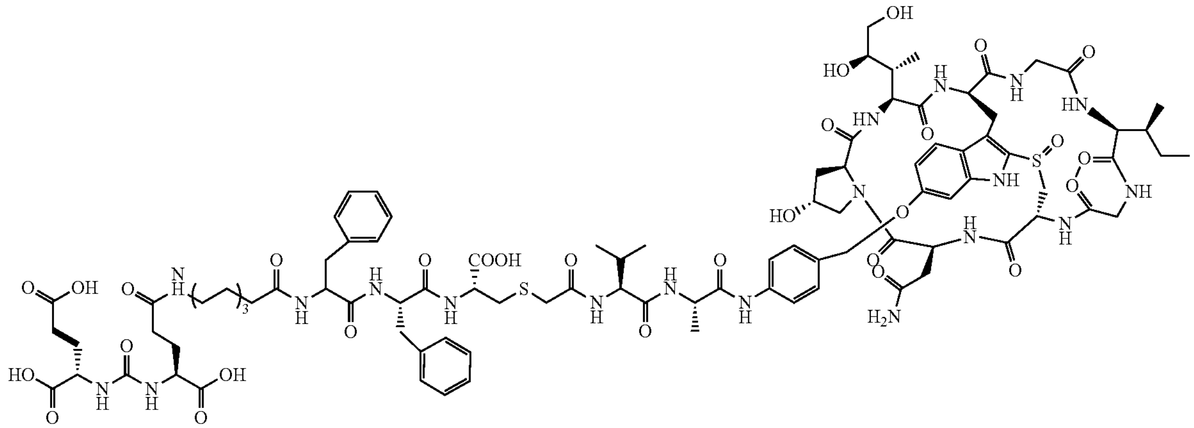

HDP 30.2515

A solution of HDP 30.1704 in ACN/$H_2O$ (1:1, v:v) (2.60 mg, 2 μmol, 4 mM) and a solution of HDP 30.2225 in ACN/$H_2O$ (1:1, v:v) (1.71 mg, 2 μmol, 4 mM) were mixed and diluted with a $Na_2CO_3$/$NaHCO_3$ buffer (100 mM, pH=9.3, 750 μl) to reach a pH=9.0, resulting in a final concentration of HDP 30.2225 equal to 1.14 mM. Reaction mixture was stirred at room temperature for 1 hour and half and the product purified by preparative RP-HPLC on a C18 column [λ=305 nm; gradient: 0-5 min 5% B; 20-25 min 100% B; 27-35 min 5% B; A=water with 0.05% TFA; B=methanol with 0.05% TFA]. Product was isolated as 2.61 mg (62%) of white powder.

MS(ESI−): m/z found: 1045.42, calc.: 1045.66 $[M-2H]^{2-}$; found: 696.67, calc.: 696.77 $[M-3H]^{3-}$.

Example 41
6'-O-[6-(2-((DUPA-Aoc-Phe-Phe-Cys)-sulfanyl)-acetamido)-hexyl]-α-amantin (HDP 30.2523)
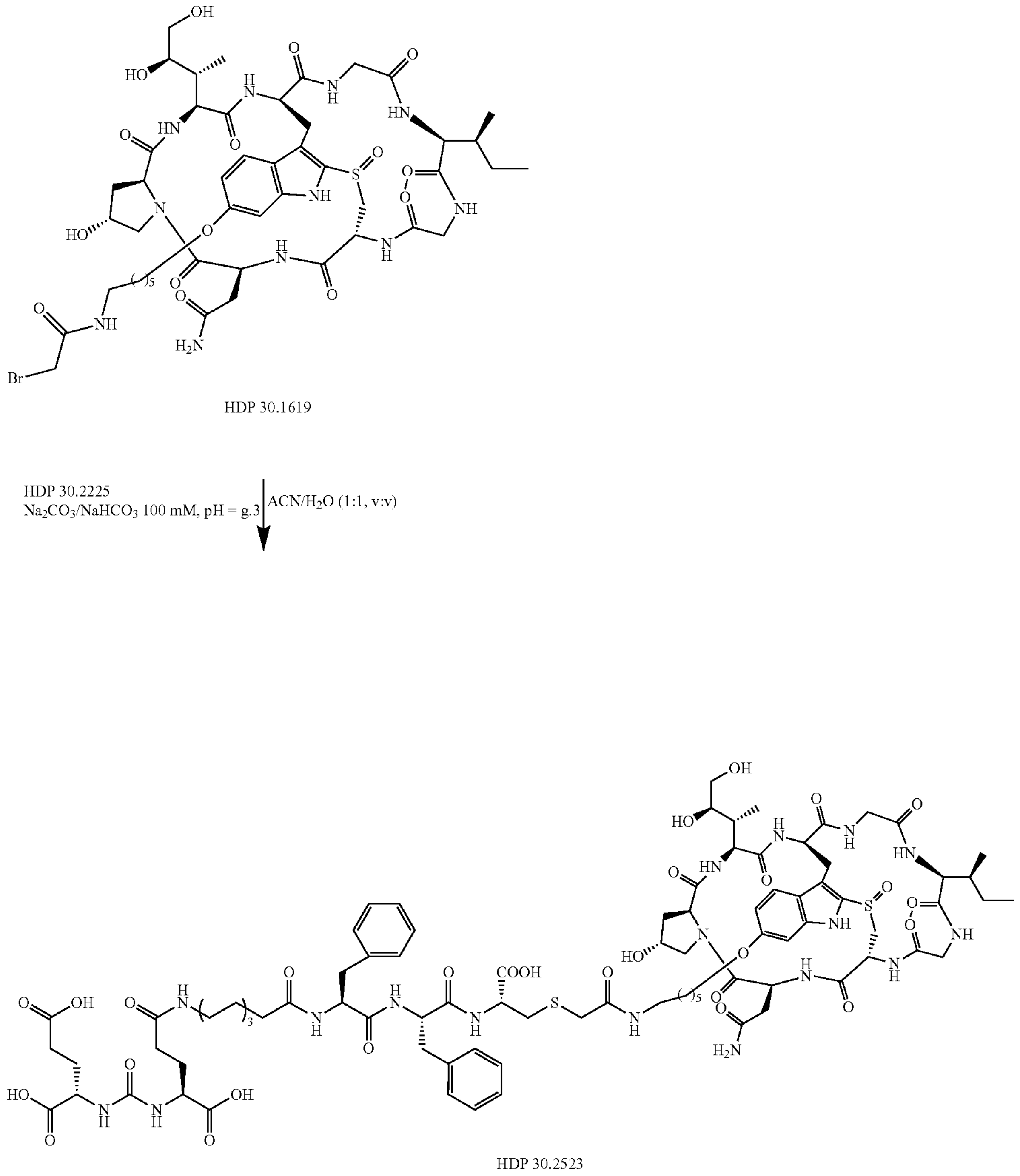
HDP 30.2523 was prepared as described herein in example 40, starting from HDP 30.1619 as amanitin precursor. The product was isolated as white powder (5.68 mg, 67%).
MS(ESI−): m/z found: 1915.75, calc.: 1916.15 $[M-H]^-$; found: 957.42, calc.: 957.57 $[M-2H]^{2-}$.

Example 42

6'-O-[2-((DUPA-Aoc-Phe-Phe-(His-Glu)$_2$-Cys)-sulfanyl)-acetamido-Val-Ala-PAB]-α-amantin (HDP 30.2594)

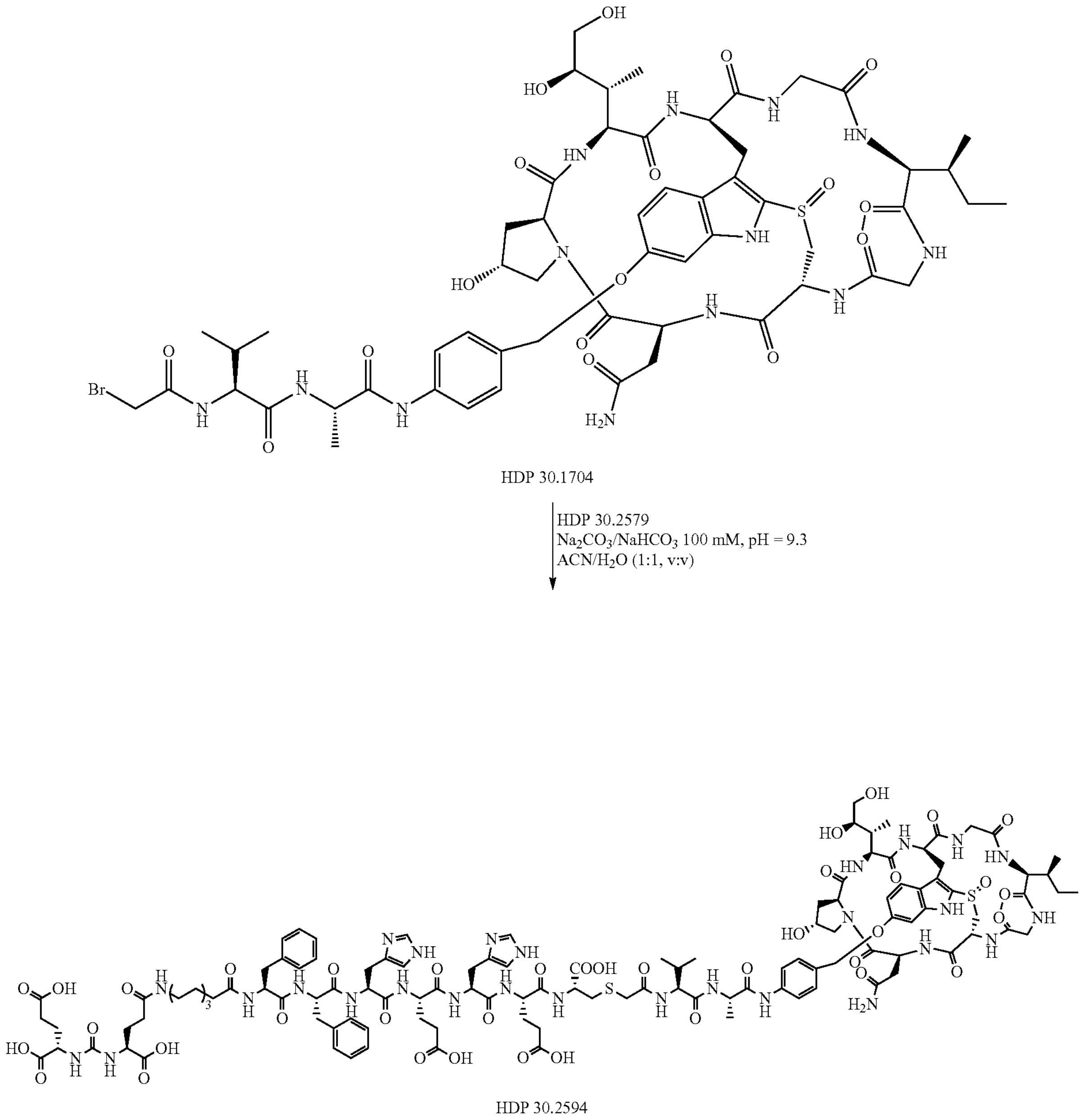

HDP 30.1704

HDP 30.2594

HDP 30.2594 was prepared as described herein in example 40, starting from HDP 30.1704 as amanitin precursor. The product was isolated as white powder (1.24 mg).

MS(ESI−): m/z found: 2623.83 calc.: 2624.84 $[M-H]^-$; found: 1311.50 calc.: 1311.92 $[M-2H]^{2-}$; found: 874.00 calc.: 874.72 $[M-3H]^{3-}$.

C. Data Relating to DUPA-Amatoxin Conjugates

FIGS. 2 to 5 show the results from cytotoxicity studies, and Table 8 shows the selectivity (S) and targeting indexes (TI) values of efficient DUPA-α-amanitin conjugates.

TABLE 8 shows the selectivity (S) and targeting indexes (TI) values of efficient DUPA-α-amanitin conjugates

| Compound code | Structural characteristics | $IC_{50}$ (M) LNCaP (PSMA+) | $IC_{50}$ (M) PC3 (PSMA−) | S | TI for LNCaP |
|---|---|---|---|---|---|
| α-amanitin | unconjugated toxin | $4.79 \times 10^{-7}$ | $2.13 \times 10^{-7}$ | — | — |
| HDP 30.2284 | monovalent Cys(S-maleimidocaproyl) linkage chemistry Val-Ala-PAB | $8.63 \times 10^{-10}$ | $1.57 \times 10^{-6}$ | 1819 | 555 |
| HDP 30.2537 | monovalent DUPA-Aoc-Phe-Phe-Cys(S-maleimidocaproyl)-Val-Cit-PAB | $2.102 \times 10^{-9}$ | $3.102 \times 10^{-7}$ | 148 | 371 |
| HDP 30.2535 | monovalent DUPA-Aoc-Phe-Phe-Cys(S-maleimidopropyl)-Val-Ala-PAB | $1.894 \times 10^{-9}$ | $3.614 \times 10^{-7}$ | 191 | 253 |
| HDP 30.2515 | monovalent DUPA-Aoc-Phe-Phe-Cys(S-acetamide)-Val-Ala-PAB | $4.51 \times 10^{-9}$ | $6.63 \times 10^{-7}$ | 147 | 106 |
| HDP 30.2301 | monovalent DUPA-Aoc-Phe-Phe-Cys(S-maleimidocaproyl) stable linker | $6.11 \times 10^{-9}$ | $1.52 \times 10^{-6}$ | 249 | 78 |
| HDP 30.2523 | monovalent DUPA-Aoc-Phe-Phe-Cys(S-acetamide)-C6 | $6.76 \times 10^{-9}$ | $1.80 \times 10^{-6}$ | 266 | 71 |
| HDP 30.2448 | bivalent (DUPA-Aoc-Phe-Phe-$PEG_4$-S)$_2$-disubstituted maleimidopropyl Val-Ala-PAB | $7.84 \times 10^{-9}$ | $5.31 \times 10^{-8}$ | 6.8 | 61 |
| HDP 30.2490 | bivalent (DUPA-Aoc-Phe-Phe-$PEG_8$-S)$_2$-disubstituted maleimidopropyl Val-Ala-PAB | $7.692 \times 10^{-9}$ | $4.037 \times 10^{-7}$ | 52.5 | 62 |
| HDP 30.2589 | Monovalent DUPA-Aoc-Phe-Phe-Cys-S-S-C(Me)-C5 stable linker | $9.01 \times 10^{-9}$ | $2.03 \times 10^{-7}$ | 22.5 | 53 |

D. Synthesis and Characterization of Half-Life Extended DUPA-Amatoxin Conjugates

Example 43

Figure 6:
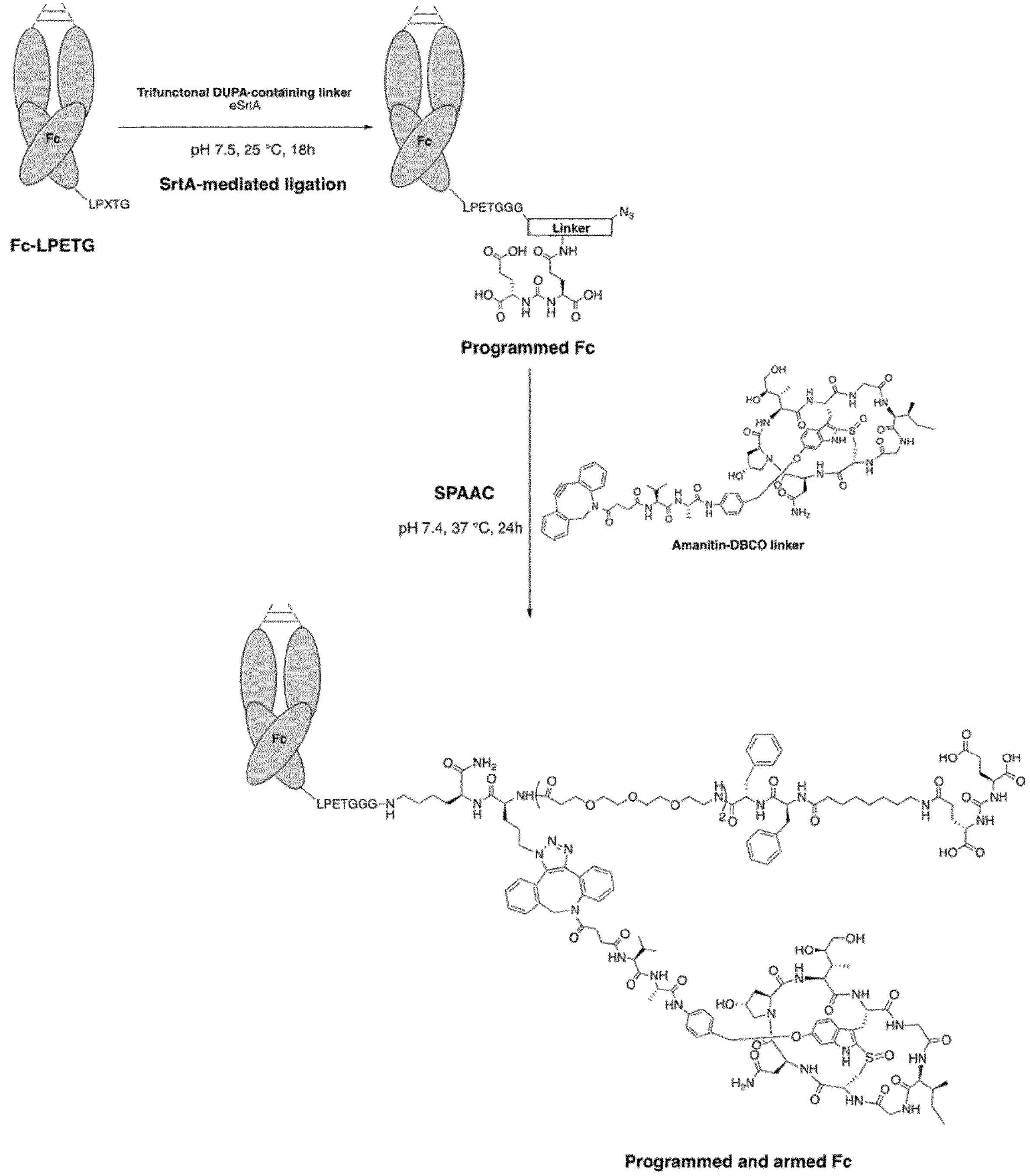
FIG. 6 shows the two-step "program and arm"-strategy for production of DUPA-Fc-amanitin conjugates.
Figure 9:
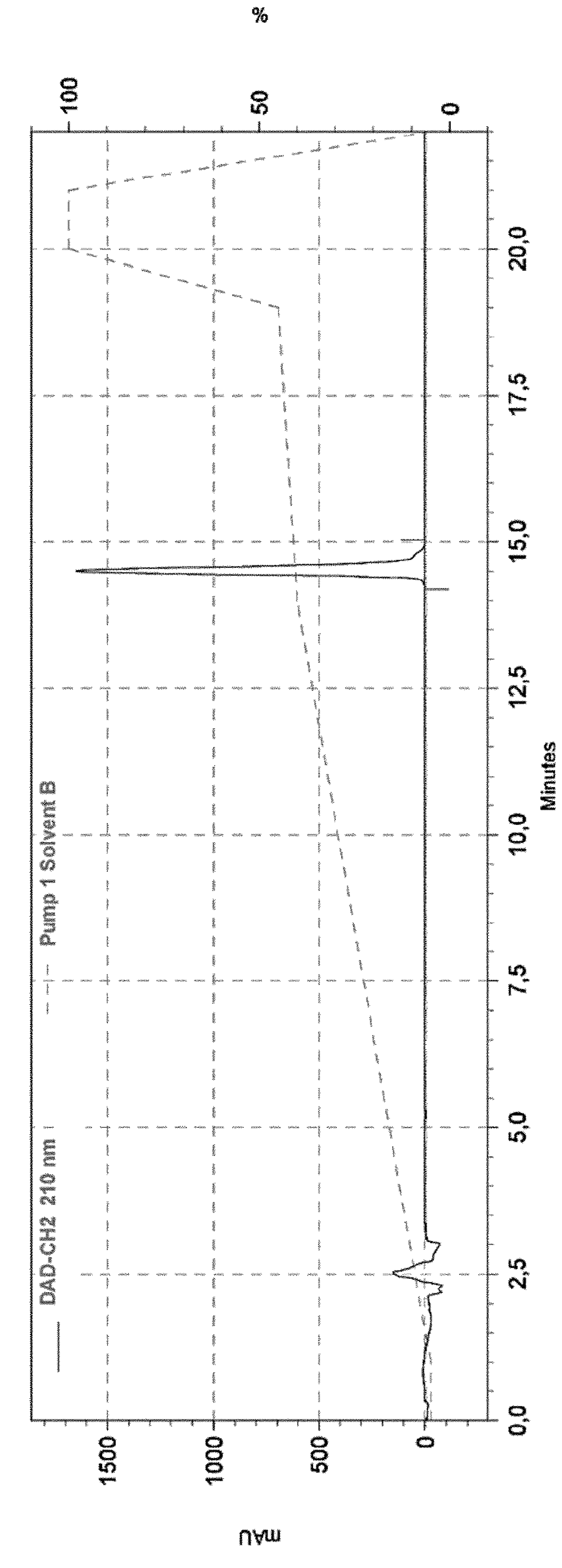
FIG. 9 shows an analytical RP-HPLC of trifunctional DUPA-containing linker (λ=210 nm; gradient: 0-1 min 5% B; 1-14 min 40% B; 14-19 min 45% B; 19-20 min 100% B; 20-21 min 100% B; 21-22 min 5% B; A=water with 0.05% TFA; B=acetonitrile; flow rate=1.4 ml/min).
Figure 10:
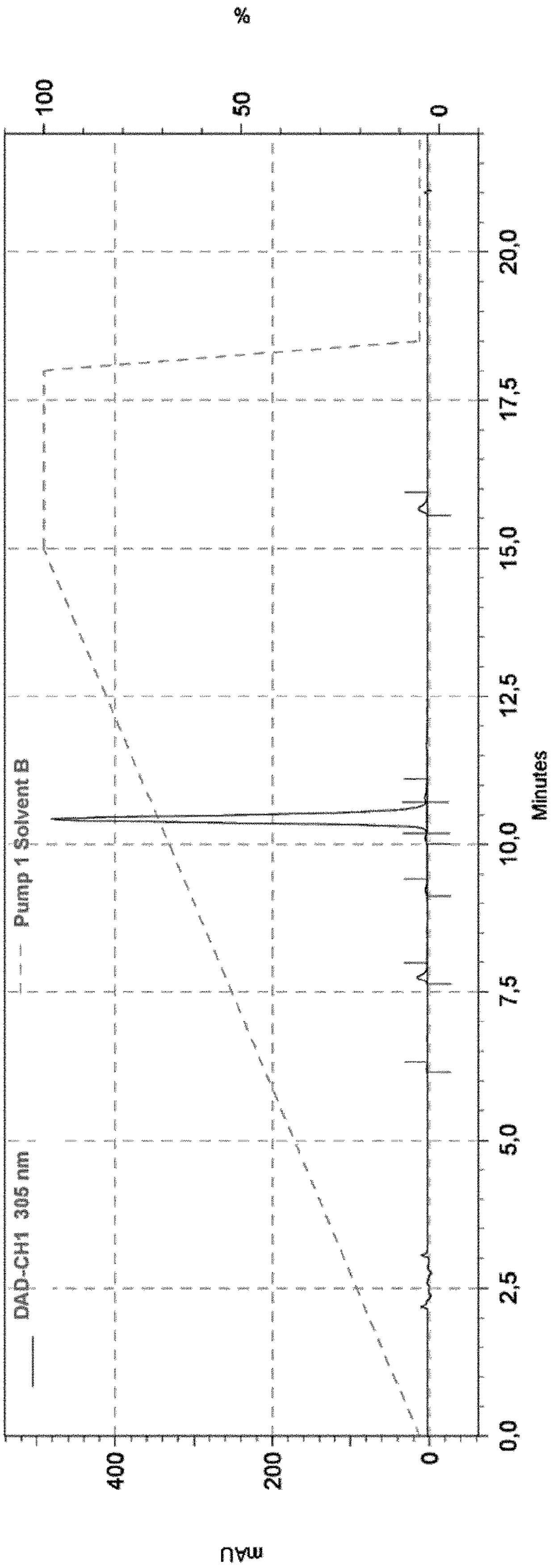
FIG. 10 shows an analytical RP-HPLC of DBCO-amanitin linker (λ=305 nm; gradient: 0 min 5% B; 0-15 min 100% B; 15-18 min 100% B; 18-18.50 min 100% B; 18.50-22 min 5% B; A=water with 0.05% TFA; B=acetonitrile flow rate=1.4 ml/min).
Figure 11:
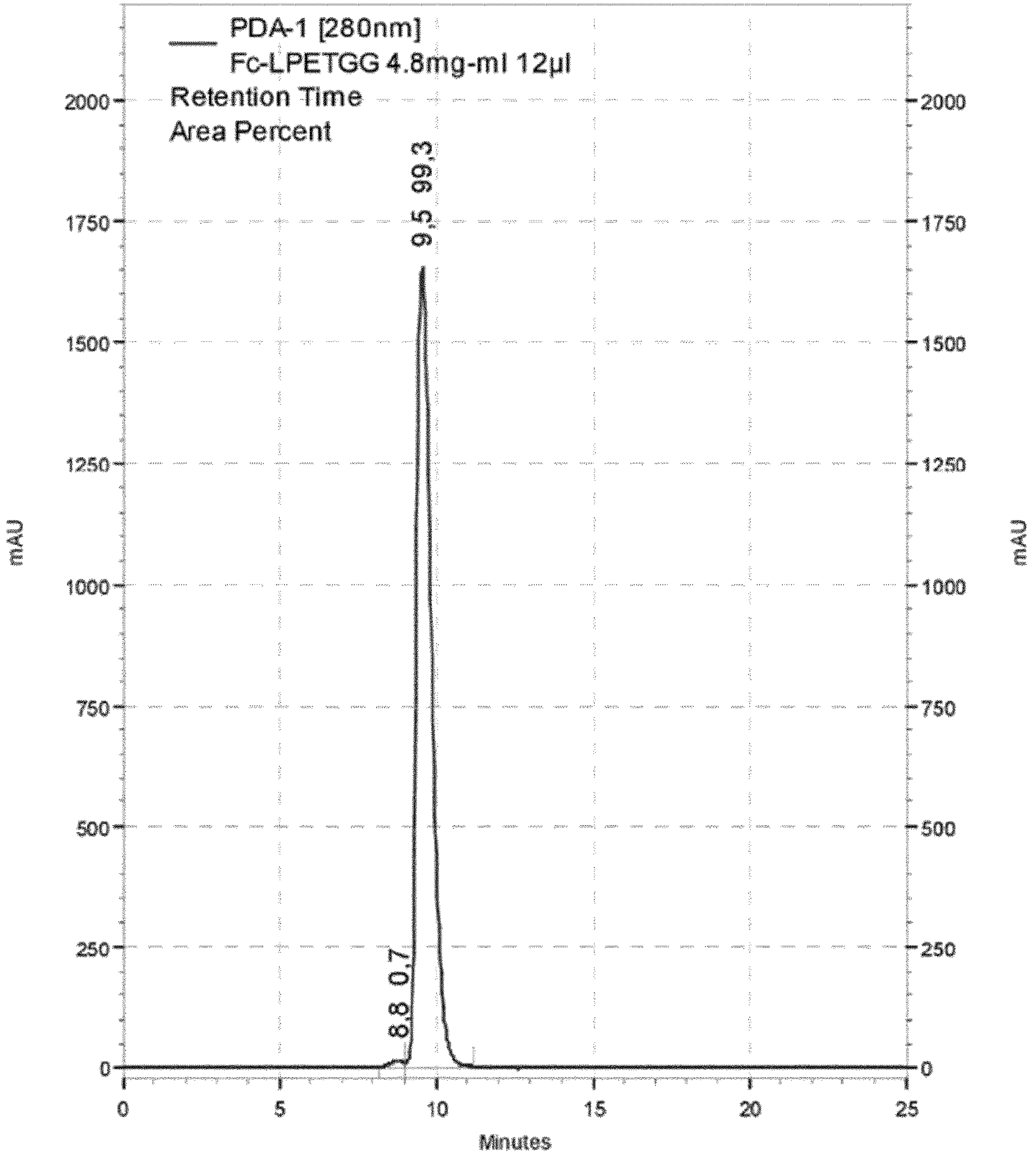
FIG. 11 shows an SEC-HPLC of purified Fc-LPETG under native non-reducing conditions (λ=280 nm; buffer: 0.05% $NaN_3$+0.1 mol/l $Na_2SO_4$ in 0.1 mol/l $NaPO_4$ pH 6.7; flow rate: 0.35 ml/min).
Figure 12:
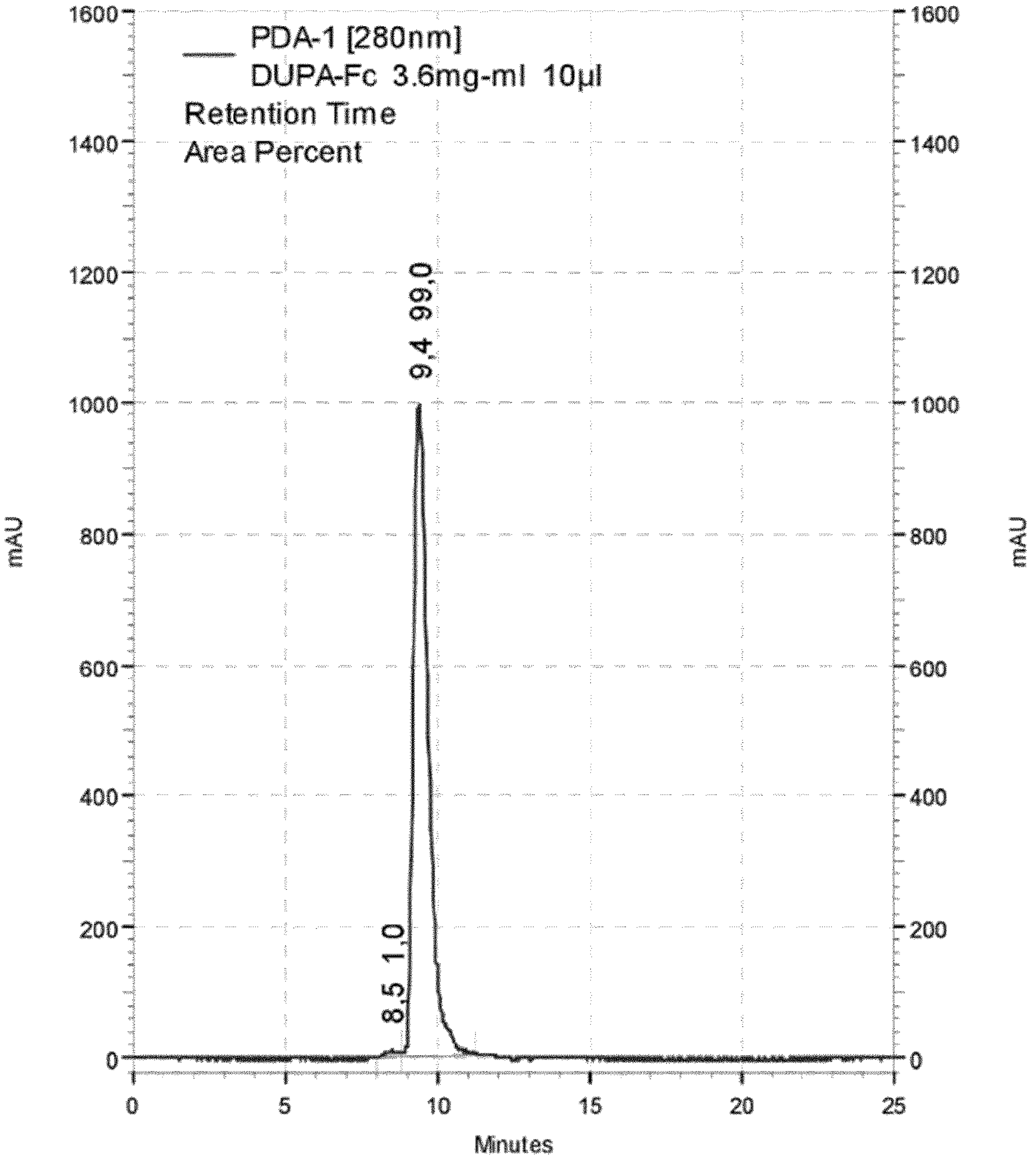
FIG. 12 shows an SEC-HPLC of purified DUPA-Fc under native non-reducing conditions (λ=280 nm; buffer: 0.05% $NaN_3$+0.1 mol/l $Na_2SO_4$ in 0.1 mol/l $NaPO_4$ pH 6.7; flow rate: 0.35 ml/min).
Figure 13:
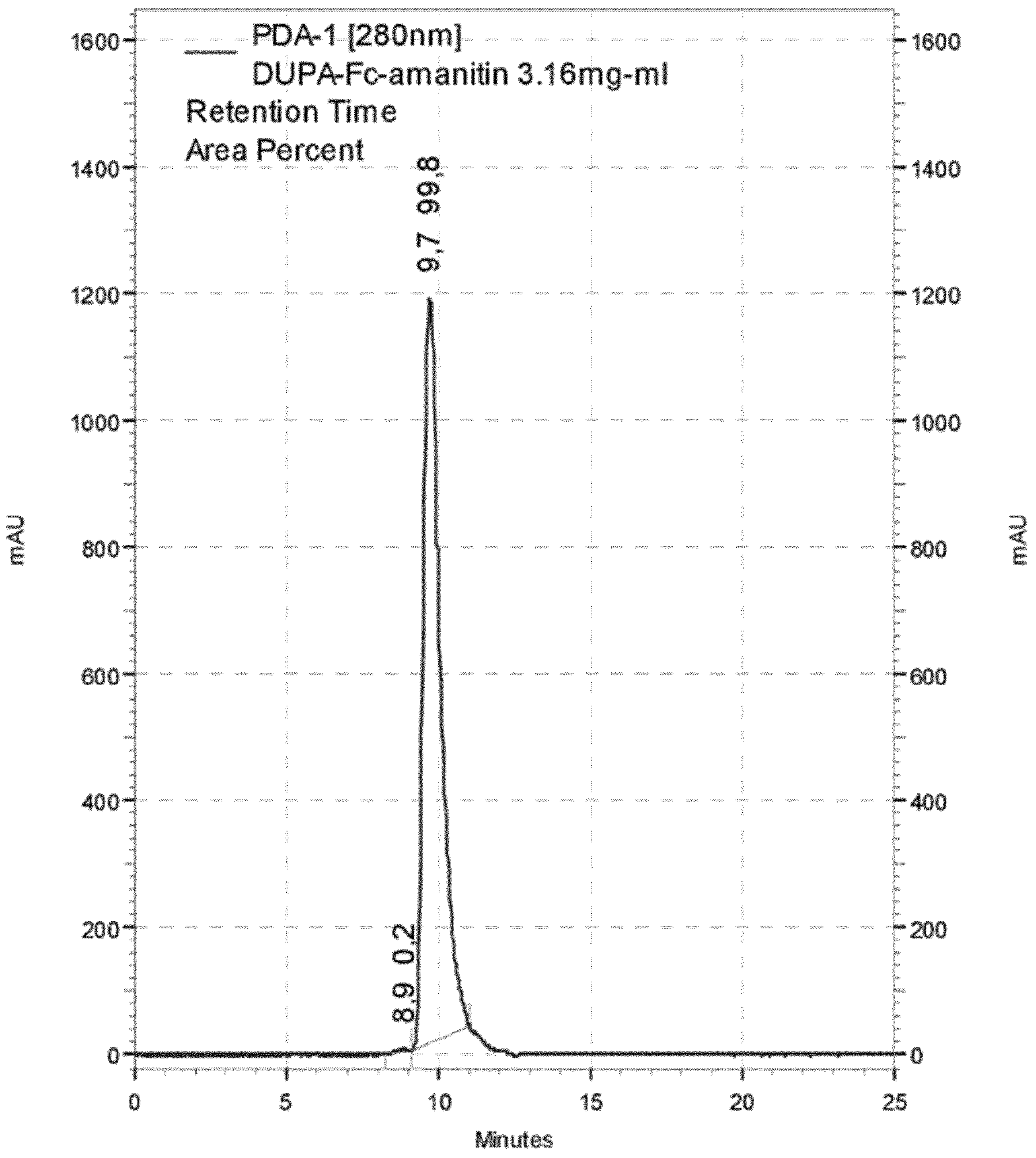
FIG. 13 shows an SEC-HPLC of purified DUPA-Fc-amanitin (A) under native non-reducing conditions at A=280 nm and (B) λ=310 nm (buffer: 0.05% $NaN_3$+0.1 mol/l $Na_2SO_4$ in 0.1 mol/l $NaPO_4$ pH 6.7; flow rate: 0.35 ml/min).

The inventors developed a two step "program and arm" strategy for grafting the DUPA-amanitin conjugate onto a human IgG1 Fc, as illustrated in FIG. 6. The Fc protein was first programmed to target PSMA-expressing cells by sortase A (SrtA)-mediated ligation of a trifunctional linker containing the PSMA-targeting moiety, the SrtA substrate and an azide handle (FIG. 7). SrtA is a transpeptidase from *Staphylococcus aureus* widely used for site-specific modifications of antibody and antibody fragments (Swee L. K., Guimares C. P., Sehrawat S., Spooner E., Barrasa M. I., Ploegh H. L. *Proc. Natl. Acad. Sci. USA* 2013, 110, 1428-1433; Kornberger P., Skerra A. *mAbs* 2014, 6, 354-366; Wagner K., Kwakkenbos M. J., Claassen Y. B., Maijoor K., Bohne M., van der Sluijs K. F., Witte M. D., van Zoelen D., J., Cornelissen L. A., Beaumont T., Bakker A. Q., Ploegh H. L., Spits H. *Proc. Natl. Acad. Sci. USA* 2014, 111, 16820-16825; Dickgiesser S., Rasche N., Nasu D., Middel S., Hörner S., Avrutina O., Diederichsen U., Kolmar H. *ACS Chem. Biol.* 2015, 10(9), 2158-2165). The reaction catalyzed by SrtA leads to the formation of a new amide bond between a C-terminal sorting motif LPXTG (X is equal to any amino acid) and an N-terminal oligoglycine (Chen L. et al. Sci. Rep. 2016, 6, article number: 31899).

An expression plasmid encoding human IgG1 Fc fragment with the C-terminal SrtA recognition sequence LPETG was cloned and used for transient expression in Expi293F™ cells. To prevent the formation of N-terminal truncations, an additional N-terminal TEV protease (Tobacco Etch Virus nuclear-inclusion-a endopeptidase) cleavage site was introduced. Furthermore, the unique glycosylation site at $N_{297}$ in the CH2 domains was genetically removed to avoid the heterogeneity issue which occurs when mammalian cells are used as production system and simplify the manufacturing and analysis process (Dmitrij Hristodorov, Rainer Fischer, Lars Linden *Mol. Biotechnol.* 2013, 54, 1056-1068). The construct was purified over protein A prior to its chemical modification, and resulted in the production of ca. 122.5 mg/L of C-termini SrtA tag-containing IgG1 Fc fragment, designated as Fc-LPETG (FIG. 6), with monomeric purity >99%.

A trifunctional DUPA-containing linker (FIG. 7A), using N-terminal GGG for Fc-LPETG transpeptidation and an azide functionality for toxin conjugation, was designed by adding the $PEG_3$-$PEG_3$-Orn($N_3$)-Lys(Gly-Gly-Gly) linker to the PSMA-targeting moiety and was assembled by SPPS.

Figure 14A:
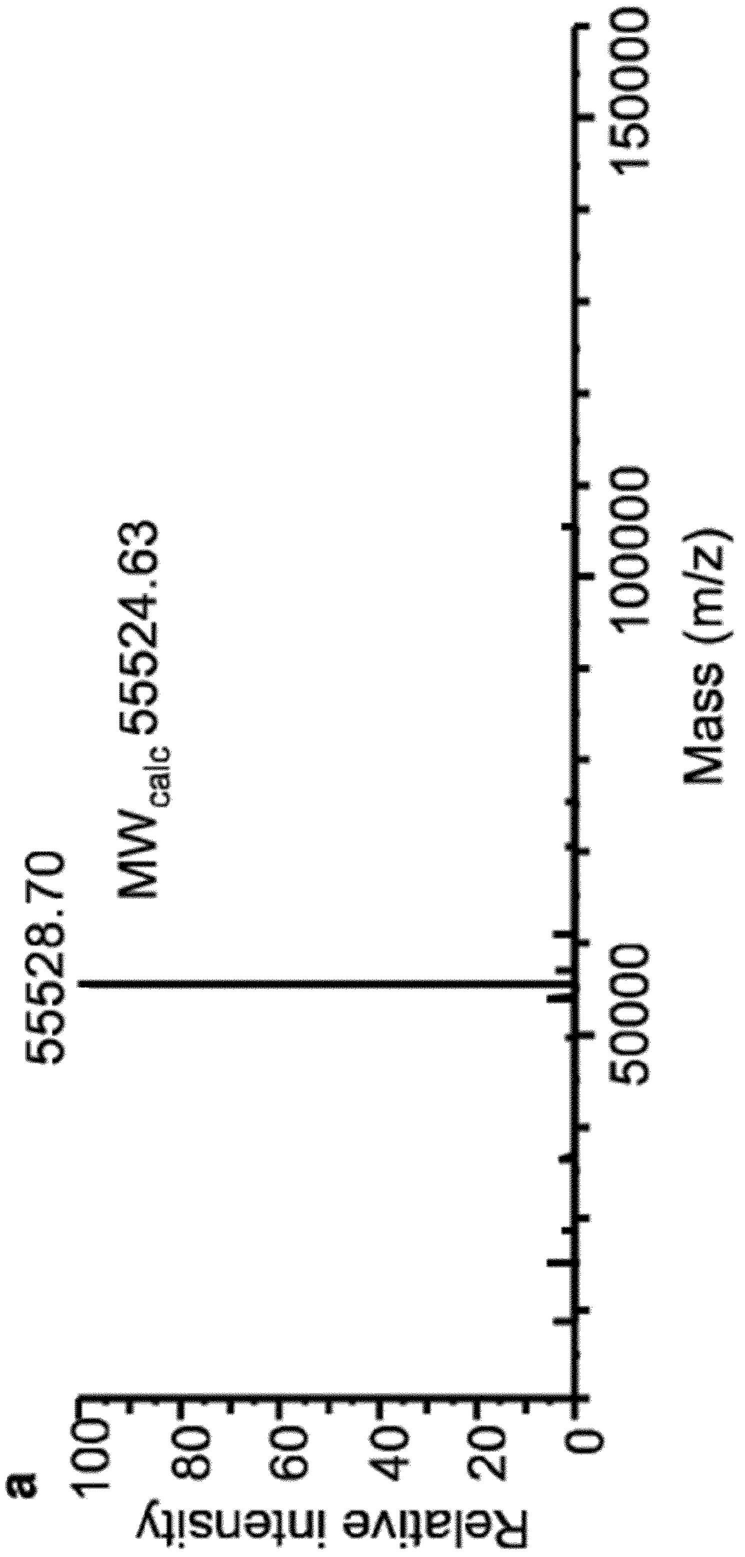
FIG. 14A shows an HRESI-MS analysis after deconvolution of Fc-LPETGG (panel a), DUPA-Fc (panel b) and DUPA-Fc-amanitin (panel c).

To this end, the Fc-LPETG construct (FIG. 6) was reacted with a large excess of trifunctional DUPA-containing linker (FIG. 7A) under the catalysis of an activity-optimized SrtA (eSrtA) (Chen I., Dorr B., Liu D. R. *Proc. Natl. Acd. Sci. USA* 2011, 108, 1139-11404). Ligation conditions were optimized to ensure maximum conjugation yield and minimize reversed reaction. Reaction proceeded smoothly with nearly quantitative conversion according to SDS-PAGE analysis (FIG. 14B). Excess reagents were removed by size exclusion chromatography under native, non-reducing conditions. DUPA-Fc conjugate (Programmed Fc; FIG. 6) was confirmed to be a disulfide-linked Fc dimer by SDS-PAGE under reducing and non-reducing conditions (FIG. 14). ESI-MS analysis under non-reducing conditions (FIG. 14A, panel b) further confirmed the expected molecular weight for a Fc dimer. However, deconvolution results revealed two different peaks, which were assigned to versions of Fc modified with one to two molecules of linker, resulting in an average linker-to-antibody ratio (LAR) of 1.62 (FIG. 14A, panel b).

Following the SrtA-mediated conjugation, the inventors subsequently explored the strain-promoted azide alkyne cycloaddition (SPAAC), a mild and chemoselective reaction preserving the stoichiometry and residue specificity of DUPA-Fc conjugates (Thomas J. D., Cui H., North J. P., Hofer T., Rader C., Burke Jr T. R. *Bioconjugate Chem.* 2012, 23(10), 2007-2013), to “arm” the DUPA-Fc construct with the dibenzocyclooctyne (DBCO)-amanitin derivative (FIG. 7B). For this proof-of-concept study, we selected the cathepsin B-cleavable linker strategy owing to its potential to release and deliver unmodified α-amanitin to target cells.

The conjugation reaction was performed at a 20-fold excess of DBCO-amanitin followed by purification by size-exclusion—fast protein liquid chromatography (SEC-FPLC) to remove excess of free toxin derivative, yielding ca. 19 mg/L of total DUPA-Fc-amanitin conjugate (Programmed and armed Fc; FIG. 6).

Incorporation of α-amanitin in the final conjugate was confirmed by SDS-PAGE under non-reducing conditions, which showed migration to higher molecular weight in comparison to DUPA-Fc, and by Western blot analysis with immunodetection of α-amanitin (FIGS. 14B and 14C). Heterogeneity from DUPA-Fc with respect to the number of attached linker molecules led to formation of heterogenous species with drug-to-antibody ratio (DAR) ranging from one to two, as showed by SDS-PAGE and confirmed by deconvoluted mass spectrum. The average DAR was calculated as equal to 1.72, consistent to the LAR value reported for DUPA-Fc (FIG. 14A, panel c).

Step 1: Synthesis of the Trifunctional DUPA-Containing Linker

AmphiSpheres® 40 RAM resin (703 mg, 0.267 mmol) was swollen 1 h in DCM, washed with and resuspended in DMF for 30 min. Resin was deprotected with 20% piperidine in DMF (30 s, rt for 2 min, 30 W, 50° C.) and then shaked with Fmoc-Lys(Mtt)-OH (4.0 equiv), 2-(1H-Benzotriazole-1-yl)-1,1,3,3-tetramethylaminium tetrafluoroborate (TBTU; 3.99 equiv), DIPEA (8.0 equiv) in DMF (8 ml) for 1 h at rt and then under MW irradiation (30 W, 50° C., 3 min). Coupling was repeated twice with several DMF washing in between. Fmoc was removed by suspending the resin in 20% piperidine in DMF (3 ml) under the conditions described above. Each coupling was then performed by shaking the resin with Fmoc-protected amino acid (4.0 equiv), TBTU (3.99 equiv), DIPEA (8.0 equiv) in DMF (8 ml) under MW irradiation (30 W, 50° C., 3 min, ×3), followed by Fmoc-removal in the conditions mentioned herein. Protected DUPA reagent (3.0 equiv) was coupled by using TBTU (2.99 equiv), DIPEA (6.0 equiv) under MW irradiation (30 W, 50° C., 3 min, ×3). Prior to cleavage, Mtt was removed by suspending the resin-bound peptide in DCM/TIS/TFA (97:2:1, 4 ml) and shaking at rt for 10 min. Procedure was repeated as far as no Mtt-OH could be detected in the filtrate by HPLC (approximately 20 cycles). Lysine side chain was then reacted with the pre-assembled Fmoc-Gly-Gly-Gly-OH. Resin was then extensively washed with DCM and dry in vacuo. Peptide was cleaved from the resin and totally deprotected with TFA/anisole/TIS/$H_2O$ (94:2:2:2, 20 ml) cocktail for 2 h at rt. Mixture was precipitated in four portions in pre-cooled MTBE (40 ml) and pellet collected by centrifugation at 0° C. for 10 minutes. Pellet were collected, dried in vacuo and dissolved in ACN/$H_2O$ (1:1, v:v) for purification by RP-HPLC [λ=210 nm; gradient: 0 min 5% B; 14 min 40% B; 19 min 45% B; 20-21 min 100% B; 22 min 5% B; A=water with 0.05% TFA, B=acetonitrile; flow rate: 30 ml/min]. Desired compound was lyophilized directly affording 119.46 mg (28%) of desired linker as white powder.

RP-HPLC tR=14.51 min.

ESI-MS m/z: calcd for $[M-H]^-$: 1598.81 found 1598.83; calcd for $[M-2H]^{2-}$: 798.90; found 799.00.

The following scheme shows the MW-assisted SPPS of trifunctional DUPA-containing linker.

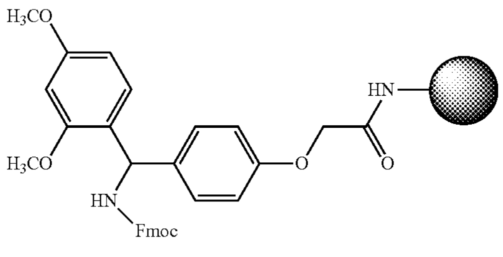

AmphiSpheres 40 RAM resin

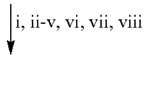

-continued

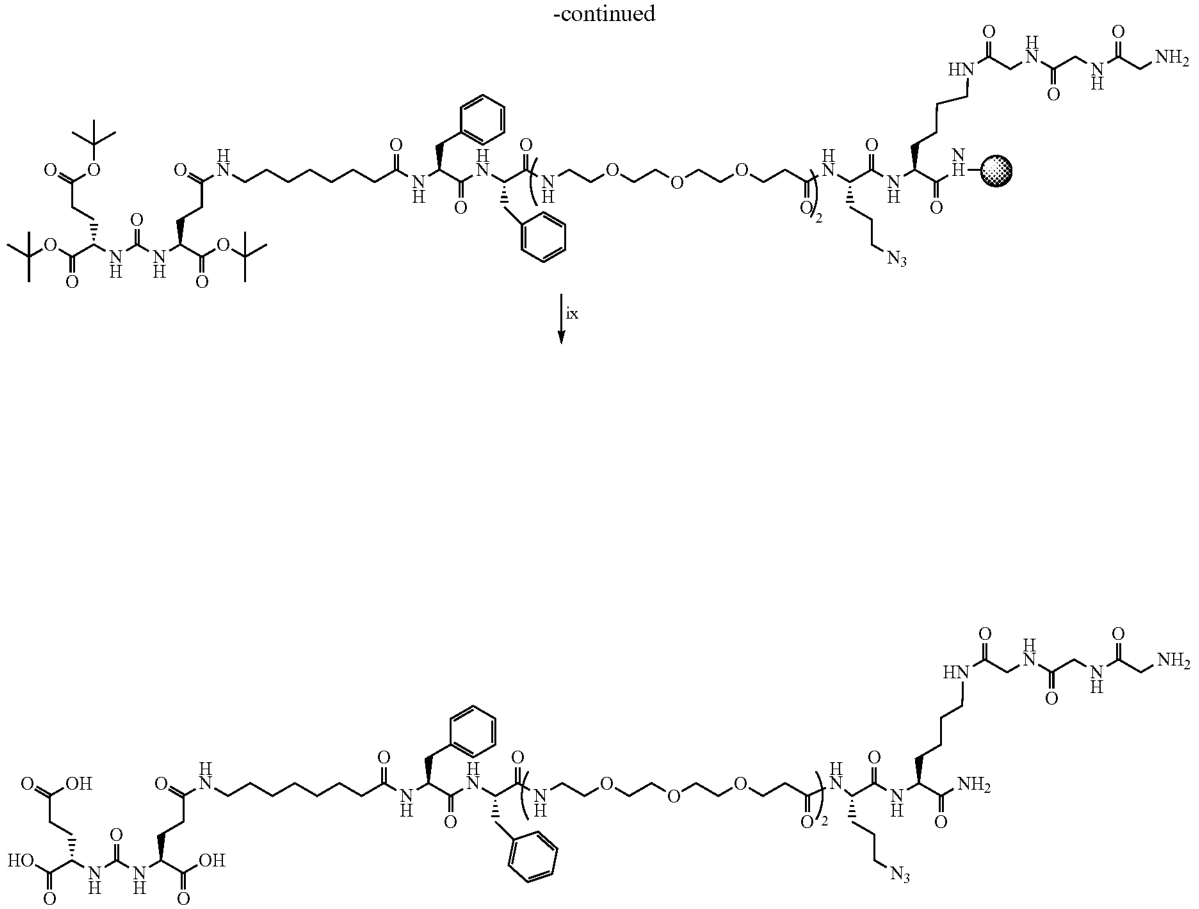

i) a-20% piperidine in DMF, rt, 30 s (×1), W=30, T=50° C., 3 min (×2), b-Fmoc-Lys(Mtt)-OH (4 equiv), TBTU (3.99 equiv), DIPEA (8 equiv), rt, 1 h, W=30, T=50° C., 3 min (×1); ii-v) a-20% piperidine in DMF, rt, 30 s (×1), W=30, T=50° C., 3 min (×2), b-c-AA-OH (4 equiv), TBTU (3.99 equiv), DIPEA (8 equiv), W=30, T=50° C., 3 min (×3); vi) a-20% piperidine in DMF, rt, 30 s (×1), W=30, T=50° C., 3 min (×2), b-4, (3.0 equiv), TBTU (2.99 equiv), DIPEA (6.0 equiv), W=30, T=50° C., 3 min (×3); vii) a-TFA/TIS/DCM (1/2/97, 4 ml), rt, 10 min (×20), viii) a-Fmoc-Gly-Gly-Gly-OH (4 equiv), TBTU (3.99 equiv), DIPEA (8 equiv), 1 h, rt, W=30, T=50° C., 3 min (×3), b-20% piperidine in DMF, rt, 30 s (×1), W=30, T=50° C., 3 min (×2) [×3]; ix) TFA/anisole/TIS/$H_2O$ (94/2/2/2, 20 ml), rt, 2 h.

Step 2: Synthesis of Amanitin-DBCO Linker

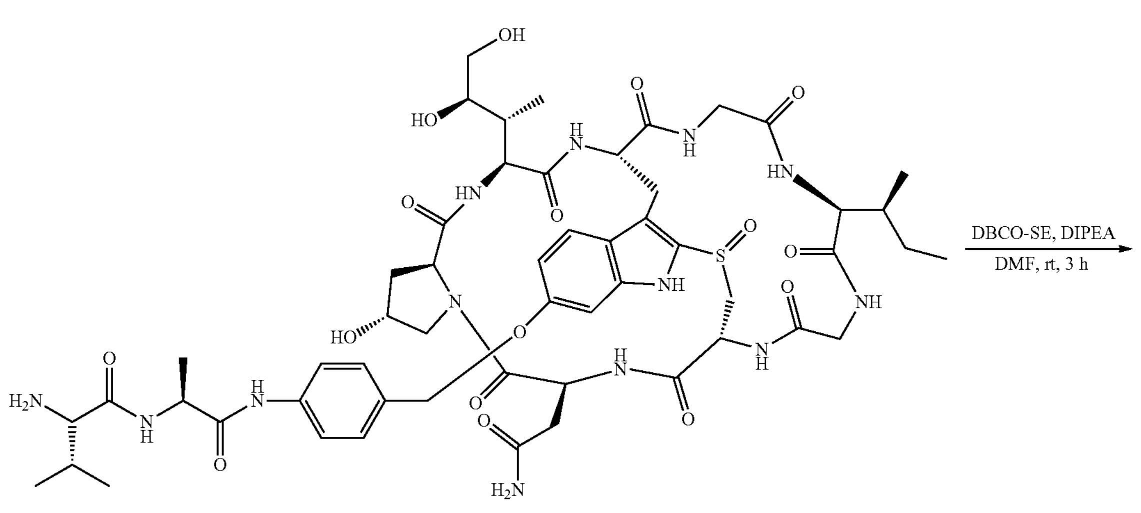

HDP 30.1702

-continued

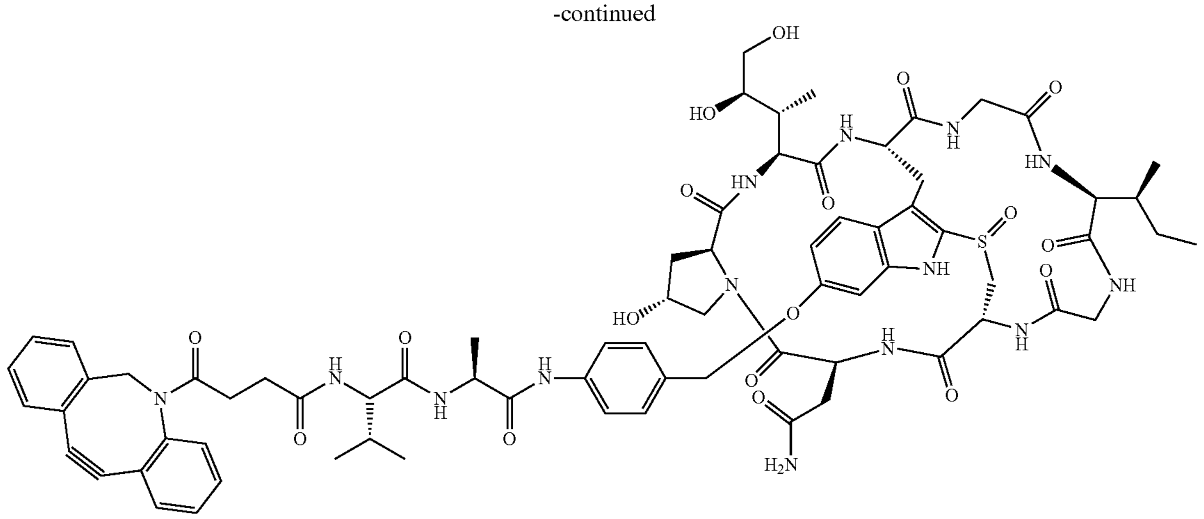

DBCO-amanitin linker

The amanitin-DBCO derivative was synthetized, as shown in the scheme above, from amanitin precursor HDP 30.1702 whose synthesis was accomplished according to the procedure described herein above (Example 18). Precusor HDP 30.1702 (80.32 mg, 0.067 mmol) was dissolved in absolute DMF (1.6 ml). Dibenzocyclooctine-N-succinimidyl ester (DBCO-SE) (29.8 mg, 0,074 mmol) was dissolved in DMF (1.6 ml) and DIPEA (22.9 µl, 0.13 mmol) was added to the solution. Reaction mixture was stirred at rt for 2.5 h.

Reaction was quenched by adding $H_2O$ (100 µl) and DMF was evaporated in vacuo. Residue was dissolved in methanol (MeOH) (2 ml) and dripped into pre-cooled MTBE (40 ml) and centrifuged at 0° C. The pellet was washed with MTBE (40 ml), collected and dried in vacuo. The compound was purified by RP-HPLC [λ=305 nm; gradient: 0-15 min 5% B; 18 min 100% B; 1,5-22 min 5% B; A=water with 0.05% TFA, B=acetonitrile; flow rate: 30 ml/min]. Fractions corresponding to the product were directly lyophilized affording 77.88 mg (78%) of amanitin-DBCO derivative as white powder.

ESI-MS m/z: calcd for $[M+H]^+$: 1481.62, found 1481.42; calcd for $[M+2H]^{2+}$: 741.32, found 741.42.

Step 3: Cloning of Plasmid for Protein Expression

The plasmid vector pEXPR-TEV-G5-H20C-Fc-LPETGG (provided by Prof. H. Kolmar, T U Darmstadt, Germany) encodes the amino acid sequence of SEQ ID No. 1. The plasmid was used for expression of the Fc-LPETG polypeptide composed of a TEV cleavage site, the $H_2O$ region, an Fc domain representing the $CH_2$ and $CH_3$ regions of an immunoglobulin, and the SrtA tag (see FIG. 8).

```
SEQ ID No. 1:
AENLYFQGGGGGEPKSCDKTHTCPPCPAPELLGGPSVFLFPPKPKDTLMI

SRTPEVTCVVVDVSHEDPEVKFNWYVDGVEVHNAKTKPREEQYASTYRVV

SVLTVLHQDWLNGKEYKCKVSNKALPAPIEKTISKAKGQPREPQVYTLPP

SRDELTKNQVSLTCLVKGFYPSDIAVEWESNGQPENNYKTTPPVLDSDGS

FFLYSKLTVDKSRWQQGNVFSCSVMHEALHNHYTQKSLSLSPGGS
```

-continued

```
SEQ ID No. 2:
LPETGG

SEQ ID No. 3:
AENLYFQGGGGGEPKSCDKTHTCPPCPAPELLGGPSVFLFPPKPKDTLMI

SRTPEVTCVVVDVSHEDPEVKFNWYVDGVEVHNAKTKPREEQYASTYRVV

SVLTVLHQDWLNGKEYKCKVSNKALPAPIEKTISKAKGQPREPQVYTLPP

SRDELTKNQVSLTCLVKGFYPSDIAVEWESNGQPENNYKTTPPVLDSDGS

FFLYSKLTVDKSRWQQGNVFSCSVMHEALHNHYTQKSLSLSPGGSLPETG

G
```

Step 4: Expression and Purification of Protein Fc-LPETGG

Expi 293F™ cells were transiently transfected with the Fc-LPETGG construct using PEI reagent (polyethyleneimine) in accordance to the manufacturer's instructions. Expi293F™ cells were cultivated in 2 l flasks with a final volume of 500 ml of Expi293 culture medium per flask.

Transfection complex was prepared by mixing 1.5 ml of PEI reagent (1 mg/ml in $H_2O$) with 500 µg of DNA in 50 ml of Opti-MEM medium. After 15 min incubation at rt, transfection mixture was added to a suspension of Expi293F™ cells in 425 ml volume. At 16 h after transfection, cells were centrifuged at 460×g at rt for 20 min, supernatant was discarded and 500 ml of fresh Expi293F expression medium was added. At day 6 after transfection, cells were centrifuged at 3488×g and 4° C. for 40 min. Cells supernatant was centrifuged once again at 10947×g at 4° C. for 20 min. The culture medium was diluted with 500 ml of phosphate-buffered saline (PBS) solution and centrifuged through 1.2, 0.65, 0.45, 0.22 µm steril filters. The final solution was applied to a Protein A column. The column was washed with binding buffer (PBS pH 7.4) and bound fraction eluted with elution buffer (glycine 0.1 M pH 3.0) and neutralized with neutralization buffer (Tris(hydroxymethyl) aminomethane hydrochloride (Tris-HCl) 1 M pH 9.0). Collected protein sample was dialyzed against SrtA buffer (Tris-HCl 50 mM pH 7.4, NaCl 150 mM) at 4° C. overnight.

Protein concentration was determined by $Abs_{280\ nm}$ to be 4.8 mg/ml (122.5 mg/I of culture).

Step 5: Sortase a (SrtA)-Mediated Ligation of Peptide Trifunctional DUPA-Containing Linker to the Fc-LPETG Fragment eSrtA was prepared as described by Chen et al. PNAS 2011 108 (28) 11399-11404. Protein A purified Fc-LPETG (40 mg, 20.65 μM) was mixed with trifunctional DUPA-containing linker (50 equiv., 1 mM) in SrtA reaction-buffer (Tris-HCl 50 mM pH 7.5, NaCl 150 mM, $CaCl_2$) 5 mM) in presence of sortase A pentamutant (eSrtA) enzyme (0.125 eq, 2.6 μM). Reaction was allowed to proceed for 18 h at 25° C. and then purified using SEC-FPLC over a HiLoad™ 26/600 Superdex™ 200 pg column to remove eSrtA and excess of peptide. Column was first equilibrated with PBS buffer (pH 7.4) and then DUPA-containing Fc 15 eluted using the same buffer as used for column equilibration. The flow through from the column was concentrated using an Amicon® Ultra-15 Centrifugal Filter (MWCO 50000) and filtered through a 0.22 μm sterile filter (Sterile Millex® Filter). Concentration of DUPA-Fc conjugate was determined to be 3.6 mg/ml (27.87 mg) by $Abs_{280\ nm}$ (MW=58461.89 Da, $\varepsilon_{280}$=74675.1 $cm^{-1}M^{-11}$).

Step 6: Conjugation by SPAAC of DBCO-Amanitin Linker to DUPA-Fc Construct

DBCO-amanitin linker (20 equiv., 12.18 mg) was dissolved in ACN/$H_2O$ (3:1, 1.28 ml) and added to DUPA-Fc (24 mg, 48.6 μM) in PBS buffer (pH 7.4, 8.46 ml). DMSO (2.24 ml) was added. Mixture was incubated at 37° C. for 24 h. Purification was performed by SEC-FPLC over a HiLoad™ 16/600 Superdex™ 200 pg column. Conjugate was concentrated to a final volume of 7.5 ml filtered through a 0.22 μm sterile filter prior to its use in biological assays. Concentration of DUPA-Fc-amanitin conjugate was determined as 3.16 mg/ml (23.7 mg) by $Abs_{280\ nm}$ (MW=61425.21 Da, $\varepsilon_{280}$=85500 $cm^{-1}M^{-11}$).

Example 44

The cytotoxicity of the DUPA-Fc-α-amanitin conjugate was tested in four prostate cancer cell lines compared with Fc-DUPA-linker alone and conjugate in presence of a 200-fold molar excess of PSMA inhibitor 2-PMPA.

Figure 15:
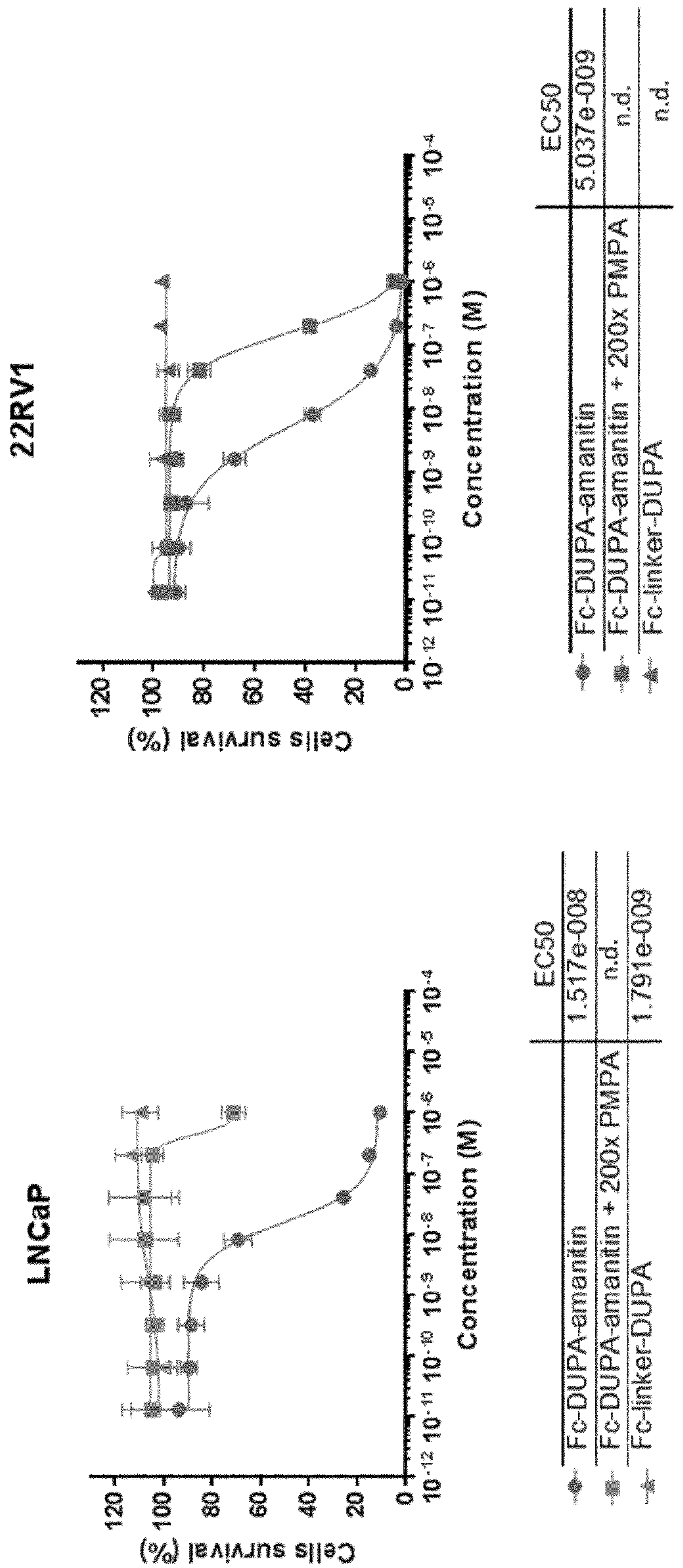
FIG. 15 shows the cytotoxicity of the DUPA-Fc-α-amanitin conjugate in four prostate cancer cell lines compared with Fc-DUPA-linker alone and conjugate in presence of a 200-fold molar excess of PSMA inhibitor 2-PMPA.

The cytotoxic effect of the DUPA-Fc-α-amanitin conjugate is observed only in PSMA expressing cell lines LNCaP and $C_{4-2}$ PSMA (+++); 22RV1 PSMA) (+). EC50 in PSMA positive cell line was observed in the range between 5.04-15.17 nM. Activity of conjugate was completely inhibited by 2-PMPA. As expected no activity of the conjugate was observed in PSMA negative PC3 cell line. The conjugate demonstrated excellent in vitro selectivity (FIG. 15).

Figure 16:
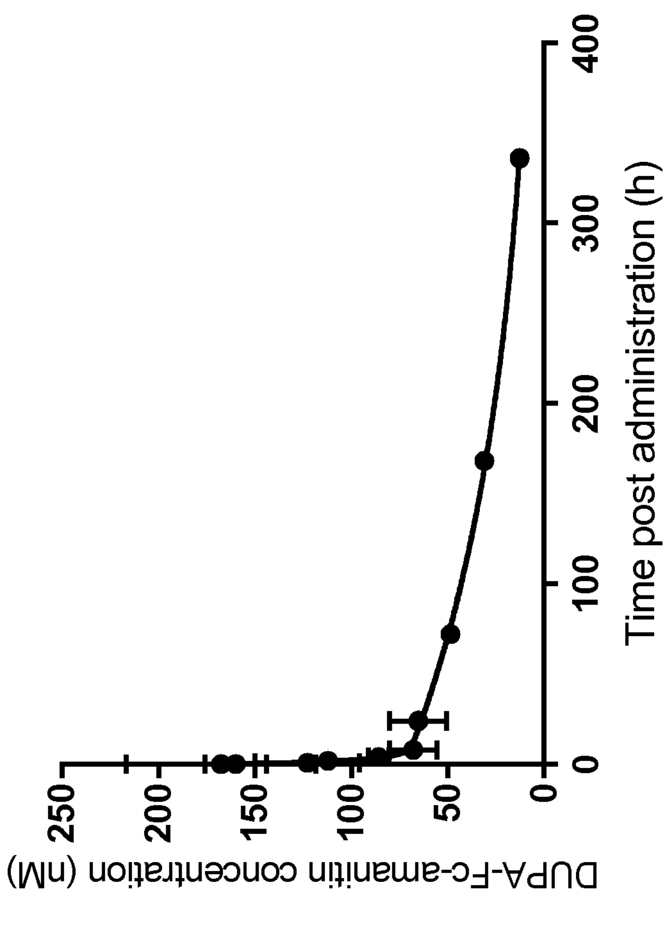
FIG. 16 shows blood pharmacokinetics of DUPA-Fc-α-amanitin conjugate in Cb17 Scid male mice (n=3). A biphasic elimination profile associated with bicompartmental model and FcRn recycling was observed.

Blood pharmacokinetics of DUPA-Fc-α-amanitin conjugate was tested in Cb17 Scid male mice (n=3). A biphasic elimination profile associated with bicompartmental model and FcRn recycling was observed. Fast elimination phase half-life was determined for 82 min and is observed at early time-points after administration 5 min.-4 h. Slow elimination phase is clearly observed from 4 h after administration onward. The half-life for this phase was determined for 5.5 day (FIG. 16).

The anti-tumor effect of DUPA-Fc-α-amanitin conjugate was tested in a Cb 17 Scid mouse LNCaP xenograft model (n=8-9)

Proposed dosing scheme was completely tolerated as indicated by relative body weight graph schemes. Observed cachexia is associated with LNCaP model and is also observed in vehicle injected group.

Figure 17:
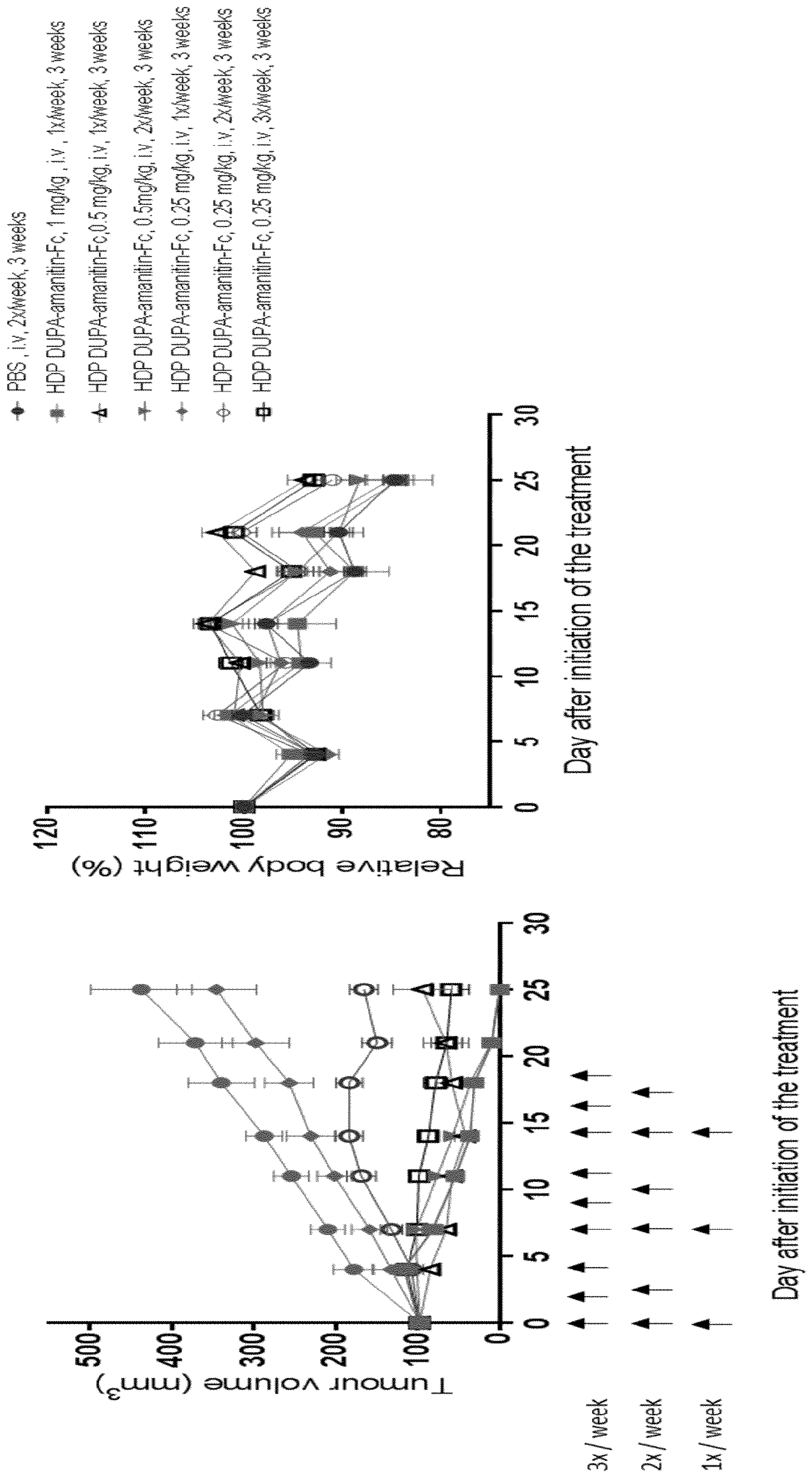
FIG. 17 shows anti-tumor effect of DUPA-Fc-α-amanitin conjugate in a Cb 17 Scid mouse LNCaP xenograft model (n=8-9) Proposed dosing scheme was completely tolerated as indicated by relative body weight graph schemes. Observed cachexia is associated with LNCaP model and is also observed in vehicle injected group.

Anti-tumor effect of DUPA-Fc-α-amanitin conjugate is clearly dose and administration frequency dependent. 1 mg/kg administered once per week and 0.5 mg/kg administered two times per week yielded complete response in all treated animals at day 25 after the therapy initiation. The 0.25 mg/kg administered three times per week and 0.5 mg/kg administered once per week yielded similar tumor responses: leaded to slight tumor regression and inhibited the tumor growth till day 25. 0.25 mg/kg administered two times per week inhibited the tumor growth during the period of administration however showed limited in vivo efficacy. 0.25 mg/kg administered once per week only slightly delayed tumor growth but in the end of the treatment period was statistically non-different than the vehicle treated arm (FIG. 17).

The invention claimed is:

1. A conjugate comprising (a) an amatoxin, (b) a PSMA-binding moiety consisting of 2-[3-(1,3-dicarboxy-propyl) ureido]pentanedioic acid or 6-amino-2-[3-(1,3-dicarboxy-propyl)ureido]-hexanoic acid, and (c) a linking moiety linking said amatoxin and said PSMA-binding moiety, the conjugate having structure VII or VIII

VII

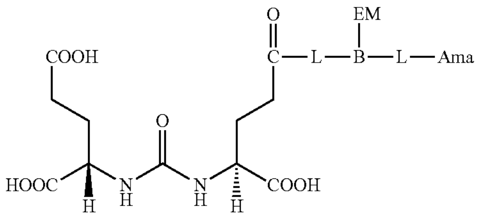

-continued

VIII

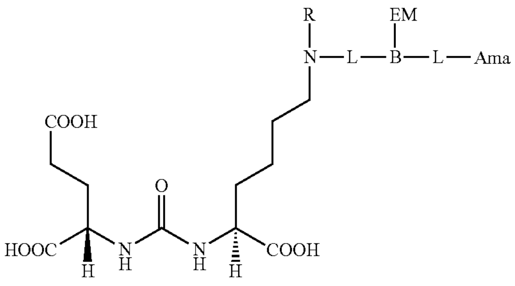

wherein each L is a linker, Ama is the amatoxin, B is a trifunctional linker element, EM is a half-life extension moiety, and R is selected from H, $C_{1-6}$-alkyl, and p-bromobenzyl, and wherein the conjugate comprises a 1,2,3-triazole resulting from a reaction of an azide moiety of the trifunctional linker B and an alkyne moiety of said linker L connecting said amatoxin to said trifunctional linker B, and wherein said alkyne moiety is selected from propiolic acid, 3-butynoic acid, 4- pentynoic acid, 5-hexynoic acid, dibenzylcyclooctyne (DiBO), dibenzylazacyclooctynone (DBCO) and bicyclo[6.1.0]non-4-yne (BCN).

2. The conjugate of claim 1, wherein the half-life extension moiety comprises an Fc moiety of an antibody.

3. The conjugate of claim 1 having the structure IX

IX

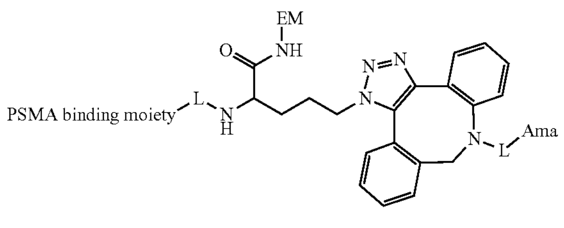

wherein each L is a linker, Ama is the amatoxin, EM is the half-life extension moiety, and the PSMA-binding moiety consists of 2-[3-(1,3-dicarboxy-propyl)ureido]pentanedioic acid or 6-amino-2-[3-(1,3-dicarboxypropyl)ureido]-hexanoic acid.

4. The conjugate of claim 1, wherein said L-Ama is selected from

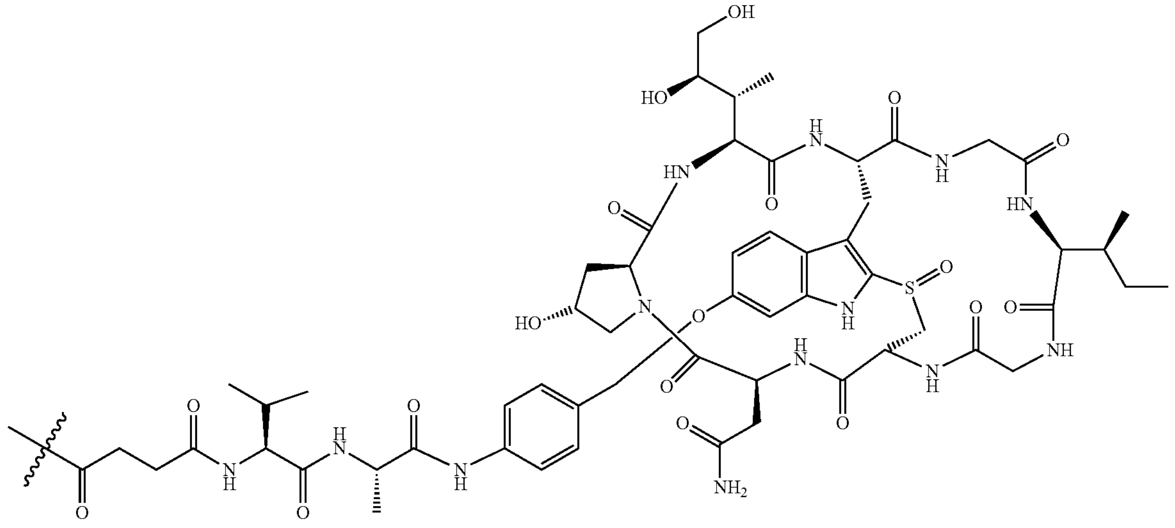

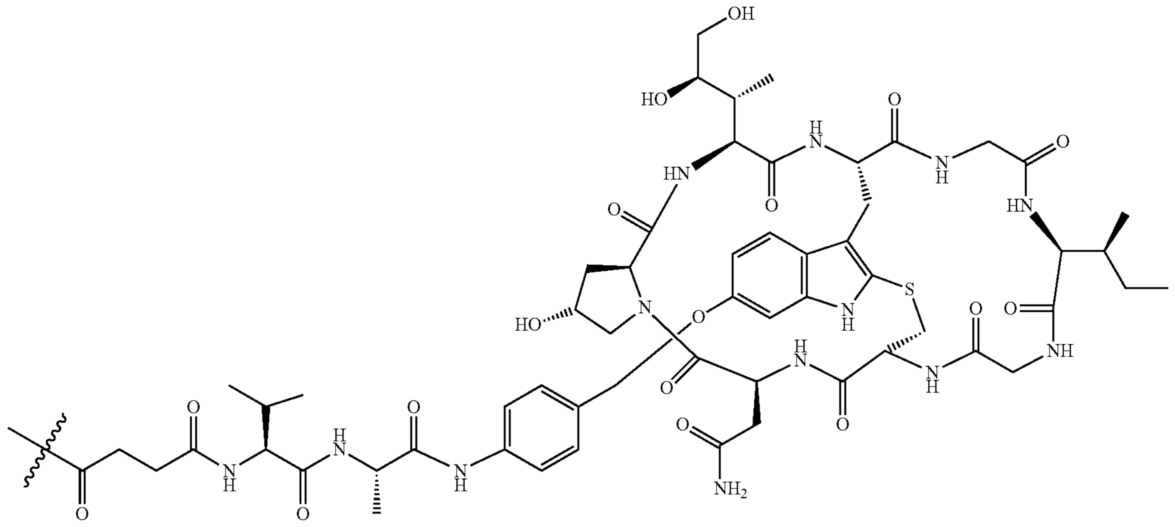

-continued
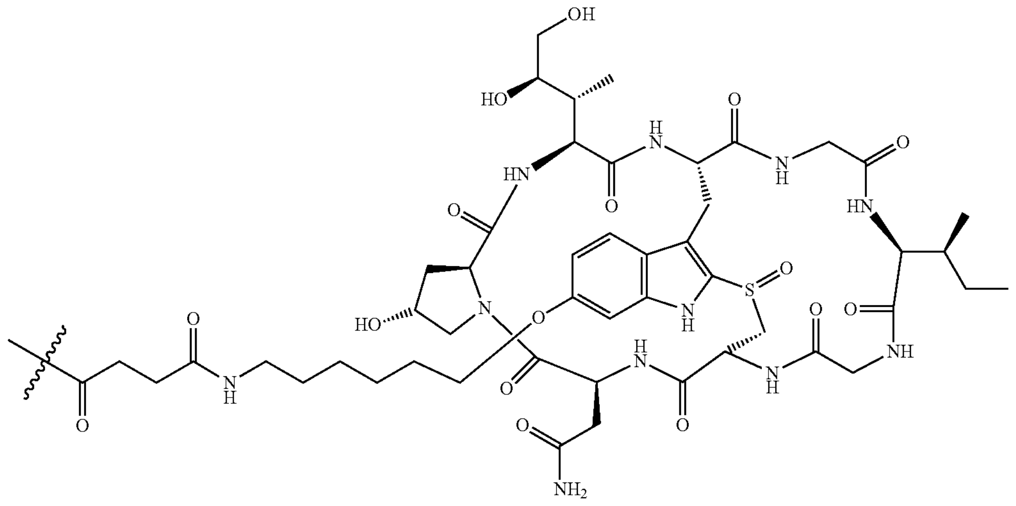
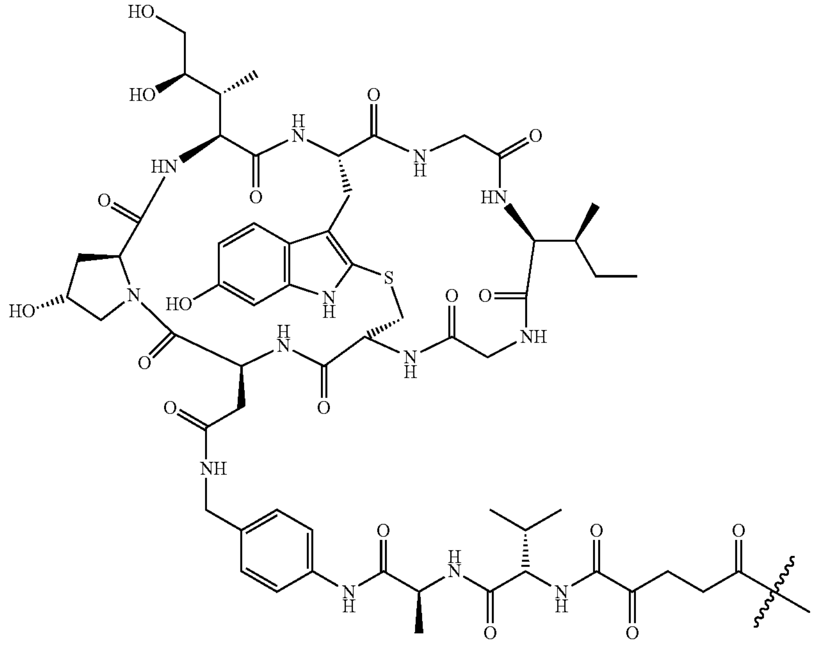

-continued
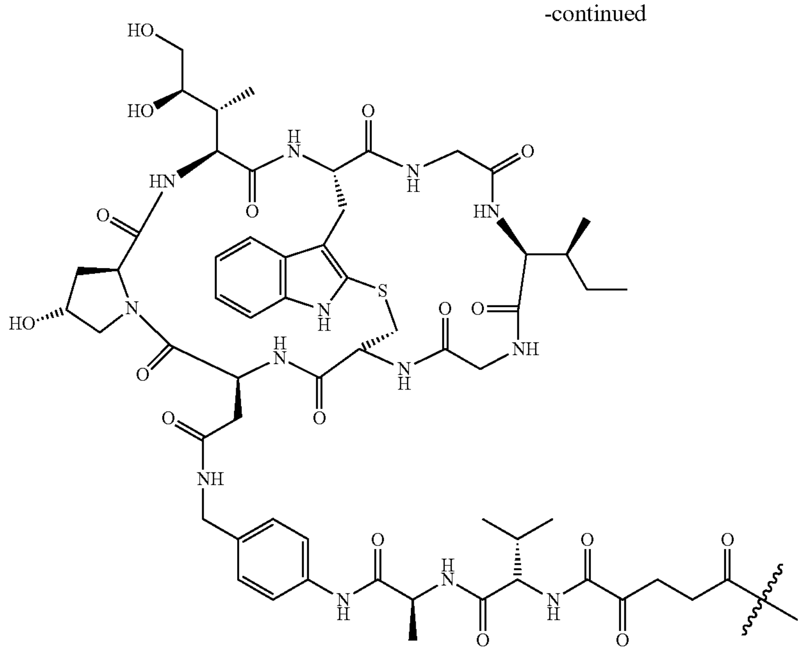
and
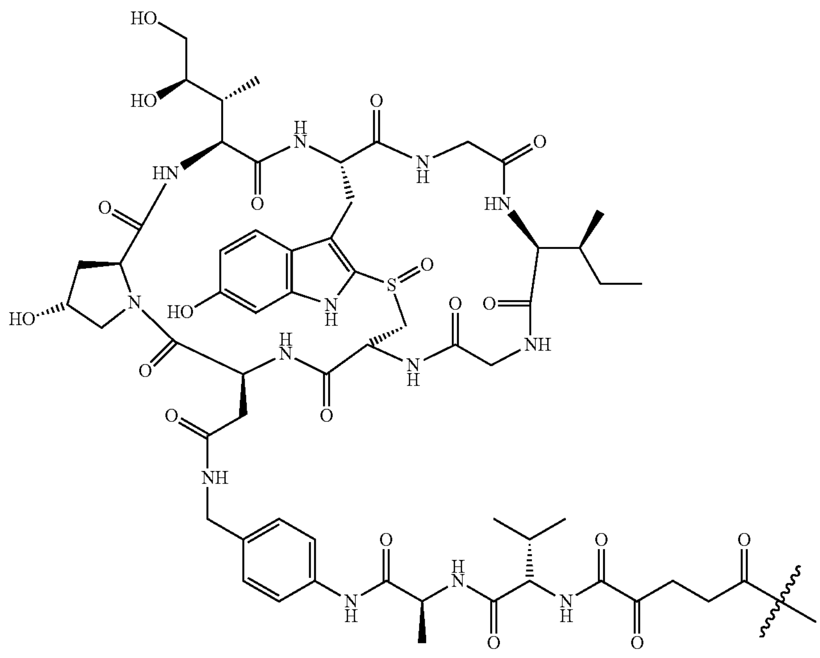
.

5. The conjugate of claim 4, wherein the conjugate is selected from
(SEQ ID NO: 4)
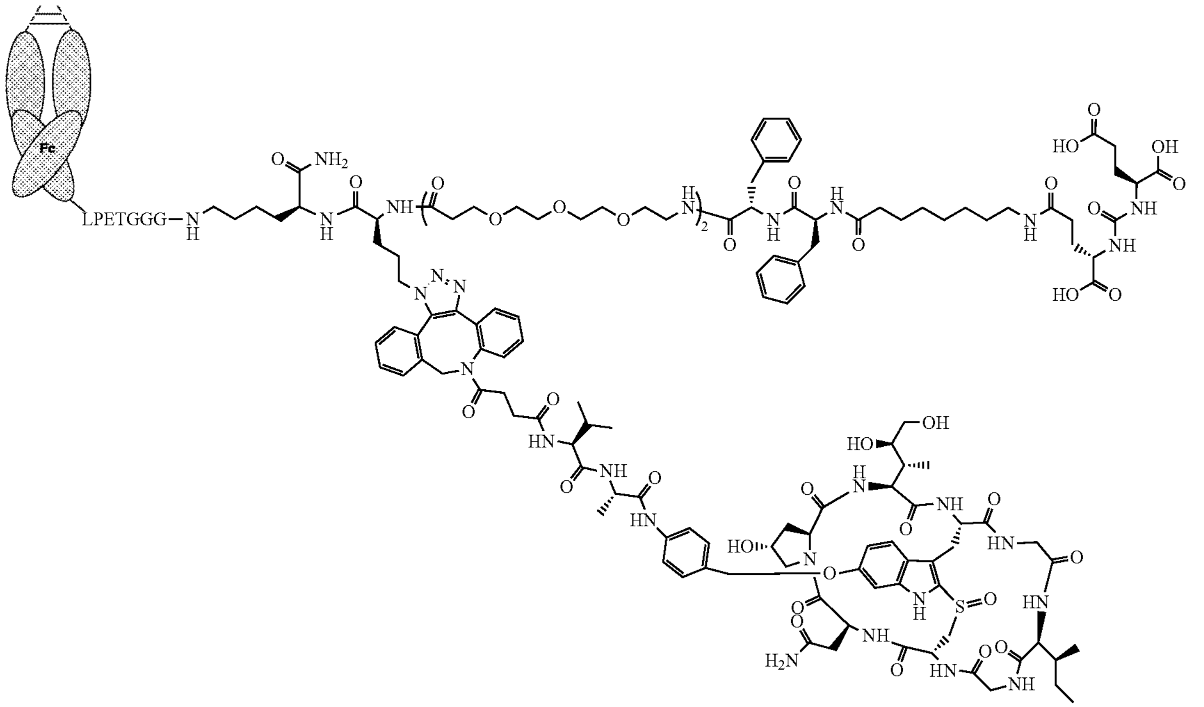
(SEQ ID NO: 4)
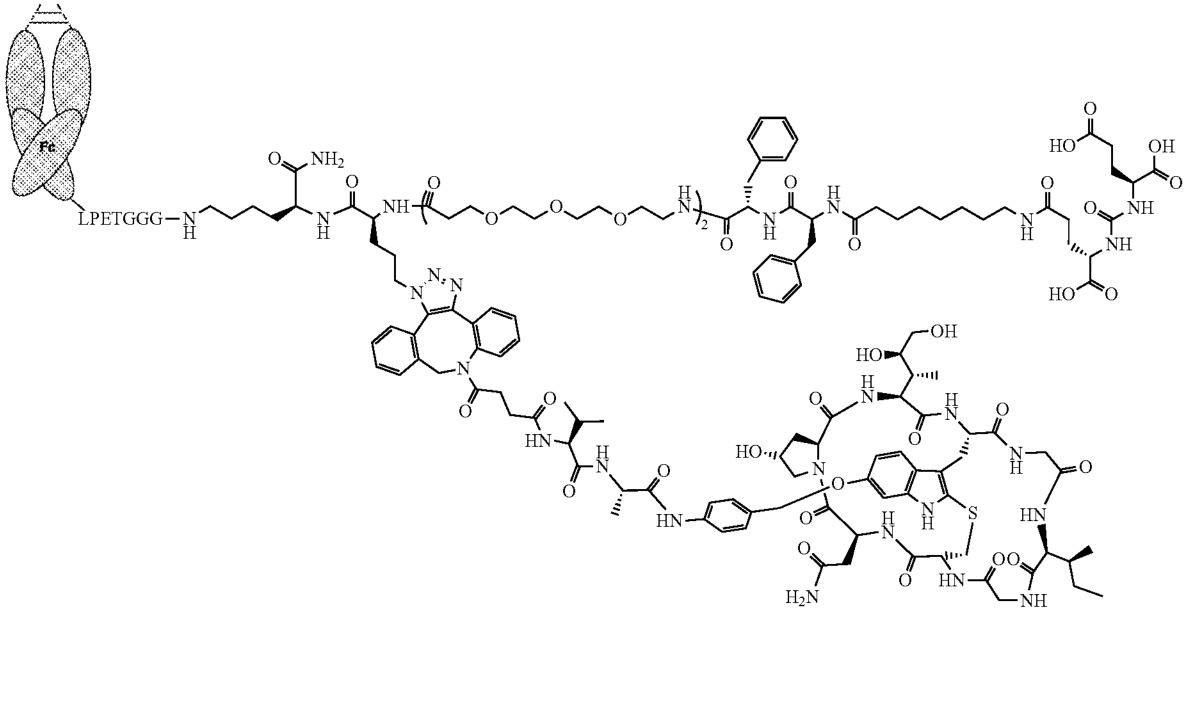

-continued
(SEQ ID NO: 4)
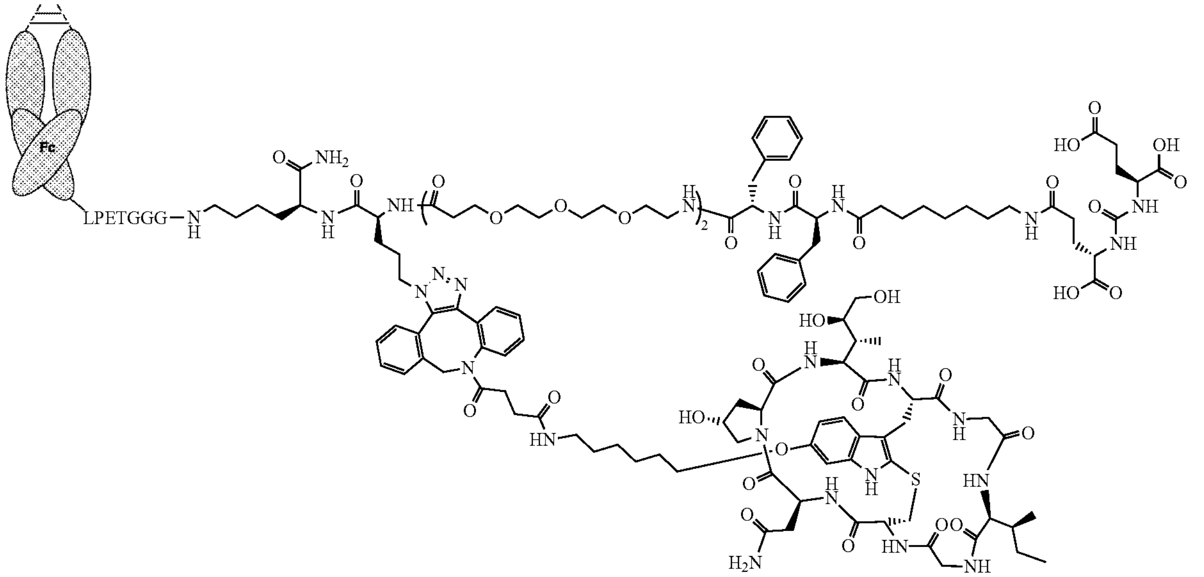
(SEQ ID NO: 4)
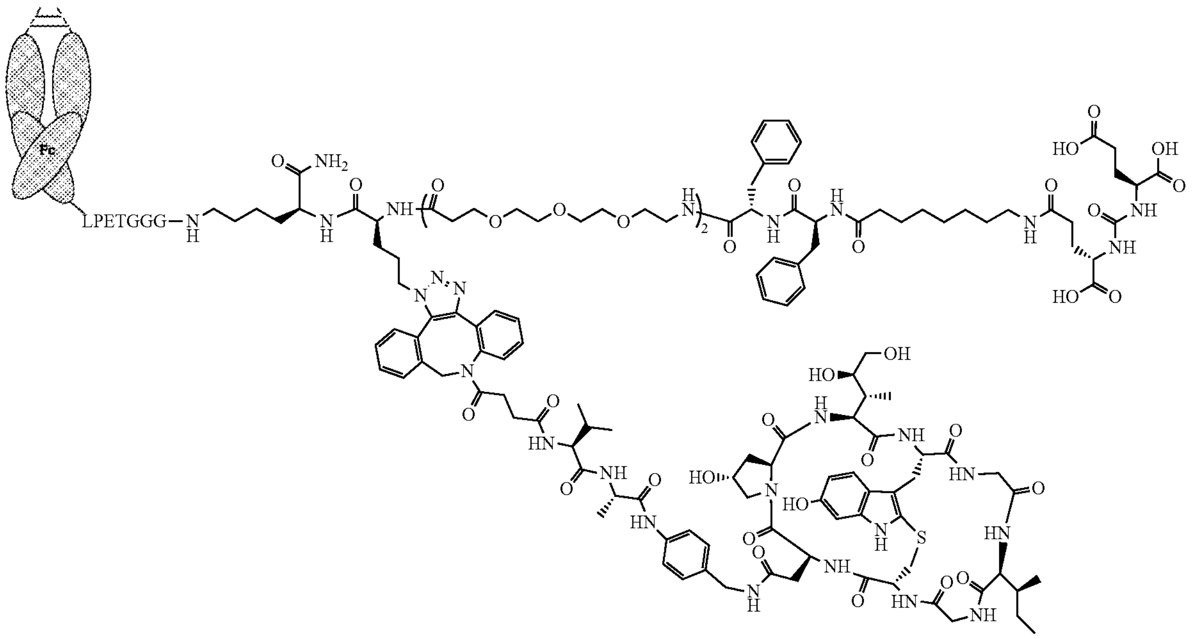

-continued (SEQ ID NO: 4)

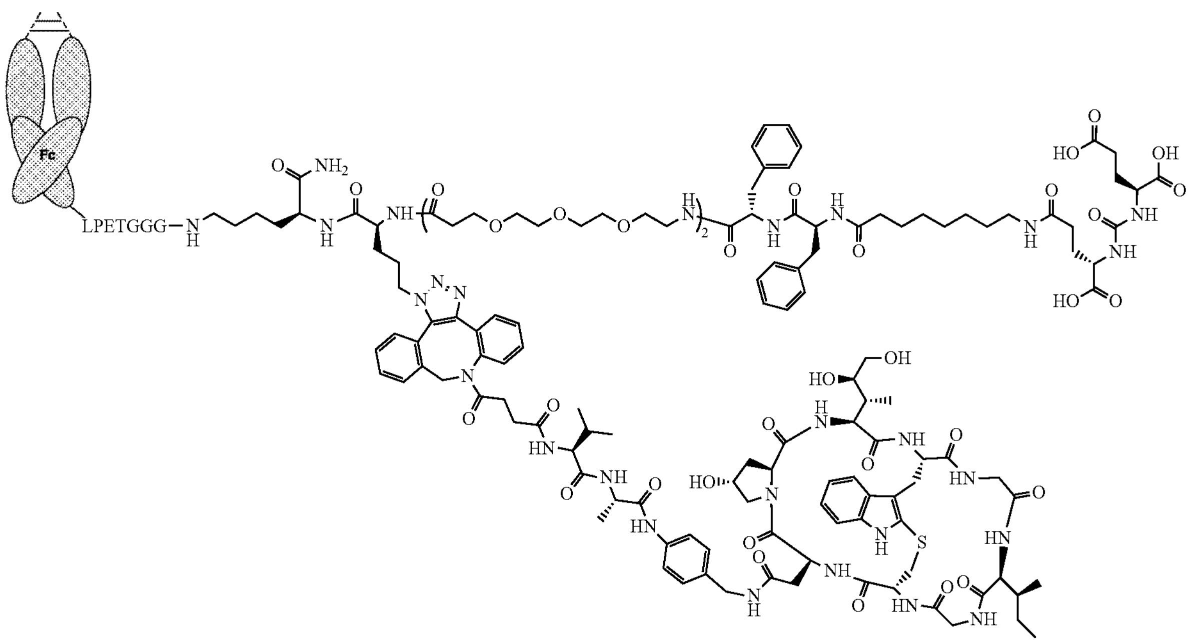

and (SEQ ID NO: 4)

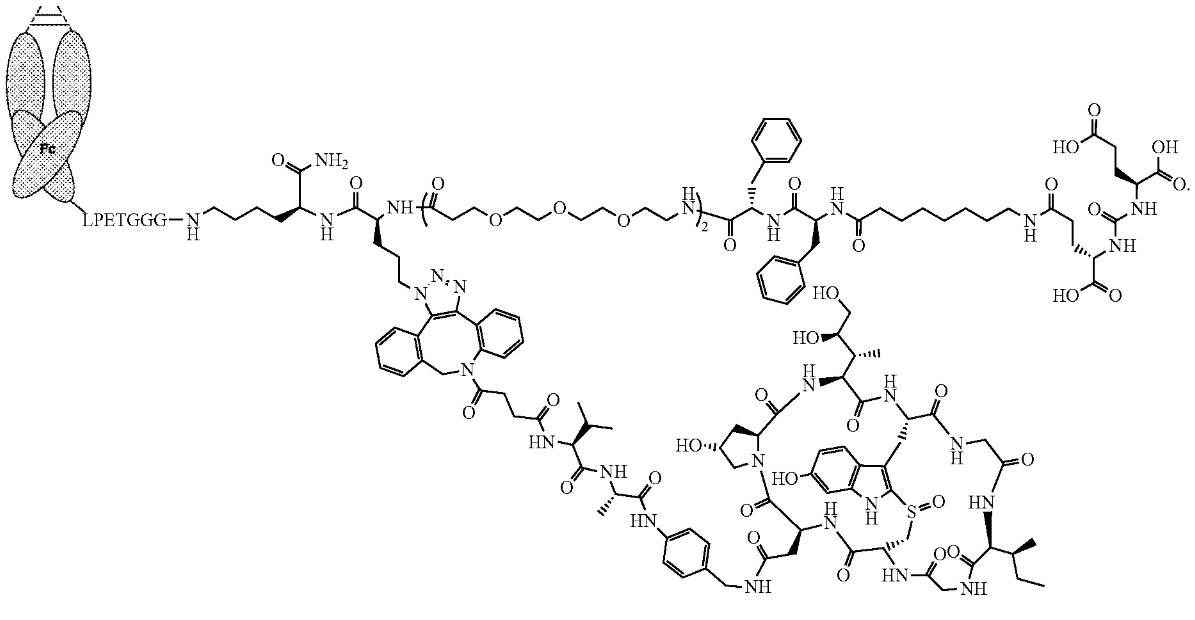

6. The conjugate of claim 2, wherein said Fc moiety consists of SEQ ID NO: 1 or SEQ ID NO: 3.

7. A pharmaceutical composition comprising a conjugate according to claim 1.

8. A method of treating cancer in a patient comprising administering a conjugate of claim 1 to the patient, wherein the cancer is selected from breast cancer, pancreatic cancer, cholangiocarcinoma, colorectal cancer, lung cancer, prostate cancer, ovarian cancer, stomach cancer, kidney cancer, malignant melanoma, leukemia, and malignant lymphoma.

9. A pharmaceutical composition comprising a conjugate according to claim 2.

10. A pharmaceutical composition comprising a conjugate according to claim 3.

11. A pharmaceutical composition comprising a conjugate according to claim 4.

12. A pharmaceutical composition comprising a conjugate according to claim 5.

13. A pharmaceutical composition comprising a conjugate according to claim 6.

14. A method of treating cancer in a patient comprising administering a conjugate of claim 2 to the patient, wherein the cancer is selected from breast cancer, pancreatic cancer, cholangiocarcinoma, colorectal cancer, lung cancer, prostate cancer, ovarian cancer, stomach cancer, kidney cancer, malignant melanoma, leukemia, and malignant lymphoma.

15. A method of treating cancer in a patient comprising administering a conjugate of claim 3 to the patient, wherein the cancer is selected from breast cancer, pancreatic cancer, cholangiocarcinoma, colorectal cancer, lung cancer, prostate cancer, ovarian cancer, stomach cancer, kidney cancer, malignant melanoma, leukemia, and malignant lymphoma.

16. A method of treating cancer in a patient comprising administering a conjugate of claim 4 to the patient, wherein the cancer is selected from breast cancer, pancreatic cancer, cholangiocarcinoma, colorectal cancer, lung cancer, prostate cancer, ovarian cancer, stomach cancer, kidney cancer, malignant melanoma, leukemia, and malignant lymphoma.

17. A method of treating cancer in a patient comprising administering a conjugate of claim 5 to the patient, wherein the cancer is selected from breast cancer, pancreatic cancer, cholangiocarcinoma, colorectal cancer, lung cancer, prostate cancer, ovarian cancer, stomach cancer, kidney cancer, malignant melanoma, leukemia, and malignant lymphoma.

18. A method of treating cancer in a patient comprising administering a conjugate of claim 6 to the patient, wherein the cancer is selected from breast cancer, pancreatic cancer, cholangiocarcinoma, colorectal cancer, lung cancer, prostate cancer, ovarian cancer, stomach cancer, kidney cancer, malignant melanoma, leukemia, and malignant lymphoma.

* * * * *

SEQUENCE LISTING

```
<160> NUMBER OF SEQ ID NOS: 4

<210> SEQ ID NO 1
<211> LENGTH: 245
<212> TYPE: PRT
<213> ORGANISM: Artificial Sequence
<220> FEATURE:
<223> OTHER INFORMATION: Synthetic

<400> SEQUENCE: 1

Ala Glu Asn Leu Tyr Phe Gln Gly Gly Gly Gly Gly Glu Pro Lys Ser
1               5                   10                  15

Cys Asp Lys Thr His Thr Cys Pro Pro Cys Pro Ala Pro Glu Leu Leu
            20                  25                  30

Gly Gly Pro Ser Val Phe Leu Phe Pro Pro Lys Pro Lys Asp Thr Leu
        35                  40                  45

Met Ile Ser Arg Thr Pro Glu Val Thr Cys Val Val Val Asp Val Ser
    50                  55                  60
```

-continued

His Glu Asp Pro Glu Val Lys Phe Asn Trp Tyr Val Asp Gly Val Glu
65 70 75 80

Val His Asn Ala Lys Thr Lys Pro Arg Glu Glu Gln Tyr Ala Ser Thr
85 90 95

Tyr Arg Val Val Ser Val Leu Thr Val Leu His Gln Asp Trp Leu Asn
100 105 110

Gly Lys Glu Tyr Lys Cys Lys Val Ser Asn Lys Ala Leu Pro Ala Pro
115 120 125

Ile Glu Lys Thr Ile Ser Lys Ala Lys Gly Gln Pro Arg Glu Pro Gln
130 135 140

Val Tyr Thr Leu Pro Pro Ser Arg Asp Glu Leu Thr Lys Asn Gln Val
145 150 155 160

Ser Leu Thr Cys Leu Val Lys Gly Phe Tyr Pro Ser Asp Ile Ala Val
165 170 175

Glu Trp Glu Ser Asn Gly Gln Pro Glu Asn Asn Tyr Lys Thr Thr Pro
180 185 190

Pro Val Leu Asp Ser Asp Gly Ser Phe Phe Leu Tyr Ser Lys Leu Thr
195 200 205

Val Asp Lys Ser Arg Trp Gln Gln Gly Asn Val Phe Ser Cys Ser Val
210 215 220

Met His Glu Ala Leu His Asn His Tyr Thr Gln Lys Ser Leu Ser Leu
225 230 235 240

Ser Pro Gly Gly Ser
245

<210> SEQ ID NO 2
<211> LENGTH: 6
<212> TYPE: PRT
<213> ORGANISM: Artificial Sequence
<220> FEATURE:
<223> OTHER INFORMATION: Synthetic

<400> SEQUENCE: 2

Leu Pro Glu Thr Gly Gly
1 5

<210> SEQ ID NO 3
<211> LENGTH: 251
<212> TYPE: PRT
<213> ORGANISM: Artificial Sequence
<220> FEATURE:
<223> OTHER INFORMATION: Synthetic

<400> SEQUENCE: 3

Ala Glu Asn Leu Tyr Phe Gln Gly Gly Gly Gly Gly Glu Pro Lys Ser
1 5 10 15

Cys Asp Lys Thr His Thr Cys Pro Pro Cys Pro Ala Pro Glu Leu Leu
20 25 30

-continued

```
Gly Gly Pro Ser Val Phe Leu Phe Pro Pro Lys Pro Lys Asp Thr Leu
        35                  40                  45

Met Ile Ser Arg Thr Pro Glu Val Thr Cys Val Val Val Asp Val Ser
    50                  55                  60

His Glu Asp Pro Glu Val Lys Phe Asn Trp Tyr Val Asp Gly Val Glu
65                  70                  75                  80

Val His Asn Ala Lys Thr Lys Pro Arg Glu Glu Gln Tyr Ala Ser Thr
                85                  90                  95

Tyr Arg Val Val Ser Val Leu Thr Val Leu His Gln Asp Trp Leu Asn
            100                 105                 110

Gly Lys Glu Tyr Lys Cys Lys Val Ser Asn Lys Ala Leu Pro Ala Pro
        115                 120                 125

Ile Glu Lys Thr Ile Ser Lys Ala Lys Gly Gln Pro Arg Glu Pro Gln
    130                 135                 140

Val Tyr Thr Leu Pro Pro Ser Arg Asp Glu Leu Thr Lys Asn Gln Val
145                 150                 155                 160

Ser Leu Thr Cys Leu Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
            180                 185                 190

Pro Val Leu Asp Ser Asp Gly Ser Phe Phe Leu Tyr Ser Lys Leu Thr
        195                 200                 205

Val Asp Lys Ser Arg Trp Gln Gln Gly Asn Val Phe Ser Cys Ser Val
    210                 215                 220

Met His Glu Ala Leu His Asn His Tyr Thr Gln Lys Ser Leu Ser Leu
225                 230                 235                 240

Ser Pro Gly Gly Ser Leu Pro Glu Thr Gly Gly
                245                 250


<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Leu Pro Glu Thr Gly Gly Gly
1               5
```